(12) United States Patent
Miller et al.

(10) Patent No.: US 7,960,398 B2
(45) Date of Patent: Jun. 14, 2011

(54) REGULATION OF TNF-ALPHA

(75) Inventors: Karen Miller, Newbury (GB); Anita Diu-Hercend, Charenton le Pont (FR); Thierry Hercend, Charenton le Pont (FR); Paul Lang, Viuz-en-Sallaz (FR); Peter Weber, Abingdon (GB); Julian Golec, Swindon (GB); Michael Mortimore, Burford (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1252 days.

(21) Appl. No.: 10/419,327

(22) Filed: Apr. 17, 2003

(65) Prior Publication Data
US 2004/0048797 A1 Mar. 11, 2004

Related U.S. Application Data

(60) Provisional application No. 60/374,434, filed on Apr. 19, 2002.

(51) Int. Cl.
*A61K 31/517* (2006.01)
(52) U.S. Cl. .................................................. 514/266.1
(58) Field of Classification Search ............... 514/266.1
See application file for complete search history.

(56) References Cited

U.S. PATENT DOCUMENTS

| | | | |
|---|---|---|---|
| 6,184,210 B1 | 2/2001 | Keana et al. .................. 514/19 |
| 6,184,244 B1 | 2/2001 | Karanewsky et al. ........ 514/419 |
| 6,187,771 B1 | 2/2001 | Karanewsky et al. ... 514/212.05 |
| 6,197,750 B1 | 3/2001 | Karanewsky et al. .......... 514/19 |
| 6,214,858 B1 | 4/2001 | Lee et al. .................... 514/ 418 |
| 6,242,422 B1 | 6/2001 | Karanewsky et al. .......... 514/19 |
| 6,355,618 B1 | 3/2002 | Cai et al. ........................ 514/19 |
| 2003/0232846 A1 | 12/2003 | Golec et al. | |

FOREIGN PATENT DOCUMENTS

| | | |
|---|---|---|
| WO | WO 00/55114 | 9/2000 |
| WO | WO 00/55127 | 9/2000 |
| WO | WO 00/61542 | 10/2000 |
| WO | WO 01/05772 | 1/2001 |
| WO | WO 01/10383 | 2/2001 |
| WO | WO 01/16093 | 3/2001 |
| WO | WO 01/42216 | 6/2001 |
| WO | WO 01/72707 | 10/2001 |
| WO | WO 01/90070 | 11/2001 |
| WO | WO 01/94351 | 12/2001 |
| WO | WO 02/22611 | 3/2002 |
| WO | WO 02/42278 | 5/2002 |

(Continued)

OTHER PUBLICATIONS

Aggarwalt, B.B. and Eessalu, T.E., "Induction of Receptors for Tumor Necrosis Factor-α by Interferons Is Not a Major Mechanism for Their Synergistic Cytotoxic Response," *The Journal of Biological Chemistry*, 262:10000-10007 (1987).

(Continued)

*Primary Examiner* — San-ming Hui
(74) *Attorney, Agent, or Firm* — Ropes & Gray LLP; James F. Haley, Jr.; Yang Xu

(57) ABSTRACT

The present invention relates to methods for identifying compounds useful for regulating TNF-alpha levels and/or activity. The invention also relates to methods for decreasing TNF-alpha levels and/or activity. Compounds and compositions according to this invention are useful for treating TNF-mediated diseases. The invention also relates to kits comprising the compounds and compositions herein and a tool for measuring TNF-alpha activity and/or levels.

1 Claim, 210 Drawing Sheets

1. A compound of the formula (I):

I where $R^1$ is hydrogen, CN, CHN$_2$, R, or -CH$_2$Y;

R is an aliphatic group, a substituted aliphatic group, an aryl group, a substituted aryl group, an aralkyl group, a substituted aralkyl group a non-aromatic heterocyclic group or a substituted non-aromatic heterocyclic group;

Y is an electronegative leaving group or -OR, -SR, -OC=O(R), or -OPO(R$^8$) (R$^9$);

$R^8$ and $R^9$ are independently selected from R or OR;

$R^2$ is CO$_2$H, CH$_2$CO$_2$H, or esters, amides or isosteres thereof;

$R^3$ is hydrogen or a C$_{1-6}$ straight chained or branched alkyl;

Ring A contains zero to two double bonds, and is optionally fused to a saturated or unsaturated five to seven membered ring containing zero to three heteroatoms;

$X_1$ and $X_2$ in Ring A are independently selected from nitrogen or carbon, and $X_3$ is selected from a valence bond, oxygen, sulfur, nitrogen or carbon, wherein any X with suitable valence may bear a substituent;

each carbon with suitable valence in Ring A, including the fused ring if present, is independently substituted by hydrogen, halo, R, OR, SR, OH, NO$_2$, CN, NH$_2$, NHR,

FOREIGN PATENT DOCUMENTS

| | | |
|---|---|---|
| WO | WO 02/085899 | 10/2002 |
| WO | WO 02/094263 | 11/2002 |

OTHER PUBLICATIONS

Ausubel, F.M., et al., *Current Protocols in Molecular Biology*, vol. 2, John Wiley & Sons, Inc., New York.

Cohen, R.B. and Dittrich, K.A., "Anti-TNF Therapy and Malignancy—A Critical Review," *Can J Gastroenterol*, 15:376-384 (2001).

Deryckere, F., et al., "Tumor Necrosis Factor α Increases Expression of Adenovirus E3 Proteins," *Immunobiol*, 193:186-192 (1995).

Levesque, A., et al., "Improved Fluorescent Bioassay for the Detection of Tumor Necrosis Factor Activity," *Journal of Immunological Methods*, 178:71-76 (1995).

Liu, X-S., et al., "The Significance of Changes in Serum Tumor Necrosis Factor (TNF) Activity in Severely Burned Patients," *Burns*, 20:40-44 (1994).

Ostrove, J.M. and Gifford, G.E., "Simulation of RNA Synthesis in L-929 Cells by Rabbit Tumor Necrosis Factor," *Proceedings of the Society for Experimental Biology and Medicine*, 160:354-358 (1979).

Roggo, S., et al., "$P_{2/3}$ Oxo Azepenio Indoles: A New Class of Potent Broad Spectrum Caspase Inhibitors with in Vivo Activity in the pMCAO Model," *American Chemical Society (ACS) National Meeting in San Diego*, Apr. 2001.

Roggo, S., et al., "Optimized Synthesis of a Highly Potent, Brain Penetrable Caspase Inhibitor," *American Chemical Society (ACS) National Meeting in San Diego*, Apr. 2001.

Scheringa, M. and Marquet, R.L., "TNF: A Bried Review with Emphasis on its Antitumor Activity," *Biotherapy*, 2:275-281 (1990).

Tracey, K.J. And Cerami, A., "Tumor Necrosis Factor: A Pleiotropic Cytokine and Therapeutic Target," *Annu. Rev. Med.*, 45:491-503.

Wallach, D., "Cell Death Induction by TNF: a Matter of Self Control," *TIBS*, 22:107-109 (1997).

Office Action mailed May 13, 2008 in U.S. Appl. No. 10/166,437.

Keisuke et al.,"Altered Cytokine Export and Apoptosis in Mice Deficient in Interlukin-1-beta Converting Enzyme", *Science*, 267(5206):2000-2003 (1995).

Randle et al, "ICE/Caspase-1 Inhibitors as novel anti-inflammatory drugs"; *Expert Opinion on Investigational Drugs*. England, 10(7): 1207-1209 (2001).

1. A compound having the Formulae I or II or III:

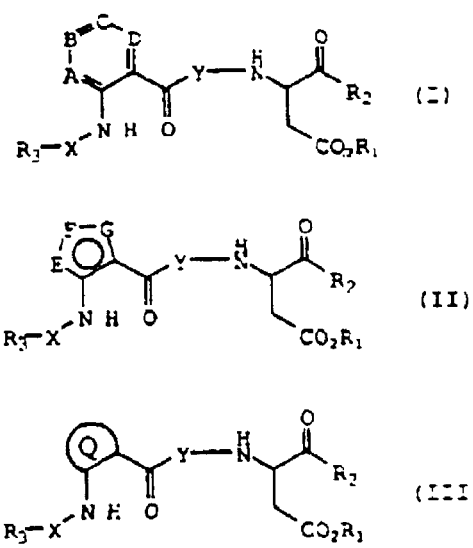

or a pharmaceutically acceptable salt or prodrug thereof, wherein:

$R_1$ is an optionally substituted alkyl or hydrogen;

$R_3$ is an N-protecting group;

$R_2$ is hydrogen or optionally substituted alkyl;

Q is an optionally substituted saturated or partially saturated carbocycle or heterocycle;

X is a peptide of 1-4 amino acids or a bond;

Y is a peptide of 1-4 amino acids or a bond;

A is $CR_6$ or nitrogen;

B is $CR_7$ or nitrogen;

C is $CR_8$ or nitrogen;

D is $CR_9$ or nitrogen;

provided that not more than two of A, B, C or D is nitrogen; and $R_6$-$R_9$ independently are hydrogen, halo, $C_1$-$C_6$ haloalkyl, $C_6$-$C_{10}$ aryl, $C_4$-$C_7$, cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl,

Fig. 1(a)

nitro, amino, cyano, $C_1$-$C_6$ acylamino, hydroxy, $C_1$-$C_6$ acyloxy, $C_1$-$C_6$ alkoxy, alkylthio, or carboxy; or one of $R_6$ and $R_7$, or $R_7$ and $R_8$, or $R_8$ and $R_9$ are taken together with the carbon atoms to which they are attached to form a carbocycle or heterocycle;

E is $C_{14}$, nitrogen, oxygen or sulfur;

F is $C_{15}$, nitrogen, oxygen or sulfur;

G is $C_{16}$, nitrogen, oxygen or sulfur;

provided that only one of E, F, G is nitrogen, oxygen or sulfur and $R_{14}$-$R_{16}$ are independently hydrogen, halo, $C_1$-$C_6$ haloalkyl, $C_6$-$C_{10}$ aryl, $C_4$-$C_7$, cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, cyano, $C_1$-$C_6$ acylamino, hydroxy, $C_1$-$C_6$ acyloxy, $C_1$-$C_6$ alkoxy, alkylthio, or carboxy; or one of $R_{14}$ and $R_{15}$, or $R_{15}$ and $R_{16}$, are taken together with the carbon atoms to which they are attached to form a carbocycle or heterocycle.

2. A compound according to claim 1, wherein $R_3$ is t-butyloxycarbonyl, acetyl or benzyloxycarbonyl.

3. A compound according to claim 1, wherein $R_1$ is H, Me, Et or acetoxymethyl.

4. A compound according to claim 1, wherein $R_2$ is hydrogen, fluoromethyl, acyloxymethyl, arylacyloxymethyl or aminomethyl.

5. A compound according to claim 1, wherein X is a bond.

6. A compound according to claim 1, wherein A, B, C and D are CH.

Fig. 1(b)

7. A compound according to claim 1, wherein A is nitrogen, and B, C and D are CH.

8. A compound according to claim 1, wherein G is sulfur, and E and F are CH.

9. A compound according to claim 1, wherein Q is cyclohexyl or cyclopentyl.

10. A compound according to claim 1, wherein said compound has the Formula IV:

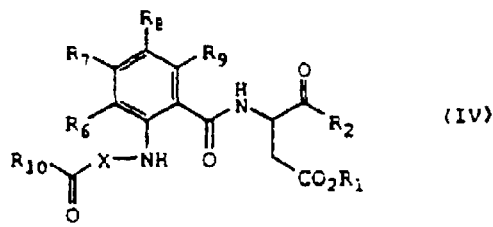

(IV)

or a pharmaceutically acceptable salt or prodrug thereof, wherein $R_2$ is hydrogen or optionally substituted alkyl, wherein the substituent is halo, hydroxy, alkoxy, aryloxy, alkylthio, arylthio, amino, acyloxy, or arylacyloxy:

$R_6$-$R_9$ independently are hydrogen, halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, cyano, $C_1$-$C_6$ acylamino, hydroxy, $C_1$-$C_6$ acyloxy, $C_1$-$C_6$ alkoxy, alkylthio, or carboxy; or one of $R_6$ and $R_7$, or $R_7$ and $R_8$, or $R_8$ and $R_9$ are taken together with the carbon atoms to which they are attached to form a carbocycle or heterocycle, selected from the group consisting of —$OCH_2O$—, —$OCF_2O$—, —$(CH_2)_3$—, —$(CH_2)_4$—, —$OCH_2CH_2O$—, —$CH_2N(R_{13})CH_2$—, —$CH_2CH_2N(R_{13})CH_2$—, —$CH_2N(R_{13})CH_2CH_2$— and —CH=CH—CH=CH—: wherein $R_{13}$ is hydrogen, alkyl or cycloalkyl;

Fig. 1(c)

$R_{10}$ is hydrogen, $C_1$-$C_6$ alkoxy, $C_1$-$C_6$ alkyl, $C_1$-$C_6$ haloalkyl, $C_6$-$C_{10}$ aryl, $C_4$-$C_7$ cycloalkyl, $C_6$-$C_{10}$ aryl($C_1$-$C_6$)alkyl, benzyloxy, substituted benzyloxy, or $NR_{11}R_{12}$; wherein $R_{11}$ and $R_{12}$ independently are hydrogen, $C_1$-$C_6$ alkyl, $C_1$-$C_6$ haloalkyl, $C_6$-$C_{10}$ aryl, $C_4$-$C_7$ cycloalkyl, $C_6$-$C_{10}$ aryl($C_1$-$C_6$)alkyl, or $R_{11}$ and $R_{12}$ are combined to form a heterocyclic ring system selected from the group consisting of pyrrolidine, piperidine, piperazine and morpholine.

11. A compound according to claim 10, wherein $R_2$ is hydrogen, fluoromethyl, acyloxymethyl, arylacyloxymethyl or aminomethyl.

12. A compound according to claim 10, wherein $R_{10}$ is benzyloxy.

13. A compound according to claim 10, wherein $R_1$ is H, Me or acetoxymethyl.

14. A compound according to claim 10, wherein X is a peptide of 1-2 amino acids or a bond.

Fig. 1(d)

| |
|---|
| 2-(Z-Amino)benzoyl-Asp-fmk |
| 2-(Z-Amino)-6-methylbenzoyl-Asp-fmk |
| 2-(Z-Amino)-5-methylbenzoyl-Asp-fmk |
| 2-(Z-Amino)-3-methylbenzoyl-Asp-fmk |
| 2-(Z-Amino)-3-methylbenzoyl-Asp-fmk |
| 2-(Z-Amino)-5-fluorobenzoyl-Asp-fmk |
| cis-2-(Z-Amino)cyclohexanecarboxyl- Asp-fmk |
| 2-(Z-Amino)-3,5-dimethylbenzoyl- Asp-fmk |
| 2-(Z-Amino)-5-chlorobenzoyl-Asp-fmk |
| 2-(Z-Amino)-6-chlorobenzoyl-Asp-fmk |
| 2-(Z-Amino)-4-methylbenzoyl- Asp-fmk |
| 3-(Z-Amino)thiophene-3-carboxyl- Asp-fmk |
| 3-(Methoxycarbonylamino)thiophene-2-carboxyl-Asp-fmk |
| Cis-2-(Z-Amino)cyclopentanecarboxyl- Asp-fmk |
| Trans-2-(Z-Amino)cyclohexanecarboxyl-Asp-fmk |
| Z-Glu-(2-aminobenzoyl)- Asp-fmk |
| Z-Val-(2-Aminobenzoyl)- Asp-fmk |
| 2-(Z-Amino)benzoyl-Asp-DCB-methylketone |
| Methoxycarbonyl-Val-(2-aminobenzoyl)-Asp-fmk |

Fig. 1(e)

| 1 | 2-(Z-Amino)benzoyl-Asp-fmk |
|---|---|
| 2 | 2-(Z-Amino)-6-methylbenzoyl-Asp-fmk |
| 3 | 2-(Z-Amino)-5-methylbenzoyl-Asp-fmk |
| 4 | 2-(Z-Amino)-3-methylbenzoyl-Asp-fmk |
| 5 | 2-(Z-Amino)-3-methylbenzoyl-Asp-fmk |
| 6 | 2-(Z-Amino)-5-fluorobenzoyl-Asp-fmk |
| 7 | cis-2-(Z-Amino)cyclohexanecarboxyl-Asp-fmk |
| 8 | 2-(Z-Amino)-3,5-dimethylbenzoyl-Asp-fmk |
| 9 | 2-(Z-Amino)-5-chlorobenzoyl-Asp-fmk |
| 10 | 2-(Z-Amino)-6-chlorobenzoyl- Asp-fmk |
| 11 | 2-(Z-Amino)-4-methylbenzoyl-Asp-fmk |
| 12 | 3-(Z-Amino)thiophene-3-carboxyl-Asp-fmk |
| 13 | 3-(Methoxycarbonylamino)thiophene-2-carboxyl-Asp-fmk |
| 14 | Cis-2-(Z-Amino)cyclopentanecarboxyl-Asp-fmk |
| 15 | Trans-2-(Z-Amino)cyclohexanecarboxyl-Asp-fmk |
| 16 | Z-Glu-(2-aminobenzoyl)-Asp-fmk |
| 17 | Z-Val-(2-Aminobenzoyl)-Asp-fmk |
| 18 | 2-(Z-Amino)benzoyl-Asp-DCB-methylketone |
| 19 | Methoxycarbonyl-Val-(2-aminobenzoyl)- Asp-fmk |

Z: benzyloxycarbonyl fmk: fluoromethylketone

DCB: 2,6-dichlorobenzoyloxy

Fig. 1(f)

1. A compound represented by formula 1:

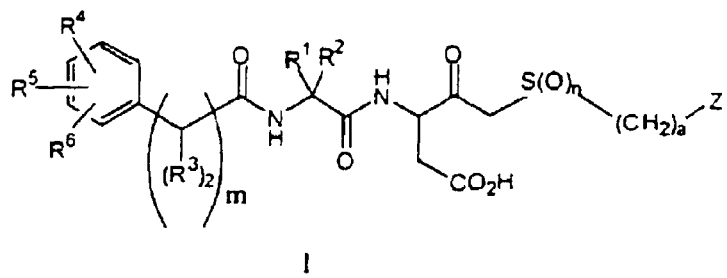

I or a pharmaceutically acceptable salt, ester or hydrate, wherein:

a is 0 or 1 and m and n are 0,1 or 2;

Z is selected from the group consisting of:

1) $C_{1-8}$ alkyl,

2) $C_{3-11}$ cycloalkyl, said alkyl and cycloalkyl groups being optionally substituted with 1-4 halo groups, 3) phenyl or naphthyl, optionally substituted by one or two groups selected from the group consisting of: halo, nitro, $C_{1-4}$alkyl and $C_{1-4}$alkoxy, said alkyl and alkoxy groups being optionally substituted with 1-3 halo groups; and 4) $HET^1$ wherein $HET^1$ represents a 5 or 6 membered aromatic or non-aromatic ring, and the benzofused analogs thereof, containing from 1-3 heteroatoms selected from O, S and N, and optionally substituted with 1-2 groups selected from halo, $C_{1-4}$alkyl and $C_{1-4}$acyl;

$R^1$ represents a member selected from the group consisting of: H, aryl, $C_{1-6}$ alkyl optionally substituted by $OR^7$, and $C_{5-7}$ cycloalkyl optionally containing one heteroatom selected from O, S and $NR^8$, and $R^2$ represents H,

Fig. 2-1(a)

or in the alternative, $R^1$ and $R^2$ are taken in combination and represent a ring of 4-7 members, said ring optionally containing one heteroatom selected from O, S and $NR^8$;

$R^7$ is selected from the group consisting of: H, $C_{1-5}$ alkyl and benzyl optionally substituted with 1-2 groups selected from halo. $C_{1-4}$ alkyl and $C_{1-4}$ alkoxy: and $R^8$ is H or $C_{1-4}$ alkyl:

each $R^3$ is independently selected from the group consisting of: H, $C_{1-4}$ alkyl optionally containing 1-2 oxo groups, $C_{1-4}$ alkoxy and halo:

$R^4$, $R^5$ and $R^6$ are independently selected from the group consisting of:

1) H,
2) halo,
3) $C_{1-4}$ alkoxy optionally substituted with 1-3 halo atoms,
4) $NO_2$,
5) OH,
6) benzyloxy, the benzyl portion of which is optionally substituted with 1-2 members selected from the group consisting of: halo, CN, $C_{1-4}$ alkyl and $C_{1-4}$ alkoxy, said alkyl and alkoxy being optionally substituted with 1-3 halo groups,
7) $NH-C_{1-4}$ acyl,
8) $C_{1-4}$ acyl,
9) $O-C_{1-4}$ alkyl-$CO_2H$, optionally esterified with a $C_{1-6}$ alkyl or $C_{5-7}$ cycloalkyl group,
10) $CH=CH-CO_2H$,
11) $C_{0-5}$ alkyl$CO_2H$,
12) $C_{0-5}$ alkyl $C(O)NH_2$, optionally substituted on the nitrogen atom by 1-2 $C_{1-4}$ alkyl groups;
13) $C_{0-2}$ alkyl$S(O)_{0-2}C_{1-4}$ alkyl;
14) $S(O)_{0-2}-C_{1-6}$ alkyl or $S(O)_{0-2}$-phenyl, said alkyl and phenyl portions thereof being optionally substituted with 1-3 members selected from the group consisting of: halo, CN, $C_{1-4}$ alkyl and $C_{1-4}$ alkoxy, said alkyl and alkoxy being optionally substituted by 1-3 halo groups,
15) benzoyl optionally substituted by 1-2 members selected from the group consisting of: halo, CN, $C_{1-4}$ alkyl and $C_{1-4}$ alkoxy, said alkyl and alkoxy groups being optionally substituted by 1-3 halo groups.

Fig. 2-1(b)

16) phenyl or naphthyl, optionally substituted with 1-2 members selected from this group consisting of: halo, CN, $C_{1-4}$alkyl and $C_{1-4}$alkoxy, said alkyl and alkoxy being optionally substituted with 1-3 halo groups,

17) CN,

18) $C_{1-4}$ alkyl-$HET^2$, wherein $HET^2$ represents a 5-7 membered aromatic or non-aromatic ring containing 1-4 heteroatoms selected from O, S and $NR^8$ and optionally containing 1-2 oxo groups, and optionally substituted with 1-3
$C_{1-4}$alkyl, OH, halo or $C_{1-4}$acyl groups:

19) -O $C_{1-4}$alkyl-$HET^3$, wherein $HET^3$ is a 5 or 6 membered aromatic or non-aromatic ring containing from 1 to 3 heteroatoms selected from O, S and N, and optionally substituted with one or two groups selected from halo and $C_{1-4}$alkyl, and optionally containing 1-2 oxo groups, and 20) $HET^1$, wherein $HET^1$ is a 5 or 6 membered aromatic or non-aromatic ring, and the benzofused analogs thereof, containing from 1 to 4 heteroatoms selected from O, S and N, and is optionally substituted by one or two groups selected from halo, $C_{1-4}$alkyl and $C_{1-4}$acyl, or $R^4$ and $R^5$ are taken in combination and represent a fused heteroaryl ring as shown below:

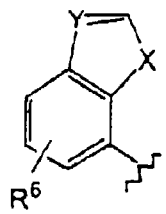

wherein Y is selected from the group consisting of CH and N, and X is selected from O, S and NH, and $R^6$ is as defined above.

2. A compound in accordance with claim 1 wherein a is 1.

3. A compound in accordance with claim 1 wherein m is 1.

Fig. 2-1(c)

4. A compound in accordance with claim 1 wherein n is 0.

5. A compound in accordance with claim 1 wherein Z is phenyl optionally substituted by one or two groups selected from halo, nitro, $C_{1-4}$alkoxy optionally substituted by up to 3 halogen atoms, or $C_{1-4}$alkyl optionally substituted by up to 3 halogen atoms.

6. A compound in accordance with claim 1 wherein $R^1$ is $C_{1-4}$alkyl optionally substituted by $OR^7$.

7. A compound in accordance with claim wherein $R^2$ is hydrogen

8. A compound in accordance with claim 1 wherein $R^3$ is hydrogen.

9. A compound in accordance with claim 1 wherein $R^2$ is H and n is 0.

10. A compound in accordance with claim 9 wherein $R^1$ represents a member selected from the group consisting of: H, $C_{1-4}$alkyl optionally substituted by $OR^7$ and $C_{5-7}$ cycloalkyl optionally containing one heteroatom selected from O, S and $NR^8$.

11. A compound in accordance with claim 1 wherein Z represents $HET^1$ and $HET^1$ represents a 5 or 6 membered aromatic ring, or the benzofused analog thereof, containing from 1-3 heteroatoms selected from O, S and N, and optionally substituted with 1-2 groups selected from halo, $C_{1-4}$alkyl and $C_{1-4}$acyl.

12. A compound in accordance with claim 11 wherein $HET^1$ represents a member selected from the group consisting of: pyridine, pyrimidine, pyridazine, furan, thiophene, thiazole and oxazole.

Fig. 2-1 (d)

13. A compound in accordance with claim 1 wherein $HET^2$ is selected from the group consisting of: butyrolactone, tetrahydrofuran, tetrahydropyran and 2-pyrrolidinone.

14. A compound in accordance with claim 1 wherein $HET^2$ is selected from pyridine and pyrimidine.

15. A compound in accordance with claim 1 wherein $HET^2$ is selected from the group consisting of: 1,2,3-oxadiazole, 1,2,4-oxadiazole, 1,3,4-oxadiazole, 1,2,3-thiadiazole, 1,2,4-thiadiazole, 1,3,4-thiadiazole, thiophene, pyrrole, pyridine, tetrazole, oxazole, thiazole, 1,2,3-triazole, 1,2,4-triazole and 1,3,4-triazole.

16. A compound in accordance with claim 1 wherein:

a and m are 1;

n is 0;

Z is phenyl optionally substituted by one or two groups selected from halo, nitro, $C_{1-4}$alkoxy optionally substituted by up to 3 halogen atoms, or $C_{1-4}$alkyl optionally substituted by up to 3 halogen atoms;

$R^1$ represents a member selected from the group consisting of: H, $C_{1-4}$alky optionally substituted by $OR^7$ and $C_{5-7}$cycloalkyl optionally containing one heteroatom selected from O, S and $NR^8$, $R^2$ is hydrogen:

$R^3$ is hydrogen

Z represents $HET^1$ and $HET^1$ represents pyridine, pyrimidine, pyridazine, furan, thiophene, thiazole or oxazole, optionally substituted with 1-2 groups selected from halo, $C_{1-4}$alkyl and $C_{1-4}$acyl;

$HET^2$ is selected from the group consisting of: butyrolactone, tetrahydrofuran, tetrahydropyran and 2-pyrrolidinone;

$HET^3$ is selected from the group consisting of: butyrolactone, tetrahydrofuran, tetrahydropyran, 2-pyrrolidinone, pyridine and pyrimidine;

and $HET^4$ is selected from the group consisting of: 1,2,3-oxadiazole, 1,2,4-oxadiazole, 1,3,4-oxadiazole, 1,2,3-thiadiazole, 1,2,4-thiadiazole, 1,3,4-thiadiazole, thiophene, pyrrole, pyridine, tetrazole, oxazole, thiazole, 1,2,3-triazole, 1,2,4-triazole and 1,3,4-triazole, and all other variables are as defined therein.

Fig. 2-1 (e)

|   | Table 1 |
|---|---------|
| 1 | 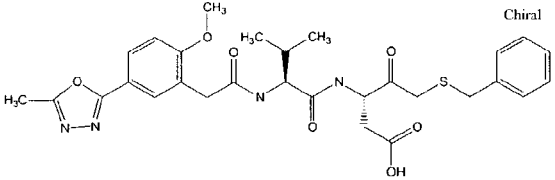 |
| 2 | 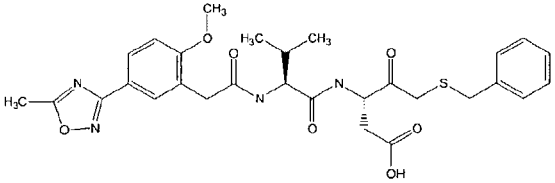 |
| 3 | 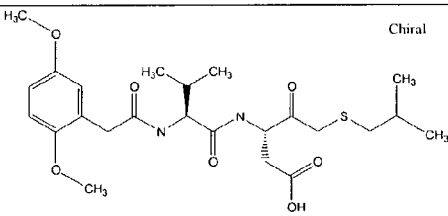 |
| 4 | 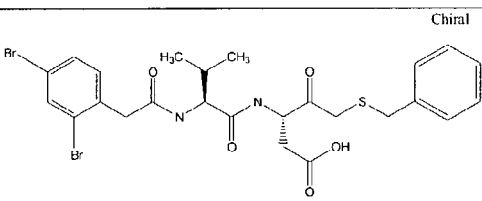 |
Fig. 2-1(f)

| 18 | 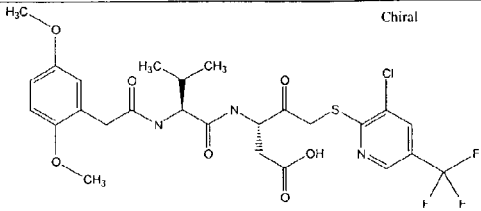 |
| 19 | 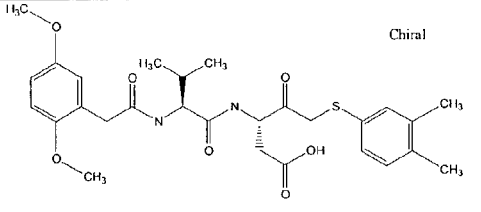 |
| 20 | 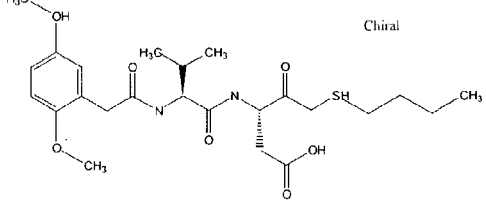 |
| 21 | 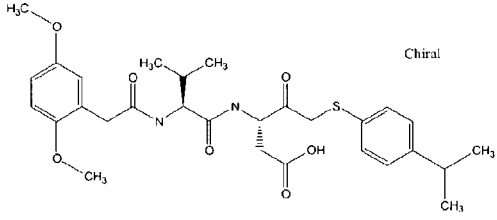 |
Fig. 2-1(j)

| 26 | 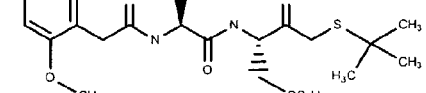 |
| 27 | 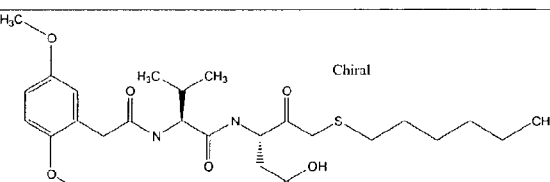 |
| 28 | 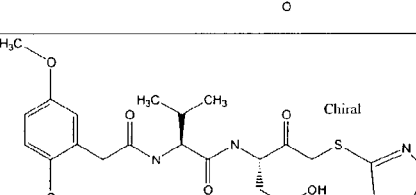 |
| 29 | 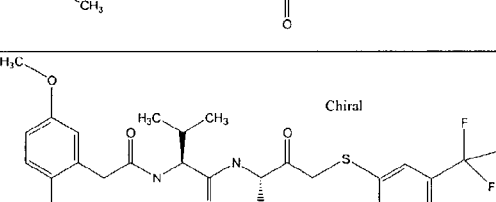 |
Fig. 2-1(l)

| 34 | 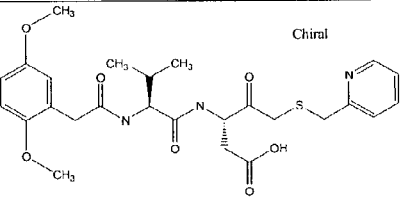 |
| 35 | 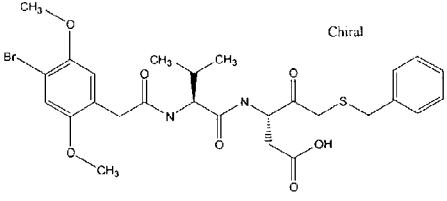 |
| 36 | 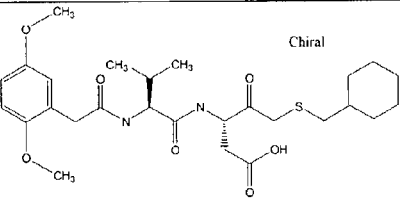 |
| 37 | 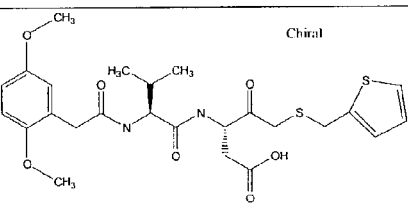 |
Fig. 2-1(n)

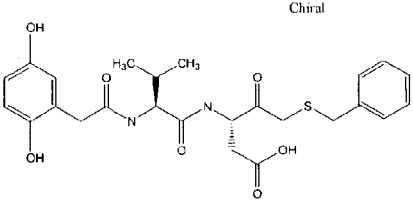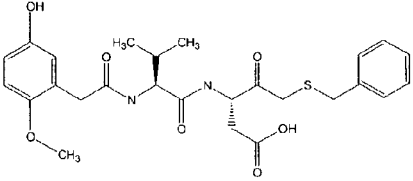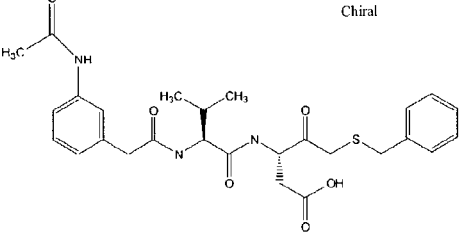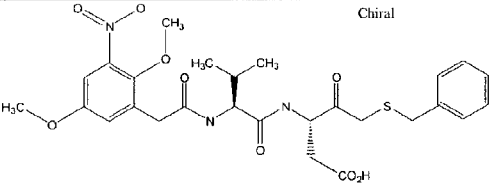
Fig. 2-1(q)

| 54 | 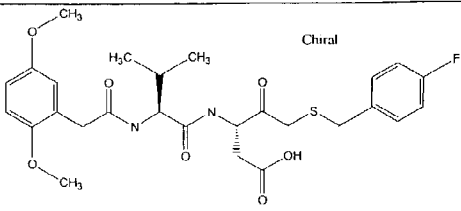 |
|---|---|
| 55 | 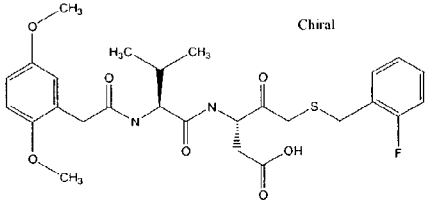 |
| 56 | 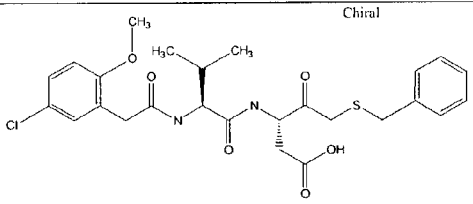 |
| 57 | 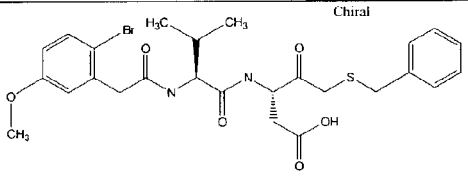 |
Fig. 2-1(s)

| 58 | 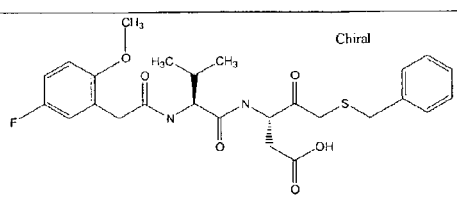 |
| 59 | 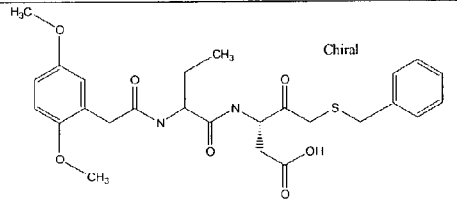 |
| 60 | 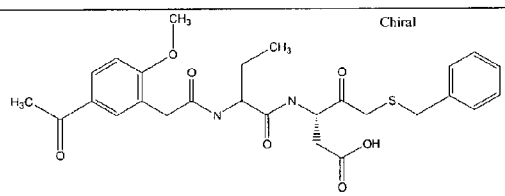 |
| 61 | 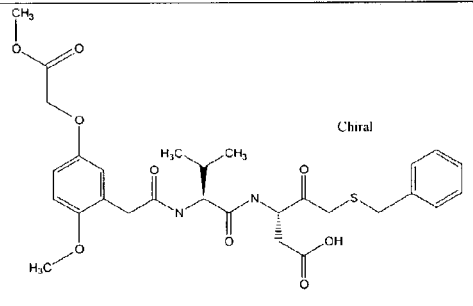 |
Fig. 2-1(t)

| 91 | 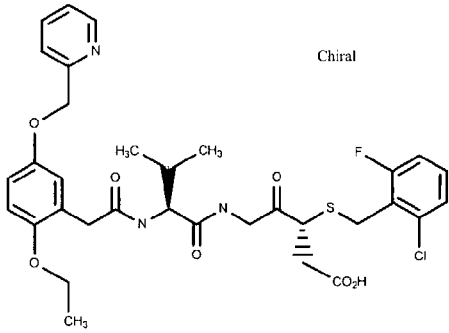 |
| --- | --- |
| 92 | 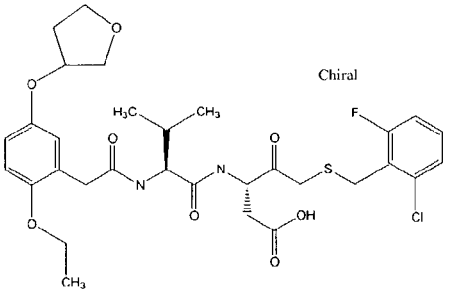 |
| 93 | 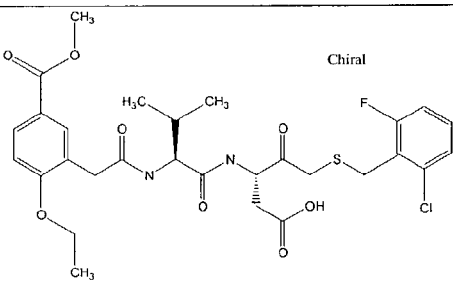 |
Fig. 2-2(d)

| 94 | 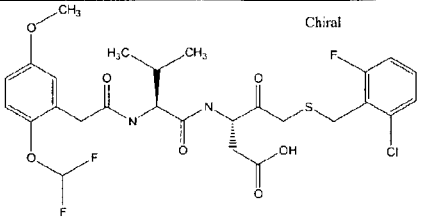 |
| 95 | 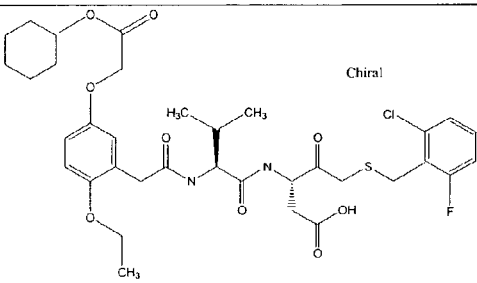 |
| 96 | 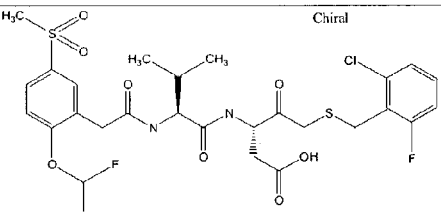 |
| 97 | 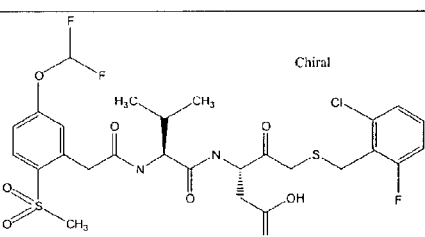 |
Fig. 2-2(e)

| 106 | 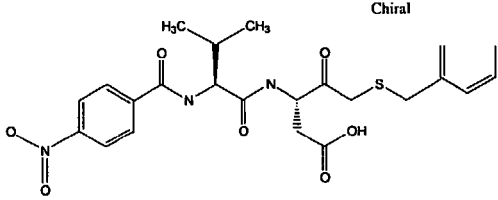 |
| 107 | 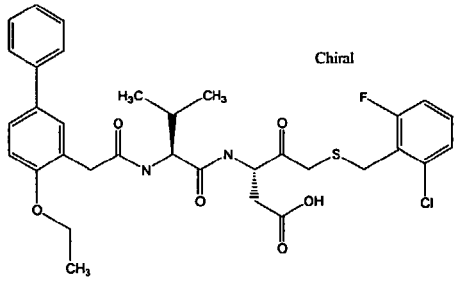 |
| 108 | 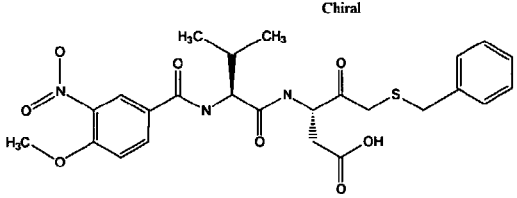 |
| 109 | 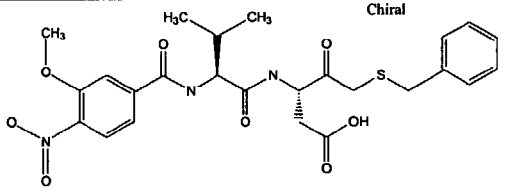 |
Fig. 2-2(h)

| 137 | 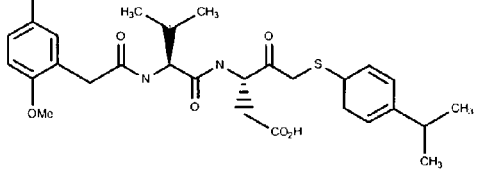 |
| 138 | 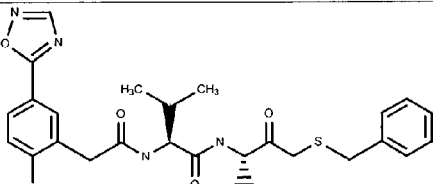 |
| 139 | 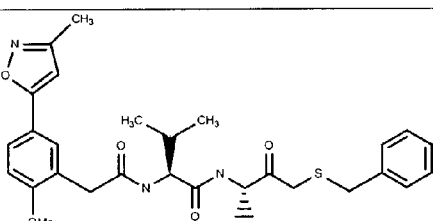 |
| 140 | 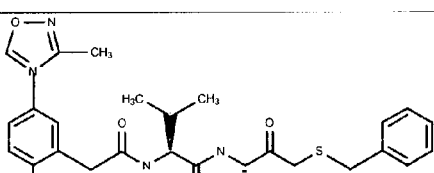 |
Fig. 2-2(p)

Fig. 2-2(q)

| 145 | 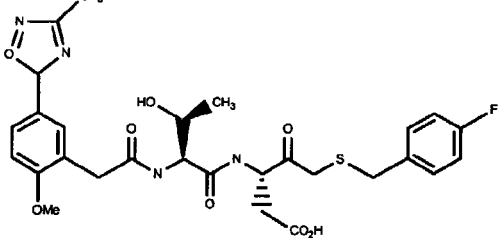 |
| --- | --- |
| 146 | 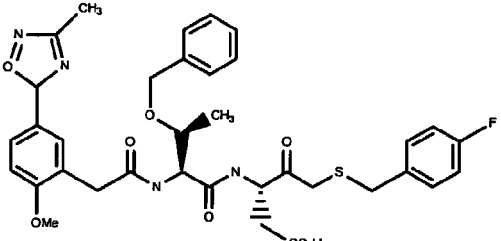 |
| 147 | 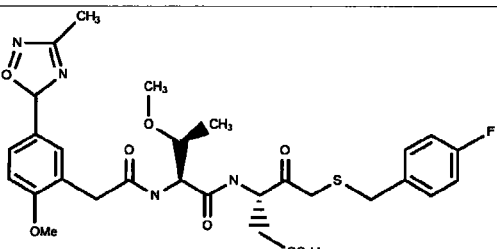 |
| 148 | 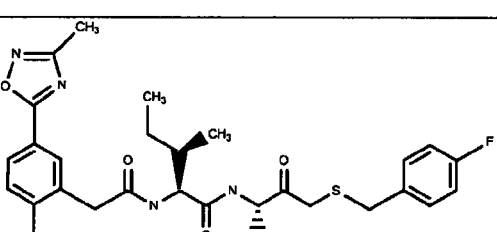 |
Fig. 2-2(r)

1. A compound having the Formula I:

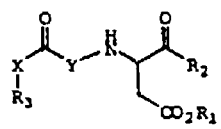

or pharmaceutically acceptable salts or prodrugs thereof, wherein:

$R_1$ is an optionally substituted alkyl or hydrogen;

$R_2$ is hydrogen or optionally substituted alkyl;

$R_3$ is an alkyl, saturated carbocyclic, partially saturated carbocyclic, aryl, saturated heterocyclic, partially saturated heterocyclic or heteroaryl group, wherein said group is optionally substituted;

X is O, S, $NR_4$ or $(CR_4R_5)_n$, where $R_4$ and $R_5$ are, at each occurrence, independently selected from the group consisting of hydrogen, alkyl and cycloalkyl, and n is 0, 1, 2 or 3; or X is $NR_4$, and $R_3$ and $R_4$ are taken together with the nitrogen atom to which they are attached to form a saturated heterocyclic, partially saturated heterocyclic or heteroaryl group, wherein said group is optionally substituted; or X is $CR_4R_5$, and $R_3$ and $R_4$ are taken together with the carbon atom to which they are attached to form a saturated carbocyclic, partially saturated carbocyclic, aryl, saturated heterocyclic, partially saturated heterocyclic or oxygen-containing heteroaryl group, wherein said group is optionally substituted; and Y is a residue of a natural or non-natural amino acid;

provided that when X is O, then $R_3$ is not unsubstituted benzyl or $t$-butyl; and when X is $CH_2$, then $R_3$ is not hydrogen.

Fig. 3(a)

2. The compound of claim 1, wherein $R_1$ is hydrogen, methyl, ethyl or acetoxymethyl.

3. The compound of claim 1, wherein $R_2$ is hydrogen, fluoromethyl, acyloxymethyl, arylacyloxymethyl, aryloxymethyl, phosphinyloxymethyl, or aminomethyl.

4. The compound of claim 1, wherein Y is valine, isoleucine, leucine, alanine, phenylalanine, cyclohexylalanine, 2-aminobutyric acid, phenylglycine or cyclohexylglycine.

5. The compound of claim 1, wherein:
$R_3$ is optionally substituted alkyl, $C_4$-$C_7$ cycloalkyl, saturated heterocyclic, partially saturated heterocyclic, aryl or heteroaryl; and
X is O, S, $NR_4$ or $(CR_4R_5)_n$, wherein $R_4$ and $R_5$ are independently hydrogen, alkyl or cycloalkyl, and n is 0, 1, 2 or 3.

6. The compound of claim 1, wherein X is O, NH or $CH_2$.

7. The compound of claim 1, wherein $R_3$ is straight-chained or branched $C_{1-6}$ alkyl.

8. The compound of claim 1, wherein $R_3$ is straight-chained or branched $C_{1-6}$ alkyl optionally substituted by hydroxy, carboxy, halogen, $C_4$-$C_7$ cycloalkyl, saturated or unsaturated heterocyclic group, aryl or heteroaryl.

9. The compound of claim 1, wherein $R_3$ is optionally substituted benzyl.

Fig. 3(b)

10. The compound of claim 1, wherein $R_3$ is optionally substituted pyridylmethyl.
11. The compound of claim 1, wherein $R_3$-X-C(O)- is an antioxidant group.
12. The compound of claim 11, wherein said antioxidant group is
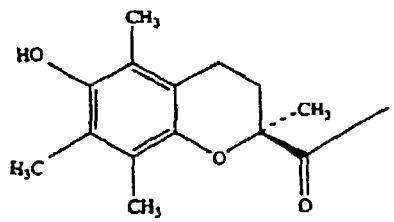
13. The compound of claim 12, wherein said compound is
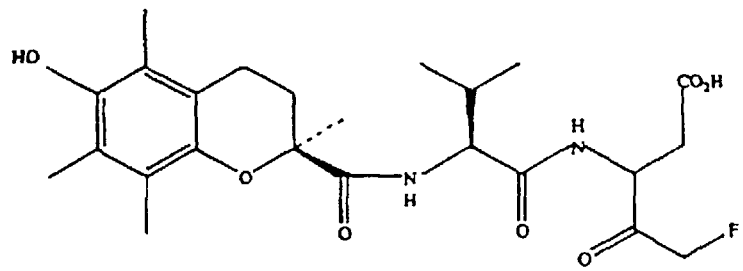
14. The compound of claim 1, wherein $R_3$-X-C(O)- is a fluorescent group.
Fig. 3(c)

15. The compound of claim 14, wherein said fluorescent group is
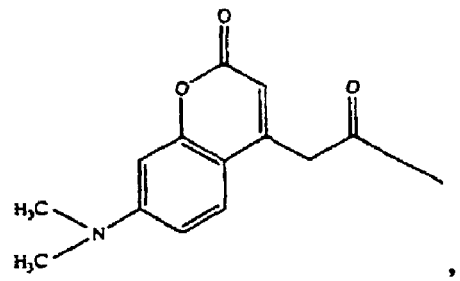
,
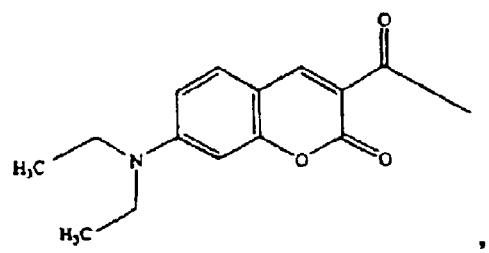
,
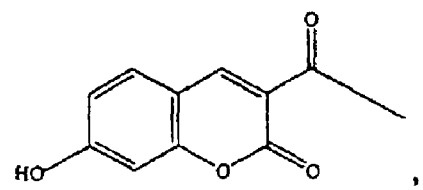
,
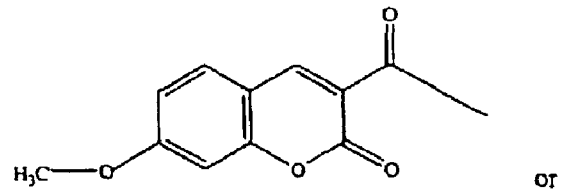 or
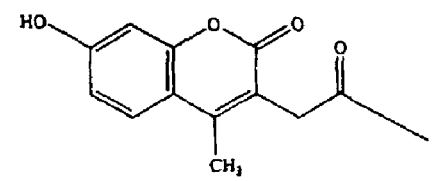
Fig. 3(d)

16. The compound of claim 14, wherein said compound is selected from the group consisting of
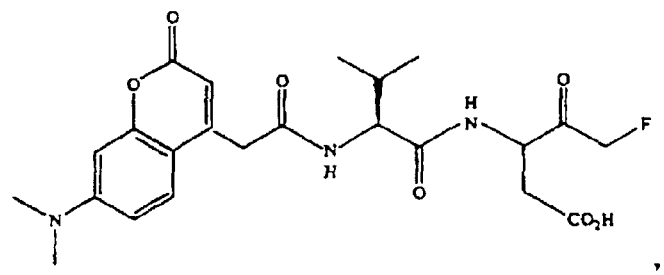
,
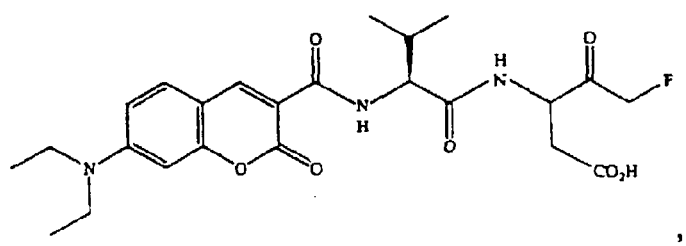
,
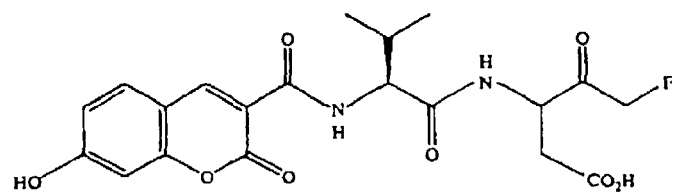
,
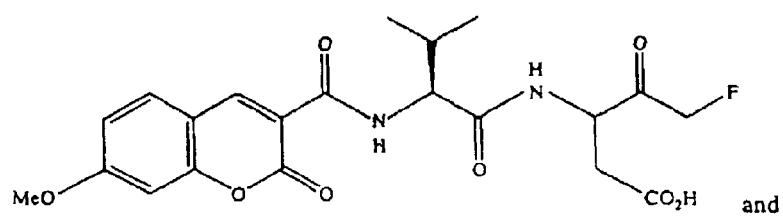 and
Fig. 3(e)

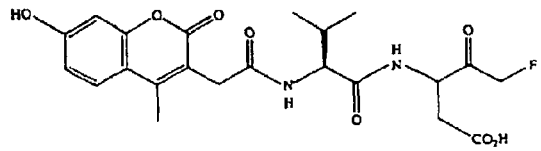

17. A compound having the Formula II:

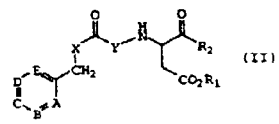

or pharmaceutically acceptable salts or prodrugs thereof wherein:

$R_1$ is an optionally substituted alkyl or hydrogen;

$R_2$ is hydrogen or optionally substituted alkyl;

X is O, S, $NR_4$ or $(CR_4R_5)_n$, wherein $R_4$ and $R_5$ are, at each occurrence, independently selected from the group consisting of hydrogen, alkyl, and cycloalkyl, and n is 0, 1, 2 or 3;

Y is a residue of a natural or non-natural amino acid;

A is $CR_6$ or nitrogen;

B is $CR_7$ or nitrogen;

C is $CR_8$ or nitrogen;

D is $CR_9$ or nitrogen;

E is $CR_{10}$ or nitrogen; provided that not more than three of A, B, C, D and E are nitrogen; and $R_6$-$R_{10}$ independently are hydrogen, halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, cyano, $C_1$-$C_6$ acylamino, hydroxy, $C_1$-$C_6$ acyloxy, $C_1$-$C_6$ alkoxy, alkylthio, or carboxy; or

Fig. 3(f)

one of $R_6$ and $R_7$, or $R_7$ and $R_8$, or $R_8$ and $R_9$, or $R_9$ and $R_{10}$ are taken together with the carbon atoms to which they are attached to form a carbocycle or heterocycle, selected from the group consisting of —$OCH_2O$—, —$OCF_2O$—, —$(CH_2)_3$—, —$(CH_2)_4$—, —$OCH_2CH_2O$—, —$CH_2N(R_{13})CH_2$—, $CH_2CH_2N(R_{13})CH_2$—, —$CH_2N(R_{13})CH_2CH_2$—, -$N(R_{13})$-CH=CH-, -CH-CH-$N(R_{13})$-, -O-CH=CH-, -CH=CH-O-, -S-CH=CH-, -CH=CH-S-, -N=CH-CH=CH-, -CH=N-CH=CH-, -CH=CH-N=CH-, -CH=CH-CH=N-, -N=CH-CH=N-, and —CH=CH—CH=CH—; wherein $R_{13}$ is hydrogen, alkyl or cycloalkyl;

provided that when X is O, A is $CR_6$, B is $CR_7$, C is $CR_8$, D is $CR_9$ and E is $CR_{10}$, then at least one of the $R_6$-$R_{10}$ is not hydrogen.

18. The compound of claim 17, wherein $R_2$ is hydrogen, fluoromethyl, acyloxymethyl, arylacyloxymethyl, aryloxymethyl, phosphinyloxymethyl, or aminomethyl.

19. The compound of claim 17, wherein $R_1$ is hydrogen, methyl, ethyl or acetoxymethyl.

20. The compound of claim 17, wherein Y is valine, Isoleucine, leucine, alanine, phenylalanine, cyclohexylalanine, 2-aminobutyric acid, phenylglycine or cyclohexylglycine.

21. The compound of claim 17, wherein X is O, A is $CR_6$, B is $CR_7$, C is $CR_8$, D is $CR_9$, and E is $CR_{10}$.

22. The compound of claim 17, wherein X is O, and one of A, B, C, D or E is nitrogen.

Fig. 3(g)

23. The compound of claim 17, wherein X is $CH_2$, A is $CR_6$, B is $CR_7$, C is $CR_8$, D is $CR_9$ and E is $CR_{10}$.

24. A compound having the Formula III:

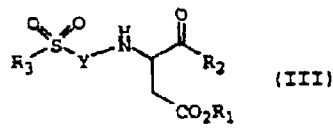

(III)

or pharmaceutically acceptable salts or prodrugs thereof, wherein:

$R_1$ is an optionally substituted alkyl or hydrogen;

$R_2$ is hydrogen or optionally substituted alkyl;

$R_3$ is an alkyl, saturated carbocyclic, partially saturated carbocyclic, aryl, saturated heterocyclic, partially saturated heterocyclic or heteroaryl group, wherein said group is optionally substituted; and Y is a residue of a natural or non-natural amino acid.

25. The compound of claim 24, wherein $R_1$ is hydrogen, methyl, ethyl or acetoxymethyl.

26. The compound of claim 24, wherein $R_2$ is hydrogen, fluoromethyl, acyloxy methyl, arylacyloxymethyl, aryloxymethyl, phosphinyloxymethyl, or aminomethyl.

27. The compound of claim 24, wherein Y is valine, isoleucine, leucine, alanine, phenylalanine, cyclohexylalanine, 2-aminobutyric acid, phenylglycine or cyclohexylglycine.

Fig. 3(h)

28. The compound of claim 24, wherein $R_3$ is straight-chained or branched $C_{1-6}$ alkyl.

29. The compound of claim 24, wherein $R_3$ is straight-chained or branched $C_{1-6}$ alkyl optionally substituted by hydroxy, carboxy, halogen $C_4$-$C_7$ cycloalkyl, saturated or unsaturated heterocyclic group, aryl or heteroaryl.

30. The compound of claim 24, wherein $R_3$ is methylphenyl or dimethylaminonaphthyl.

31. The compound of claim 1, wherein said compound is selected from the group consisting of:

2-Chlorobenzyloxycarbonyl-Val-Asp-fmk,

3-Chlorobenzyloxycarbonyl-Val-Asp-fmk,

4-Chlorobenzyloxycarbonyl-Val-Asp-fmk,

Phenethoxycarbonyl-Val-Asp-fmk,

Cyclohexylmethoxycarbonyl-Val-Asp-fmk,

Methoxycarbonyl-Val-Asp-fmk,

Ethoxycarbonyl-Val-Asp-fmk,

Isopropyloxycarbonyl-Val-Asp-fmk,

2-Chlorobenzyloxycarbonyl-Ile-Asp-fmk,

3-Chlorobenzyloxycarbonyl-Ile-Asp-fmk,

4-Chlorobenzyloxycarbonyl-Ile-Asp-fmk,

Phenylacetyl-Val-Asp-fmk,

4-Nitrobenzyloxycarbonyl-Val-Asp-fmk, 2,5-Dimethylbenzyloxycarbonyl-Val-Asp-fmk, 3,4-Dichlorobenzyloxycarbonyl-Val-Asp-fmk, 3,5-Dichlorobenzyloxycarbonyl-Val-Asp-fmk, 2,5-Dichlorobenzyloxycarbonyl-Val-Asp-fmk, 2,6-Dichlorobenzyloxycarbonyl-Val-Asp-fmk,

Fig. 3(i)

2,4-Dichlorobenzyloxycarbonyl-Val-Asp-fmk, 2,4-Dimethylbenzyloxycarbonyl-Val-Asp-fmk, 4-Ethylbenzyloxycarbonyl-Val-Asp-fmk, 4-Bromobenzyloxycarbonyl-Val-Asp-fmk, 4-Fluorobenzyloxycarbonyl-Val-Asp-fmk, Cyclopentylmethoxycarbonyl-Val-Asp-fmk, 4-Trifluoromethylbenzyloxycarbonyl-Val-Asp-fmk, 3-Phenylpropionyl-Val-Asp-fmk, Benzylaminocarbonyl-Val-Asp-fmk, 3-Phenylpropyloxycarbonyl-Val-Asp-fmk, 2,4-Difluorobenzyloxycarbonyl-Val-Asp-fmk, 3,4-Difluorobenzyloxycarbonyl-Val-Asp-fmk, 4-Morpholinecarbonyl-Val-Asp-fmk, 4-Pyridylmethoxycarbonyl-Val-Asp-fmk, 2-Pyridylmethoxycarbonyl-Val-Asp-fmk, 2,6-Dichlorobenzyloxycarbonyl-Val-Asp-DCB-methylketone, Isobutoxycarbonyl-Val-Asp-fmk, Propionyl-Val-Asp-fmk, Benzyl-glutaryl-Val-Asp-fmk, Glutaryl-Val-Asp-fmk, 3-(2-Phenyloxyphenyl)propionyl-Val-Asp-fmk, 3-(5-Bromo-2-hydroxyphenyl)propionyl-Val-Asp-fmk, 3-Fluorobenzyloxycarbonyl-Val-Asp-fmk, 2-Fluorobenzyloxycarbonyl-Val-Asp-fmk, 3-Methylbenzyloxycarbonyl-Val-Asp-fmk, 2-Chloro-4-fluorobenzyloxycarbonyl-Val-Asp-fmk, and 2-Naphthylmethoxycarbonyl-Val-Asp-fmk.

32. The compound of claim 24, wherein said compound is selected from the group consisting of:

*p*-Toluenesulfonyl-Val-Asp-fmk, and

*p*-Toluenesulfonyl-Phe-Asp-fmk.

Fig. 3(j)

Table 1
| Compound Number | |
|---|---|
| 1 | 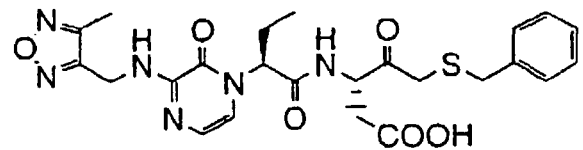 |
| 2 | 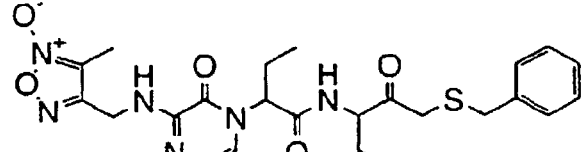 |
| 3 | 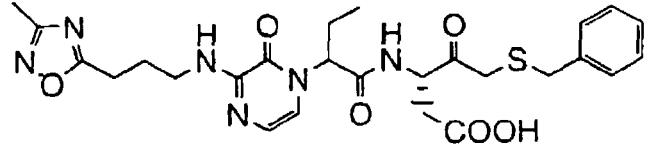 |
| 4 | 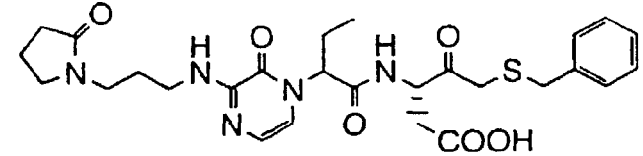 |
| 5 | 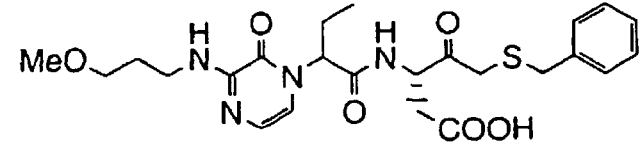 |
| 6 | 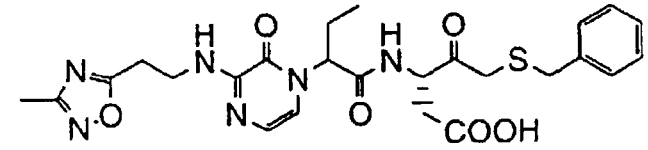 |
Fig. 4(a)

| 35 | 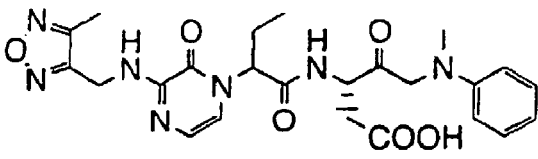 |
|---|---|
| 36 | 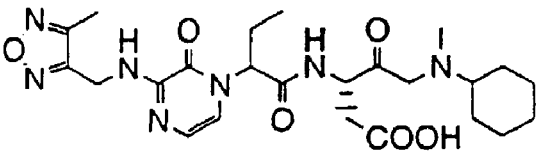 |
| 37 | 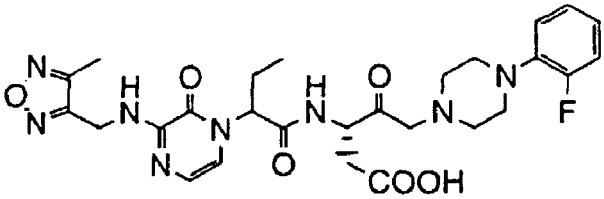 |
| 38 | 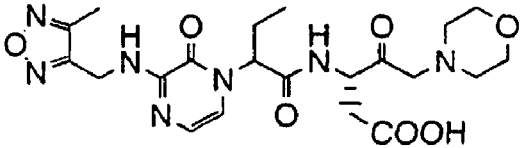 |
| 39 | 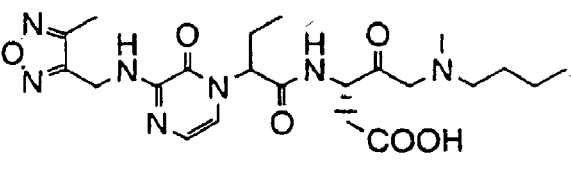 |
| 40 | 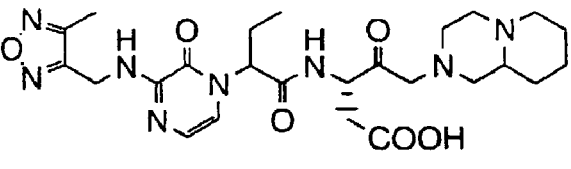 |
| 41 | 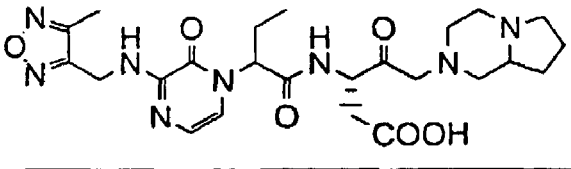 |
Fig. 4(f)

| 62 | 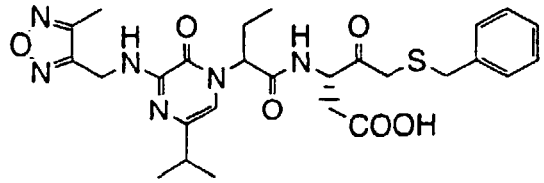 |
| 63 | 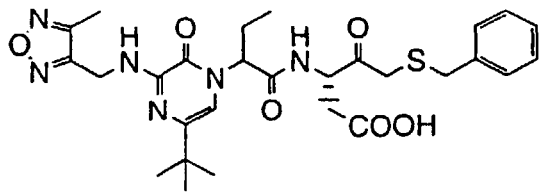 |
| 64 | 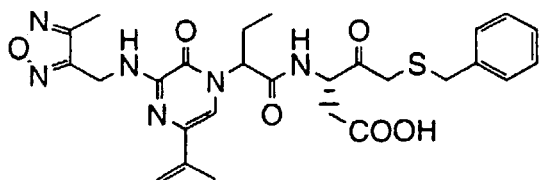 |
| 65 | 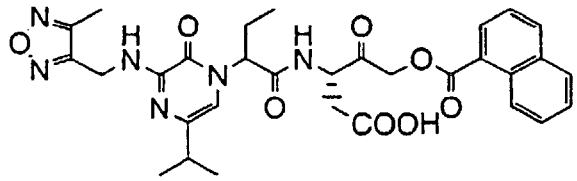 |
| 66 | 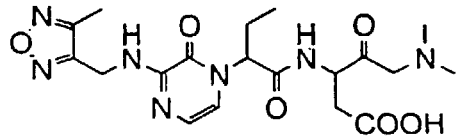 |
| 67 | 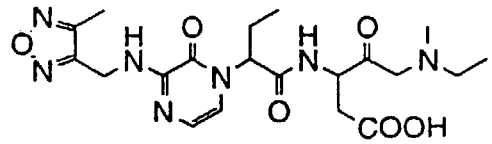 |
Fig. 4(j)

| 76 | 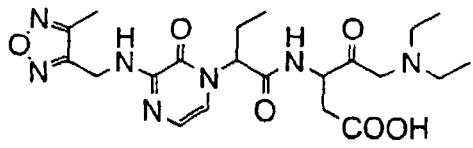 |
| 77 | 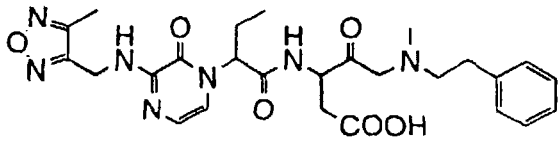 |
| 78 | 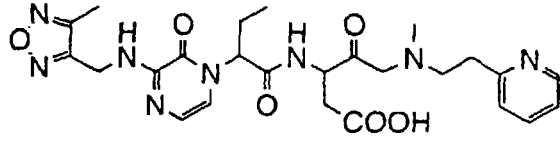 |
| 79 | 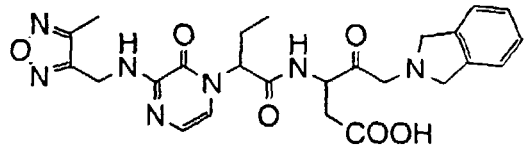 |
| 80 | 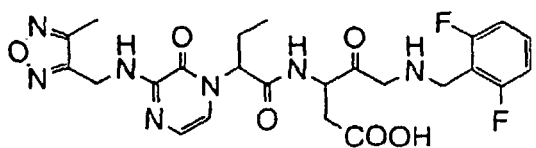 |
| 81 | 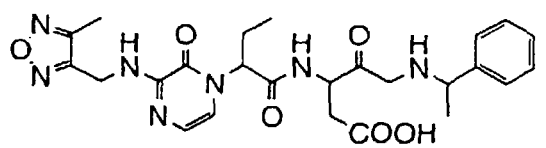 |
| 82 | 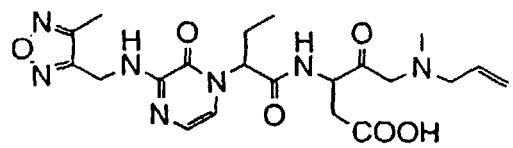 |
Fig. 4(l)

| 83 | 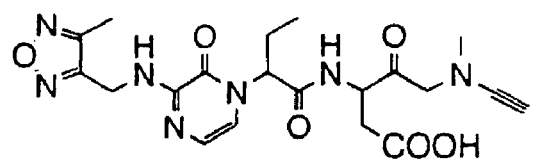 |
| 84 | 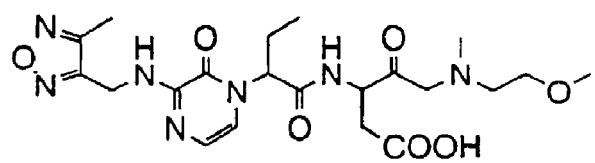 |
| 85 | 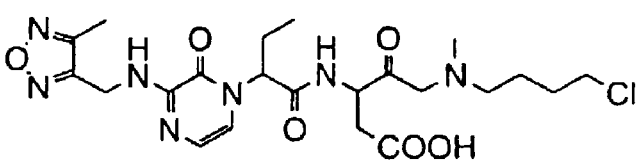 |
| 86 | 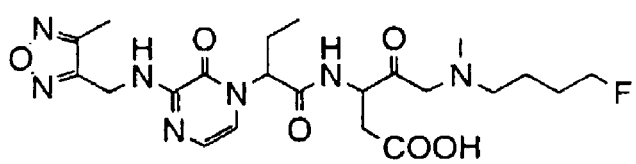 |
| 87 | 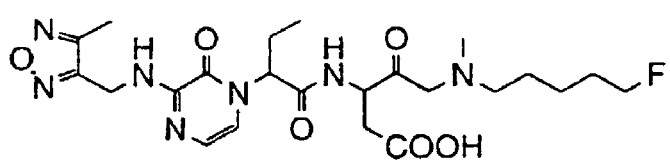 |
| 88 | 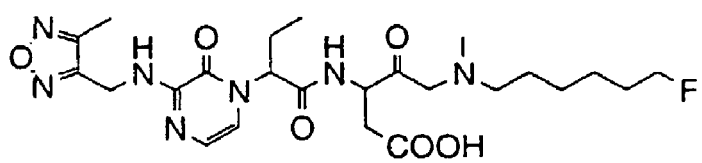 |
Fig. 4(m)

1. A compound represented by formula I:

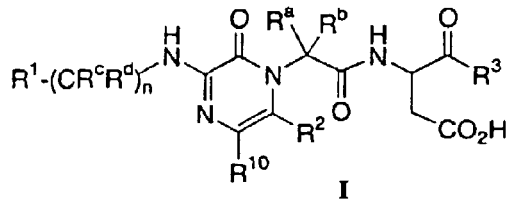

I or a pharmaceutically acceptable salt, ester, N-oxide or hydrate thereof wherein:

$R^1$ is selected from the group consisting of:

OH, $C_{1-6}$alkyl, HET, Aryl, $C_{1-6}$alkoxy, $NH_2$, $NHC_{1-6}$alkyl, $N(C_{1-6}$ alkyl$)_2$, $C_{1-6}$alkylC(O), $C_{1-6}$alkylS(O)$_y$, Aryl-S(O)$_y$, HET- S(O)$_y$ wherein y is 0, 1 or 2, Aryl-C(O) and HET-C(O), the alkyl and alkyl portions of which being optionally substituted with 1-2 members selected from the group consisting of: OH, Aryl$^1$, HET, halo, $NH_2$, $NHCH_3$, $N(CH_3)_2$, $CO_2H$, $CF_3$ and $C_{1-4}$-acyl;

Aryl represents a $C_{6-14}$ aromatic 1-3 ring system optionally substituted with 1-3 members selected from OH, $C_{1-6}$alkyl, $OC_{1-6}$ alkyl, Aryl$^1$, HET, halo, $NH_2$, $NHCH_3$, $N(CH_3)_2$, $CF_3$, $CO_2H$ and $C_{1-4}$acyl;

Aryl$^1$ represents a $C_{6-14}$ membered aromatic ring system having 1-3 rings and optionally substituted with 1-3 members selected from the group consisting of: OH, HET, halo, $NH_2$, $NHCH_3$, $N(CH_3)_2$, $CO_2H$ and $C_{1-4}$-acyl;

HET represents a 5 to 15 membered aromatic, partially aromatic or non-aromatic ring system, containing 1-4 heteroatoms selected from O, S and N, and optionally substituted with 1-2 oxo groups and 1-3 groups selected from halo, $C_{1-4}$alkyl, $C_{1-4}$alkoxy, $CF_3$ and $C_{1-4}$acyl;

FIG.4(o)

$R^a$ and $R^b$ independently represent a member selected from the group consisting of: H, Aryl, $C_{1-6}$alkyl optionally substituted by 1-3 of halo, $OR^4$, $SR^4$ and $C_{5-7}$cycloalkyl optionally containing one heteroatom selected from O, S and $NR^5$.

or in the alternative, $R^a$ and $R^b$ are taken in combination and represent a non-aromatic carbocyclic 4-7 membered ring, optionally containing one heteroatom selected from O, S and $NR^5$;

$R^4$ is selected from the group consisting of: H, $C_{1-5}$alkyl, Aryl and Aryl-$C_{1-4}$alkyl optionally substituted with 1-2 groups selected from halo and $C_{1-4}$alkyl;

$R^5$ is H, $C_{1-4}$alkyl or $C_{1-4}$acyl;

$R^c$ and $R^d$ each independently represents a member selected from the group consisting of: H, $C_{1-6}$alkyl and Aryl, or in the alternative, $R^c$ and $R^d$ are taken in combination and represent a non-aromatic carbocyclic ring of 3-7 members, optionally containing one heteroatom selected from O, S and $NR^5$;

n is an integer from 0-6 inclusive;

$R^2$ represents H, halo or $C_{1-6}$alkyl;

$R^3$ represents H, $C_{1-6}$alkyl, Aryl, HET, $C_{1-6}$alkyl$SR^6$, $C_{1-6}$alkyl$OR^6$, $C_{1-6}$alkylOC(O)$R^7$ or $C_{1-6}$alkyl$NR^8R^9$;

$R^6$ represents $C_{1-6}$alkyl, Aryl, HET or Aryl-$C_{1-6}$alkyl, said alkyl and the alkyl portions being optionally substituted with $1-3$ members selected from the group consisting of: OH, halo, $NH_2$, $NHCH_3$, $N(CH_3)_2$, $CO_2H$, $CF_3$ and $C_{1-4}$acyl;

$R^7$ represents $C_{1-8}$alkyl, Aryl or HET;

$R^8$ and $R^9$ independently represent H, $C_{1-10}$alkyl, Aryl, HET, $C_{1-6}$alkylN($C_{1-6}$alkyl)$_{0-2}$, Aryl-$C_{1-6}$alkyl, $C_{1-6}$alkylOH, or $C_{1-6}$alkylO$C_{1-6}$alkyl, or $R^8$ and $R^9$ are taken in combination with the nitrogen atom to which they are attached and represent a 3-10 membered ring system containing 1-4 heteroatoms selected from O, S, N and optionally substituted with 1-2 oxo groups, and 1-3 groups selected from $C_{1-6}$alkyl, HET, $CO_2R^c$ and $C(O)N(R^C)_2$,

FIG.4(p)

said alkyl and alkyl portions being optionally substituted with 1-3 groups selected from halo, $C_{1-3}$alkyl, hydroxy$C_{1-3}$ alkyl, $C_{1-3}$alkoxy, $C_{1-3}$alkoxy$C_{1-3}$alkyl and Aryl$^1$, and $R^{10}$ represents H, $C_{1-20}$ alkyl, aryl or HET, with aryl and HET as previously described.

2. A compound represented by formula I':

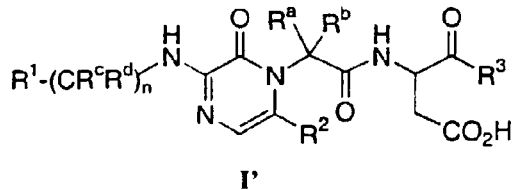

I' or a pharmaceutically acceptable salt, ester, N-oxide or hydrate thereof wherein:

$R^1$ is selected from the group consisting of:

OH, $C_{1-6}$alkyl, HET, Aryl, $C_{1-6}$alkoxy, $NH_2$, $NHC_{1-6}$alkyl, $N(C_{1-6}$ alkyl$)_2$, $C_{1-6}$alkylC(O), $C_{1-6}$alkylS(O)$_y$, Aryl-S(O)$_y$, HET- S(O)$_y$ wherein y is 0, 1 or 2,, Aryl-C(O) and HET-C(O), the alkyl and alkyl portions of which being optionally substituted with 1-2 members selected from the group consisting of: OH, Aryl$^1$, HET, halo, $NH_2$, $NHCH_3$, $N(CH_3)_2$, $CO_2H$, $CF_3$ and $C_{1-4}$-acyl;

Aryl represents a $C_{6-14}$ aromatic 1-3 ring system optionally substituted with 1-3 members selected from OH, $C_{1-6}$ alkyl, $OC_{1-6}$ alkyl, Aryl$^1$, HET, halo, $NH_2$, $NHCH_3$, $N(CH_3)_2$, $CF_3$, $CO_2H$ and $C_{1-4}$acyl;

Aryl$^1$ represents a $C_{6-14}$membered aromatic ring system having 1-3 rings and optionally substituted with 1-3 members selected from the group consisting of: OH, HET, halo, $NH_2$, $NHCH_3$, $N(CH_3)_2$, $CO_2H$ and $C_{1-4}$-acyl;

HET represents a 5 to 15 membered aromatic, partially aromatic or non-aromatic ring system, containing 1-4 heteroatoms selected from O, S and N, and optionally substituted with 1-2 oxo groups and 1-3 groups selected from halo, $C_{1-4}$alkyl, $C_{1-4}$alkoxy, $CF_3$ and $C_{1-4}$acyl;

$R^a$ and $R^b$ independently represent a member selected from the group consisting of: H, Aryl, $C_{1-6}$alkyl optionally substituted by 1-3 of halo, $OR^4$, $SR^4$ and $C_{5-7}$cycloalkyl optionally containing one heteroatom selected from O, S and $NR^5$, or in the alternative, $R^a$ and $R^b$ are taken in combination and represent a non-aromatic carbocyclic 4-7 membered ring, optionally containing one heteroatom selected from O, S and $NR^5$;

$R^4$ is selected from the group consisting of: H, $C_{1-5}$alkyl, Aryl and Aryl-$C_{1-4}$alkyl optionally substituted with 1-2 groups selected from halo and $C_{1-4}$alkyl;

$R^5$ is H or $C_{1-4}$alkyl;

$R^c$ and $R^d$ each independently represents a member selected from the group consisting of: H, $C_{1-6}$alkyl and Aryl, or in the alternative, $R^c$ and $R^d$ are taken in combination and represent a non-aromatic carbocyclic ring of 3-7 members, optionally containing one heteroatom selected from O, S and $NR^5$;

n is an integer from 0-6 inclusive;

$R_2$ represents H, halo or $C_{1-6}$alkyl;

$R^3$ represents H, $C_{1-6}$alkyl, Aryl, HET, $C_{1-6}$alkyl$SR^6$, $C_{1-6}$alkyl$OR^6$, $C_{1-6}$alkyl$OC(O)R^7$ or $C_{1-6}$alkyl$NR^8R^9$;

$R^6$ represents $C_{1-6}$alkyl, Aryl, HET or Aryl-$C_{1-6}$alkyl, said alkyl and the alkyl portions being optionally substituted with 1-3 members selected from the group consisting of: OH, halo, $NH_2$, $NHCH_3$, $N(CH_3)_2$, $CO_2H$, $CF_3$ and $C_{1-4}$ acyl;

$R^7$ represents $C_{1-8}$alkyl, Aryl or HET;

$R^8$ and $R^9$ independently represent H, $C_{1-10}$alkyl, Aryl, HET, $C_{1-6}$alkyl$N(C_{1-6}$alkyl$)_{0-2}$, Aryl-$C_{1-6}$alkyl, $C_{1-6}$alkyl$OH$, or $C_{1-6}$alkyl$OC_{1-6}$alkyl, or $R^8$ and $R^9$ are taken in combination with the nitrogen atom to which they are attached and represent a 3-10 membered ring system containing 1-4 heteroatoms selected from O, S, N and optionally substituted with 1-2 oxo groups, and 1-3 groups selected from $C_{1-6}$alkyl, HET, $CO_2R^c$ and $C(O)N(R^C)_2$, said alkyl and alkyl portions being optionally substituted with 1-3 groups selected from halo, $C_{1-3}$alkyl, hydroxy$C_{1-3}$ alkyl, $C_{1-3}$alkoxy, $C_{1-3}$alkoxy$C_{1-3}$alkyl and Aryl'.

3. A compound in accordance with claim 1 wherein $R^1$ represents HET or Aryl, said HET representing a 5 to 15 membered aromatic, partially aromatic or non-aromatic ring or ring system, containing from 1-4 heteroatoms selected from O, S and N, and optionally substituted with 1-2 groups selected from oxo, halo, $C_{1-4}$alkyl $C_{1-4}$alkoxy and $C_{1-4}$acyl, and said Aryl being selected from phenyl and naphthyl, and being optionally substituted with 1-3 members selected from the group consisting of: OH, Aryl', HET, halo, $NH_2$, $NHCH_3$, $N(CH_3)_2$, $CO_2H$ and $C_{1-4}$-acyl.

4. A compound in accordance with claim 3 wherein $R^1$ represents HET optionally substituted with 1-2 groups selected from oxo, halo, $C_{1-4}$alkyl, $C_{1-4}$alkoxy and $C_{1-4}$acyl.

5. A compound in accordance with claim 4 wherein $R^1$ represents HET substituted with 1-2 groups selected from oxo, halo, $C_{1-4}$alkyl, $C_{1-4}$alkoxy and $C_{1-4}$acyl.

6. A compound in accordance with claim 5 wherein $R^1$ represents HET selected from the group consisting of: pyridinyl, pyrazinyl, pyrrolyl, furanyl, pyrazolyl, imidazolyl, benzimidazolyl, oxathiazolyl, thiazolyl, benzothiazolyl, oxazolyl, pyrrazolyl, 1,2-diazolyl, 1,2,3- and 1,2,4-triazolyl, 1,2,4- and 1,2,5-oxadiazolyl, 1,2,4-and 1,2,5-thiadiazolyl, tetrazolyl, isoxazolyl, thienyl, azepinyl, pyrrolidinyl, piperidinyl, piperazinyl, optionally substituted with 1-2 groups selected from halo, $C_{1-4}$alkyl and $C_{1-4}$alkoxy.

FIG.4(s)

7. A compound in accordance with claim 3 wherein $R^1$ represents Aryl, said Aryl being phenyl optionally substituted with 1-3 members selected from the group consisting of: OH, $Aryl^1$, HET, halo, $NH_2$, $NHCH_3$, $N(CH_3)_2$, $CO_2H$ and $C_{1-4}$-acyl.

8. A compound in accordance with claim 1 wherein $R^c$ and $R^d$ represent H, and n is an integer of from 0-3 inclusive.

9. A compound in accordance with claim 1 wherein $R^a$ and $R^b$ independently represent H or $C_{1-6}$alkyl, optionally substituted with halo, $OR^4$, $SR^4$ or $C_{5-7}$cycloalkyl optionally containing one heteroatom selected from O, S and $NR^5$.

10. A compound in accordance with claim 9 wherein one of $R^a$ and $R^b$ represents H and the other represents $C_{1-6}$alkyl.

11. A compound in accordance with claim 10 wherein one of $R^a$ and $R^b$ represents H and the other represents ethyl.

12. A compound in accordance with claim 1 wherein $R^2$ represents H or halo.

13. A compound in accordance with claim 1 wherein:

$R^3$ is selected from the group consisting of H, $C_{1-6}$alkyl, $C_{1-6}$alkyl$SR^6$, and $C_{1-6}$alkyl$NR^8R^9$;

$R^6$ represents $C_{1-6}$alkyl, Aryl, HET or Aryl-$C_{1-6}$alkyl, said alkyl, aryl, and the alkyl group and alkyl portions being optionally substituted with 1-3 members selected from the group consisting of: OH, halo, $NH_2$, $NHCH_3$, $N(CH_3)_2$, $CO_2H$, $CF_3$ and $C_{1-4}$ acyl, and said HET being optionally substituted with 1-2 oxo groups and 1-3 groups selected from halo, $C_{1-4}$alkyl, $C_{1-4}$alkoxy, $CF_3$ and $C_{1-4}$acyl; and $R^8$ and $R^9$ independently represent H, $C_{1-10}$alkyl, Aryl, HET, $C_{1-6}$alkylN($C_{1-6}$alkyl$)_{0-2}$, Aryl-$C_{1-6}$alkyl, $C_{1-6}$alkylOH, or $C_{1-6}$alkylO$C_{1-6}$alkyl, or $R^8$ and $R^9$ are taken in combination with the nitrogen atom to which they are attached and represent a 3-10 membered ring system containing 1-4 heteroatoms selected from O,

FIG.4(t)

S, N and optionally substituted with 1-2 oxo groups, and 1-3 groups selected from $C_{1-6}$alkyl, HET, $CO_2R^c$ and $C(O)N(R^C)_2$, said alkyl and alkyl portions being optionally substituted with 1-3 groups selected from halo, $C_{1-3}$alkyl, hydroxyC$_{1-3}$ alkyl, $C_{1-3}$alkoxy, $C_{1-3}$alkoxyC$_{1-3}$alkyl and Aryl$^1$.

14. A compound in accordance with claim 13 wherein:

$R^3$ is selected from the group consisting of: H, $C_{1-6}$alkyl, $C_{1-6}$alkylSR$^6$, and $C_{1-6}$alkylNR$^8$R$^9$;

$R^6$ represents Aryl, HET or Aryl-$C_{1-6}$alkyl, said alkyl, aryl, and the alkyl group and alkyl portions being optionally substituted with 1-3 members selected from the group consisting of: OH, halo, $NH_2$, $NHCH_3$, $N(CH_3)_2$, $CO_2H$, $CF_3$ and $C_{1-4}$acyl, and said HET being optionally substituted with 1-2 oxo groups and 1-3 groups selected from halo and $C_{1-4}$alkyl; and $R^8$ and $R^9$ independently represent H, $C_{1-10}$alkyl, Aryl, HET, $C_{1-6}$alkylN($C_{1-6}$alkyl)$_{0-2}$, Aryl-$C_{1-6}$alkyl or $C_{1-6}$alkylOC$_{1-6}$alkyl, or $R^8$ and $R^9$ are taken in combination with the nitrogen atom to which they are attached and represent a 3-10 membered ring system containing 1-4 heteroatoms selected from O, S, N and optionally substituted with 1-2 oxo groups, and 1-3 groups selected from $C_{1-6}$alkyl, HET, $CO_2R^c$ and $C(O)N(R^C)_2$, said alkyl and alkyl portions being optionally substituted with 1-3 groups selected from halo, $C_{1-3}$alkyl, $C_{1-3}$alkoxyC$_{1-3}$alkyl and Aryl$^1$.

15. A compound in accordance with claim 1 wherein:

$R^1$ represents HET or Aryl, said HET representing a 5 to 15 membered aromatic, partially aromatic or non-aromatic ring or ring system, containing from 1-4 heteroatoms selected from O, S and N, and optionally substituted with 1-2 groups selected from oxo, halo, $C_{1-4}$alkyl $C_{1-4}$alkoxy and $C_{1-4}$acyl, and said Aryl being selected from phenyl and naphthyl, and being optionally substituted with 1-3 members selected from the group consisting of: OH, Aryl$^1$, HET, halo, $NH_2$, $NHCH_3$, $N(CH_3)_2$, $CO_2H$ and $C_{1-4}$-acyl;

$R^c$ and $R^d$ represent H, and n is an integer of from 0-3 inclusive;

FIG.4(u)

$R^a$ and $R^b$ independently represent H or $C_{1-6}$alkyl optionally substituted with halo, $OR^4$, $SR^4$ or $C_{5-7}$cycloalkyl optionally containing one heteroatom selected from O, S and $NR^5$;

$R^3$ is selected from the group consisting of H, $C_{1-6}$alkyl, $C_{1-6}$alkyl$SR^6$, and $C_{1-6}$alkyl$NR^8R^9$;

$R^6$ represents $C_{1-6}$alkyl, Aryl, HET or Aryl-$C_{1-6}$alkyl, said alkyl, aryl, and the alkyl group and alkyl portions being optionally substituted with 1-3 members selected from the group consisting of: OH, halo, $NH_2$, $NHCH_3$, $N(CH_3)_2$, $CO_2H$, $CF_3$ and $C_{1-4}$acyl, and said HET being optionally substituted with 1-2 oxo groups and 1-3 groups selected from halo, $C_{1-4}$alkyl, $C_{1-4}$alkoxy, $CF_3$ and $C_{1-4}$acyl; and $R^8$ and $R^9$ independently represent H, $C_{1-10}$alkyl, Aryl, HET, $C_{1-6}$alkylN($C_{1-6}$alkyl)$_{0-2}$, Aryl-$C_{1-6}$alkyl, $C_{1-6}$alkylOH, or $C_{1-6}$alkylO$C_{1-6}$alkyl, or $R^8$ and $R^9$ are taken in combination with the nitrogen atom to which they are attached and represent a 3-10 membered ring system containing 1-4 heteroatoms selected from O, S, N and optionally substituted with 1-2 oxo groups, and 1-3 groups selected from $C_{1-6}$alkyl, HET, $CO_2R^c$ and $C(O)N(R^C)_2$.

said alkyl and alkyl portions being optionally substituted with 1-3 groups selected from halo, $C_{1-3}$alkyl, hydroxy$C_{1-3}$ alkyl, $C_{1-3}$alkoxy, $C_{1-3}$alkoxy$C_{1-3}$alkyl and $Aryl^1$. Within this subset, all other variables are as originally defined.

16. A compound in accordance with claim 1 wherein n represents 1-6.

FIG. 4(v)

1. A compound of fourmula

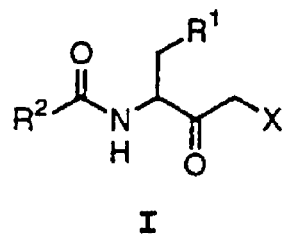

I wherein X is F or Cl;

R¹ is COOH, COO(alkyl), or an isostere thereof; and

R² is an aryl group.

2. The compound of claim 1 having one or more of the following features: (a) X is F; (b) R¹ is COOH; and/or (c) R² is an optionally substituted group selected from phenyl, naphthyl, or a five, six, nine or ten membered heteroaryl having one or two heteroatoms.

3. The compound of claim 2 having the following features: (a) X is F; (b) R¹ is COOH; and (c) R² is an optionally substituted group selected from phenyl, naphthyl, or five, six, nine or ten membered heteroaryl having one or two heteroatoms.

Fig. 5(a)

| 1 | 3-Benzoylamino-5-fluoro-4-oxo-pentanoic acid |
|---|---|
| 2 | 5-Fluoro-3-(3-methyl-benzoylamino)-4-oxo-pentanoic acid |
| 3 | 5-Fluoro-3-(4-methyl-benzoylamino)-4-oxo-pentanoic acid |
| 4 | 3-(2-Chlorobenzoylamino)-5-fluoro-4-oxo-pentanoic acid |
| 5 | 3-(3-Chlorobenzoylamino)-5-fluoro-4-oxo-pentanoic acid |
| 6 | 3-(4-Chlorobenzoylamino)-5-fluoro-4-oxo-pentanoic acid |
| 7 | 3-(3,4-Dichlorobenzoylamino)-5-fluoro-4-oxo-pentanoic acid |
| 8 | 3-(3,5-Dichlorobenzoylamino)-5-fluoro-4-oxo-pentanoic acid |
| 9 | 5-Fluoro-3-(2-fluorobenzoylamino)-4-oxo-pentanoic acid |
| 10 | 5-Fluoro-3-(3-fluorobenzoylamino)-4-oxo-pentanoic acid |
| 11 | 5-Fluoro-3-(4-fluorobenzoylamino)-4-oxo-pentanoic acid |
| 12 | 5-Fluoro-4-oxo-3-(3-trifluoromethylbenzoylamino)-pentanoic acid |
| 13 | 5-Fluoro-3-(4-trifluoromethylbenzoylamino)-4-oxo-pentanoic acid |
| 14 | 3-(Biphenyl-3-carboxamido)-5-fluoro-4-oxo-pentanoic acid |
| 15 | 3-(Biphenyl-4-carboxamido)-5-fluoro-4-oxo-pentanoic acid |
| 16 | 5-Fluoro-3-(3-methoxybenzoylamino)-4-oxo-pentanoic acid |
| 17 | 5-Fluoro-3-(4-methoxy-benzoylamino)-4-oxo-pentanoic acid |
| 18 | 2-(3-Acetylaminobenzoylamino)-4-fluoro-3-oxo-butyric acid |
| 19 | 3-(3-Cyanobenzoylamino)-5-fluoro-4-oxo-pentanoic acid |
| 20 | 3-(4-Cyano benzoylamino)-5-fluoro-4-oxo-pentanoic acid |
| 21 | 5-Fluoro-3-(3-iodo-benzoylamino)-4-oxo-pentanoic acid |
| 22 | 5-Fluoro-3-(naphthyl-1-carboxamido)-4-oxo-pentanoic acid |
| 23 | 5-Fluoro-3-(naphthyl-2-carboxamido]-4-oxo-pentanoic acid |
| 24 | 5-Fluoro-4-oxo-3-(pyridyl-4-carboxamido)-pentanoic acid trifluoroacetate salt |
| 25 | 5-Fluoro-4-oxo-3-(pyridyl-3-carboxamido)-pentanoic acid trifluoroacetate salt |
| 26 | 5-Fluoro-3-(furyl-3-carboxamido-4-oxo-pentanoic acid |
| 27 | 5-Fluoro-3-(1-methyl-1*H*-pyrrolyl-2-carboxamido)-4-oxo-pentanoic acid |

Fig. 5(b)

| 28 | 5-Fluoro-4-oxo-3-(thienyl-2-carboxamido)-pentanoic acid |
|---|---|
| 29 | 5-Fluoro-4-oxo-3-(thienyl-3-carboxamido)-pentanoic acid |
| 30 | 5-Fluoro-4-oxo-3-(thiazolyl-2-carboxamido)-pentanoic acid |
| 31 | 5-Fluoro-3-(1H-indolyl-2-carboxamido)-4-oxo-pentanoic acid |
| 32 | 3-(3-Carboxybenzoylamino)-5-fluoro-4-oxo-pentanoic acid |
| 33 | 3-(4-Methylamidobenzoylamino)-5-fluoro-4-oxo-pentanoic acid |
| 34 | 5-Fluoro-3-(5-phenyl-furyl-2-carboxamido)-4-oxo-pentanoic acid |
| 35 | 3-(3-Benzyloxybenzoylamino)-5-fluoro-4-oxo-pentanoic acid |
| 36 | 3-(3-(2-Phenylethoxy)benzoylamino)-5-fluoro-4-oxo-pentanoic acid |
| 37 | 5-Fluoro-4-oxo-3-(3-phenoxybenzoylamino)-pentanoic acid |
| 38 | 5-Fluoro-3-(1-naphthylacetamido)-4-oxo-pentanoic acid |
| 39 | 3-Benzoylamino-5-chloro-4-oxo-pentanoic acid |

Fig. 5(c)

1. A compound having the Formula I:

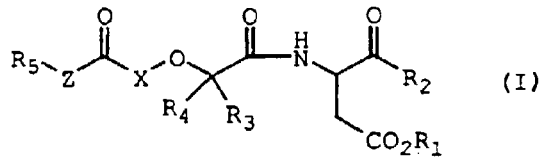

or a pharmaceutically acceptable salt or prodrug thereof, wherein $R_1$ is an optionally substituted alkyl or hydrogen;

$R_2$ is hydrogen or optionally substituted alkyl;

$R_3$ and $R_4$ independently are hydrogen, optionally substituted aryl, optionally substituted heterocyclic, optionally substituted heteroaryl, optionally substituted carbocyclic, optionally substituted alkyl, optionally substituted alkenyl, or optionally substituted alkynyl;

$R_5$ is an optionally substituted alkyl, optionally substituted carbocyclic, optionally substituted heterocyclic, optionally substituted aryl or optionally substituted heteroaryl;

Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1 -2 amino acids or a bond.

2. The compound of claim 1, wherein $R_3$ and $R_4$ independently are hydrogen, aryl, heterocyclic, heteroaryl, $C_{1-10}$alkyl, alkenyl, alkynyl, or $C_{1-10}$alkyl substituted by one or more hydroxy, halogen, carboxy, amino, amide, ester, guanadino, thiol, alkylthiol, aryl, heterocyclic, or heteroaryl groups; and $R_5$ is an optionally substituted alkyl, $C_4$-$C_7$ cycloalkyl, saturated or unsaturated heterocyclic, aryl or heteroaryl group.

3. A compound according to claim 1, wherein $R_1$ is H, Me, Et or acetoxymethyl.

Fig. 6(a)

4. A compound according to claim 1, wherein R is hydrogen, fluoromethyl, acyloxymethyl, arylacyloxymethyl, aryloxymethyl, heteroaryloxymethyl, or aminomethyl.

5. A compound according to claim 1, wherein X is a bond.

6. A compound according to claim 1, wherein Z is O, S, NH or $CH_2$.

7. A compound according to claim 1, wherein $R_3$ is hydrogen and $R_4$ is straight-chained or branched $C_{1-6}$ alkyl, cycloalkyl, aryl or heteoaryl.

8. A compound according to claim 1, wherein $R_3$ is hydrogen and $R_4$ is straight-chained or branched $C_{1-6}$ alkyl optionally substituted by hydroxy, halogen, carboxy, amino, amide, ester, guanadino, thiol, alkylthiol, aryl, heterocyclic or heteroaryl.

9. A compound according to claim 1, wherein $R_5$ is optionally substituted benzyl.

10. A compound according to claim 1, wherein $R_5$ is optionally substituted phenyl, naphthyl or heteroaryl.

11. A compound according to claim 1, wherein said compound has the Formula II:

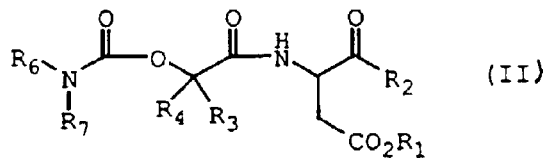

(II)

or a pharmaceutically acceptable salt or prodrug thereof wherein

Fig. 6(b)

$R_6$ and $R_7$ independently are hydrogen, alkyl, optionally substituted alkyl, $C_4$-$C_7$ cycloalkyl, heterocyclic, aryl, heteroaryl, or $R_6$ and $R_7$ are combined together with the nitrogen to form a heterocycle.

12. A compound according to claim 11, wherein $R_2$ is hydrogen, fluoromethyl, acyloxymethyl, arylacyloxymethyl, aryloxymethyl, heteroaryloxymethyl, or aminomethyl.

13. A compound according to claim 11, wherein $R_1$ is H, Me, Et or acetoxymethyl.

14. A compound according to claim 11, wherein $R_3$ is hydrogen and $R_4$ is straight-chained or branched $C_{1-6}$ alkyl, cycloalkyl, aryl or heteoaryl.

15. A compound according to claim 11, wherein $R_3$ is hydrogen and $R_4$ is straight-chained or branched $C_{1-6}$ alkyl optionally substituted by hydroxy, halogen, carboxy, amino, amide, ester, guanadino, thiol, alkylthiol, aryl, heterocyclic or heteroaryl.

16. A compound according to claim 11, wherein $R_6$ is hydrogen and $R_7$ is optionally substituted phenyl, naphthyl, heteroaryl or benzyl.

17. A compound according to claim 11, wherein $R_6$ is hydrogen and $R_7$ is an optionally substituted alkyl.

18. A compound according to claim 1, wherein said compound is selected from the group consisting of:
1-(Carbonyl-Asp-CH$_2$F)ethyl N-phenylcarbamate,
1-(Carbonyl-Asp-CH$_2$F)ethyl N-benzylcarbamate,
2-Methyl-1-(carbonyl-Asp-CH$_2$F)propyl N-phenylcarbamate,
2-Methyl-1-(carbonyl-Asp-CH$_2$F)propyl N-benzylcarbamate,

Fig. 6(c)

2-Methyl-1-(carbonyl-Asp-CH₂F)propyl N-(2.6-dichlorophenyl)carbamate,

2-Methyl-1-(carbonyl-Asp-CH₂F)propyl N-(2,5-dichlorophenyl)-carbamate,

2-Methyl-1-(carbonyl-Asp-CH₂F)propyl N-(2,4-dichlorophenyl)-carbamate,

2-Methyl-1-(carbonyl-Asp-CH₂DCB)propyl N-phenylcarbamate,

2-Methyl-1-(carbonyl-Asp-CH₂DCB)propyl N-(2,6-dichlorophenyl)-carbamate,

2-Methyl-1-(carbonyl-Asp-CH₂PTP)propyl N-phenylcarbamate,

2-Methyl-1-(carbonyl-Asp-CH₂PTP)propyl N-(2,6-dichlorophenyl)-carbamate,

2-Methyl-1-(carbonyl-Asp-CH₂DPP)propyl N-phenylcarbamate,

2-Methyl-1-(carbonyl-Asp-CH₂DPP)propyl N-(2,6-dichlorophenyl)-carbamate,

2-Methyl-1-(carbonyl-Asp-CH₂F)propyl N-(2-methyl-1-methoxycarbonyl-propyl)carbamate, and Z-Valine 2-methyl-1-(carbonyl-Asp-CH₂F) propyl ester.

19. A compound according to claim 1, wherein said compound is selected from the group consisting of:

2-Methyl-1-(carbonyl-Asp-CH₂F)propyl N-(3-fluorophenyl)carbamate,

2-Methyl-1-(carbonyl-Asp-CH₂F)propyl N-(4-fluorophenyl)carbamate,

2-Methyl-1-(carbonyl-Asp-CH₂F)propyl N-(3,4-difluorophenyl)carbamate,

2-Methyl-1-(carbonyl-Asp-CH₂F)propyl N-(4-phenoxyphenyl)carbamate, 1-(Carbonyl-Asp-CH₂F)propyl N-phenylcarbamate, 1-(Carbonyl-Asp-CH₂F)butyl N-phenylcarbamate, 1-(Carbonyl-Asp-CH₂F)-2-propenyl N-phenylcarbamate, 2-(4-Imidazolyl)-1-(carbonyl-Asp-CH₂F)ethyl N-phenylcarbamate, 2-Phenyl-1-(carbonyl-Asp-CH₂F)ethyl N-phenylcarbamate, 2-Methyl-1-(carbonyl-Asp-CH₂F)butyl N-phenylcarbamate, 3-Methyl-1-(carbonyl-Asp-CH₂F)butyl N-phenylcarbamate, 1-Phenyl-1-(carbonyl-Asp-CH₂F)methyl N-phenylcarbamate, 1-(2-Chlorophenyl)-1-(carbonyl-Asp-CH₂F)methyl N-phenylcarbamate, 1-(4-Chlorophenyl)-1-(carbonyl-Asp-CH₂F)methyl N-phenylcarbamate,

Fig. 6(d)

1-Cyclohexyl-1-(carbonyl-Asp-CH$_2$F)methyl N-phenylcarbamate,

2-Chloro-1-(carbonyl-Asp-CH$_2$F)ethyl N-phenylcarbamate, and 2,2,2-trifluoro-1-(carbonyl-Asp-CH,F)ethyl N-phenylcarbamate.

Fig. 6(e)

| 1 | S-1-(Cabornyl-Asp-CH$_2$F)ethyl N-Phenylcarbamate |
|---|---|
| 2 | 2-Methyl-1-(carbonyl-Asp-CH$_2$F)propyl N-Phenylcarbamate |
| 3 | S-2-Methyl-1-(carbonyl-Asp-CH$_2$F)propyl N-Phenylcarbamate |
| 4 | S-1-(Carbonyl-Asp-CH$_2$F)ethyl N-Benzylcarbamate |
| 5 | 2-Methyl-1-(carbonyl-Asp-CH$_2$F)propyl N-Benzylcarbamate |
| 6 | S-2-Methyl-1-(carbonyl-Asp-CH$_2$F)propyl N-Benzylcarbamate |
| 7 | S,S-2-Methyl-1-(carbonyl-Asp-CH$_2$F)propyl N-(2-Methyl-1-methoxycarbonylpropyl)-carbamate |
| 8 | S-2-Methyl-1-(carbonyl-Asp-CH$_2$DCB)propyl N-Phenylcarbamate |
| 9 | S-2-Methyl-1-(carbonyl-Asp-CH$_2$F)propyl N-(3 Fluorophenyl)carbamate |
| 10 | S-2-Methyl-1-(carbonyl-Asp-CH$_2$F)propyl N-(4 Fluorophenyl)carbamate |
| 11 | S-2-Methyl-1-(carbonyl-Asp-CH$_2$F)propyl N-(3,4-Difluorophenyl)carbamate |
| 12 | S-2-Methyl-1-(carbonyl-Asp-CH$_2$F)propylN-(4-Phenoxyphenyl)carbamate |
| 13 | S-1-Cyclohexyl-1-(carbonyl-Asp-CH$_2$F)methyl N-Phenylcarbamate |
| 14 | S-2-Methyl-1-(carbonyl-Asp-CH$_2$F)propyl N-(2,5-Dichloroyphenyl)carbamate |
| 15 | S-2-Methyl-1-(carbonyl-Asp-CH$_2$F)propyl N-(2,4-Dichloroyphenyl)carbamate |
| 16 | S-2-Methyl-1-(carbonyl-Asp-CH$_2$F)propyl N-(2,5-Dichloroyphenyl)carbamate |
| 17 | S-2-Methyl-1-(carbonyl- Asp-CH$_2$PTP)propyl N-Phenylcarbamate |

Asp: Aspartic acid

Fig. 6(f)

1. A compound of the formula (I):

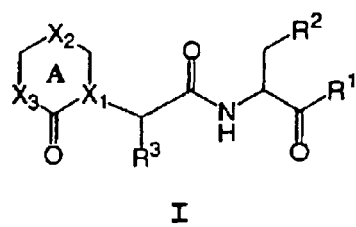

I where $R^1$ is hydrogen, CN, $CHN_2$, R, or -$CH_2Y$;

R is an aliphatic group, a substituted aliphatic group, an aryl group, a substituted aryl group, an aralkyl group, a substituted aralkyl group a non-aromatic heterocyclic group or a substituted non-aromatic heterocyclic group;

Y is an electronegative leaving group or -OR, -SR, -OC=O(R), or -OPO($R^8$) ($R^9$);

$R^8$ and $R^9$ are independently selected from R or OR;

$R^2$ is $CO_2H$, $CH_2CO_2H$, or esters, amides or isosteres thereof;

$R^3$ is hydrogen or a $C_{1-6}$ straight chained or branched alkyl;

Ring A contains zero to two double bonds, and is optionally fused to a saturated or unsaturated five to seven membered ring containing zero to three heteroatoms;

$X_1$ and $X_3$ in Ring A are independently selected from nitrogen or carbon, and $X_2$ is selected from a valence bond, oxygen, sulfur, nitrogen or carbon, wherein any X with suitable valence may bear a substituent;

each carbon with suitable valence in Ring A, including the fused ring if present, is independently substituted by hydrogen, halo, R, OR, SR, OH, $NO_2$, CN, $NH_2$, NHR,

Fig.7(a)

N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, NHS(O)$_2$R, =O, =S, =NNHR, =NNR$_2$, =N-OR, =NNHCOR, =NNHCO$_2$R, =NNHSO$_2$R, or =NR;

each substitutable nitrogen in Ring A is substituted by hydrogen, R, COR, S(O)$_2$R, or CO$_2$R;

provided that when X$_3$ is a carbon, a substituent on X$_3$ is attached by an atom other than nitrogen;

and further provided that at least one X in Ring A is a nitrogen.

2. The compound of claim 1 where R$^2$ is CO$_2$H or an ester, amide or carboxylic acid isoster.

3. The compound of claim 2 where R$^1$ is CH$_2$Y and Y is F, OR, SR, or -OC=O(R).

4. The compound of claim 3 where R$^3$ is hydrogen or C$_{1-3}$ alkyl.

5. A compound of formula IA:

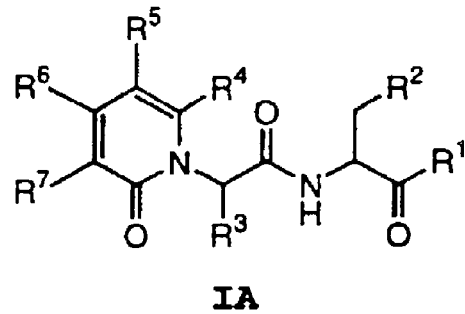

IA where R$^1$ is hydrogen, CN, CHN$_2$, R, -CH$_2$Y;

R is an aliphatic group, a substituted aliphatic group, an aryl group, a substituted aryl group, an aralkyl group, a substituted aralkyl group, a non-aromatic

Fig. 7(b)

heterocyclic group or a substituted non-aromatic heterocyclic group;

Y is an electronegative leaving group, -OR, -SR, -OC=O(R), or -OPO($R^8$) ($R^9$);

$R^8$ and $R^9$ are each independently selected from R or OR;

$R^2$ is $CO_2H$, $CH_2CO_2H$, or esters, amides or isosteres thereof;

$R^3$ is hydrogen or a $C_{1-6}$ straight chained or branched alkyl;

each of $R^4$-$R^6$ is independently selected from hydrogen, halo, R, OR, SR, aryl, substituted aryl, OH, $NO_2$, CN, $NH_2$, NHR, $N(R)_2$, NHCOR, NHCONHR, NHCON$(R)_2$, NRCOR, NHCO$_2$R, CO$_2$R, CO$_2$H, COR, CONHR, CON$(R)_2$, S(O)$_2$R, SONH$_2$, S(O)R, SO$_2$NHR, or NHS(O)$_2$R; and $R^7$ is selected from hydrogen, halo, R, OR, SR, aryl, substituted aryl, OH, CN, CO$_2$R, CO$_2$H, COR, CONHR, CON$(R)_2$, S(O)$_2$R, SONH$_2$, S(O)R, or SO$_2$NHR.

6. The compound of claim 5 where $R^1$ is CH$_2$Y and Y is F, -OR, -SR, or -OC=O(R); $R^2$ is CO$_2$H or esters, amides or isosteres thereof; $R^3$ is hydrogen or $C_{1-3}$ alkyl, each of $R^4$-$R^6$ is independently selected from hydrogen, R, phenyl or substituted phenyl; and $R^7$ is hydrogen, R, phenyl or substituted phenyl.

7. A compound of formula IB:

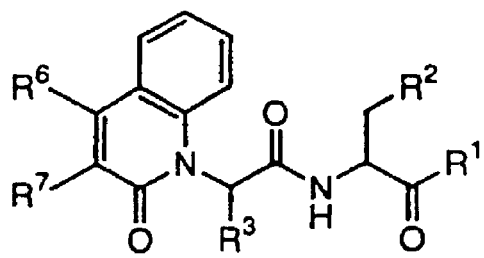

Fig. 7(c)

where $R^1$ is hydrogen CN, $CHN_2$, R, or $-CH_2Y$;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R), or $-OPO(R^8)(R^9)$;

$R^8$ and $R^9$ are each independently selected from R or OR;

$R^2$ is $CO_2H$, $CH_2CO_2H$, or esters, amides or isosteres thereof;

$R^3$ is hydrogen or a $C_{1-6}$ straight chained or branched alkyl;

$R^6$ is selected from hydrogen, halo, R, OR, SR, aryl, substituted aryl, OH, $NO_2$, CN, $NH_2$, NHR, $N(R)_2$, NHCOR, NHCONHR, $NHCON(R)_2$, NRCOR, $NHCO_2R$, $CO_2R$, $CO_2H$, COR, CONHR, $CON(R)_2$, $S(O)_2R$, $SONH_2$, S(O)R, $SO_2NHR$, or $NHS(O)_2R$; and $R^7$ is selected from hydrogen, halo, R, OR, SR, aryl, substituted aryl, OH, CN, $CO_2R$, $CO_2H$, COR, CONHR, $CON(R)_2$, $S(O)_2R$, $SONH_2$, S(O)R, or $SO_2NHR$.

8. The compound of claim 7 where $R^1$ is $CH_2Y$ and Y is F, -OR, -SR, or -OC=O(R); $R^2$ is $CO_2H$ or esters, amides or isosteres thereof; and $R^3$ is hydrogen or $C_{1-3}$ alkyl, $R^6$ and $R^7$ are each hydrogen.

9. A compound of formula IC:

Fig. 7(d)

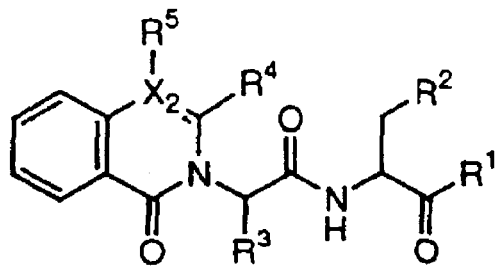

IC where $R^1$ is hydrogen, CN, CHN$_2$, R, or -CH$_2$Y;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R) , or -OPO($R^8$) ($R^9$) ;

$R^8$ and $R^9$ are independently selected from R or OR;

$R^2$ is CO$_2$H, CH$_2$CO$_2$H, or esters, amides or isosteres thereof;

$R^3$ is hydrogen or a C$_{1-6}$ straight chained or branched alkyl;

$R^4$ and $R^5$ are each independently selected from hydrogen, halo, R, OR, SR, aryl, substituted aryl, OH, NO$_2$, CN, NH$_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, NHS(O)$_2$R, =O, =S, =NNHR, =NNR$_2$, =N-OR, =NNHCOR, =NNHCO$_2$R, =NNHSO$_2$R, or =NR.

10. The compound of claim 9 where $R^1$ is CH$_2$Y and Y is F, -OR, -SR, or -OC=O(R); $R^2$ is CO$_2$H or esters, amides or isosteres thereof; $R^3$ is hydrogen or C$_{1-3}$ alkyl; $R^4$ is hydrogen; and $R^5$ is hydrogen when X$_2$ is nitrogen or carbon.

11. A compound of formula ID:

Fig. 7(e)

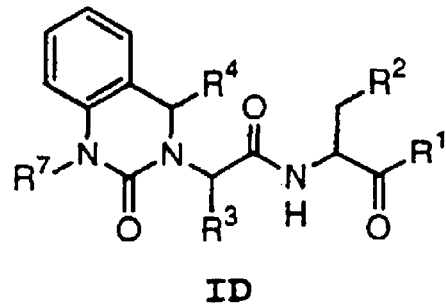

ID where $R^1$ is hydrogen, CN, CHN$_2$, R, -CH$_2$Y;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R), or -OPO($R^8$) ($R^9$);

$R^8$ and $R^9$ are independently selected from R or OR;

$R^2$ is CO$_2$H, CH$_2$CO$_2$H, or esters, amides or isosteres thereof;

$R^3$ is hydrogen or a C$_{1-6}$ straight chained or branched alkyl;

$R^4$ is independently selected from hydrogen, halo, R, OR, SR, aryl, substituted aryl, OH, NO$_2$, CN, NH$_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, or NHS(O)$_2$R;

$R^7$ is selected from hydrogen, halo, R, OR, SR, aryl, substituted aryl, OH, CN, CO$_2$R, CO$_2$H, COR, CONHR, CON(R)$_2$, S(O)$_2$R, SONH$_2$, S(O)R, or SO$_2$NHR.

12. The compound of claim 11 where $R^1$ is CH$_2$Y and Y is F, -OR, -SR, or -OC=O(R); $R^2$ is CO$_2$H or esters, amides or isosteres thereof; $R^3$ is hydrogen or C$_{1-3}$ alkyl; R$_4$ is hydrogen and $R^7$ is aralkyl.

Fig. 7(f)

13. A compound of formula IE:

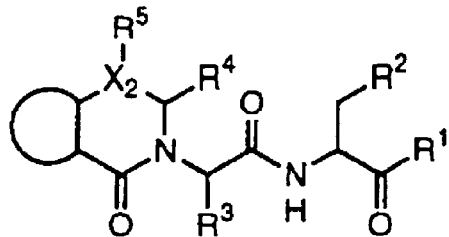

IE where $R^1$ is hydrogen, CN, $CHN_2$, R, $-CH_2Y$;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R), or $-OPO(R^8)(R^9)$;

$R^8$ and $R^9$ are independently selected from R or OR;

$R^2$ is $CO_2H$, $CH_2CO_2H$, or esters or isosteres thereof;

$R^3$ is hydrogen or a $C_{1-6}$ straight chained or branched alkyl;

$R^4$ and $R^5$ are each independently selected from hydrogen, halo, R, OR, SR, aryl, substituted aryl, OH, $NO_2$, CN, $NH_2$, NHR, $N(R)_2$, NHCOR, NHCONHR, $NHCON(R)_2$, NRCOR, $NHCO_2R$, $CO_2R$, $CO_2H$, COR, CONHR, $CON(R)_2$, $S(O)_2R$, $SONH_2$, S(O)R, $SO_2NHR$, or $NHS(O)_2R$; and the fused ring is an aromatic or non-aromatic heterocyclic ring.

14. The compound of claim 13 where $R^1$ is $CH_2Y$ and Y is F, -OR, -SR, -OC=O(R), $R^2$ is $CO_2H$ and esters, amides or isosteres thereof, $R^3$ is H or $C_{1-3}$ alkyl, and the

Fig. 7(g)

fused ring is a five or six membered heterocycle having one ring heteroatom.

15. A compound of formula IF:

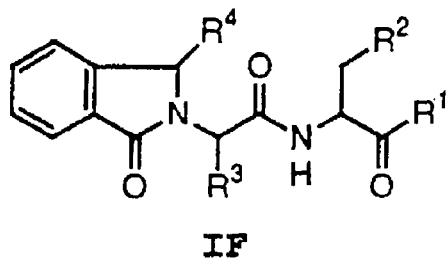

IF where $R^1$ is hydrogen, CN, $CHN_2$, R, or -$CH_2Y$;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R), or -OPO($R^8$) ($R^9$);

$R^8$ and $R^9$ are independently selected from R or OR;

$R^2$ is $CO_2H$, $CH_2CO_2H$, or esters, amides or isosteres thereof;

$R^3$ is hydrogen or a $C_{1-6}$ straight chained or branched alkyl; and $R^4$ is independently selected from hydrogen, halo, R, OR, SR, aryl, substituted aryl, OH, $NO_2$, CN, $NH_2$, NHR, N(R)$_2$, NHCOR, NHCONHR, NHCON(R)$_2$, NRCOR, NHCO$_2$R, CO$_2$R, CO$_2$H, COR, CONKR, CON(R)$_2$, S(O)$_2$R, SONH$_2$, S(O)R, SO$_2$NHR, or NHS(O)$_2$R.

16. The compound of claim 15 where $R^1$ is $CH_2Y$ and Y is F, -OR, -SR, or -OC=O(R); $R^2$ is $CO_2H$ or esters, amides or isosters thereof; $R^3$ is hydrogen or $C_{1-3}$ alkyl; and $R^4$ is $H_2$ or =O.

Fig. 7(h)

17. A compound of formula IG:

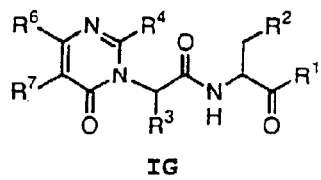

IG where $R^1$ is hydrogen, CN, $CHN_2$, R, or $-CH_2Y$;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or -OR, -SR, -OC=O(R), or $-OPO(R^8)(R^9)$;

$R^8$ and $R^9$ are independently selected from R or OR;

$R^2$ is $CO_2H$, $CH_2CO_2H$, or esters, amides or isosteres thereof;

$R^3$ is hydrogen or a $C_{1-6}$ straight chained or branched alkyl;

each of $R^4$ and $R^6$ is independently selected from hydrogen, halo, R, OR, SR, aryl, substituted aryl, OH, $NO_2$, CN, $NH_2$, NHR, $N(R)_2$, NHCOR, NHCONHR, $NHCON(R)_2$, NRCOR, $NHCO_2R$, $CO_2R$, $CO_2H$, COR, CONHR, $CON(R)_2$, $S(O)_2R$, $SONH_2$, S(O)R, $SO_2NHR$, or $NHS(O)_2R$; and $R^7$ is selected from hydrogen, halo, R, OR, SR, aryl, substituted aryl, OH, CN, $CO_2R$, $CO_2H$, COR, CONHR, $CON(R)_2$, $S(O)_2R$, $SONH_2$, S(O)R, or $SO_2NHR$.

18. The compound of claim 17 where $R^1$ is $CH_2Y$ and Y is F, -OR, -SR, or -OC=O(R); $R^2$ is $CO_2H$ or esters, amides or isosters thereof; $R^3$ is hydrogen or $C_{1-3}$ alkyl; and $R^4$, $R^6$ and $R^7$ are each hydrogen.

Fig. 7(i)

| 1. | 5-Fluoro-4-oxo-3-[(S)-2-(2-oxo-2*H*-pyridin-1-yl)-propionylamino]-pentanoic acid |
|---|---|
| 2. | 5-Fluoro-3-[2-(2-oxo-2*H*-pyridin-1-yl)-acetylamino]-4-oxo-pentanoic acid |
| 3. | 5-Fluoro-3-[2-(6-methyl-2-oxo-2*H*-pyridin-1-yl)-acetylamino]-4-oxo-pentanoic acid |
| 4. | 5-Fluoro-3-[2-(4-phenyl-2-oxo-2*H*-pyridin-1-yl)-acetylamino]-4-oxo-pentanoic acid |
| 5. | 5-Fluoro-3-[2-(3-phenyl-2-oxo-2H-pyridin-1-yl)-acetylamino]-4-oxo-pentanoic acid |
| 6. | 5-Fluoro-4-oxo-3-[(S)-2-(2-oxo-2*H*-quinolin-1-yl)-propionylamino]-pentanoic acid |
| 7. | 5-Fluoro-4-oxo-3-[(S)-(R)-2-(2-oxo-2*H*-quinolin-1-yl)-acetylamino]-pentanoic acid |
| 8. | 5-Fluoro-4-oxo-3-[2-(1-oxo-1*H*-isoquinolin-2-yl)-acetylamino]-pentanoic acid |
| 9. | 5-Fluoro-4-oxo-3-[(S)-2-(1-oxo-1*H*-isoquinolin-2-yl)-propionylamino]-pentanoic acid |
| 10. | 5-Fluoro-4-oxo-3-[2-(1-oxo-1*H*-isoquinolin-2-yl)-acetylamino]-pentanoic acid |
| 11. | 5-Fluoro-4-oxo-3-[2-(1-oxo-3,4-dihydro-1*H*-isoquinolin-2-yl)-acetylamino]-pentanoic acid (1C-4) |
| 12. | 5-Fluoro-4-oxo-3-[2-(4-oxo-4*H*-thieno[2,3-*d*]pyrimidin-3-yl)-acetylamino]-pentanoic acid |
| 13. | 5-Fluoro-4-oxo-3-[2-(1-oxo-1,3-dihydro-isoindol-2-yl)-acetylamino]-pentanoic acid |
| 14. | 5-Fluoro-4-oxo-3-[(2S)-2-(1-oxo-1,3-dihydro-isoindol-2-yl)-propionylamino]-pentanoic acid |
| 15. | 5-Fluoro-4-oxo-3-[(2S)-2-(1,3-dioxo-1,3-dihydro-isoindol-2-yl)-propionylamino-pentanoic acid |
| 16. | 2,6-Dichloro-benzoic acid 4-carboxy-2-oxo-3-[2-(1-oxo-1*H*-isoquinolin-2-yl)-propionylamino]-butyl ester (IC-S)Step I: 2,6-dichloro-benzoic acid 4-*tert*-butoxycarbonyl-2-hydroxy-3-[2-(1-oxo-1*H*-isoquinolin-2-yl)-propionylamino]-butyl ester |
| 17. | 5-Fluoro-3-[2-(6-ethyl-2-oxo-2*H*-pyridin-1-yl)-acetylamino]-4-oxo-pentanoic acid |

Fig. 7(j)

| 18. | 5-Fluoro-4-oxo-3-[(2S)-2-(4-oxo-4*H*-quinazolin-3-yl)-propionylamino]-pentanoic acid |
|---|---|
| 19. | 2,6-Dichloro-benzoic acid 4-carboxy-2-oxo-3-[2-(4-oxo-4H-quinazolin-3-yl)-propionylamino]-butyl ester |
| 20. | 5-Fluoro-4-oxo-3-[2-(1-oxo-1*H*-[2,6]naphthyridin-2-yl)-acetylamino-pentanoic acid |
| 21. | 5-Fluoro-4-oxo-3-[(2S)-2-(4-oxo-4*H*-quinazolin-3-yl)-butyrylamino]-pentanoic acid |
| 22. | 5-Fluoro-4-oxo-3-[(2S)-2-(6-methoxy-4-oxo-4H-quinazolin-3-yl)-butyrylamino]-pentanoic acid |
| 23. | 5-Fluoro-4-oxo-3-[(2S)-3-methyl-2-(-4-oxo-4H-quinazolin-3-yl)-butyrylamino]-pentanoic acid |
| 24. | 5-Fluoro-4-oxo-3-[(2S)-2-(4-oxo-4H-quinazolin-3-yl)-pentanoylamino]-pentanoic acid |
| 25. | 5-Fluoro-4-oxo-3-[(2S)-2-(6-oxo-6H-pyrimidin-1-yl)-butyrylamino]-pentanoic acid |
| 26. | (3S)-4-Oxo-3[(2S)-2-(4-oxo-4H-quinazolin-3-yl)-butyrylamino]-butanoic acid |
| 27. | 5-Fluoro-4-oxo-3-[(2S)-2-[1-(3-chlorobenzyl)-2-oxo-1,4-dihydro-2H-quinazolin-3-yl]-3-methyl-butyrylamino]-pentanoic acid |

Fig. 7(k)

22. A compound of formula I:

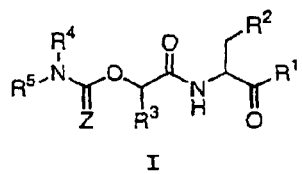

I or a pharmaceutically-acceptable derivative thereof, wherein:

Z is oxygen or sulfur;

$R^1$ is hydrogen, $-CHN_2$, $-R$, $-CH_2OR$, $-CH_2SR$, or $-CH_2Y$;

R is a $C_{1-12}$ aliphatic, aryl, aralkyl, heterocyclyl, or heterocyclylalkyl;

Y is an electronegative leaving group;

$R^2$ is $CO_2H$, $CH_2CO_2H$, or esters, amides or isosteres thereof;

$R^3$ is a group capable of fitting into the S2 sub-site of a caspase; and $R^4$ and $R^5$ taken together with the intervening nitrogen form a mono-, bi- or tricyclic hetero ring system having 1-6 heteroatoms selected from nitrogen, oxygen or sulfur.

23. The compound of claim 22 wherein the compound has one or more of the following features:

Fig. 8(a)

(i) Z is oxygen;
(ii) $R^1$ is hydrogen, -R, -$CH_2OR$, -$CH_2SR$, or -$CH_2Y$;
(iii) $R^2$ is $CO_2H$ or an ester, amide or isostere thereof;
(iv) $R^3$ is a group having a molecular weight up to 140 Daltons; or
(v) $R^4$ and $R^5$ taken together with the intervening nitrogen form a monocyclic, bicyclic or tricyclic ring system wherein each ring of the system has 5-7 ring atoms.

24. The compound of claim 23 wherein the compound has the following features:

(i) Z is oxygen;
(ii) $R^1$ is hydrogen, -R, -$CH_2OR$, -$CH_2SR$, or -$CH_2Y$;
(iii) $R^2$ is $CO_2H$ or an ester, amide or isosteres thereof;
(iv) $R^3$ is a group having a molecular weight up to 140 Daltons; and
(v) $R^4$ and $R^5$ taken together with the intervening nitrogen form a monocyclic, bicyclic or tricyclic heterocyclic or heteroaryl ring system wherein each ring of the system has 5-7 ring atoms.

25. The compound of claim 24 wherein $R^1$ is -$CH_2Y$.

26. The compound of claim 25 wherein $R^1$ is -$CH_2F$ and $R^3$ is a $C_{1-4}$ alkyl group.

27. The compound of claim 26 wherein $R^4$ and $R^5$ taken together with the intervening nitrogen form a bicyclic or

Fig. 8(b)

tricyclic heterocyclic or heteroaryl ring system wherein each ring of the system has 5-7 ring atoms.

28. The compound of claim 27 wherein $R^4$ and $R^5$ taken together with the intervening nitrogen form a tricyclic heterocyclic or heteroaryl ring system wherein each ring of the system has 5-7 ring atoms.

29. The compound of claim 28 wherein the middle ring of the tricyclic ring system is a five- or six-membered ring.

30. The compound of claim 22 wherein the compound has one or more of the following features:

(i) Z is oxygen;

(ii) $R^1$ is -CH$_2$OR, -CH$_2$SR, or -CH$_2$Y;

(iii) $R^2$ is CO$_2$H or an ester, amide or isostere thereof;

(iv) $R^3$ is C$_{1-4}$ alkyl; or (v) $R^4$ and $R^5$ taken together with the intervening nitrogen form a ring selected from indole, isoindole, indoline, indazole, purine, dihydropyridine, benzimidazole, imidazole, imidazoline, pyrrole, pyrrolidine, pyrroline, pyrazole, pyrazoline, pyrazolidine, triazole, piperidine, morpholine, thiomorpholine, piperazine, carbazole, phenothiazine, phenoxazine, dihydrophenazine, dihydrocinnoline, dihydroquinoxaline, tetrahydroquinoline, tetrahydroisoquinoline, dihydronaphthyridine, tetrahydronaphthyridine, dihydroacridine, (ß⁻ carboline, pyrido[4,3-b]indole, 2,3,9-

Fig. 8(c)

triazafluorene, 9-thia-2,10-diazaanthracene, 3,6,9-triazafluorene, thieno[3,2-b]pyrrole, or dihydrophenanthridine.

31. The compound of claim 30 wherein the compound has one or more of the following features:

(i) Z is oxygen;
(ii) $R^1$ is -CH$_2$OR, -CH$_2$SR, or -CH$_2$Y;
(iii) $R^2$ is CO$_2$H or an ester, amide or isostere thereof;
(iv) $R^3$ is C$_{1-4}$ alkyl; or
(v) $R^4$ and $R^5$ taken together with the intervening nitrogen form a ring selected from indole, isoindole, indoline, indazole, benzimidazole, imidazole, pyrrolidine, pyrazole, triazole, piperidine, morpholine, thiomorpholine, piperazine, carbazole, phenothiazine, phenoxazine, dibenzoazepine, dihydro-dibenzoazepine, dihydrophenazine, dihydrocinnoline, dihydroquinoxaline, tetrahydroquinoline, tetrahydroisoquinoline, dihydronaphthyridine, tetrahydronaphthyridine, dihydroacridine, ß-carboline, pyrido[4,3-b]indole, 2,3,9-triazafluorene, 9-thia-2,10-diazaanthracene, 3,6,9-triazafluorene, thieno[3,2-b]pyrrole, or dihydrophenanthridine.

32. The compound of claim 31 wherein the compound has one or more of the following features:

(i) Z is oxygen;
(ii) $R^1$ is -CH$_2$OR, -CH$_2$SR, or -CH$_2$Y;

Fig. 8(d)

(iii) $R^2$ is $CO_2H$ or an ester, amide or isostere thereof;

(iv) $R^3$ is $C_{1-4}$ alkyl; or (v) $R^4$ and $R^5$ taken together with the intervening nitrogen form a substituted or unsubstituted ring system selected from carbazole, phenothiazine, indole, indoline, 5H-dibenzo[b,f]azepine, 10,11-dihydro-5H-dibenzo[b,f]azepine, ß-carboline, pyrido[4,3-b]indole, 2,3,9-triazafluorene, 9-thia-2,10-diazaanthracene, 3,6,9-triazafluorene, thieno [3,2-b]pyrrole, or dihydrophenanthridine.

33. The compound of claim 32 wherein Z is oxygen; $R^1$ is -$CH_2OR$, -$CH_2SR$, or -$CH_2Y$; $R^2$ is $CO_2H$ or an ester, amide or isostere thereof; $R^3$ is $C_{1-4}$ alkyl; and $R^4$ and $R^5$ taken together with the intervening nitrogen form a substituted or unsubstituted ring system selected from carbazole, phenothiazine, indole, indoline, 5H-dibenzo[b,f]azepine, 10,11-dihydro-5H-dibenzo[b,f]azepine, ß-carboline, pyrido[4, 3-b]indole, 2,3,9-triazafluorene, 9-thia-2,10-diazaanthracene, 3,6,9-triazafluorene, thieno[3,2-b]pyrrole, or dihydrophenanthridine.

34. The compound of claim 33 wherein $R^1$ is -$CH_2Y$.

35. The compound of claim 34 wherein $R^1$ is -$CH_2F$.

36. The compound of claim 22 wherein the compound is selected from those compounds listed in Table 1.

37. The compound of claim 22 wherein the compound is selected from the following:

Fig. 8(e)

38. A pharmaceutical composition comprising a compound according to any of claims 22-37 and a pharmaceutically acceptable carrier.

| 1. | [3S/R]-5-Fluoro-4-oxo-3-[(S)-3-methyl-2-(carbazole-carbamoyloxy-butyrylamino]-pentanoic acid |
|---|---|
| 2. | [3S/R]-5-Fluoro-4-oxo-3-[(S)-3-methyl-2-(3-chlorocarbazole)-carbamoyloxy-butyrylamino]-pentanoic acid |
| 3. | [3S/R]-5-Fluoro-4-oxo-3-[(S)-3-methyl-2-(3,6-dichlorocarbazole)-carbamoyloxy-butyrylamino]-pentanoic acid |
| 4. | [3S/R]-5-Fluoro-4-oxo-3-[(S)-3-methyl-2-(carbazole-carbamoyloxy-butyrylamino]-pentanoic acid |
| 5. | [3S/R]-5-Fluoro-4-oxo-3-[(S)-3-methyl-2-(2,3-dichlorocarbazole)-carbamoyloxy-butyrylamino]-pentanoic acid |
| 6. | [3S/R]-5-Fluoro-4-oxo-3-[(S)-3-methyl-2-(2-trifluoromethyl)-carbazole-carbamoyloxy-butyrylamino]-pentanoic acid |
| 7. | [3S/R]-5-Fluoro-4-oxo-3-[(S)-3-methyl-2-(2-methylcarbazole)-carbamoyloxy-butyrylamino]-pentanoic acid |
| 8. | [3S/R]-5-Fluoro-4-oxo-3-[(S)-2-(carbazole-carbamoyloxy)-butyrylamino]-pentanoic acid |
| 9. | [3S/R]-5-Fluoro-4-oxo-3-[(S)-3,3-dimethyl-2-(carbazole-carbamoyloxy)-butyrylamino]-pentanoic acid |
| 10. | [3S/R]-5-Fluoro-4-oxo-3-[(S)-2-(2-chlorocarbazole)-carbamoyloxy-butyrylamino]-pentanoic acid |
| 11. | [3S/R]-5-Fluoro-4-oxo-3-[(S)-3-methyl-2-(indole)-carbamoyloxy-butyrylamino]-pentanoic acid |
| 12. | [3S/R]-5-Fluoro-4-oxo-3-[(S)-3-methyl-2-()-carbamoyloxy-butyrylamino]-pentanoic acid |
| 13. | [3S/R]-5-Fluoro-4-oxo-3-[(S)-3-methyl-2-(2-chlorophonothiazine)-carbamoyloxy-butyrylamino]-pentanoic acid |
| 14. | [3S/R]-5-Fluoro-4-oxo-3-[(S)-3-methyl-2-(3-chlorophonothiazine)-carbamoyloxy-butyrylamino]-pentanoic acid |
| 15. | [3S/R]-5-Fluoro-4-oxo-3-[(S)-3-methyl-2-(3,7-dichlorophonothiazine)-carbamoyloxy-butyrylamino]-pentanoic acid |
| 16. | [3S/R]-5-Fluoro-4-oxo-3-[(S)-3-methyl-2-(3,4-dichlorophonothiazine)-carbamoyloxy-butyrylamino]-pentanoic acid |
| 17. | [3S/R]-5-Fluoro-4-oxo-3-[(S)-3-methyl-2-(9,10-Dihydrophenanthridine)-carbamoyloxy-butyrylamino]-pentanoic acid |

Fig. 8(g)

| | |
|---|---|
| 18. | Dibenzo[b,f]azepine-5-carboxylic acid 1-(1-carboxymethyl-3-fluoro-2-oxo-propylcarbamoyl)-2-methyl-propyl-ester |
| 19. | 10,11-Dihydro-dibenzo[b,f]azepine-5-carboxylic acid 1-(1-carboxymethyl-3-fluoro-2-oxo-propylcarbamoyl)-2-methyl-propyl ester |
| 20. | [3S/R]-5-Fluoro-4-oxo-3-((S)-2,3-dihydroindole-1-carbamoyloxy-3-methyl-butyrylamino)-pentanoic acid |
| 21. | 21)[3S/R]-5-Fluoro-4-oxo-3-[(S)-3-methyl-2-(carbazole)-carbamoyloxy-butyrylamino]-pentanoic acid, diethylamide |
| 22. | [3S/R]-5-Fluoro-4-oxo-3-[(S)-3-methyl-2-(carbazole)-carbamoyloxy-buryrylamino]-pentanoic acid, ethyl amide |
| 23. | [3S/R]-5-Fluoro-4-oxo-3-[(S)-3-methyl-2-(carbazole)-carbarnoyloxy-butyrylamino]-pentanoic acid, piperazine amide |
| 24. | [3S/R]-5-Fluoro-4-oxo-3-[(S)-3-methyl-2-(carbazole)-carbamoyloxy-butyrylamino]-pentanoic acid, N, N-dimethylaminoethyl amide |
| 25. | [3S/R]-5-Fluoro-4-oxo-3-[(S)-3-methyl-2-(carbazole)-carbamoyloxy-butyrylamino]-pentanoamide |
| 26. | [3S/R]-5-Fluoro-4-oxo-3-[(S)-3-methyl-2-(carbazole)-carbamoyloxy-butyrylamino]-pentanoic acid, cyclohexy ester |
| 27. | [3S/R]-5-Fluoro-4-oxo-3-[(S)-3-methyl-2-(carbazole)-carbamoyloxy-butyrylamino]-pentanoic acid, n-propyl ester |
| 28. | [3S/R]-5-Fluoro-4-oxo-3-[(S)-3-methyl-2-(carbazole)-carbamoyloxy-butyrylamino]-pentanoic acid, isopropyl ester |
| 29. | [3S/R]-5-Fluoro-4-oxo-3-[(S)-3-methyl-2-(carbazole)-carbamoyloxy-butyrylamino]-pentanoic acid, methyl ester |
| 30. | [3S/R]-5-Fluoro-4-oxo-3-[(S)-3-methyl-2-(carbazole)-carbamoyloxy-butyrylamino]-pentanoic acid, cholesterol ester |

Fig. 8(h)

1. A compound of formula

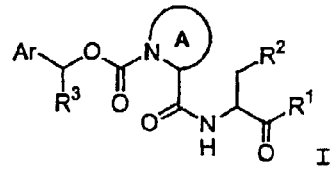

wherein:

Ring A is an optionally substituted piperidine, tetrahydroquinoline or tetrahydroisoquinoline ring;

$R^1$ is hydrogen, $CHN_2$, R, or $-CH_2Y$;

R is an optionally substituted group selected from an aliphatic group, an aryl group, an aralkyl group, a heterocyclic group, or an heterocyclylalkyl group;

Y is an electronegative leaving group;

$R^2$ is $CO_2H$, $CH_2CO_2H$, or esters, amides or isosteres thereof;

Ar is an optionally substituted aryl group; and $R^3$ is hydrogen, an optionally substituted $C_{1-6}$ alkyl, $F_2$, CN, aryl or $R^3$ is attached to Ar to form an unsaturated or partially saturated five or six membered fused ring having 0-2 heteroatoms.

2. The compound of claim 1 having one or more of the following features:

(a) $R^1$ is $CH_2F$;

(b) $R^2$ is $CO_2H$ or esters, amides or isosteres thereof;

(c) $R^3$ is hydrogen or an optionally substituted $C_{1-6}$ alkyl; and (d) Ar is an optionally substituted aryl.

Fig. 9(a)

3. The compound of claim 2 having the following features: (a) $R^1$ is $CH_2F$; (b) $R^2$ is $CO_2H$ or esters, amides or isosteres thereof; (c) $R^3$ is hydrogen or an optionally substituted $C_{1-6}$ alkyl; and (d) Ar is an optionally substituted aryl.

4. The compound of claim 3 where Ring A is a piperidine ring.

5. The compound of claim 3 where Ring A is a tetrahydroquinoline ring.

6. The compound of claim 3 where Ring A is a tetrahydroisoquinoline ring.

7. The compound of claim 1, wherein the compound is selected from the compounds listed in Table 1.

Fig. 9(b)

| | |
|---|---|
| 1. | [3S/R, (2S)]-3-(1-Benzyloxyzcarbonyl-2-piperidinecarboxamido)-5-fluoro-4-oxo-pentanoic acid |
| 2. | [3S/R, (2S)]-3-(1-(2-Chlorobenzyloxycarbonyl)-2-piperidinecarbonoxamido)-5-fluoro-4-oxo-pentanoic acid |
| 3. | [3S/R, (2S)]-3-(1-Benzyloxycarbonyl-1,2,3,4-tetarahydro-quinolinyl-2-carbonoxamido)-5-fluoro-4-oxo-pentanoic acid |
| 4. | [3S/R,(2S)]-5-Fluoro-4-oxo-3-(1-(2-trifluoromethyl benzyloxycarbonyl)-2-piperidinecarbonoxamido)-pentanoic acid |
| 5. | [3S/R, (2S) ]-3-1-(3-Chlorobenzyloxycarbonyl)-2-piperidinecarboxamido)-5-fluoro-4-oxo-pentanoic acid |
| 6. | [3S/R, (2S) ]-5-Fluoro-4-oxo-3-(1-(3-trifluoromethyl benzyloxycarbonyl)-2-piperidinecarboxamido)-pentanoic acid |
| 7. | [3S/R, (2S) ]-3-(1-(3,4-Dichlorobenzyloxycarbonyl)-2-piperidinecarboxamido)-5-fluoro-4-oxo-pentanoic acid |
| 8. | [3S/R, (2S) ]-5-Fluoro-3-(1-(3-methoxybenzyloxycarbonyl)-2-piperidinecarboxamido)-4-oxo-pentanoic acid |
| 9. | [3S/R, (2S, α-R) ]-5-Fluoro-3-(1-(α-trifluoromethyl benzyloxycarbonyl)-2-piperidinecarboxamido)-4-oxo-pentanoic acid |
| 10. | [3S/R, (2S) ]-5-Fluoro-4-oxo-3-(1-(2-pyridinylmethoxycarbonyl)-2-piperidinecarboxamido)-pentanoic acid |
| 11. | [3S/R, (2S) ]-5-Fluoro-4-oxo-3-(1-(3-thienylmethoxycarbonyl)-2-piperidinecarboxamido-pentanoic acid |
| 12. | [3S/R, (2S) ]-3-(1-(3-Bromobenzyloxycarbonyl)-2-piperidinecarboxamido)-5-fluoro-4-oxo-pentanoic acid |
| 13. | [3S/R, (2S) ]-3-(1-(2,4-Dichlorobenzyloxycarbonyl)-2-piperidinecarboxamido)-5-fluoro-4-oxo-pentanoic acid |
| 14. | [3S/R, (2S) ]-3-(1-(3,5-Dichlorobenzyloxycarbonyl)-2-piperidinecarboxamido)-5-fluoro-4-oxo-pentanoic acid |
| 15. | [3S/R, (2S)-3-(1-(2,4-Bis(trifluoromethyl)benzyloxycarbonyl)-2-piperidinecarboxamidok)-5-Fluoro-4-oxo-pentanoic acid |
| 16. | [3S/R, (2S)]-3-(1-(4-Chlorobenzyloxycarbonyl)-1,2,3,4-tetrahydro-quinolinyl-2-carboxamido)-5-fluoro-4-oxo-pentanoic acid |
| 17. | [3S/R, (2S) ]-3-(1-(3,4-Dichlorobenzyloxycarbonyl)-1,2,3,4-tetrahydro-quinolinyl-2-carboxamido)-5-fluoro-4-oxo-pentanoic acid |

Fig. 9(c)

| 18. | [3S/R, (2S) ]-3-(1-(3-Trifluoromethylbenzyloxycarbonyl)-1,2,3,4-tetrahydro-quinolinyl-2-carboxamido)-5-fluoro-4-oxo-pentanoic acid |
|---|---|
| 19. | [3S/R, (2S) ]-5-Fluoro-3-(1-(3-methylsulphonylbenzyloxycarbonyl)-2-piperidinecarboxamido)-4-oxo-pentanoic acid |
| 20. | [3S/R, (2S) ]-5-Fluoro-4-oxo-3-(1-(3-phenylbenzyloxycarbonyl)-2-piperidinecarboxamido)-pentanoic acid |
| 21. | [3S/R, (2S) ]-5-Fluoro-3-(1-(23-nitrobenzyloxycarbonyl)-2-piperidinecarboxamido)-4-oxo-pentanoic acid |
| 22. | [3S/R, (2S) ]-5-Fluoro-3-(1-(2,3-dichlorobenzyloxycarbonyl)-2-piperidinecarboxamido)-4-oxo-pentanoic acid |
| 23. | [3S/R, (2S) ]-5-Fluoro-3-(1-(2,5-dichlorobenzyloxycarbonyl)-2-piperidinecarboxamido)-4-oxo-pentanoic acid |
| 24. | [3S/R, (2S) ]-5-Fluoro-4-oxo-3-(1-(2-phenoxybenzyloxycarbonyl)-2-piperidinecarboxamido)-pentanoic acid |
| 25. | [3S/R, (2S)]-3-(1-(2-Chlorobenzyloxycarbonyl)-1,2,3,4-tetrahydro-quinolinyl-2-carboxamido)-5-fluoro-4-oxo-pentanoic acid |
| 26. | [3S/R, (2S)]-3-(1-(3-Chlorobenzyloxycarbonyl)-1,2,3,4-tetrahydro-quinolinyl-2-carboxamido)-5-fluoro-4-oxo-pentanoic acid |
| 27. | [3S/R, (2S) ]-3-(1-(2-trifluoro methylbenzyloxycarbonyl)-1,2,3,4-tetrahydro-quinolinyl-2-carboxamido)-5-fluoro-4-oxo-pentanoic acid |
| 28. | [3S/R, (2S)]-3(1-(2-Chlorobenzyloxycarbonyl)-1,2,3,4-tetrahydro-isoquinolinyl-2-carboxamido)-5-fluoro-4-oxo-pentanoic acid |
| 29. | [3S/R, (2S)]-3-(1-(Benzyloxycarbonyl)-1,2,3,4-tetrahydro-isoquinolinyl-2-carboxamido)-5-fluoro-4-oxo-pentanoic acid |
| 30. | [3S/R, (2S) ]-5-Fluoro-3-(1-(3-acetamidobenzyloxycarbonyl))-2-piperidinecarboxamido)-4-oxo-pentanoic acid |
| 31. | [3S/R, (2S) ]-5-Fluoro-3-(1-(3-methanesulfonamido) benzyloxycarbonyl)-2-piperidinecarboxamido)-4-oxo-pentanoic acid |
| 32. | [3S/R, (2S)]-5-Fluoro-4-oxo-3-(1-(3k-chloro-2-thienylmethoxycarbonyl)-2-piperidinecarboxamido)-pentanoic acid |
| 33. | 2-(1-Carboxymethyl-3-fluoro-2-oxo-propylcarbamoyl)-piperidine-1-carboxylic acid 2,2,2-trifluoro-1-naphthalen-1-yl-ethyl ester |
| 34. | [3S/R, (2S,α-R) ]-5-Fluoro-3-(1-(α-trifluoromethyl (3-chloro benzyloxycarbonyl)-2-piperidinecarboxamido)-4-oxo-pentanoic acid |

Fig. 9(d)

| 35. | [3S/R, (2S, α-R) ]-5-Fluoro-3-(1-(α-pentafluoromethyl (benzyloxycarbonyl)-2-piperidinecarboxamido)-4-oxo-pentanoic acid |
|---|---|
| 36. | [3S/R, (2S, α-R) ]-5 Fluoro-3-(1-(α-trifluoromethyl benzyloxycarbonyl-1,2,3,4-tetrahydro-quinolinyl-2-carboxamido)-4-oxo-pentanoic acid |
| 37. | [3S/R, (2S, α-R) ]-5-Fluoro-3-(1-(α-trifluoromethyl-(3-chloro benzyloxycarbonyl-1,2,3,4-tetrahydroquinolinyl-2-carboxamido)-4-oxo-pentanoic acid |
| 38. | 2-(1-Carbamoylmethy-3-fluoro-2-oxo-propylcarbamoyl)-piperidine-1-carboxylic acid 3,4-dichloro-benzyl ester |
| 39. | 2-(1-Ethylcarbamoylmethyl-3-fluoro-2-oxo-propylcarbamoyl)-piperidine-1-carboxylic acid 3,4-dichloro-benzyl ester |
| 40. | 2-(1-Diethylcarbamoylmethyl-3-fluoro-2-oxo-propylcarbamoyl)-piperidine-1-carboxylic acid 3,4-dichloro-benzyl ester |
| 41. | 2-{1-[(2-Dimethylamino-ethylcarbamoyl)-methyl]-3-fluoro-2-oxo-propylcarbamoyl}-piperidine-1-carboxylic acid 3,4-dichloro-benzyl ester |
| 42. | 2-{3-Fluoro-1-[2-(4-methylk-piperazin-1-yl)-2-oxo-ethyl]-2-oxo-propylcarbamoyl}-piperidine-1-carboxylic acid 3,4-dichloro-benzyl ester |
| 43. | [3S/R, (2S) ]-3-(1-(3,4-Dichlorobenzyloxycarbonyl)-2-piperidinecarboxamido)-5-fluoro-4-oxo-pentanoate, N-(4-hydroxy-2-isopropyl disulfanyl-1-methyl-butene)-N- methylformamide ester |
| 44. | [3S/R, (2S) ]-3-(1-(5-Chloro-2-fluorobenzyloxycarbonyl)-2-piperidinecarboxamido)-5-fluoro-4-oxo-pentanoic acid |

Fig. 9(e)

1. A compound of formula

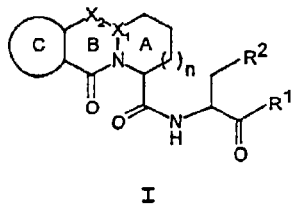

I or a pharmaceutically acceptable derivative thereof, wherein:

$R^1$ is hydrogen, $CHN_2$, R, or -$CH_2Y$;

R is an aliphatic group, an aryl group, an aralkyl group, a heterocyclic group, or a heterocyclylalkyl group;

Y is an electronegative leaving group;

$R^2$ is $CO_2H$, $CH_2CO_2H$, or esters, amides or isosteres thereof;

$X_2$-$X_1$ is $N(R^3)$-$C(R^3)$, $C(R^3)_2$-$C(R^3)$, $C(R^3)_2$-N, N=C, $C(R^3)$=N, $C(R^3)$=C, C(=O)-N, or C(=O)-$C(R^3)$;

each $R^3$ is independently selected from hydrogen or $C_{1-6}$ aliphatic,

Ring C is a fused aryl ring;

n is 0, 1 or 2; and each methylene carbon in Ring A is optionally and independently substituted by =O, or by one or more halogen, $C_{1-4}$ alkyl, or $C_{1-4}$ alkoxy.

2. The compound of claim 1 having one or more of the following features:

(a) $R^1$ is -$CH_2Y$ wherein Y is a halogen, OR, SR, or -OC=O(R), wherein R is an aryl group or heterocyclic group;

Fig. 10(a)

(b) $R^2$ is $CO_2H$ or esters, amides or isosteres thereof;

(c) $X_2$-$X_1$ is N=C, $C(R^3)$=C, or C(=O)-N;

(d) Ring C is a fused five or six-membered aromatic ring having zero to two heteroatoms; and (e) n is 0 or 1.

3. The compound of claim 2 wherein:

(a) $R^1$ is -$CH_2Y$ wherein Y is a halogen, OR, SR, or -OC=O(R), wherein R is an aryl group or heterocyclic group;

(b) $R^2$ is $CO_2H$ or esters, amides or isosteres thereof;

(c) $X_2$-$X_1$ is N=C, $C(R^3)$=C, or C(=O)-N;

(d) Ring C is a fused five or six-membered aromatic ring having zero to two heteroatoms; and (e) n is 0 or 1.

4. The compound of claim 3 wherein $R^1$ is -$CH_2Y$ wherein Y is F; $R^2$ is $CO_2H$ or an ester or amide thereof;

$X_2$-$X_1$ is N=C, CH=C, or C(=O)-N; Ring C is benzene ring;

and n is 0 or 1.

5. The compound of claim 1, said compound selected from the compounds listed in Table 2.

Fig. 10(b)

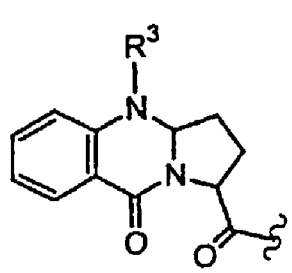 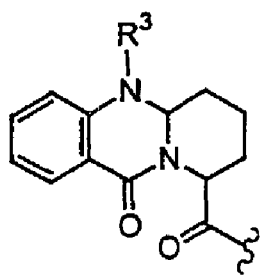 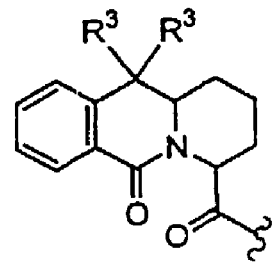
a          b          c
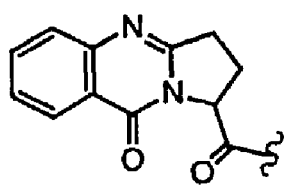 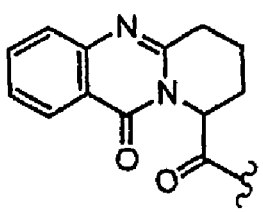 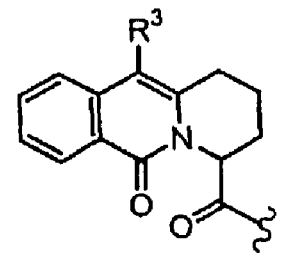
d          e          f
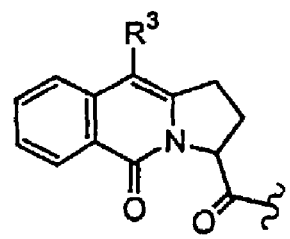 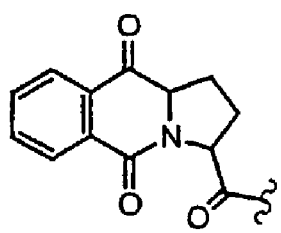 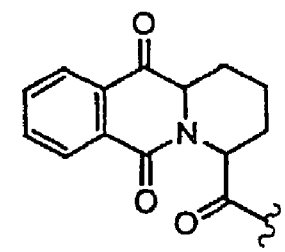
g          h          i
Fig. 10(c)

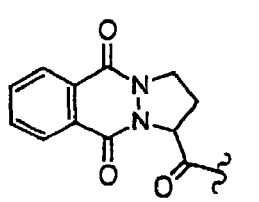
j
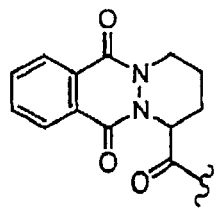
k
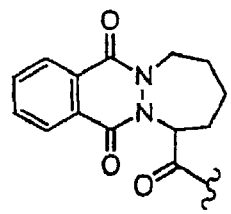
l
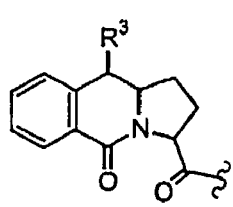
m
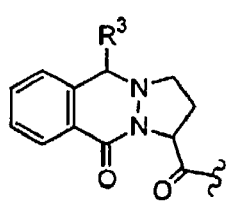
n
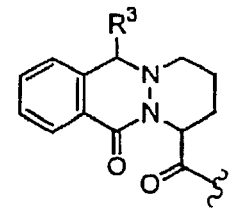
o
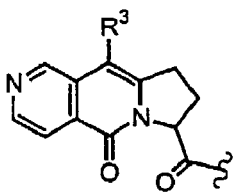
p
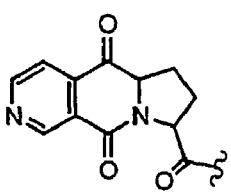
q
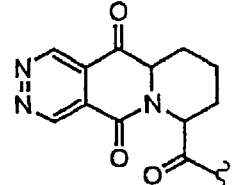
r
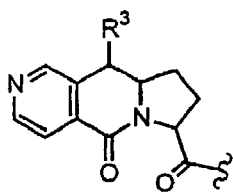
s
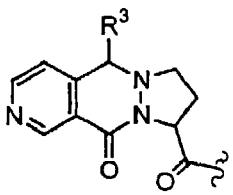
t
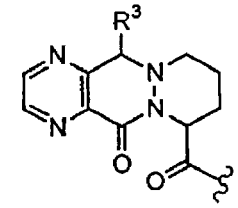
u
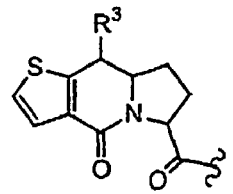
v
Fig. 10(d)

| Example | R¹ | R² | Ring C | N | X₁ | X₂ |
|---------|-----|-----|--------|---|----|----|
| 1. | CH₂F | CO₂H | benzo | 0 | C | N |
| 2. | CH₂F | CO₂H | benzo | 1 | C | N |
| 3. | CH₂F | CO₂H | benzo | 0 | C | C-H |
| 4. | CH₂F | CO₂H | benzo | 1 | C | C-H |
| 5. | CH₂F | CO₂H | benzo | 1 | N | C=O |
| 6. | CH₂F | CO₂H | pyrazino | 1 | N | C=O |

Table 2 compounds of Fig. 10(b)

a compound of formula I:

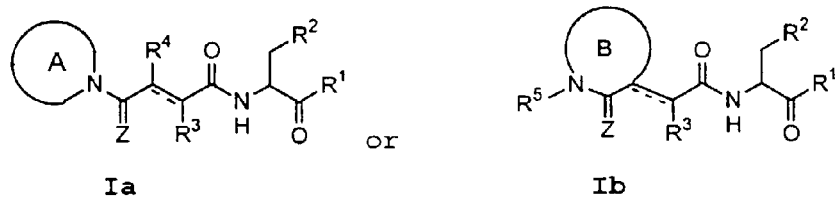

Ia or Ib or a pharmaceutically-acceptable derivative thereof, wherein:

--- between $R^3$ and $R^4$ represents a single or double bond;

Z is oxygen or sulfur;

$R^1$ is hydrogen, -$CHN_2$, -R, -$CH_2OR$, -$CH_2SR$, or -$CH_2Y$;

R is a $C_{1-12}$ aliphatic, aryl, aralkyl, heterocyclyl, or heterocyclylalkyl;

Y is an electronegative leaving group;

$R^2$ is $CO_2H$, $CH_2CO_2H$, or esters, amides or isosteres thereof;

$R^3$ is a group capable of fitting into the S2 sub-site of a caspase;

$R^4$ is hydrogen or a $C_{1-6}$ aliphatic group that is optionally interrupted by -O-, -S-, -$SO_2$-, -CO-, -H-, or -N($C_{1-4}$ alkyl)-, or $R^3$ and $R^4$ taken together with their intervening atoms optionally form a 3-7 membered ring

Fig. 11(a)

having 0-2 heteroatoms selected from nitrogen, oxygen or sulfur;

Ring A is a nitrogen-containing mono-, bi- or tricyclic ring system having 0-5 additional ring heteroatoms selected from nitrogen, oxygen or sulfur;

Ring B is a nitrogen-containing 5-7 membered ring having 0-2 additional ring heteroatoms selected from nitrogen, oxygen or sulfur;

$R^5$ is $R^6$, $(CH_2)_nR^6$, $COR^6$, $CO_2R^6$, $SO_2R^6$, $CON(R^6)_2$, or $SO_2N(R^6)_2$;

n is one to three; and each $R^6$ is independently selected from hydrogen, an optionally substituted $C_{1-4}$ aliphatic group, an optionally substituted $C_{6-10}$ aryl group, or a mono- or bicyclic heteroaryl group having 5-10 ring atoms.

2. The compound of claim 1 where --- between $R^3$ and $R^4$ represents a single bond and Z is oxygen.

3. The conpound of claim 2 wherein the compound is a compound of formula Ia.

4. The compound of claim 3 wherein the compound has one or more of the following features:

(i) $R^1$ is hydrogen, -R, -CH$_2$OR, -CH$_2$SR, or -CH$_2$Y;

(ii) $R^2$ is CO$_2$H or an ester, amide or isostere thereof;

(iii) $R^3$ is a group having a molecular weight up to 140 Daltons;

(iv) $R^4$ is hydrogen or $C_{1-6}$ alkyl; and (v) Ring A is a monocyclic, bicyclic or tricyclic ring system wherein each ring of the system has 5-7 ring atoms.

Fig.11(b)

5. The compound of claim 4 wherein the compound has the following features:

(i) $R^1$ is hydrogen, -R, -CH$_2$OR, -CH$_2$SR, or -CH$_2$Y;

(ii) $R^2$ is CO$_2$H or an ester, amide or isosteres thereof;

(iii) $R^3$ is a group having a molecular weight up to 140 Daltons;

(iv) $R^4$ is hydrogen or C$_{1-6}$ alkyl; and (v) Ring A is a monocyclic, bicyclic or tricyclic heterocyclic or heteroaryl ring system wherein each ring of the system has 5-7 ring atoms.

6. The compound of claim 5 wherein $R^1$ is -CH$_2$Y

7. The compound of claim 6 wherein $R^1$ is -CH$_2$F.

8. The compound of Claim 7 wherein $R^3$ is a C$_{1-4}$ alkyl group.

9. The compound of claim 8 wherein Ring A is a tricyclic heterocyclic or heteroaryl ring system wherein each ring of the system has 5-7 ring atoms.

10. The compound of claim 9 wherein the middle ring of the tricyclic ring system is a five- or six-membered ring.

11. The compound of claim 4 wherein Ring A is selected from indole, isoindole, indoline, indazole, purine, dihydropyridine, benzimidazole, imidazole, imidazoline,

Fig. 11(c)

pyrrole, pyrrolidine, pyrroline, pyrazole, pyrazoline, pyrazolidine, triazole, piperidine, morpholine, thiomorpholine, piperazine, carbazole, iminostilbene, phenothiazine, phenoxazine, dihydrophenazine, dihydrocinnoline, dihydroquinoxaline, tetrahydroquinoline, tetrahydroisoquinoline, dihydronaphthyridine, tetrahydronaphthyridine, dihydroacridine, β-carboline, pyrido [4,3-b]indole, 2,3,9-triazafluorene, 9-thia-2,10-diazaanthracene, 3,6,9-triazafluorene, thieno[3,2-b]pyrrole, or dihydrophenanthridine.

12. The compound of claim 5 wherein Ring A is selected from indole, isoindole, indoline, indazole, purine, dihydropyridine, benzimidazole, imidazole, imidazoline, pyrrole, pyrrolidine, pyrroline, pyrazole, pyrazoline, pyrazolidine, triazole, piperidine, morpholine, thiomorpholine, piperazine, carbazole, iminostilbene, phenothiazine, phenoxazine, dihydrophenazine, dihydrocinnoline, dihydroquinoxaline, tetrahydroquinoline, tetrahydroisoquinoline, dihydronaphthyridine, tetrahydronaphthyridine, dihydroacridine, β-carboline, pyrido[4,3-b]indole, 2,3,9-triazafluorene, 9-thia-2,10-diazaanthracene, 3,6,9-triazafluorene, thieno[3,2-b]pyrrole, or dihydrophenanthridine.

13. The compound of claim 12 wherein Ring A is selected from carbazole, phenothiazine, β-carboline, pyrido[4,3-b]indole, 2,3,9-triazafluorene, 9-thia-2,10-diazaanthracene, 3 , 6 , 9-triazafluorene, phenoxazine,

Fig. 11(d)

dibenzoazepine, dihydro-dibenzoazepine, dihydrophenazine, dihydroacridine, or dihydrophenanthridine.

14. The compound of claim 1 wherein the compound is selected from the compounds listed in Table 1.

15. The compound of claim 2 wherein the compound is a compound of formula Ib.

16. The compound of claim 15 wherein the compound has one or more of the following features:

(i)    $R^1$ is -$CH_2OR$, -$CH_2SR$, or -$CH_2Y$;

(ii)    $R^2$ is $CO_2H$ or an ester, amide or isostere thereof;

(iii)    $R^3$ is a group having a molecular weight up to about 140 Daltons;

(iv)    Ring B is a nitrogen-containing five to seven membered ring having 0-1 additional ring heteroatoms selected from nitrogen, oxygen or sulfur; and (v)    $R^5$ is an optionally substituted $C_{1-6}$ aliphatic group, an optionally substituted phenyl or an optionally substituted benzyl group.

17. The compound of claim 16 wherein the compound has the following features:

(i)    $R^1$ is -$CH_2OR$, -$CH_2SR$, or -$CH_2Y$;

(ii)    $R^2$ is $CO_2H$ or an ester, amide or isostere thereof;

(iii)    $R^3$ is a group having a molecular weight up to about 140 Daltons;

Fig. 11(e)

(iv) Ring B is a nitrogen-containing five to seven membered ring having 0-1 additional ring heteroatoms selected from nitrogen, oxygen or sulfur; and (v) $R^5$ is an optionally substituted $C_{1-6}$ aliphatic group, an optionally substituted phenyl or an optionally substituted benzyl group.

18. The compound of claim 17 wherein $R^1$ is -$CH_2Y$.

19. The compound of claim 18 wherein $R^1$ is -$CH_2F$.

20. The compound of claim 19 wherein $R^3$ is a $C_{1-4}$ alkyl group.

21. The compound of claim 2 wherein the compound is selected from the compounds listed

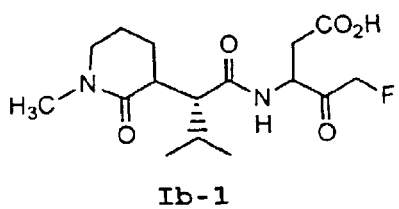
Ib-1

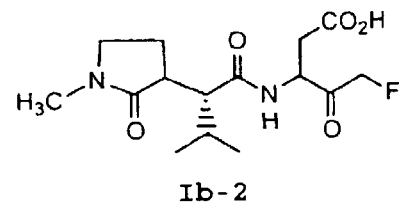
Ib-2

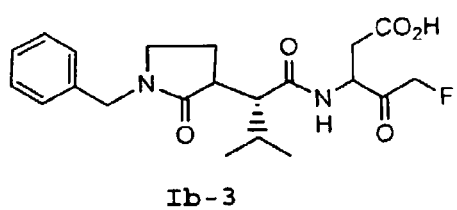
Ib-3

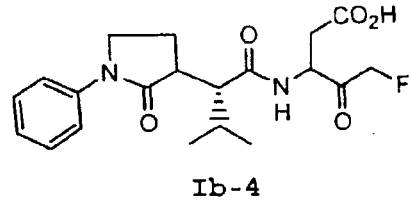
Ib-4

Fig.11(f)

26. A compound of formula Ia:

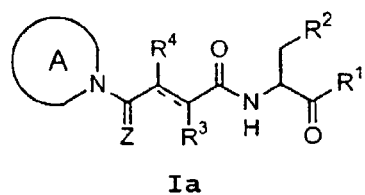

Ia or a pharmaceutically-acceptable derivative thereof, wherein:

--- between $R^3$ and $R^4$ represents a single or double bond;

Z is oxygen or sulfur;

$R^1$ is $CH_2Y$;

Y is an electronegative leaving group;

$R^2$ is $CO_2H$, $CH_2CO_2H$, or esters, amides or isosteres thereof;

$R^3$ is a group capable of fitting into the S2 sub-site of a caspase;

$R^4$ is hydrogen or a $C_{1-6}$ aliphatic group that is optionally interrupted by -O-, -S-, -SO$_2$-, -CO-,-NH-, or -N($C_{1-4}$ alkyl)-, or $R^3$ and $R^4$ taken together with their intervening atoms optionally form a 3-7 membered ring

Fig.11(g)

having 0-2 heteroatoms selected from nitrogen, oxygen or sulfur;

Ring A is a nitrogen-containing mono-, bi- or tricyclic ring system having 0-5 additional ring heteroatoms selected from nitrogen, oxygen or sulfur;

27. The compound of claim 26 wherein Z is oxygen and --- between $R^3$ and $R^4$ represents a single bond.

28. The compound of claim 27 wherein $R^3$ is a $C_{1-4}$ alkyl group.

29. The compound of claim 28 wherein Ring A is selected from indole, isoindole, indoline, indazole, purine, dihydropyridine, benzimidazole, imidazole, imidazoline, pyrrole, pyrrolidine, pyrroline, pyrazole, pyrazoline, pyrazolidine, triazole, piperidine, morpholine, thiomorpholine, piperazine, carbazole, iminostilbene, phenothiazine, phenoxazine, dihydrophenazine, dihydrocinnoline, dihydroquinoxaline, tetrahydroquinoline, tetrahydroisoquinoline, dihydronaphthyridine, tetrahydronaphthyridine, dihydroacridine, β-carboline, pyrido [4,3-b]indole, 2 , 3 , 9-triazafluorene, 9-thia-2, 10-diazaanthracene, 3,6,9-triazafluorene, thieno [3,2-b]pyrrole, or dihydrophenanthridine .

30. The compound of claim 29 wherein Ring A is selected from carbazole, phenothiazine, β-carboline, pyrido[4,3-b]indole, 2, 3, 9-triazafluorene, 9-thia-2, 10-diazaanthracene, 3, 6, 9-triazafluorene, phenoxazine,

Fig. 11(h)

dibenzoazepine, dihydro-dibenzoazepine, dihydrophenazine, dihydroacridine, or dihydrophenanthridine.

31. The compound of claim 30 wherein Ring A is selected from carbazole, phenothiazine or dihydrophenanthridine.

Fig. 11(i)

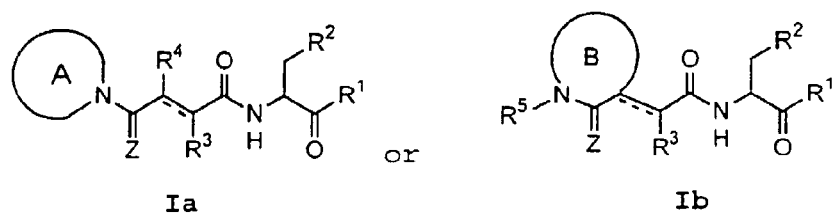

wherein Z is oxygen or sulfur; $R^1$ is hydrogen, $-CHN_2$, R, $CH_2OR$, $CH_2SR$, or $-CH_2Y$; --- between $R^3$ and $R^4$ represents a single or double bond; Y is an electronegative leaving group; $R^2$ is $CO_2H$, $CH_2CO_2H$, or esters, amides or isosteres thereof; $R^3$ is a group capable of fitting into the S2 subsite of a caspase enzyme; $R^4$ is a hydrogen or $C_{1-6}$ alkyl or $R^3$ and $R^4$ taken together form a ring; Ring A and Ring B are each heterocyclic rings, and R and $R^5$ are as described

Fig. 11(j)

Examples of monocyclic rings for Ring A include triazole, piperidine, morpholine, thiomorpholine, imidazole, pyrrolidine, pyrazole, and piperazine. Examples of preferred bicyclic rings for Ring A include indole, isoindole, indoline, indazole, benzimidazole, thieno[3,2-b]pyrrole, dihydroquinoxaline, dihydrocinnoline, dihydronaphthyridine, tetrahydronaphthyridine, tetrahydroquinoline, and tetrahydroisoquinoline, most preferably indole or indoline. Examples of tricyclic rings for Ring A include carbazole, phenothiazine, β-carboline, pyrido[4,3-b]indole, 2, 3, 9-triazafluorene, 9-thia-2, 10-diazaanthracene, 3, 6, 9-triazafluorene, phenoxazine, dibenzoazepine, dihydro-dibenzoazepine, dihydrophenazine, dihydroacridine, or dihydrophenanthridine, carbazole,

Fig. 11(k)

| No. | Structure |
|---|---|
| Ia-1 | 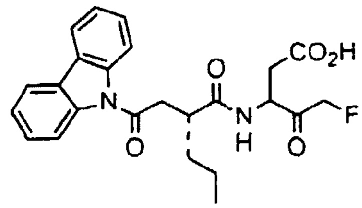 |
| Ia-2 | 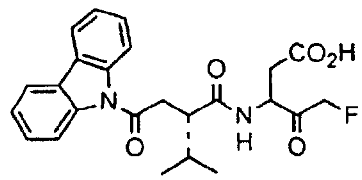 |
| Ia-3 | 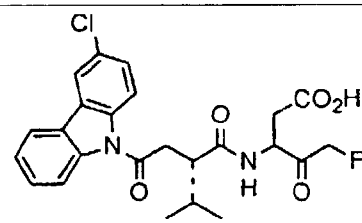 |
| Ia-4 | 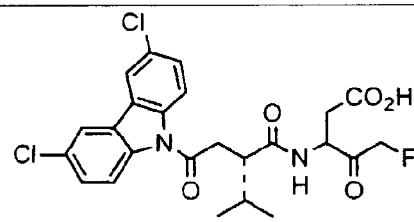 |
| Ia-5 | 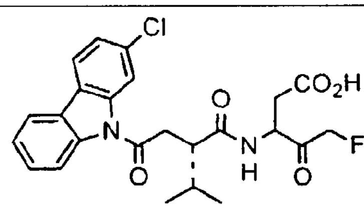 |
| Ia-6 | 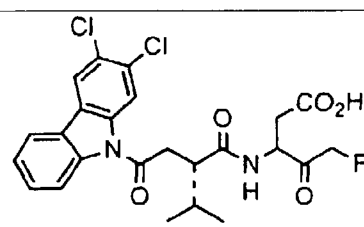 |

Fig.11(l)

| No. | Structure |
|---|---|
| Ia-7 | carbazole-CF3 substituted compound with isopropyl, amide, CO2H and CH2F ketone |
| Ia-8 | carbazole-CH3 substituted compound with isopropyl, amide, CO2H and CH2F ketone |
| Ia-9 | carbazole compound with ethyl, amide, CO2H and CH2F ketone |
| Ia-10 | carbazole compound with tert-butyl, amide, CO2H and CH2F ketone |
| Ia-11 | carbazole-Cl substituted compound with ethyl, amide, CO2H and CH2F ketone |
| Ia-12 | indole compound with isopropyl, amide, CO2H and CH2F ketone |

Fig. 11(m)

| No. | Structure |
|---|---|
| Ia-13 | 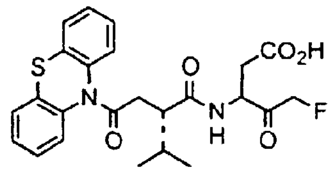 |
| Ia-14 | 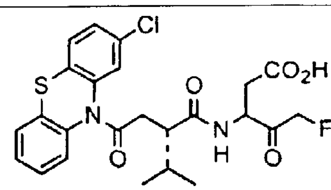 |
| Ia-15 | 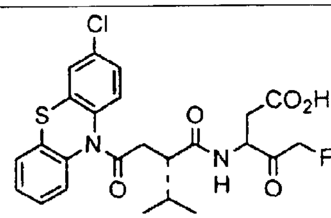 |
| Ia-16 | 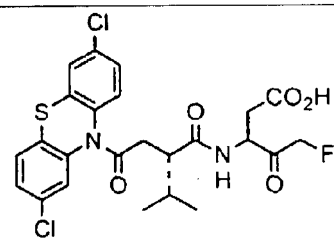 |
| Ia-17 | 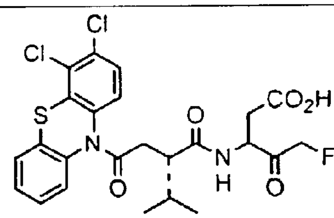 |
| Ia-18 | 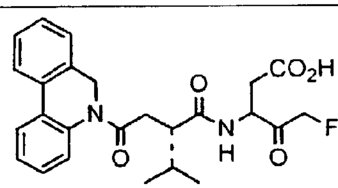 |

Fig. 11(n)

| No. | Structure |
|---|---|
| Ia-19 | 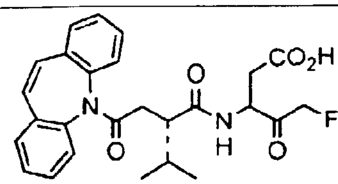 |
| Ia-20 | 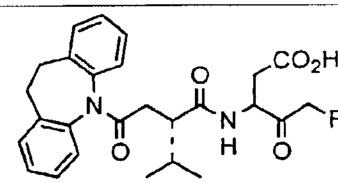 |
| Ia-21 | 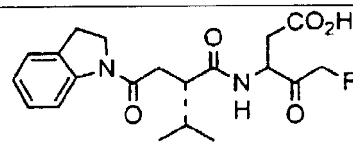 |
| Ia-22 | 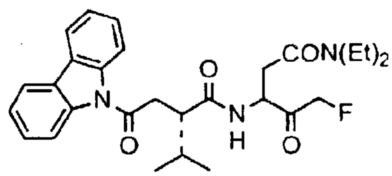 |
| Ia-23 | 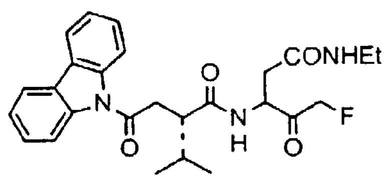 |
| Ia-24 | 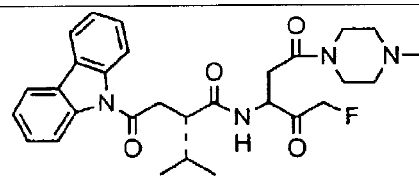 |
| Ia-25 | 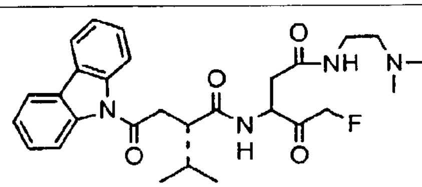 |

Fig. 11(o)

| No. | Structure |
|---|---|
| Ia-26 | 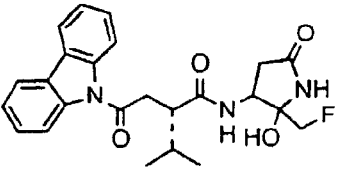 |
| Ia-27 | 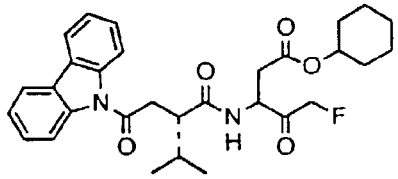 |
| Ia-28 | 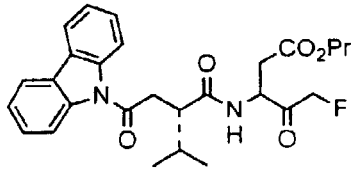 |
| Ia-29 | 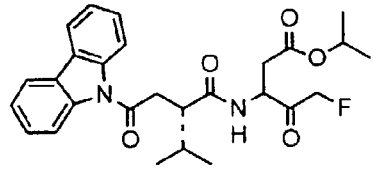 |
| Ia-30 | 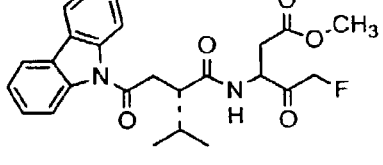 |
| Ia-31 | 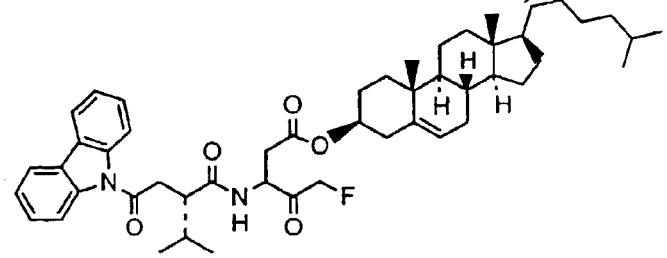 |
Fig. 11(p)

| No. | Structure |
|---|---|
| Ia-32 | 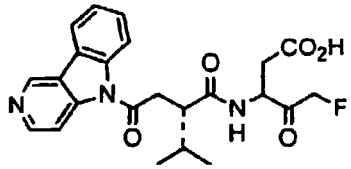 |
| Ia-33 | 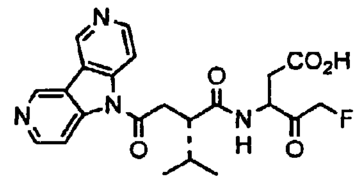 |
| Ia-34 | 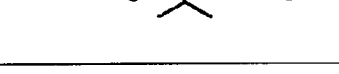 |
| Ia-35 | 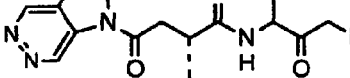 |
| Ia-36 | 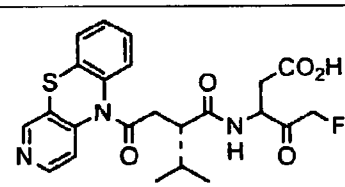 |
| Ia-37 | 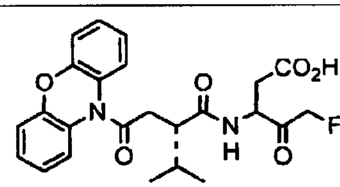 |
| Ia-38 | 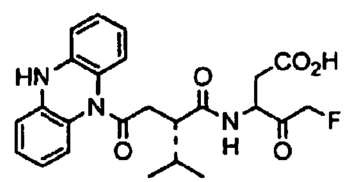 |
Fig. 11(q)

| No. | Structure |
|---|---|
| Ia-39 | 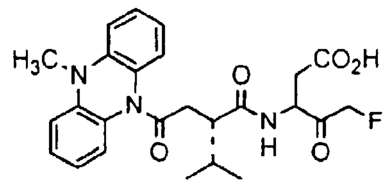 |
| Ia-40 | 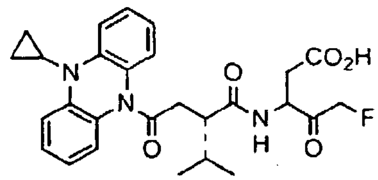 |
| Ia-41 | 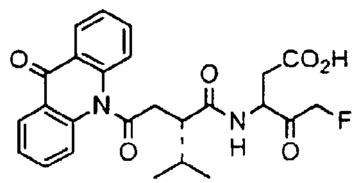 |
| Ia-42 | 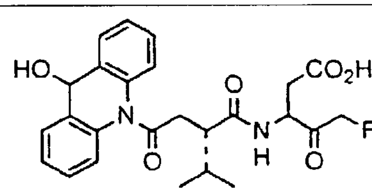 |
| Ia-43 | 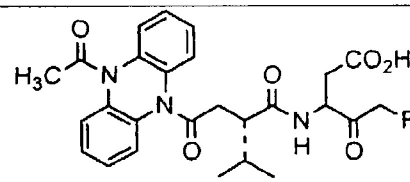 |
| Ia-44 | 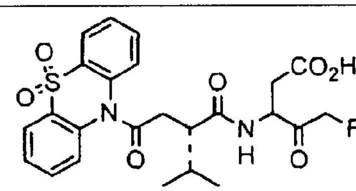 |

Fig. 11(r)

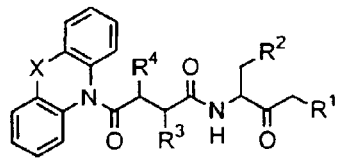

II where X is a bond, -S-, -O-, -CH$_2$-, or -NH-, and R$^1$, R$^2$, R$^3$ and R$^4$ are as described above. Where X is -CH$_2$-, each of the methylene hydrogens may be optionally and independently replaced by -OR, -OH, -SR, protected OH (such as acyloxy), -CN, -NH$_2$, -NHR, -N(R)$_2$, -NHCOR, -NHCONHR, -NHCON(R)$_2$, -NRCOR, -NHCO$_2$R, -CO$_2$R, -CO$_2$H, -COR, -CONHR, -CON(R)$_2$, -S(O)$_2$R, -SONH$_2$, -S(O)R, -SO$_2$NHR, -NHS(O)$_2$R, =O, = S, =NNHR, =NNR$_2$, =N-OR, =NNHCOR, =NNHCO$_2$R, =NNHSO$_2$R, or =NR where R is a C$_{1-4}$ aliphatic group. Where X is -NH-, the NH hydrogen may be replaced by alkyl, CO(alkyl), CO$_2$(alkyl), or SO$_2$(alkyl).

Another embodiment of this invention relates to compounds of formula Ib that have one or more, and preferably all, of the following features:

(i)     R$^1$ is hydrogen, -R, -CH$_2$OR, -CH$_2$SR, or -CH$_2$Y. More preferably, R$^1$ is -CH$_2$OR, -CH$_2$SR, or -CH$_2$Y. An even more preferred R$^1$ is -CH$_2$Y. Most preferably, R$^1$ is -CH$_2$F.

(ii) R$^2$ is CO$_2$H or an ester, amide or isostere thereof.

Fig. 11(s)

1. A compound of formula I:

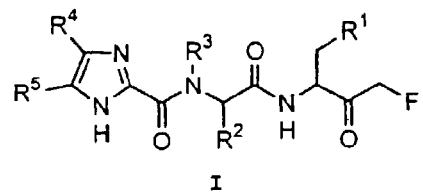

wherein:

$R^1$ is $CO_2H$, $CH_2CO_2H$, or esters, amides or isosteres thereof;

$R^2$ is hydrogen or an optionally substituted $C_1$-$C_6$ aliphatic group;

$R^3$ is hydrogen or an optionally substituted $C_1$-$C_6$ aliphatic group; and $R^4$ and $R^5$ are each independently selected from hydrogen, an optionally substituted $C_1$-$C_6$ aliphatic group, or $R^4$ and $R^5$ taken together with the ring to which they are attached form an optionally substituted bicyclic ring, said bicyclic ring selected from the following:

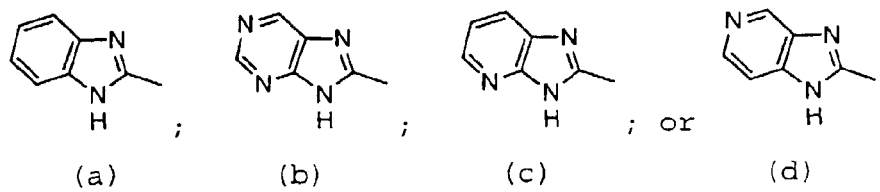

2. The compound of claim 1 where $R^2$ is an optionally substituted $C_{1-6}$ straight or branched alkyl group.

3. The compound of claim 1 having one or more features selected from the group consisting of:

Fig. 12(a)

a) $R^1$ is $CO_2H$ or esters, amides or isosteres thereof;

b) $R^2$ is a $C_1$-$C_6$ straight chain or branched alkyl group;

c) $R^3$ is hydrogen; and d) $R^4$ and $R^5$ are each hydrogen, or $R^4$ and $R^5$ together with the ring to which they are attached form a benzimidazole ring.

4. The compound of claim 3 having the following features:

a) $R^1$ is $CO_2H$ or esters, amides or isosteres thereof;

b) $R^2$ is a $C_1$-$C_6$ straight chain or branched alky group;

c) $R^3$ is hydrogen; and d) $R^4$ and $R^5$ are each hydrogen, or $R^4$ and $R^5$ together with the ring to which they are attached form a benzimidazole ring.

5. A compound selected from the group consisting of:

[3S/R,(2S)]-5-Fluoro-3-{2-[(1H-imidazole-2-carbonyl)-amino]-propionylamino}-4-oxo-pentanoic acid;

[3S/R, (2S)]-5-Fluoro-3-{2- [(1H-imidazole-2-carbonyl)-amino]-propionylamino}-4-oxo-pentanoic acid tert-butyl ester;

[3S/R, (2S)]-3-{2-[(1H-Benzoimidazole-2-carbonyl)-amino]-propionylamino}-5-fluoro-4-oxo-pentanoic acid;

[3S/R,(2S)]-5-Fluoro-3-{2-[(1H-imidazole-2-carbonyl)-amino]-butyrylamino}-4-oxo-pentanoic acid;

[3S/R,(2S)]-5-Fluoro-3-{2-[(1H-imidazole-2-carbonyl)-amino]-3-methylbutyrylamino}-4-oxo-pentanoic acid;

[3S/R, (2S)]-3-{2-[(1H-Benzoimidazole-2-carbonyl)-amino]-3-methylbutyrylamino}-5-fluoro-4-oxo-pentanoic acid;

Fig. 12(b)

| 1. | [3S/R, (2S)]-5-Fluoro-3-{2-[1H-imidazole-2-carbonyl)-amino]-propionylamino}-4-oxo-pentanoic acid, trifluoroacetate salt |
|---|---|
| 2. | [3S/R, (2S)]-3-Fluoro-2-{2-[1H-Benzoimidazole-2-carbonyl)-amino]-propionylamino}-5-fluoro-4-oxo-pentanoic acid, trifluoroacetate salt |
| 3. | [3S/R, (2S)]-5-Fluoro-3-{2-[1H-imidazole-2-carbonyl)-amino]-butyrylamino}-4-oxo-pentanoic acid, trifluoroacetate salt |
| 4. | [3S/R, (2S)]-5-Fluoro-3-{2-[1H-imidazole-2-carbonyl)-amino]-3-methylbutyrylamino}-4-oxo-pentanoic acid |
| 5. | [3S/R, (2S)]-3-Fluoro-3-{2-[1H-Benzoimidazole-2-carbonyl)-amino]-3-methylbutyrylamino}-5-fluoro-4-oxo-pentanoic acid |

Fig. 12(c)

1. A compound of formula II:

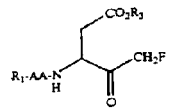

or a pharmaceutically acceptable salt thereof, wherein, $R_1$ is an N-terminal protecting group selected from the group consisting of t-butoxycarbonyl (Boc), acetyl (Ac) and benzyloxycarbonyl (Cbz);

$R_3$ is alkyl or hydrogen; and

AA is a residue of an amino acid selected from the group consisting of valine (Val), isoleucine (Ile) and leucine (Leu).

2. The compound of claim 1, wherein $R_3$ is methyl or hydrogen.

3. The compound of claim 2, which is Cbz-Val-Asp-$CH_2F$ or a pharmaceutically acceptable salt thereof.

4. The compound of claim 2, which is Cbz-Leu-Asp- $CH_2F$ or a pharmaceutically acceptable salt thereof.

5 The compound of claim 2, which is Cbz-Ile-Asp- $CH_2F$ or a pharmaceutically acceptable salt thereof.

6. The compound of claim 2, which is Ac-Val-Asp- $CH_2F$ or a pharmaceutically acceptable salt thereof.

7. The compound of claim 2, which is Ac-Leu-Asp- $CH_2F$ or a pharmaceutically acceptable salt thereof.

8. The compound of claim 2, which is Ac-Ile-Asp- $CH_2F$ or a pharmaceutically acceptable salt thereof.

9. The compound of claim 2, which is Boc-Val-Asp- $CH_2F$ or a pharmaceutically acceptable salt thereof.

10. The compound of claim 2, which is Boc-Leu-Asp- $CH_2F$ or a pharmaceutically acceptable salt thereof.

11. The compound of claim 2, which is Boc-Ile-Asp- $CH_2F$ or a pharmaceutically acceptable salt thereof.

12. The compound of claim 2, which is Cbz-Val-Asp (OMe)- $CH_2F$.

13. The compound of claim 2, which is Cbz-Leu-Asp (OMe)- $CH_2F$.

14. The compound of claim 2, which is Cbz-Ile-Asp (OMe)-$CH_2F$.

15. A pharmaceutical composition comprising the compound of any one of claims 1-14, and a pharmaceutically acceptable carrier.

Fig. 13(a)

| 1.  | t-Butyl 5-fluoro-4-hydroxy-3-nitropentanoate |
|-----|----------------------------------------------|
| 2.  | t-Butyl 3-amino-5-fluoro-4-hydroxy-pentanoate |
| 3.  | t-Butyl 3-(Cbz-Val-amido)-5-fluoro-4-hydroxy-pentanoate |
| 4.  | Z-Val-Asp-fmk t-butyl ester |
| 5.  | Z-Val-Asp-fmk |
| 6.  | Z-Leu-Asp-fmk |
| 7.  | Z-Ile-Asp-fmk |
| 8.  | Z-Ala-Asp-fmnk |
| 9.  | Ac-Val-Asp-fmk |
| 10. | Z-N-Me-Val-Asp-fmk |
| 11. | Z-β-Ala-Asp-fmk |
| 12. | Z-Gly-Asp-fmk |
| 13. | Z-Phe-Asp-fink |
| 14. | Z-Glu-Asp-fmk |
| 15. | Z-Pro-Asp-fmk |
| 16. | Z-His-Asp-fmk |
| 17. | Z-Tyr-Asp-fmk |
| 18. | Z-Val-Asp-fmk Methyl Ester |
| 19. | Z-Leu-Asp-fmk Methyl Ester |
| 20. | Z-Ile-Asp-fmk Methyl Ester | fmk: fluoromethylketone
Glu: Glutamic acid
Z: benzyloxycarbonyl
Pro: Proline
Val: Valine
His: Histidine
Asp: Aspartic acid
Tyr: Tyrosine
Leu: Leucine
Ile: Isoleucine
Ala: Alanine
Gly: Glycine
Phe: Phenylalanine

Fig.13(b)

compounds having the general Formula I:

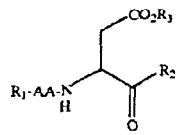

or pharmaceutically acceptable salts or prodrugs thereof, wherein:

$R_1$ is an N-terminal protecting group including t-butyloxycarbonyl, acetyl, and benzyloxycarbonyl; AA is a residue of any natural or non-natural α-amino acid, or β-amino acid, or a derivative of an α-amino acid or β-amino acid, e.g. Gly, Thr, Glu, Lys, Arg, Ser, Asn, Gln, Val, Ala, Leu, Ile, Met, and β-amino acids such as β-Ala, and which is not His, Tyr, Pro or Phe; $R_2$, is H or $CH_2R_4$, $R_4$, is an electronegative leaving group such as F, Cl, TsO-, MeO-, ArO-, ArCOO, ArN-, and ArS-; and $R_3$ is alkyl or H.

With respect to $R_3$, preferred alkyl groups are $C_{1-6}$ alkyl groups, e.g. methyl, ethyl, propyl, isopropyl, isobutyl, pentyl and hexyl groups.

Formula II:

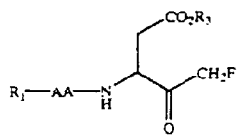

or pharmaceutically acceptable salts or prodrugs thereof wherein AA, $R_1$ and $R_3$ are as defined previously with respect to Formula I.

Preferred $R_1$ is t-butyloxycarbonyl, acetyl and benzyloxycarbonyl. Preferred $R_3$ is H, Me, Et or t-Bu. Preferred AA is Val, Ala, Leu, Ile, Met, and β-amino acids such as β-Ala.

Exemplary preferred inhibitors of apoptosis having Formula I include, without limitation:

Boc-Ala-Asp-$CH_2$F,  Boc-Ala-Asp(OMe)-$CH_2$F,
Boc-Val-Asp-$CH_2$F,  Boc-Val-Asp(OMe)-$CH_2$F,
Boc-Leu-Asp-$CH_2$F,  Boc-Leu-Asp(OMe)-$CH_2$F,
Ac-Val-Asp-$CH_2$F,  Ac-Val-Asp(OMe)-$CH_2$F,
Ac-Ile-Asp-$CH_2$F,  Ac-Ile-Asp(OMe)-$CH_2$F,
Ac-Met-Asp-$CH_2$F,  Ac-Met-Asp(OMe)-$CH_2$F,
Cbz-Val-Asp-$CH_2$F,  Cbz-Val-Asp(OMe)-$CH_2$F,
Cbz-β-Ala-Asp-$CH_2$F  Cbz-β-Ala-Asp(OMe)-$CH_2$F
Cbz-Leu-Asp-$CH_2$F,  Cbz-Leu-Asp(OMe)-$CH_2$F, and
Cbz-Ile-Asp-$CH_2$F,  Cbz-Ile-Asp(OMe)-$CH_2$F.

Fig. 13(c)

1. A compound of the following formula:

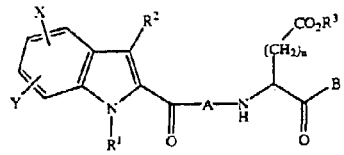

wherein:
n is 1 or 2;
$R^1$ is alkyl, cycloalkyl, (cycloalkyl)alkyl, phenyl, substitutedphenyl, phenylalkyl, substituted phenylalkyl, heteroaryl, (heteroaryl)alkyl of $(CH_2)_mCO_2R^4$, wherein m=1-4, and $R^4$ is as defined below;
$R^2$ is a hydrogen atom, chloro, alkyl, cycloalkyl, (cycloalkyl)alkyl, phenyl, substitutedphenyl, phenylalkyl, substituted phenylalkyl, heteroaryl, (heteroaryl)alkyl or $(C_2)_pCO_2R^5$, wherein p=0-4, and $R^5$ is as defined below;
$R^3$ is a hydrogen atom, alkyl, cycloalkyl, (cycloalkyl) alkyl, phenylalkyl, or substituted phenylalkyl;
$R^4$ is a hydrogen atom, alkyl, cycloalkyl, (cycloalkyl) alkyl, phenylalkyl, or substituted phenylalkyl;
$R^5$ is a hydrogen atom, alkyl, cycloalkyl, (cycloalkyl) alkyl, phenylalkyl, or substituted phenylalkyl;
A is a natural or unnatural amino acid;
B is a hydrogen atom, a deuterium atom, alkyl, cycloalkyl, (cycloalkyl)alkyl, phenyl, substituted phenyl, phenylalkyl, substituted phenylalkyl, heteroaryl, (heteroaryl)alkyl, halomethyl, $CH_2ZR^6$, $CH_2OCO(aryl)$, or $CH_2OCO$ (heteroaryl), or $CH_2OPO(R^7)R^8$, where Z is an oxygen, OC(=O) or a sulfur atom;
$R^6$ is phenyl, substituted phenyl, phenylalkyl, (substituted phenyl)alkyl, heteroaryl or (heteroaryl) alkyl;
$R^7$ and $R^8$ are independently selected from a group consisting of alkyl, cycloalkyl, phenyl, substituted phenyl, phenylalkyl, (substituted phenyl)alkyl and (cycloalkyl)alkyl; and
X and Y are independently selected from the group consisting of a hydrogen atom, halo, trihalomethyl, amino, protected amino, an amino salt, mono-substituted amino, di-substituted amino, carboxy, protected carboxy, a carboxylate salt, hydroxy, protected hydroxy, a salt of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl; or a pharmaceutically acceptable salt or stereoisomer thereof.

2. The compound of claim 1 wherein B is $CH_2ZR^6$.
3. The compound of claim 2 wherein B is $CH_2OC(=O)R^6$.
4. The compound of claim 3 wherein $R^6$ is substituted phenyl.
5. The compound of claim 3 wherein $R^6$ is heteroaryl.
6. The compound of claim 2 wherein B is $CH_2OR^6$.
7. The compound of claim 6 wherein $R^6$ is substituted phenyl.
8. The compound of claim 7 wherein $R^6$ is tetra(halo) phenyl.
9. The compound of claim 8 wherein $R^6$ is optionally substituted naphthyl.
10. The compound of claim 9 wherein $R^6$ is naphthyl substituted with one or more heteroaryl groups.

Fig. 14(a)

| 1. | (3S)-3-[(l-Methylindole-2-Carbonyl)Alaninyl] Amino-4-Oxobutanoic Acid, t-Butyl Ester Semicarbazone |
|---|---|
| 2. | (3S)-3-[(l-Methylindole-2-Carbonyl)Alaninyl] Amino-4-Oxobutanoic Acid, Semicarbazone |
| 3.. | (3S)-3-[(l-Methylindole-2-Carbonyl)Alaninyl] Amino-4-Oxobutanoic Acid |
| 4. | (3S)-3-(l-Methylindole-2-Carbonyl)Prolinyl]Amino-4-Oxo-Butanoic Acid, t-Butyl Ester Semicarbazone |
| 5. | (3S)-3-[(l-Methylindole-2-Carbonyl)Prolinyl] Amino-4-Oxo-Butanoic Acid, Semicarbazone |
| 6. | (3S)-3-[(l-Methylindole-2-Carbonyl)Prolinyl] Amino-4-Oxo-Butanoic Acid |
| 7. | (3S)-3-[l(l-Methylindole-2-Carbonyl)Valinyl] Amino-4-Oxo-Butanoic Acid, t-Butyl Ester Semicarbazone |
| 8. | (3S)-3[l-Methylindole-2-Carbonyl)Valinyl] Amino-4-Oxo-Butanoic Acid Semicarbazone |
| 9. | (3S)-3[l-Methylindole-2-Carbonyl)Valinyl] Amino-4-Oxo-Butanoic Acid |
| 10. | (3S)-3-[(l-Methylindole-2-Carbonyl)Leucinyl] Amino-4-Oxo-Butanoic Acid, t-Butyl Enter Semicarbazone |
| 11. | (3S)-3-[l-Methylindole-2-Carbonyl)Leucinyl] Amino-4-Oxo-Butanoic Acid Semicarbazone |
| 12. | (3S)-3-[(l-Methylindole-2- Carbonyl)Leucinyl] Amino-4-Oxo-Butanoic Acid |
| 13. | (3S)-3-[(l-Methylindole-2-Carbonyl)Phenylalaninyl] Amino-4-Oxabutanoic acid, t-Butyl Ester Semicarbazone |
| 14. | (3S)-3-[(l-Methylindole-2-Carbonyl)Phenylalaninyl] Amino-4-Oxobutanoic Acid Semicarbazone |
| 15. | (3S)-3-[(l-Methylindole-2-Carbonyl)(Phenylalaninyl] Amino-4-Oxobutanoic Acid |
| 16. | (l-Methylindole-2-Carbonyl)Glycine, Methyl Ester |
| 17. | (1-Methylindole-2-Carbonyl)Glycine |

Fig. 14(b)

| 18. | (3S)-3-[(1-Methylindole-2-Carbonyl)Glycine] Amino-4-Oxo-Butanoic Acid, t-Butyl Ester Semicarbazone |
|---|---|
| 19. | (3S)-3-[(1-Methylindole-2-Carbonyl)Glycinyl] Amino-4-Oxo-Butanoic Acid, Semicarbazone |
| 20. | (3S)-3-[(1-Methylindole-2-Carbonyl)Glycinyl]-Amino-4-Oxo-Butanoic Acid |
| 21. | (3S)-3-[(1-Benzylindole-2-Carbonyl)Alaninyl] Amino-4-Oxo-Butanoic Acid, t-Butyl Ester Semicarbazone |
| 22. | (3S)-3-[(1-Benzylindole-2-Carbonyl)Alaninyl] Amino-4-Oxo-Butanoic Acid, Semicarbazone |
| 23. | (3S)-3-[(1-Benzylindole-2-Carbonyl)Alaninyl] Amino-4-Oxo-Butanoic Acid |
| 24. | (3S)-3-(1-(4'-Butenyl)Indole-2-Carbonyl)Valinyl] Amino-4-Oxobutanoic Acid, t-Butyl Ester Semicarbazone |
| 25. | (3S)-3-[(1-4'-Butenyl)Indole-2-Carbonyl)Valinyl] Amino-4-Oxobutanoic Acid, Semicarbazone |
| 26. | (3S)-3-[(1-(4'-Butenyl)indole-2-Carbonyl)Valinyl] Amino-4-Oxobutanoic Acid |
| 27. | (3S)-3-[(1-(2'-(1'-t-Butoxy-[1'-Oxo)Ethyl)Indole-2-Carbonyl)Alaninyl] Amino-4-Oxobutanoic Acid, t-Butyl Ester Semicarbazone |
| 28. | (3S)-3-[(1-(Carboxymethyl)-Indole-2-Carbonyl)Alaninyl] Amino-4-Oxabutanoic Acid, Semicarbazone |
| 29. | (3S)-3-[(1-(Carboxymethyl)Indole-2-Carbonyl)Alaninyl] Amino-4-Oxobutanoic Acid |
| 30. | (3S)-3-[(1-(3'-(1'-t-Butoxy-1'-Oxo)Proply)Indole-2-Carbonyl)Alaninyl] Amino-4-Oxobutanoic Acid, t-Butyl Ester Semicarbazone |
| 31. | (3S)-3-[1-(2'-Carboxyethyl)Indole-2-Carbonyl)Alaninyl] Amino-4-Oxobutanoic Acid, Semicarbazone |
| 33. | (3S)-3-(1-(2'-Carboxyethyl)Indole-2-Carbonyl)Alaninyl] Amino-4-Oxobutanoic Acid |
| 34. | 2,6-Dichlorobenzyloxyethanol |

Fig. 14(c)

| 35. | 5-(2'-6'-Dichlorobenzyloxy)-4-Hydroxy-3-Nitro-Pentanoic Acid, t-Butyl Ester |
|---|---|
| 36. | 3-Amino-5-(2',6'-Dichlorobezyloxy)-4-Hydroxy-Pentanoic Acid, t-Butyl Ester |
| 37. | N-(1,3-Dimethylindole-2-Carbonyl)Valine |
| 38. | N-[(1,3-Dimethylindole-2-Carbonyl)Valinyl]-3-Amino-4-Hydroxy-5(2',6'-Dichlorobenzyloxy) Pentanoic Acid, t-Butyl Ester |
| 39. | N-[(1,3-Dimethylindole-2-Carbonyl)Valinyl]-3-Amino-4-Oxo-5-(2'6'-Dichlorobenzyloxy)Pentanoic Acid, t-Butyl Ester |
| 40. | N-[1,3-Dimethylindole-2-Carbonyl)Valinyl]-3-Amino-4-Oxo-5-(2',6'-Dichlorobenzyloxy)Pentanoic Acid |
| 41. | N-[1,3-Dimethylindole-2-Carbonyl)Valinyl]-3-Amino-4-Hydroxy-5-Fluoropentanoic Acid, t-Butyl Ester |
| 42. | N-[(1,3-Dimethylindole-2-Carbonyl)Valinyl]-3-Amino-4-Oxo-5-Fluoropentanoic Acid, t-Butyl Ester |
| 43. | N-[(1,3-Dimethylindole-2-Carbonyl)Valinyl]-3-Amino-4-Oxo-5-Fluoropentanoic Acid |
| 44. | N-[(1-Methylindole-2-Carbonyl)Valinyl]-3-Amino-4-Hydroxy-5-Fluoropentanoic Acid, t-Butyl Ester |
| 45. | N-[(3-Chloro-1-Methylindole-2-Carbonyl)Valinyl]-3-Amino-4-Oxo-5-Fluoropentanoic Acid, t-Butyl Ester |
| 46. | N-[(3-Chloro-1,Methylindole-2-Carbonyl)Valinyl]-3-Amino-4-Oxo-5-Fluoropentanoic Acid |
| 47. | N-[(5-Fluoro-[1-Methylindole-2-Carbonyl)Valinyl]-3-Amino-4-Hydroxy-5-Fluoropentanoic Acid, t-Butyl Ester |
| 48. | N-[(3-Chloro-5-Fluoro-1-Methylindole-2-Carbonyl)Valinyl]-3-Amino-4-Oxo-5-Fluoropentanoic Acid, t-Butyl Ester |
| 49. | N-[(3-Chloro-5-Fluoro-1-Methylindole-2-Carbonyl)Valinyl]-3-Amino-4-Oxo-5-Fluoropentanoic Acid |
| 50. | N-[(1-(3'-Phenylpropyl)Indole-2-Carbonyl)Valinyl]-3-Amino-4-Hydroxy-5-Fluoropentanoic Acid, t-Butyl Ester |
| 51. | N-(1-(3'-Phenylpropyl)Indole-2-Carbonyl)Valinyl]-3-Amino-4-Oxo-5-Fluoropentanoic Acid, t-Butyl Ester |

Fig. 14(d)

| 51 | N-(l-(3'-Phenylpropyl)Indole-2-Carbonyl)Valinyl]-3-Amino-4-Oxo-5-Fluoropentanoic Acid, t- Butyl Ester |
|---|---|
| 52 | N-[(l-(3'-Phenylpropyl)Indole-2-Carbonyl)Valinyl]-3-Amino-4-Oxo-5-Fluoropentanoic Acid |
| 53 | N-[(l-Phenylindole-2-Carbonyl)Valinyl]-3-Amino-4-Hydroxy-5-Fluoropentanoic Acid, t-Butyl Ester |
| 54 | N-[(l-Phenylindole-2-Carbonyl)Valinyl]-3-Amino-4-Oxo-5-Fluoropentanoic Acid, t-Butyl Ester |
| 55 | N-[(l-Phenylindole-2-Carbonyl)Valinyl]-3-Amino-4-Oxo-5-Fluoropentanoic Acid |
| 56 | N-[ 1 -(2'-(( 1 '-t-Butoxy- 1 t-Oxo)Ethyl)Indole-2-Carbonyl)Valinyl]-3-Amino-4-Hydroxy-5-Fluoropentanoic Acid, t-Butyl Ester |
| 57 | N-[(l-(2'((l '-t-Butoxy-l'-Oxo)Ethyl)Indole-2-Carbonyl(Valinyl]-3-Amino-4-Oxo-5-Fluoropentanoic Acid, t-Butyl Ester |
| 58 | N-[(l-(Carboxymethyl)Indole-2-Carbonyl)Valinyl]-3-Amino-4-Oxo-5-Fluoropentanoic Acid |
| 59 | N-[(l-Methylindole-2-carbonyl)valinyl]-3-amino-4-hydroxy-5-fluoropentanoic acid, t-butyl ester |
| 60 | N-(l-Methylindole-2-carbonyl)valinyl]-3-amino-4-oxo-5-fluoropentanoic acid, t-butyl ester |
| 61 | N-[(l-Methylindole-2-carbonyl)valinyl]-3-amino-4-oxo-5-fluoropentanoicacid |
| 62 | N-[ 1(1 ,3-Dimethyl-5-fluoroindole-2-carbonyl)valinyl]-3-amino-4-oxo-5-fluoropentanoic acid |
| 63 | N-[l-homoallylindole-2-carbonyl)valinyl)-3-amino-4-oxo-5-fluoropentanoic acid |
| 64 | N-[ 1 -Methyl-5-fluoroindole-2-carbonyl)valinyl]-3-amino-4-oxo-5-fluoropentanoic acid |
| 65 | N-[(l-Methyl-3-isobutylindole-2-carbonyl)valinyl]-3-amino-4-oxo-5-fluoropentanoic acid |
| 66 | N-[(l-Methyl-3-phenethylindolo-2-carbonyl)valinyl]-3-amino-4-oxo-5-fluoropentanoic acid |

Fig. 14(e)

| 67 | N-[(l-Methyl-5-O-benzylindole-2-carbonyl)valinyl]-3-amino-4-oxo-5-fluoropentanoic acid |
|---|---|
| 68 | N-(1,3-Dimenthyl-indole-2-carbonyl)-Valinyl-3-Amino-5-Bromo-4-Oxo-Pentanoic Acid, t-Butyl Ester |
| 69 | N-[(1,3-Dimethyl-indole-2-carbonyl)-Valinyl]-3-amino-5(2,6-dichlorobenzoyl)oxy-4-oxo-pentanoic acid, t-butyl ester |
| 70 | N-[N-(1,3-Dimethyl-indole-2-carbonyl)-Valinyl]-3-amino-5-(2,6-dichlorobenzoyl)oxy-4-oxo-pentanoicacid |
| 71 | N-( 1 ,3-Dimethyl-indole-2-carbonyl)-Valinyl-3-amino-5-(diphenylphosphinyl)oxy-4-oxo-pentanoic acid |
| 72 | N-(1,3-Dimcthyl-indole-2-carbonyl)-Valinyl-3-amino-5-(l-phenyl-3-(trifluoromethyl)pyrazo]-5-yl)oxy-4-oxo-pentanoic acid |
| 73 | N-( 1 ,3-Dimethyl-indole-2-carbonyl)- Valinyl-3 -amino-5 -(3 -(N-phenyl)aminocarbonyl-2-naphthyl)oxy-4-oxo-pentanoic acid |
| 74 | N-(1,3-Dimethyl-indole-2-carbonyl)-Valinyl-3-amino-5-(2-aminocarbonyl-l-phenyl)oxy-4-oxo-pentanoic acid |
| 75 | N-(1,3-Dimethyl-indole-2-carbonyl)-Valinyl-3-amino-5-(dimethylphosphinyl)oxy-4-oxo-pentanoic acid |
| 76 | N-(valinyl)aspartic acid, a-methyl, [3-tert-butyl diester |
| 77 | N-[1,3-dimethyl-indole-2-carbonyl)valinyl]aspartic acid, p-tert-butyl ester |
| 78 | N-[(1,3-dimethyl-indole-2-carbonyl)valinyl]-3-amino-5-bromo-4-oxo-pentanoic acid, tert-butyl ester |
| 79 | N-[(1,3-dimethyl-indole-2-carbonyl)valinyl]-3-amino-5-[3-(imidazol-2-yl)-naphtyl-2-oxy]-4-oxo-pentanoic acid, tert-butyl ester |
| 80 | N-[(1,3-dimethyl-indole-2-carbonyl)valinyl]-3-amino-5[3-(imidazol-2-yl)-naphthyl-2-oxy]-4-oxo-pentanoic acid |
| 81 | N-[(l-methyl-3-isobutyl-indole-2-carbonyl)valinyl]-3-amino-5-bromo-4-oxo-N-pentanoic acid, tert-butyl ester |
| 82 | N-[(l-methyl-3-isobutyl-indole-2-carbonyl)valinyl]-3-amino-4-oxo-5-(2, 3,5,6-tetrafluorophenyloxy)-pentanoic acid, tert-butyl ester |

Fig. 14(f)

| 83 | N-[(l-methyl-3-isobutyl-indole-2-carbonyl)valinyl]-3-amino-4-oxo-5-(2,3-5,6-(tetrafluorophenyloxy)-pentanoic acid |
|---|---|
| 84 | N-[(l-methyl-3-isobutyl-indole-2-carbonyl)valinyl]-3-amino-4-oxo-5-(4-fluorophenyloxy)-pentanoic acid, tert-butyl ester |
| 85 | N-[(l-methyl-3-isobutyl-indole-2-carbonyl)valinyl]-3-amino-4-oxo-5-(4-fluorophenyloxy)-pentanoic acid |
| 86 | N-[(l-methyl-3-isobutyl-indole-2-carbonyl)valinyl]-3-amino-4-oxo-5-(2-fluorophenyloxy)-pentanoic acid, tert-butyl ester |
| 87 | N-[(l-methyl-3-isobutyl-indole-2-carbonyl)valinyl]-3-amino-4-oxo-5-(2-fluorophenyloxy)-pentanoic acid |
| 88 | N-[(l-methyl-3-isobutyl-indole-2-carbonyl)leucinyl]-3-amino-5-bromo-4-oxo-pentanoic acid, tert-butyl ester |
| 89 | N-[l(l-methyl-3-isobutyl-indole-2-carbonyl)leucinyl]-3-amino-5-(2,6-dichlorobenzoyl)oxy-4-oxo pentanoic acid, tert-butyl ester |
| 90 | N-[(l-methyl-3-isobutyl-indole-2-carbonyl)leucinyl]-3-amino-5-(2,6-dichlorobenzoyl)oxy-4-oxo pentanoic acid |
| 91 | N-[(l-methyl-3-isobutyl-indole-2-carbonyl)leucinyl]-3-amino-4-oxo-5-(2,3,5,6-tetrafluorophenyloxy)-pentanoic acid, tert-butyl ester |
| 92 | N-[(l-methyl-3-isobutyl-indole-2-carbonyl)leucinyl]-3-amino-4-oxo-5-(2,3,5,6-tetrafluorophenyloxy)-pentanoic acid |
| 93 | N-[(l-methyl-3-isobutyl-indole-2-carbonyl)leucinyl]-3-amino-5-(diphenylphosphoroxy)-4-oxo-pentanoic acid, tert-butyl ester |
| 94 | N-[(l-methyl-3-isobutyl-indole-2-carbonyl)leucinyl]-3-amino-5-(diphenylphosphoroxy)-4-oxo-pentanoic acid |
| 95 | N-[(l-methyl-3-isobutyl-indole-2-carbonyl)cyclohexylaaninyl]-3-amino-5-bromo-4-oxo-pentanoic acid, tert-butyl ester |
| 96 | N-[(l-methyl-3-isobutyl-indole-2-carbonyl)cyclohexylaianinyl]-3-amino-4-oxo-5-(2,3,5,6-tetrafluorophenyloxy)-pentanoic acid, tert-butyl ester |
| 97 | N-[(l-methyl-3-isobutyl-indole-2-carbonyl)cyclohexylaianinyl]-3-amino-4-oxo-5-(2,3,5,6-tetrafluorophenyloxy)-pentanoic acid |
| 98 | N-[(l-methyl-3-isobutyl-indole-2-carbonyl)cyclohexylalaninyl]-3-amino- 5(2,6-dichlorobenzoyl)oxy-4-oxo-pentanoic acid, tert-butyl ester |

Fig. 14(g)

| 99 | N-[(1-methyl-3-isobutyl-indole-2-carbonyl)cyclohexylalaninyl]-3-amino -5-(2,6-dichlorobenzoyl)oxy-4-oxo-pentanoic acid |
|---|---|
| 100 | N-[(1-methyl-3-isobutyl-indole-2-carbonly)cyclohexylalaninyl]-3-amino-4-oxo-5-1-phenyl-3-(trifluoromethyl)pyrazol-5-yloxy]-pentanoic acid, tert-butyl ester |
| 101 | N-[(1-methyl-3-isobutyl-indole-2-carbonyl)cyclohexylalaninyl]-3-amino-4-oxo-5-[1-phenyl-3-(trifluoromethyl)pyrazol-5-yloxy]-pentanoic acid |
| 102 | N-[(carbobenzyloxycarbonyl)-valinyl]aspartic acid, p-tert-butyl ester |
| 103 | N-[(carbobenzyloxycarbonyl)valinyl]-3-amino-5-bromo-4-oxo-pentanoic acid, tert-butyl ester |
| 104 | N-[(carbobenzyloxycarbonyl)valinyl]-3-amino-4-oxo-5-(2,3,5,6-tetrafluorophenyloxy)-pentanoic acid, tert-butyl ester |
| 105 | N-[(carbobenzyloxycarbonyl)valinyl]-3-amino-4-hydroxy-5-(2,3,5,6-tetrafluorophenyloxy)-pentanoic acid, tert-butyl ester |
| 106 | N-(valinyl)-3-amino-4-hydroxy-5-(2,3,5,6-tetrafluorophenyloxy)-pentanoic acid, tert-butyl ester |
| 107 | N-[(1,3-dimethyl-indole-2-carbonyl)valinyl]-3-amino-4-hydroxy-5-(2,3,5,6-tetrafluorophenyloxy)-pentanoic acid, tert-butyl ester |
| 108 | N-[(1,3-dimethyl-indole-2-carbonyl)valinyl]-3-amino-4-oxo-5-(2,3,5,6-tetrafluorophenyloxy)-pentanoic acid, tert-butyl ester |
| 109 | N-[(1,3-dimethyl-indole-2-carbonyl)valinyl]-3-amino-4-oxo-5-(2,3,5,6-tetrafluorophenyloxy)-pentanoic acid |
| 110 | N-[(1-methyl-indole-2-carbonyl)valinyl]-3-amino-4-hydroxy-5-(2,3,5,6-tetrafluorophenyloxy)-pentanoic acid, tert-butyl ester |
| 111 | N-[(1-methyl-indole-2-carbonyl)valinyl]-3-amino-4-oxo-5-(2,3,5,6-tetrafluorophenyloxy)-pentanoic acid, tert-butyl ester |
| 112 | N-[(1-methyl-indole-2-carbonyl)valinyl]-3-amino-4-oxo-5-(2,3,5,6-tetrafluorophenyloxy)-pentanoic acid |
| 113 | N-[(5-fluoro-1-methyl-indole-2-carnonyl)valinyl]-3-amino-4-hydroxy-5-(2,3,5,6-tetrafluorophenyloxy)-pentanoic acid, tert-butyl ester |
| 114 | N-[(5-fluoro-methyl-indole-2-carbonyl)valinyl]-3-amino-4-oxo-5-(2,3,5,6-tetrafluorophenyloxy)-penanoic acid, tert-butyl ester |
| 115 | N-[(5-fluoro-1-methyl-indole-2-carbonyl)valinyl]-3-amino-4-oxo-5-(2,3,5,6-tetrafluorophenyloxy)-pentanoic acid |

Fig. 14(h)

| 115 | N-[(5-fluoro-1-methyl-indole-2-carbonyl)valinyl]-3-amino-4-oxo-5-(2, 3,5,6-tetrafluorophenyloxy)-pentanoic acid |
|---|---|
| 116 | N-{[1-(tert-butyl)oxycarbonylmethyl-indole-2-carbonyl]valinyl}-3-amino-4-hydroxy-5-(2,3,5,6-tetrafluorophenyloxy)-pentanoic acid, tert-butyl ester |
| 117 | N-{[1-(tert-butyl)oxycarbonylmethyl-indole-2-carbonyl]valinyl}-3-amino-4-oxo-5-(2,3,5,6-tetrafluorophenyloxy)-pentanoic acid, tert-butyl ester |
| 118 | N-{[1-(carboxymethyl)-indole-2-carbonyl]valinyl}-3-amino-4-oxo-5-(2,3,5,6-tetrafluorophenyloxy)-pentanoic acid |

Fig. 14(i)

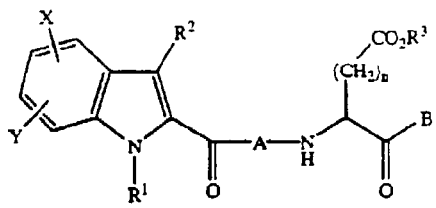

wherein:
n is 1 or 2;

R¹ is alkyl, cycloalkyl, (cycloalkyl)alkyl, phenyl, (substituted)phenyl, phenylalkyl, (substituted) phenylalkyl, heteroaryl, (heteroaryl)alkyl or $(CH_2)_mCO_2R^4$, wherein m=1-4, and R⁴ is as defined below;

R² is a hydrogen atom, chloro, alkyl, cycloalkyl, cycloalkyl)alkyl, phenyl, (substituted)phenyl, phenylalkyl, (substituted)phenylalkyl, heteroaryl, (heteroaryl)alkyl or $(CH_2)_pCO_2R^5$, wherein p=0-4, and R⁵ is as defined below;

R³ is a hydrogen atom, alkyl, cycloalkyl, (cycloalkyl)alkyl, phenylalkyl, or (substituted)phenylalkyl;

R⁴ is a hydrogen atom, alkyl, cycloalkyl, (cycloalkyl)alkyl, phenylalkyl, or (substituted)phenylalkyl;

R⁵ is a hydrogen atom, alkyl, cycloalkyl, (cycloalkyl)alkyl, phenylalkyl, or (substituted)phenylalkyl;

A is a natural or unnatural amino acid;

B is a hydrogen atom, a deuterium atom, alkyl, cycloalkyl, (cycloalkyl)alkyl, phenyl, (substituted) phenyl, phenylalkyl, (substituted)phenylalkyl, heteroaryl, (heteroaryl)alkyl, halomethyl, $CH_2ZR^6$, $CH_2OCO(aryl)$, or $CH_2OCO(heteroaryl)$, or $CH_2OPO(R^7)R^8$, where Z is an oxygen, OC(=O) or a sulfur atom;

R⁶ is phenyl, substituted phenyl, phenylalkyl, (substituted phenyl)alkyl, heteroaryl or (heteroaryl)alkyl;

R⁷ and R⁸ are independently selected from a group consistent of alkyl, cycloalkyl, phenyl, substituted phenyl, phenylalkyl, (substituted phenyl)alkyl and (cycloalkyl)alkyl; and X and Y are independently selected from the group consisting of a hydrogen atom, halo, trihalomethyl, amino, protected amino, an amino salt, mono-substituted amino, di-substituted amino, carboxy, protected carboxy, a carboxylate salt, hydroxy, protected hydroxy, a salt of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl;

or a pharmaceutically acceptable salt or stereoisomer thereof.

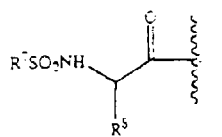

R[1] is a hydrogen atom, alkyl or phenylalkyl;

R[2] is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl;

R[3] is alkyl, cycloalkyl, (cycloalkyl)alkyl, phenylalkyl, or (mono- or di-substituted phenyl)alkyl;

R[4] is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl;

R[5] is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl;

R[6] is alkyl, cycloalkyl, (cycloalkyl)alkyl, phenylalkyl, or (mono- or di-substituted phenyl)alkyl;

1. A compound of the following formula:

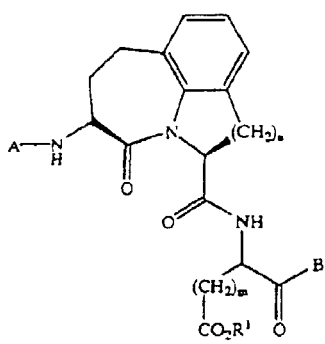

wherein:

n is 1 or 2;
m is 1 or 2;
A is R[2]CO—, R[3]—O—CO—, or R[4]SO$_2$—,
or a group of the formula:

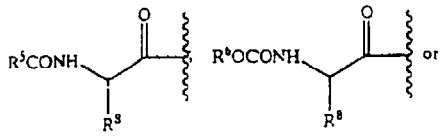

R[7] is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl; and R[8] is an amino acid side chain of a naturally occurring α-amino acid or a non-protein α-amino acid; and B is a hydrogen atom, a deuterium atom, alkyl, cycloalkyl, (cycloalkyl)alkyl, phenyl, phenylalkyl, substituted phenyl, (mono- or di-substituted phenyl)alkyl, five- or six-membered heteroaryl, (five- or six-membered heteroaryl)alkyl, or halomethyl;

a group of the formula:

—CH$_2$XR[9];

a group of the formula:

—CH$_2$—O—CO— (five- or six-membered heteroaryl); or a group of the formula:

—CH$_2$—O—PO—(R[10])R[11];

R[9] is phenyl, substituted phenyl, phenylalkyl, (mono- or di-substituted phenyl)alkyl five- or six-membered heteroaryl, or (five- or six-membered heteroaryl)alkyl; and X is an oxygen or a sulfur atom; and R[10] and R[11] are independently alkyl, cycloalkyl, phenyl, substituted phenyl, phenylalkyl or (mono- or di-substituted phenyl)alkyl;

or a pharmaceutically-acceptable salt thereof.

Fig. 15(a)

1. A compound of the following formula:

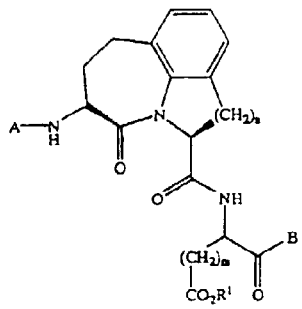

wherein:
n is 1 or 2;
m is 1 or 2;
A is $R^2CO-$, $R^3-O-CO-$, or $R^4SO_2-$,
or a group of the formula:

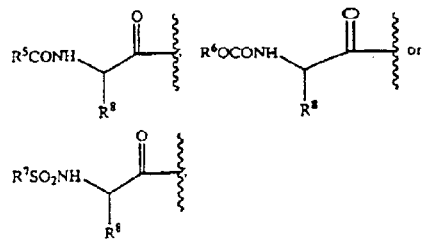

$R^1$ is a hydrogen atom, alkyl or phenylalkyl, $R^2$ is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl;

$R^3$ is alkyl, cycloalkyl (cycloalkyl)alkyl, phenylalkyl, or (mono- or di-substituted phenyl)alkyl;

$R^4$ is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl;

$R^5$ is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl;

$R^6$ is alkyl, cycloalkyl, (cycloalkyl)alkyl, phenylalkyl or (mono- or di-substituted phenyl)alkyl;

$R^7$ is alkyl, cycloalkyl, (cycloalkyl)alkyl, phenyl, phenylalkyl, substituted phenyl, (mono- or di-substituted phenyl)alkyl, five- or six-membered heteroaryl, or (five- or six-membered heteroaryl)alkyl; and $R^8$ is an amino acid side chain of a naturally occurring α-amino acid or a non-protein α-amino acid; and B is a hydrogen atom, a deuterium atom, alkyl, cycloalkyl, (cycloalkyl)alkyl, phenyl, phenylalkyl, substituted phenyl, (mono- or di-substituted phenyl)alkyl, five- or six-membered heteroaryl, (five- or six-membered heteroaryl)alkyl, or halomethyl;

a group of the formula:

a group of the formula:

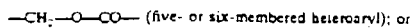

a group of the formula:

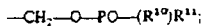

$R^9$ is phenyl, substituted phenyl, phenylalkyl, (mono- or di-substituted phenyl)alkyl, five- or six-membered heteroaryl, or (five- or six-membered heteroaryl)alkyl; and X is an oxygen or a sulfur atom; and $R^{10}$ and $R^{11}$ are independently alkyl, cycloalkyl phenyl, substituted phenyl, phenylalkyl, or (mono- or di-substituted phenyl)alkyl;

or a pharmaceutically-acceptable salt thereof.

Fig. 15(b)

| 1 | (2S-cis)-[5-Benzyloxycarbonylamino- 1,2,4,5, 6,7-hexahydro-4-oxoazepino[3,2,1-hi]indole-2-carbonyl)amino]-4-oxobutanoic acid tert-butyl ester semicarbazone |
|---|---|
| 2 | (2-cis)-[5-Benzyloxycarbonylammo-1,2,4,5,6,7-hexahydro-4-oxoazepino[3,2,1-hi]indole-2-carbonyl)-amino]-4-oxo-butanoic acid semicarbazone |
| 3 | (2S-cis)-5-[Benzyloxycarbonylamino-1,2,4,5,6,7-hexahydro-4-oxoazepino[3,2,1-hi]indole-2-carbonyl)amino]-4-oxo-butanoic acid |
| 4 | (2S-cis)-[5-Amino-1,2,3,4,5,6,7-hexahydro-4-Oxoazepino[3,2,1-hi]indole-2-carbonyl)-amino]-4-oxo-butanoic acid tert-butyl ester semicarbazone |
| 5 | (2S-cis)-[5-(N-Acetyl-(S)-aspartyl-p-tert-butylester)-amino-1, 2,3,4,5,6,7-hexahydro-4-oxoazepino[3,2,1-hi]indole-2-carbonyl)-amino]-4-oxp-butanoic acid tert-butyl ester semicarbazone |
| 6 | (2S-cis)-[5-(N-Aceryl-(S)-aspartyl)amino-1,2,3,4,5,6,7-hexahydro-4-oxoazepino[3,2, 1 -hi]indole-2-carbonyl)-amino]-4-oxo-butanoic acid semicarbazone |
| 7 | (2S-cis)-[5-(N-Acetyl-(S)-aspartyl)amino-1,2,3,4,5,6,7-hexahydroJ4-oxoazepino[3,2,1-hi]indole-2-carbonyl)-amino]-4-oxo-butanoic acid |
| 8 | (2S-cis)-[5-Succinylamino-1,2,3,4,5,6,7-hexahydro-4-oxoazepino[3,2,1-hi]indole-2-carbonyl)-amino]-4-oxo-butanoic acid tert-butyl ester Semicarbazone |
| 9 | (2S-cis)-[5-Succinylamino-1,2,3,4,5,6,7-hexahydro-4-oxoazepino[l3,2,1-hi]indole-2-carbonyl)-amino]-4-oxo-butanoic acid semicarbazone |
| 10 | (2S-cis)-[5-Succinylamino-1,2,3,4,5,6,7-hexahydro-4-oxoazepino[i3,2,1-hi]indole-2-carbonyl)-amino]-4-oxo-butanoic acid |
| 11 | (2S-cis)-[5-(N-Benzyloxycarbonyl-(S)-aspartyl)-tert-butyl ester)amino-1,2,3,4,5,6,7-hexahydro-4-oxoazepino[3,2,1-hi]indole-2-carbonyl)-amino]-4-oxo-butanoic acid tert-butyl ester semicarbazone |
| 12 | (2S-cis)-[5-(N-Benzyloxycarbonyl-(S)-aspartyl)amino- 1,2,3, 4,5, 6,7 -hexahydro-4-oxoazepino[3,2,1-hi]indole-2-carbonyl)-amino]-4-oxo-butanoic acid semicarbazone |
| 13 | (2S-cis)-[5-(N-Benzyloxycarbonyl-(S)-aspartyl)amino-1,2,3,4,5,6,7-hexahydro-4-oxoazepino[3,2,1-hi]indole-2-carbonyl)-amino]-4-oxo-butanoic acid |

Fig. 15(c)

| 14 | (2S-cis)-[5-Dihydrocinnamylamino-1,2,3,4,5,6,7-hexahvdro-4-oxoazepino[3,2,1-hi]indole-2-carbonyl)-amino]-4-oxo-butanoic acid tert-butyl ester scmicarbazone |
|---|---|
| 15 | (2S-cis)-[5-Dihydrocinnamylamino-1,2,3,4,5,6,7-hexahydro-4-oxoazepino[3,2,1-hi]indole-2-carbonyl)-amino]-4-oxo-butanoic acjd semicarbazone |
| 16 | (2S-cis)-[5-Dihydrocinnamylamino-1,2,3,4,5,6,7-hexahydro-4-oxoazepino[3,2,1-hi]indole-2-carbonyl)-amino]-4-oxo-butanoicacidtcrt-butyl cster |
| 17 | (2S-cis)-[5-Acetylamino-1,2,3,4,5,6,7-hexahydro-4-oxoazepino[3,2,1-hi]indole-2-carbonyl)-amino]-4-oxo-butanoic acid tert-butyl ester semicarbazone |
| 18 | (2S-cis)-[5-Acetylamino-1,2,3,4,5,6,7-hexahydro-4-oxoazepino[3,2,1-hi]indole-2-carbonyl)-amino]-4-oxo-butanoic acid semicarbazone |
| 19 | (2S-cis)-[5-Acetylamino-1,2,3,4,5,6,7-hexahydro-4-oxoazepino[3,^,1-hi]indole-2-carbonyl)-amino]-4-oxo-butanoicacid |
| 20 | (2S-cis)-[5-(1-Naphthoyl)amino-1,2,3,4,5,6,7-hexahydro-4-oxoaze3ino[3,2,1-hi]indole-2-carbonyl)-amino]-4-oxo-butanoic acid tert-butyl ester semicarbazone |
| 21 | (2S-cis)-[5-(1-Naphthoyl)amino-152,3,4,5,6,7-hexahydro-4-oxoazeoino[3,2,1-hi]indole-2-carbonyl)-amino]-4-oxo-butanoic acid semicarbazone |
| 22 | (2S-cis)-[5-(1-Naphthoyl)amino-1,2,3,4,5,6,7-hexahydro-4-oxoazcpino[3,2,1-hi]indole-2-carbonyl)-amino]-4-oxo-butanoic acid |
| 23 | (2S-cis)-[5-Benzoylamino-1,2,3,4,5,6,7-hexahydro-4-oxoazepino[;i,2,1-hi]indole-2-carbonyl)-amino]-4-oxo-butanoic acid tert-butyl ester semicarbazone |
| 24 | (2S-cis)-[5-Benzoylamino-1,2,3,4,5,6,7-hexahydro-4-oxoazepino['i,2,1-hi]indole-2-carbonyl)-amino]-4-oxo-butanoic acid semicarbazone |
| 25 | (2S-cis)-[5-Benzoylamino-1, 2,3,4,5, 6,7-hexahydro-4-oxoazepino[;!,2,1-hi]indole-2-carbonyl)-amino] -4-oxo-butanoic acid |
| 26 | (3R,S-cis)-6-Benzyloxycarbonylammo-5-oxo-2,3,4,5,6,7,8-hexahydro-1H-azepino[3,2, 1 -hi]quinoline-3-carbonyl)-amino]-4-oxo-butanoic acid tert-butyl ester semicarbazone |
| 27 | (3R,S-cis)-6-Bcnzyloxycarbonylamino-5-oxo-2,3,4,5,6,7,8-hexahydro-1H-azepino[3,2,1-hi]quinoline-3-carbonyl)-amino]-4-oxo-butanoic acid semicarbazone |

Fig. 15(d)

| 28 | (3R,S-cis)-6-Benzyloxycarbonylamino-5-oxo-2,3,4,5,6,7,8-hexahydro-IH-azepino[3,2,1-hi]quinoline-3-carbonyl)-amino]-4-oxo-butanoic acid |
|---|---|
| 29 | 3{(2S-cis)-[5-Benzyloxycarbonylamino-1,2,3,4,5,6,7,-hexahydro-4-oxoazepino[3,2,1-hi]indole-2-carbonyl)-amino] } -S-fluoro-4-hydroxy-pentanoic acid tert-butyl ester |
| 30 | 3{(2S-cis)-[5-Benzyloxycarbonylamino-1,2,3,4,5,6,7,-hexahydro-4-oxoazepino[3,2,1-hi]indole-2-carbonyl)-amino]}-5-fluoro-4-oxo-pi5ntanoic acid tert-butyl ester |
| 31 | 3{(2S-cis)-[5-Benzyloxycarbonylamino-1,2,3,4,5,6,7,-hexahydro-4-oxoazepino[3,2,1-hi]indole-2-carbonyl)-amino]}-5-fluoro-4-oxo-pi:ntanoic acid |
| 32 | 3{(2S-cis)-[5-Benzyloxycarbonylamino-1,2,3,4,5,6,7,-hexahydro-4-oxoazepino[3,2,1-hi]indole-2-carbonyl)-amino]}-5-bromo-4-oxo-pentanoic acid, tert-butyl ester |
| 34 | 3 {(2S-cis)-[5-Benzyloxycarbonylamino-1,2,3,4,5,6,7,-hexahydro-^ -oxoazepino[3,2,1-hi]indole-2-carbonyl)-amino]}-5-(diphenylphosphinyl)oxy-4-oxo-pentanoic acid, tert-butyl ester |
| 35 | 3 {(2S-cis)-[5-Benzyloxycarbonylamino-1,2,3,4,5,6,7,-hexahydro-^ -oxoazepino[3,2,1-hi]indole-2-carbonyl]-amino]}-5-(diphenylphosphinyl)oxy-4-oxo-pentanoic acid |

Fig. 15(e)

Formula 1:

compounds of the

FORMULA 1

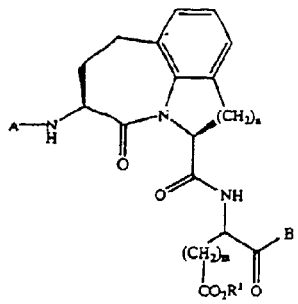

wherein:
n is 1 or 2;
m is 1 or 2;
A is $R^2CO-$, $R^3-O-CO-$, or $R^4SO_2-$;
a group of the formula:

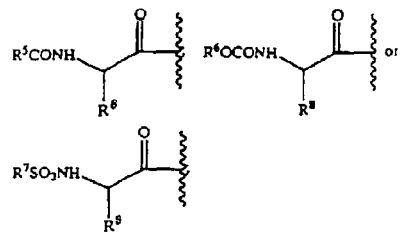

further wherein:
$R^1$ is a hydrogen atom, alkyl or phenylalkyl;
$R^2$ is alkyl, cycloalkyl, (cycloalkyl)alkyl, phenyl, phenylalkyl, substituted phenyl, (substituted phenyl)alkyl, heteroaryl, or (heteroaryl)alkyl;
$R^3$ is alkyl, cycloalkyl, (cycloalkyl)alkyl, phenylalkyl, or (substituted phenyl)alkyl;
$R^4$ is alkyl, cycloalkyl, (cycloalkyl)alkyl, phenyl, phenylalkyl, substituted phenyl, (substituted phenyl)alkyl, heteroaryl, or (heteroaryl)alkyl;
$R^5$ is alkyl, cycloalkyl, (cycloalkyl)alkyl, phenyl, phenylalkyl, substituted phenyl, (substituted phenyl)alkyl, heteroaryl, or (heteroaryl)alkyl;
$R^6$ is alkyl, cycloalkyl, (cycloalkyl)alkyl, phenylalkyl, or (substituted phenyl)alkyl;
$R^7$ is alkyl, cycloalkyl, (cycloalkyl)alkyl, phenyl, phenylalkyl, substituted phenyl, (substituted phenyl)alkyl, heteroaryl, or (heteroaryl)alkyl;
$R^8$ is an amino acid side chain chosen from the group consisting of natural and unnatural amino acids;
B is a hydrogen atom, a deuterium atom, alkyl, cycloalkyl, (cycloalkyl)alkyl, phenyl, phenylalkyl, (substituted)phenyl, (substituted)phenylalkyl, heteroaryl, (heteroaryl)alkyl, or halomethyl;

a group of the formula
$-CH_2XR^9$;

wherein $R^9$ is phenyl, phenylalkyl, substituted phenyl, (substituted phenyl)alkyl, heteroaryl, or (heteroaryl) alkyl; and X is an oxygen or a sulfur atom;
a group of the formula:
$-CH_2-O-CO-(aryl)$;

a group of the formula:
$-CH_2-O-CO-(heteroaryl)$;

a group of the formula:
$-CH_2-O-PO-(R^{10})R^{11}$;

wherein $R^{10}$ and $R^{11}$ are independently selected from a group consisting of alkyl, cycloalkyl, phenyl, substituted phenyl, phenylalkyl, and (substituted phenyl) alkyl;
or a pharmaceutically-acceptable salt thereof.

Fig. 15(f)

1. A compound of the following formula:

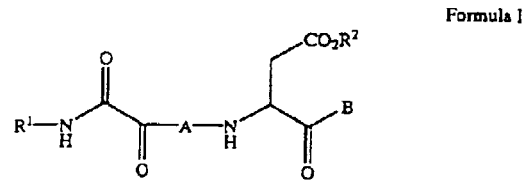

Formula I wherein:

A is a natural or unnatural amino acid of Formula IIa-i:

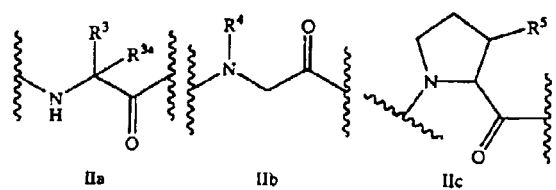

-continued

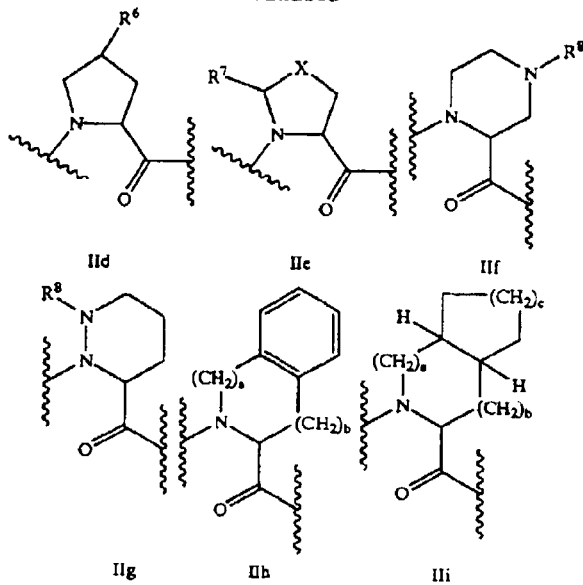

B is a hydrogen atom, a deuterium atom, $C_{1-10}$ straight chain or branched alkyl, cycloalkyl, phenyl, substituted phenyl, naphthyl, substituted naphthyl, 2-benzoxazolyl, substituted 2-oxazolyl, $(CH_2)_n$ cycloalkyl, $(CH_2)_n$phenyl, $(CH_2)_n$(substituted phenyl), $(CH_2)_n$(1 or 2-naphthyl), $(CH_2)$(beteroaryl), halomethyl, $CO_2R^{12}$, $CONR^{13}R^{14}$, $CH_2ZR^{15}$,

Fig. 16(a)

CH₂OCO(aryl), CH₂OCO(heteroaryl), or CH₂OPO(R¹⁶)R¹⁷, where Z is an oxygen or a sulfur atom, or B is a group of the Formula IIIa–c:

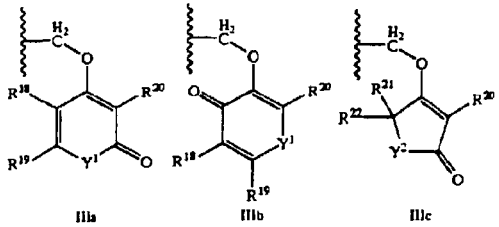

R¹ is alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, (heteroaryl)alkyl, R¹ᵃ(R¹ᵇ)N, R¹ᶜO, 2-phenoxyphenyl or 2- or 3- benzylphenyl; and R² is hydrogen, lower alkyl, cycloalkyl, (cycloalkyl)alkyl, phenylalkyl, or substituted phenylalkyl; and wherein:

R¹ᵃ and R¹ᵇ are independently hydrogen, alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, or (heteroaryl)alkyl, with the proviso that R¹ᵃ and R¹ᵇ cannot both be hydrogen;

R¹ᶜ is alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, or (heteroaryl)alkyl;

R³ is C₁₋₆ lower alkyl, cycloalkyl, phenyl, substituted phenyl, (CH₂)ₙNH₂, (CH₂)ₙNHCOR⁹, (CH₂)ₙN(C=NH)NH₂, (CH₂)ₘCO₂R², (CH₂)ₘOR¹⁰, (CH₂)ₘSR¹¹, (CH₂)ₙcycloalkyl, (CH₂)ₙphenyl, (CH₂)ₙ(substituted phenyl), (CH₂)ₙ(1 or 2-naphthyl) or (CH₂)ₙ(heteroaryl), wherein heteroaryl includes pyridyl, thienyl, furyl, thiazolyl, imidazolyl, pyrazolyl, isoxazolyl, pyrazinyl, pyrimidyl, triazinyl, tetrazolyl, and indolyl;

R³ᵃ is hydrogen or methyl, or R³ and R³ᵃ taken together are —(CH₂)ₐ— where d is an integer from 2 to 6;

R⁴ is phenyl, substituted phenyl, (CH₂)ₘphenyl, (CH₂)ₘ(substituted phenyl), cycloalkyl, or benzofused cycloalkyl;

R⁵ is hydrogen, lower alkyl, cycloalkyl, phenyl, substituted phenyl, (CH₂)ₙcycloalkyl, (CH₂)ₙphenyl, (CH₂)ₙ(substituted phenyl), or (CH₂)ₙ(1 or 2-naphthyl);

R⁶ is hydrogen, fluorine, oxo, lower alkyl, cycloalkyl, phenyl, substituted phenyl, naphthyl, (CH₂)ₙcycloalkyl, (CH₂)ₙphenyl, (CH₂)ₙ(substituted phenyl), (CH₂)ₙ(1 or 2-naphthyl), OR¹⁰, SR¹¹ or NHCOR⁹;

R⁷ is hydrogen, oxo, lower alkyl, cycloalkyl, phenyl, substituted phenyl, naphthyl, (CH₂)ₙcycloalkyl, (CH₂)ₙphenyl, (CH₂)ₙ(substituted phenyl), or (CH₂)ₙ(1 or 2-naphthyl);

R⁸ is lower alkyl, cycloalkyl, (CH₂)ₙcycloalkyl, (CH₂)ₙphenyl, (CH₂)ₙ(substituted phenyl), (CH₂)ₙ(1 or 2-naphthyl), or COR⁹;

R⁹ is hydrogen, lower alkyl, cycloalkyl, phenyl, substituted phenyl, naphthyl, (CH₂)ₙcycloalkyl, (CH₂)ₙphenyl, (CH₂)ₙ(substituted phenyl), (CH₂)ₙ(1 or 2-naphthyl), OR¹², or NR¹³R¹⁴;

R¹⁰ is hydrogen, lower alkyl, cycloalkyl, phenyl, substituted phenyl, naphthyl, (CH₂)ₙcycloalkyl, (CH₂)ₙphenyl, (CH₂)ₙ(substituted phenyl), or (CH₂)ₙ(1 or 2-naphthyl);

R¹¹ is lower alkyl, cycloalkyl, phenyl, substituted phenyl, naphthyl, (CH₂)ₙcycloalkyl, (CH₂)ₙphenyl, (CH₂)ₙ(substituted phenyl), or (CH₂)ₙ(1 or 2-naphthyl);

R¹² is lower alkyl, cycloalkyl, (CH₂)ₙcycloalkyl, (CH₂)ₙphenyl, (CH₂)ₙ(substituted phenyl), or (CH₂)ₙ(1 or 2-naphthyl);

R¹³ is hydrogen, lower alkyl, cycloalkyl, phenyl, substituted phenyl, naphthyl, substituted naphthyl, (CH₂)ₙcycloalkyl, (CH₂)ₙphenyl, (CH₂)ₙ(substituted phenyl), or (CH₂)ₙ(1 or 2-naphthyl);

R¹⁴ is hydrogen or lower alkyl;

or R¹³ and R¹⁴ taken together form a five to seven membered carbocyclic or heterocyclic ring, such as morpholine, or N-substituted piperazine;

R¹⁵ is phenyl, substituted phenyl, naphthyl, substituted naphthyl, heteroaryl, (CH₂)ₙphenyl, (CH₂)ₙ(substituted phenyl), (CH₂)ₙ(1 or 2-naphthyl), or (CH₂)ₙ(heteroaryl);

R¹⁶ and R¹⁷ are independently lower alkyl, cycloalkyl, phenyl, substituted phenyl, naphthyl, phenylalkyl, substituted phenylalkyl, or (cycloalkyl)alkyl;

R¹⁸ and R¹⁹ are independently hydrogen, alkyl, phenyl, substituted phenyl, (CH₂)ₙphenyl, (CH₂)ₙ(substituted phenyl), or R¹⁸ and R¹⁹ taken together are —(CH=CH)₂—;

R²⁰ is hydrogen, alkyl, phenyl, substituted phenyl, (CH₂)ₙphenyl, (CH₂)ₙ(substituted phenyl);

R²¹, R²² and R²³ are independently hydrogen, or alkyl;

X is CH₂, (CH₂)₂, (CH₂)₃, or S;

Y¹ is O or NR²³;

Y² is CH₂, O, or NR²³;

a is 0 or 1 and b is 1 or 2, provided that when a is 1 then b is 1;

c is 1 or 2, provided that when c is 1 then a is 0 and b is 1;

m is 1 or 2; and n is 1, 2, 3 or 4;

or a pharmaceutically acceptable salt thereof.

2. The compound of claim 1 wherein A is

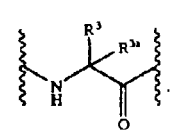

3. The compound of claim 2 wherein

R¹ is lower alkyl, cycloalkyl, phenyl, substituted phenyl, (CH₂)ₙNH₂, (CH₂)ₘOR¹⁰, (CH₂)ₘSR¹¹, (CH₂)ₙcycloalkyl, (CH₂)ₙphenyl, (CH₂)ₙ(substituted phenyl), or (CH₂)ₙ(1 or 2-naphthyl); and R³ᵃ is hydrogen.

4. The compound of claim 1 wherein A is

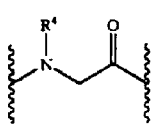

IIb

5. The compound of claim 4 wherein $R^4$ is phenyl, substituted phenyl, $(CH_2)_m$phenyl,$(CH_2)_m$(substituted phenyl), cycloalkyl, or 2-indanyl.

6. The compound of claim 1 wherein A is

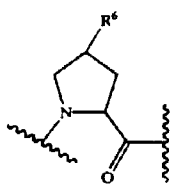

IId

7. The compound of claim 6 wherein $R^6$ is hydrogen, fluorine, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{10}$, or $SR^{11}$ 8. The compound of claim 1 wherein A is

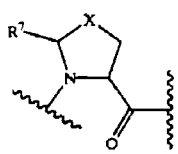

IIe

9. The compound of claim 8 wherein $R^7$ is hydrogen, oxo, cycloalkyl, phenyl, substituted phenyl, or naphthyl; and X=$CH_2$, $(CH_2)_2$, $(CH_2)_3$, or S.

10. The compound of claim 1 wherein A is

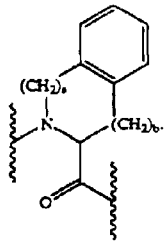

11. The compound of claim 10 wherein a is 0.

12. The compound of claim 1 wherein B is hydrogen, 2-benzoxazolyl, substituted 2-oxazolyl, $CH_2ZR^{15}$, $CH_2OCO$(aryl), or $CH_2OPO(R^{16})R^{17}$, and wherein Z is an oxygen or a sulfur atom.

13. The compound of claim 1 wherein B is

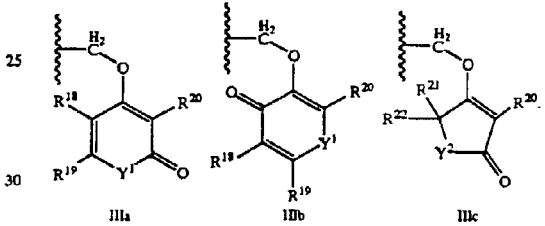

IIIa   IIIb   IIIc

14. The compound of claim 13 wherein $R^{18}$ and $R^{19}$ are independently hydrogen, alkyl, or phenyl, or wherein $R^{18}$ and $R^{19}$ taken together are —(CH=CH)$_2$—.

15. The compound of claim 1 wherein $R^1$ is phenyl, substituted phenyl, phenylalkyl, substituted phenylalkyl, naphthyl, substituted naphthyl, (1 or 2 naphthyl)alkyl, heteroaryl, or (heteroaryl)alkyl.

16. The compound of claim 3 wherein $R^3$ is methyl, isopropyl, isobutyl, cyclohexylmethyl, t-butyl, cyclohexyl or phenyl.

17. The compound of claim 16 wherein B is $CH_2O$(2,3, 5,6-tetrafluorophenyl).

18. The compound of claim 1 wherein $R^1$ is 1-naphthyl and A is valine.

19. The compound of claim 1 wherein $R^1$ is 1-naphthyl and B is $CH_2O$(2,3,5,6-tetrafluorophenyl).

20. A composition comprising a compound of claim 1 in combination with a pharmaceutically acceptable carrier.

Fig. 16(c)

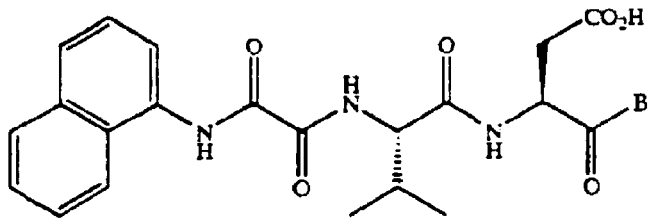

| Ex. | B | Formula | MW | MS(ES) pos. | MS(ES) neg. |
|---|---|---|---|---|---|
| 5 | CH₂O(2,6-diF—Ph) | C₂₈H₂₇F₂N₃O₇ | 555.53 | 578(M + Na) | 554(M − H) |
| 6 | CH₂O(2,4,6-triF—Ph) | C₂₈H₂₆F₃N₃O₇ | 573.52 | 596(M + Na) | 572(M − H) |
| 7 | CH₂O(2,3,5,6-tetraF—Ph) | C₂₈H₂₅F₄N₃O₇ | 591.51 | 614(M + Na) | 590(M − H) |
| 8 | CH₂O(6-Me-2-pyron-4-yl) | C₂₈H₂₉N₃O₉ | 551.55 | 574(M + Na) | 550(M − H) |
| 9 | CH₂O(2-Ph-5,6-benzopyran-4-on-3-yl) | C₃₇H₃₃N₃O₉ | 663.68 | 686(M + Na) | 662(M − H) |
| 10 | CH₂OPO(Me)Ph | C₂₉H₃₂N₃O₈P | 581.56 | 582(M + H) 604(M + Na) | 580(M − H) 694(M + TFA) |
| 11 | CH₂OPOPh₂ | C₃₄H₃₄N₃O₈P | 643.63 | 666(M + Na) | 642(M − H) |
| 12 | CH₂O(2-CF₃-pyrimidin-4-yl) | C₂₇H₂₆F₃N₅O₇ | 589.53 | 612(M + Na) | 588(M − H) |
| 13 | CH₂O(5-CO₂Me-isoxazol-3-yl) | C₂₇H₂₈N₄O₁₀ | 568.54 | 591(M + Na) | 567(M − H) |
| 14 | CH₂OPO(Me)(1-naphthyl) | C₃₃H₃₄N₃O₈P | 631.62 | 654(M + Na) | 630(M − H) 744(M + TFA) |

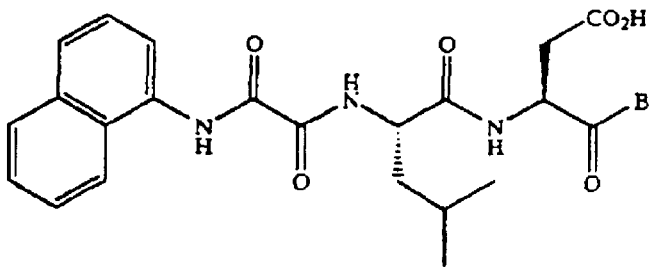

| Ex. | B | Formula | MW | MS(ES) pos. | MS(ES) neg. |
|---|---|---|---|---|---|
| 16 | CH₂OCO(2,6-diCl—Ph) | C₃₀H₃₀Cl₂N₃O₈ | 630.48 | 652/654(M + Na) | 628/630(M − H) |
| 17 | CH₂O(2,4,6-triF—Ph) | C₂₉H₂₈F₃N₃O₇ | 587.55 | 610(M + Na) | 586(M − H) |
| 18 | CH₂O(2,3,5,6-tetraF—Ph) | C₂₉H₂₇F₄N₃O₇ | 605.54 | 628(M + Na) | 604(M − H) |
| 19 | CH₂OPO(Me)Ph | C₃₀H₃₄N₃O₈P | 595.59 | 596(M + H) 618(M + Na) | 594(M − H) 708(M + TFA) |

Fig. 16(d)

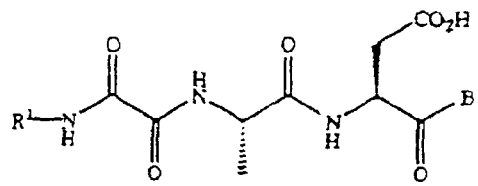

| Ex. | R¹ | B | Formula | MW | MS(ES) pos. | neg. |
|---|---|---|---|---|---|---|
| 20 | (2-Ph)Ph | CH₂O(2-F—Ph) | C₂₈H₂₆FN₃O₇ | 535.53 | 558(M + Na) | |
| 21 | (2-Ph)Ph | CH₂OCO(2,6-di-Cl—Ph) | C₂₉H₂₅Cl₂N₃O₈ | 614.44 | 652/654(M + K) | 534(M − H) 612/614(M − H) |
| 22 | (2-Ph)Ph | CH₂OPOPh₂ | C₃₄H₃₂N₃O₈P | 641.61 | 664(M + Na) | 640(M − H) |
| 23 | (2-t-Bu)Ph | CH₂O(2-F—Ph) | C₂₆H₃₀FN₃O₇ | 515.54 | 680(M + K) 516(M + H) 538(M + Na) | 514(M − H) |
| 24 | (2-t-Bu)Ph | CH₂OPOPh₂ | C₃₂H₃₆N₃O₈P | 621.63 | 554(M + K) 644(M + Na) | 620(M − H) |
| 25 | 1-naphthyl-CH₂ | CH₂O(2,3,5,6-tetra-F—Ph) | C₂₇H₂₃F₄N₃O₇ | 577.48 | 666(M + K) 600(M + Na) | 576(M − H) |
| 26 | 1-naphthyl-CH₂ | CH₂OCO(2,6-di-Cl—Ph) | C₂₈H₂₅Cl₂N₃O₈ | 602.42 | 616(M + K) 624/626(M + Na) 640/642(M + K) | 600/602(M − H) |
| 27 | 1-naphthyl-CH₂ | CH₂OPOPh₂ | C₃₃H₃₂N₃O₈P | 629.60 | 652(M + Na) 668(M + K) | 714/716(M + TFA) 628(M − H) |

Fig. 16(e)

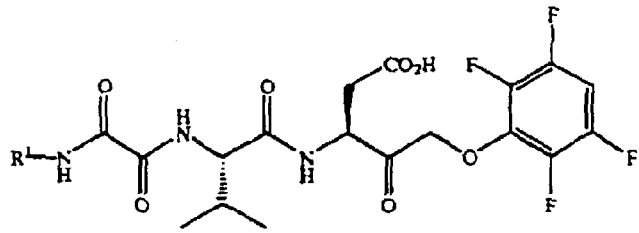

| Ex. | R¹ | Formula | MW | MS(ES) pos. | MS(ES) neg. |
|---|---|---|---|---|---|
| 29 | PhCH$_2$ | C$_{25}$H$_{25}$F$_4$N$_3$O$_7$ | 555.48 | 556(M + H) 578(M + Na) | 554(M - H) |
| 30 | Ph(CH$_2$)$_2$ | C$_{26}$H$_{27}$F$_4$N$_3$O$_7$ | 569.51 | 592(M + Na) | 568(M - H) |
| 31 | Ph$_2$CH | C$_{31}$H$_{29}$F$_4$N$_3$O$_7$ | 631.58 | 654(M + Na) | 630(M - H) |
| 32 | Ph | C$_{24}$H$_{23}$F$_4$N$_3$O$_7$ | 541.46 | 564(M + Na) | 540(M - H) |
| 33 | (2-Ph)Ph | C$_{30}$H$_{27}$F$_4$N$_3$O$_7$ | 617.55 | 640(M + Na) | 616(M - H) 730(M + TFA) |
| 34 | (2-PhCH$_2$)Ph | C$_{31}$H$_{29}$F$_4$N$_3$O$_7$ | 631.58 | 654(M + Na) | 630(M - H) |
| 35 | (3-PhO)Ph | C$_{30}$H$_{27}$F$_4$N$_3$O$_8$ | 633.55 | 634(M + H) 656(M + Na) | 632(M - H) |
| 36 | 4-Cl-1-naphthyl | C$_{28}$H$_{24}$ClF$_4$N$_3$O$_7$ | 625.96 | 648/650(M + Na) | 624/626(M - H) |
| 37 | 2-anthryl | C$_{32}$H$_{27}$F$_4$N$_3$O$_7$ | 641.57 | 642(M + H) | 640(M - H) |
| 38 | 2-benzimidazolyl | C$_{25}$H$_{23}$F$_4$N$_5$O$_7$ | 581.48 | 582(M + H) 604(M + Na) | 580(M - H) |
| 39 | 1-adamantanyl | C$_{28}$H$_{33}$F$_4$N$_3$O$_7$ | 599.58 | 600(M + H) | 598(M - H) |
| 40 | (2-F)Ph | C$_{24}$H$_{22}$F$_5$N$_3$O$_7$ | 559.45 | 582(M + Na) | 558(M - H) 672(M + TFA) |
| 41 | (4-F)Ph | C$_{24}$H$_{22}$F$_5$N$_3$O$_7$ | 559.45 | 582(M + Na) | 558(M - H) 672(M + TFA) |
| 42 | (2-CF$_3$)Ph | C$_{25}$H$_{22}$F$_7$N$_3$O$_7$ | 609.45 | 632(M + Na) | 608(M - H) 722(M + TFA) |
| 43 | (2-t-Bu)Ph | C$_{28}$H$_{31}$F$_4$N$_3$O$_7$ | 597.56 | 620(M + Na) | 596(M - H) 710(M + TFA) |
| 44 | (4-n-heptyl)Ph | C$_{31}$H$_{37}$F$_4$N$_3$O$_7$ | 639.64 | 662(M + Na) | 638(M - H) |
| 45 | (2-CH$_3$O)Ph | C$_{25}$H$_{25}$F$_4$N$_3$O$_8$ | 571.48 | 594(M + Na) | 570(M - H) |
| 46 | (2-PhO)Ph | C$_{30}$H$_{27}$F$_4$N$_3$O$_8$ | 633.55 | 656(M + Na) | 632(M - H) 746(M + TFA) |
| 47 | 2-naphthyl | C$_{28}$H$_{25}$F$_4$N$_3$O$_7$ | 591.51 | 614(M + Na) | 590(M - H) |
| 48 | 5,6,7,8-tetrahydro-1-naphthyl | C$_{28}$H$_{29}$F$_4$N$_3$O$_7$ | 595.55 | 618(M + Na) | 594(M - H) |
| 49 | 1-anthryl | C$_{32}$H$_{27}$F$_4$N$_3$O$_7$ | 641.57 | 664(M + Na) | 640(M - H) |
| 50 | 2-pyridinyl | C$_{23}$H$_{22}$F$_4$N$_4$O$_7$ | 542.44 | 543(M + H) | 541(M - H) |
| 51 | 4-pyridinyl | C$_{23}$H$_{22}$F$_4$N$_4$O$_7$ | 542.44 | 543(M + H) | 541(M - H) |
| 52 | 2,3,5,6-tetrafluoro-4-pyridinyl | C$_{23}$H$_{18}$F$_8$N$_4$O$_7$ | 614.40 | 615(M + H) | 613(M - H) |
| 53 | 2-pyrazinyl | C$_{22}$H$_{21}$F$_4$N$_5$O$_7$ | 543.43 | 544(M + H) | 542(M - H) |
| 54 | 1,2,3,4-tetrahydro-1-naphthyl | C$_{28}$H$_{29}$F$_4$N$_3$O$_7$ | 595.55 | 596(M + H) 618(M + Na) 634(M + K) | 594(M - H) 708(M + TFA) |
| 55 | (2-Cl)Ph | C$_{24}$H$_{22}$ClF$_4$N$_3$O$_7$ | 575.90 | 598/600(M + Na) | 574/576(M - H) |
| 56 | (2-Br)Ph | C$_{24}$H$_{22}$BrF$_4$N$_3$O$_7$ | 620.35 | 644/642(M + Na) | 620/618(M - H) 734/732(M + TFA) |
| 57 | (2-I)Ph | C$_{24}$H$_{22}$F$_4$IN$_3$O$_7$ | 667.35 | 690(M + Na) 706(M + K) | 666(M - H) 780(M + TFA) |
| 58 | (2,6-di-F)Ph | C$_{24}$H$_{21}$F$_6$N$_3$O$_7$ | 577.44 | 600(M + Na) | 576(M - H) 690(M + TFA) |
| 59 | (2,5-di-t-Bu)Ph | C$_{32}$H$_{39}$F$_4$N$_3$O$_7$ | 653.67 | 654(M + H) 676(M + Na) 692(M + K) | 652(M - H) 688(M + Cl) 766(M + TFA) |

Fig. 16(f)

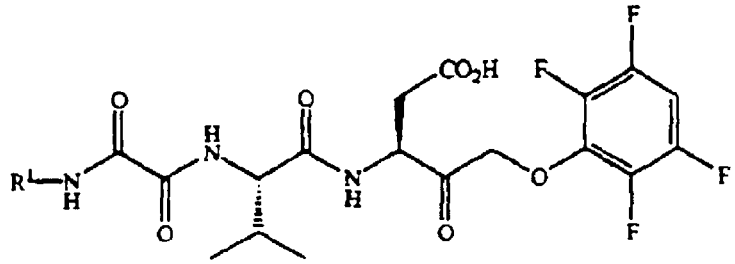

| Ex. | R¹ | Formula | MW | MS(ES) pos. | MS(ES) neg. |
|---|---|---|---|---|---|
| 60 | 5-indanyl | $C_{27}H_{27}F_4N_3O_7$ | 581.52 | 604(M + Na)<br>620(M + K) | 580(M − H)<br>694(M + TFA) |
| 61 | (3,4,5-tri-MeO)PhCH₂ | $C_{28}H_{31}F_4N_3O_{10}$ | 645.56 | 646(M + H)<br>668(M + Na)<br>684(M + K) | 644(M − H) |
| 62 | methyl | $C_{19}H_{21}F_4N_3O_7$ | 479.38 | 502(M + Na) | 478(M − H)<br>592(M + TFA) |
| 63 | n-heptyl | $C_{25}H_{33}F_4N_3O_7$ | 563.55 | 586(M + Na)<br>602(M + K) | 562(M − H)<br>676(M + TFA) |
| 64 | t-octyl | $C_{26}H_{35}F_4N_3O_7$ | 577.57 | 600(M + Na) | 576(M − H) |
| 65 | cyclo-hexyl | $C_{24}H_{29}F_4N_3O_7$ | 547.50 | 548(M + H)<br>570(M + Na)<br>586(M + K) | 546(M − H)<br>660(M + TFA) |
| 66 | 5-Ph-3-pyrazolyl | $C_{27}H_{25}F_4N_5O_7$ | 607.52 | 630(M + Na)<br>646(M + K) | 606(M − H) |
| 67 | (2-F-4-I)Ph | $C_{24}H_{21}F_5IN_3O_7$ | 685.34 | 686(M + H)<br>708(M + Na)<br>724(M + K) | 684(M − H)<br>720(M + Cl) |
| 68 | (2,3,4,5-tetra-F)Ph | $C_{24}H_{19}F_8N_3O_7$ | 613.41 | 614(M + H)<br>636(M + Na)<br>652(M + K) | 612(M − H)<br>726(M + TFA) |
| 69 | (2,3,4,6-tetra-F)Ph | $C_{24}H_{19}F_8N_3O_7$ | 613.41 | 614(M + H)<br>636(M + Na)<br>652(M + K) | 612(M − H)<br>726(M + TFA) |
| 70 | (2,3,5,6-tetra-Cl)Ph | $C_{24}H_{19}Cl_4F_4N_3O_7$ | 679.23 | 700/702/704(M + Na)<br>716/718/720(M + K) | 676/678/680(M − H)<br>790/792/794(M + TFA) |
| 71 | (2,3,4,5,6-penta-F)Ph | $C_{24}H_{18}F_9N_3O_7$ | 631.40 | 654(M + Na)<br>670(M + K) | 630(M − H)<br>666(M + Cl) |
| 72 | Ph₂N | $C_{30}H_{28}F_4N_4O_7$ | 632.57 | 633(M + H)<br>655(M + Na) | 631(M − H)<br>745(M + TFA) |
| 73 | PHCH₂(Ph)N | $C_{31}H_{30}F_4N_4O_7$ | 646.59 | 647(M + H)<br>669(M + Na)<br>685(M + K) | 645(M − H)<br>681(M + Cl) |
| 74 | PhCH₂O | $C_{25}H_{25}F_4N_3O_7$ | 571.48 | 594(M + Na) | 570(M − H)<br>684(M + TFA) |

Fig. 16(g)

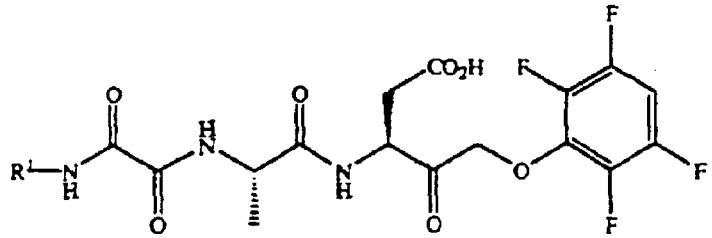

| Ex. | R¹ | Formula | MW | MS(ES) pos. | MS(ES) neg. |
|---|---|---|---|---|---|
| 76 | (2-CF₃)Ph | C₂₃H₁₈F₇N₃O₇ | 581.40 | 604(M + Na) | 580(M − H) |
| 77 | (2-Ph)Ph | C₂₈H₂₃F₄N₃O₇ | 589.50 | 612(M + Na) | 588(M − H) |
| 78 | (2-PhCH₂)Ph | C₂₉H₂₅F₄N₃O₇ | 603.53 | 604(M + H) | 602(M − H) |
| 79 | (2-PhO)Ph | C₂₈H₂₃F₄N₃O₈ | 605.50 | 628(M + Na) | 604(M − H) |
| 80 | (3-PhO)Ph | C₂₈H₂₃F₄N₃O₈ | 605.50 | 628(M + Na) | 604(M − H) |
| 81 | 5,6,7,8-tetrahydro-2-naphthyl | C₂₆H₂₅F₄N₃O₇ | 567.49 | 590(M + Na) | 566(M − H) |
| 82 | 1-naphthyl | C₂₆H₂₁F₄N₃O₇ | 563.46 | 586(M + Na) 608(M + K) | 562(M − H) |
| 83 | Ph | C₂₂H₁₉F₄N₃O₇ | 513.40 | 552(M + K) | 512(M − H) |
| 84 | (2,6-di-F)Ph | C₂₂H₁₇F₆N₃O₇ | 549.38 | 572(M + Na) | 548(M − H) 662(M + TFA) |
| 85 | (4-Ph)Ph | C₂₈H₂₃F₄N₃O₇ | 589.50 | — | 588(M − H) |
| 86 | (4-MeO)Ph | C₂₃H₂₁F₄N₃O₈ | 543.43 | 582(M + K) | 542(M − H) |
| 87 | Ph₂CH | C₂₉H₂₅F₄N₃O₇ | 603.53 | 642(M + K) | 602(M − H) |

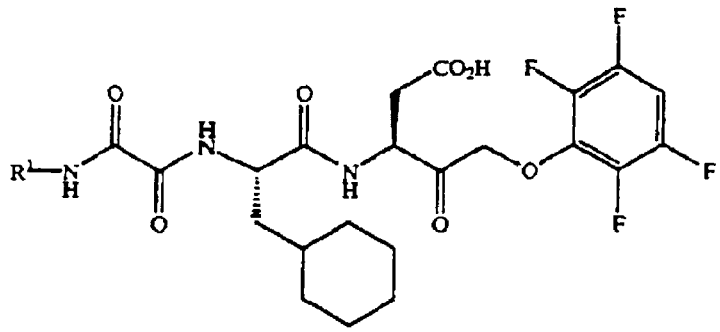

| Ex. | R¹ | Formula | MW | MS(ES) pos. | MS(ES) neg. |
|---|---|---|---|---|---|
| 89 | (2-Ph)Ph | C₃₄H₃₃F₄N₃O₇ | 671.64 | 672(M + H) 694(M + Na) | 670(M − H) 784(M + TFA) |
| 90 | (2-PhCH₂)Ph | C₃₅H₃₅F₄N₃O₇ | 685.67 | 708(M + Na) | 684(M − H) 798(M + TFA) |
| 91 | 1-naphthyl | C₃₂H₃₁F₄N₃O₇ | 645.61 | 668(M + Na) | 644(M − H) 758(M + TFA) |

Fig. 16(h)

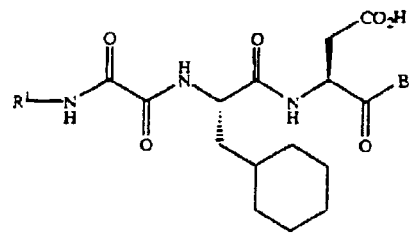

| Ex. | R¹ | B | Formula | MW | MS(ES) pos. | neg. |
|---|---|---|---|---|---|---|
| 93 | 5,6,7,8-tetrahydro-1-naphthyl | CH₂O(2,3,5,6-tetra-F-Ph) | C₃₂H₃₅F₄N₃O₇ | 649.64 | 672(M + Na) | 648(M − H) |
| 94 | 5,6,7,8-tetrahydro-1-naphthyl | CH₂OPO(Me)Ph | C₃₃H₄₂N₃O₈P | 639.68 | 662(M + Na) | 638(M − H) 752(M + TFA) |
| 95 | 5,6,7,8-tetrahydro-1-naphthyl | CH₂OPOPh₂ | C₃₈H₄₄N₃O₈P | 701.75 | 724(M + Na) 740(M + K) | 700(M + H) |
| 96 | (2-PhCH₂)Ph | CH₂OPO(Me)Ph | C₃₆H₄₂N₃O₈P | 675.72 | 698(M + Na) 714(M + K) | 674(M − H) 788(M + TFA) |
| 97 | (2-PhCH₂)Ph | CH₂OPOPh₂ | C₄₁H₄₄N₃O₈P | 737.79 | 760(M + Na) 776(M + K) | 736(M − H) 850(M + TFA) |
| 98 | (2-Ph)Ph | CH₂OPO(Me)Ph | C₄₁H₄₂N₃O₈P | 661.68 | 684(M + Na) 700(M + K) | 660(M − H) 774(M + TFA) |
| 99 | (2-Ph)Ph | CH₂OPOPh₂ | C₃₃H₄₀N₃O₈P | 723.75 | 746(M + Na) 762(M + K) | 722(M − H) 836(M + TFA) |

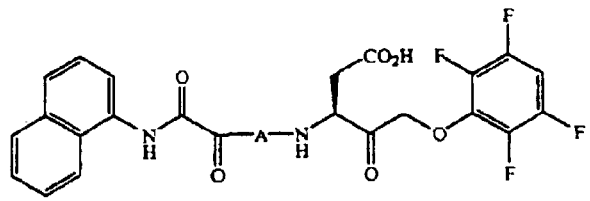

| Ex. | A | Formula | MW | MS(ES) pos. | neg. |
|---|---|---|---|---|---|
| 103 | norleucine | C₂₉H₃₇F₄N₃O₇ | 605.54 | 628(M + Na) 644(M + K) | 604(M − H) 640(M + Cl) 718(M + TFA) |
| 104 | (t-butyl)glycine | C₂₉H₂₇F₄N₃O₇ | 605.54 | 606(M + H) 628(M + Na) 644(M + K) | 604(M − H) 640(M + Cl) 718(M + TFA) |
| 105 | (t-butyl)alanine | C₃₀H₂₉F₄N₃O₇ | 619.57 | 620(M + H) 642(M + Na) 658(M + K) | 618(M − H) 732(M + TFA) |
| 106 | phenylglycine | C₃₁H₂₃F₄N₃O₇ | 625.53 | 626(M + H) 648(M + Na) 664(M + K) | 624(M − H) 660(M + Cl) 738(M + TFA) |
| 107 | phenylalanine | C₃₂H₂₅F₄N₃O₇ | 639.56 | 640(M + H) 662(M + Na) 678(M + K) | 638(M − H) 674(M + Cl) 712(M + TFA) |
| 108 | homophenylalanine | C₃₃H₂₇F₄N₃O₇ | 653.59 | 654(M + H) 676(M + Na) 692(M + K) | 652(M − H) 688(M + Cl) 766(M + TFA) |
| 109 | 1-aminocyclopentane carboxylic acid | C₂₉H₂₃F₄N₃O₇ | 603.53 | 626(M + Na) 642(M + K) | 602(M − H) |

Fig. 16 (i)

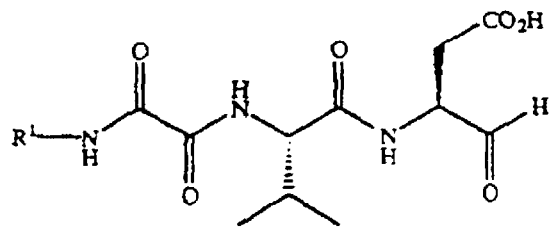

| Ex. | R¹ | Formula | MW | MS(ES) pos. | neg. |
|---|---|---|---|---|---|
| 114 | Ph | $C_{17}H_{21}N_3O_6$ | 363.37 | 386(M + Na)  402(M + K) | 362(M − H) |
| 115 | PhCH$_2$ | $C_{18}H_{23}N_3O_6$ | 377.40 | 400(M + Na) | 376(M − H) |
| 116 | Ph(CH$_2$)$_2$ | $C_{19}H_{25}N_3O_6$ | 391.42 | 414(M + Na)  430(M + K) | 390(M − H)  504(M + TFA) |
| 117 | (2-CF$_3$)Ph | $C_{18}H_{20}F_3N_3O_6$ | 431.37 | 454(M + Na) | 430(M − H) |
| 118 | (2-t-Bu)Ph | $C_{21}H_{29}N_3O_6$ | 419.48 | 442(M + Na)  458(M + K) | 418(M − H)  532(M + TFA) |
| 119 | (2-Ph)Ph | $C_{23}H_{25}N_3O_6$ | 439.47 | 462(M + Na)  478(M + K) | 438(M − H)  552(M + TFA) |
| 120 | (2-PhCH$_2$)Ph | $C_{24}H_{27}N_3O_6$ | 453.49 | 476(M + Na)  492(M + K) | 452(M − H)  566(M + TFA) |
| 121 | (2-PhO)Ph | $C_{23}H_{25}N_3O_7$ | 455.47 | 478(M + Na)  494(M + K) | 454(M − H)  568(M + TFA) |
| 122 | 2-naphthyl | $C_{21}H_{23}N_3O_6$ | 413.43 | 436(M + Na)  452(M + K) | 412(M − H)  526(M + TFA) |
| 123 | 1-naphthyl | $C_{21}H_{23}N_3O_6$ | 413.43 | 436(M + Na)  452(M + K) | 412(M − H)  526(M + TFA) |
| 124 | 4-Cl-1-naphthyl | $C_{21}H_{22}ClN_3O_6$ | 447.87 | 470/472 (M + Na)  486/488 (M + K) | 446/448(M − H) |
| 125 | 5,6,7,8-tetrahydro-1-naphthyl | $C_{21}H_{27}N_3O_6$ | 417.46 | 440(M + Na)  456(M + K) | 416(M − H)  530(M + TFA) |
| 126 | 1,2,3,4-tetrahydro-1-naphthyl | $C_{21}H_{27}N_3O_6$ | 417.46 | 440(M + Na)  456(M + K) | 416(M − H)  530(M + TFA) |
| 127 | (1-naphthyl)CH$_2$ | $C_{22}H_{25}N_3O_6$ | 427.46 | 450(M + Na)  466(M + K) | 426(M − H)  540(M + TFA) |

Fig. 16(j)

| | |
|---|---|
| 1 | (3S)-3-[N-(N'-(l-Naphthyl)Oxamyl)Leucinyl] Amino-4-Oxobutanoic Acid |
| 2 | (3RS)-3-[N-(N'-(l-Naphthyl)Oxamyl)Leucinyl] Amino-5-Fluoro-4-Oxopentanoic Acid |
| 3 | (3RS)-3-[N-(N'-(l-Naphthyl)Oxamyl)Valinyl] Amino-5-Fluoro-4-Oxopentanoic Acid |
| 4 | (3S)-3-[N-(N'-(l-Naphthyl)Oxamyl)Valinyl]Amino-5-(2',6l-Dichlorobenzoyloxy)-4-Oxopentanoic Acid |
| 15 | (3S)-3-[N-(N'-(l-Naphthyl)Oxamyl)Leucinyl] Amino-5(Diphenylphosphinyloxy)-4-Oxopentanoic Acid |
| 28 | (3S)-3[N-(Nl-(l-Naphthylmethyl)Oxamyl)Valinyl)Amino-5-(2',3',5l,6'-Tetrafluorophenoxy)-4-Oxopentanoic Acid |
| 75 | (3S)-3-[N-(N'-(2-tert-Butylphenyl)Oxamyl)Alaninyl]Amino-5-(2',3l,5',6l-Tetraflluorophenoxy)-4-Oxopentanoic Acid |
| 88 | (3S)-3-[N-(N'-(2-Phenoxyphenyl)Oxamyl)Cyclohexylalaninyl]Amino-5-(2',3',5',6'-Tetraflluorophenoxy)-4-Oxopentanoic Acid |
| 92 | (3S)-3-[N-(N'-(5,6,7,8-Tetrahydro-l-Naphthyl)Oxamyl)-Cyclohcxylalaninyl] Ammo-5-(2',6'-Dichlorobenzoyloxy)-4-Oxopentanoic Acid |
| 100 | (3S)-3-[N-(N'-Naphthyl)Oxamyl)Homoprolmyl] Amino-5-(2',3l,5',6'-Tetrafluorophenoxy)-4-Oxopentanoic Acid |
| 101 | (3S)-3-[N-(N'-(l-Naphthyl)Oxamyl)Indoline-2-Carbonyl]Amino-5-(2l,3',5l,6'-Tetrafluorophenoxy)-4-Oxopentanoic Acid |
| 102 | (3S)-3-[N-(N'-(l-Naphthyl)Oxamyl)Cyclohexylglycinyl]Amino-5-(2',3t,5',6l-Tetrafluorophenoxy)-4-Oxopentanoic Acid |
| 110 | (3S)-3-[N-(N'-(l-Naphthyl)Oxamyl)Mcthioninyl](Sulfoxidc)]Amino-5-(2',3',5',6'-Tetrafluorophenoxy)-4-Oxopentanoic Acid |
| 111 | (3S)-3-[N-(N'-(l-Naphthyl)Oxamyl)Homoprolinyl]Amino-4-Oxobutanoic Acid |
| 112 | (3S-3-[N-(N'-(2-(lH-Tetrazol-5-yl)Phenyl)Oxamyl)Valinyl]Amino-4-Oxobutanoic Acid |
| 113 | (3S)-3-[N-(N'-(l-Adamantanyl)Oxamyl)Valinyl] Amino-4-Oxybutanoic Acid |

Fig. 16(k)

the compounds of the Formula I:

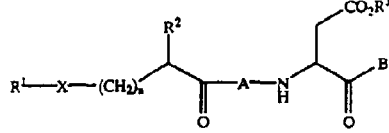

Formula I wherein:

n is 0, 1 or 2;
X is $CH_2$, C=O, O, S or NH;
A is a natural or unnatural amino acid of Formula IIa-i:

IIa

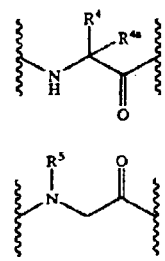

IIb

IIc

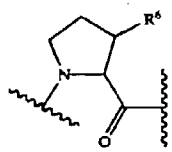

IId

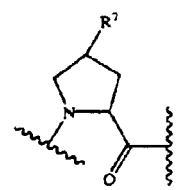

IIe

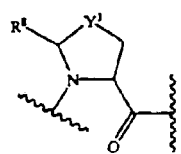

-continued

IIf

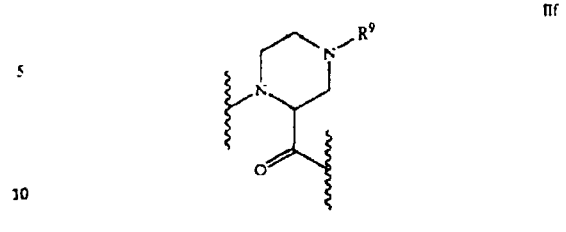

IIg

IIh

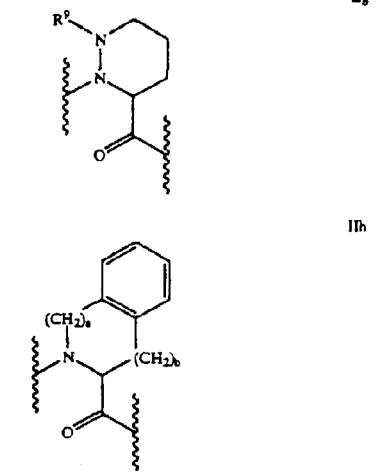

IIi

B is a hydrogen atom, a deuterium atom, $C_{1-10}$ straight chain or branched alkyl, cycloalkyl, phenyl, substituted phenyl, naphthyl, substituted naphthyl, 2-benzoxazolyl, substituted 2-oxazolyl, $(CH_2)_m$ ycloalkyl, $(CH_2)_m$phenyl, $(CH_2)_m$(substituted phenyl), $(CH_2)_m$(1 or 2-naphthyl), $(CH_2)_m$heteroaryl, halomethyl, $CO_2R^{13}$, $CONR^{14}R^{15}$, $CH_2ZR^{16}$, $CH_2OCO(aryl)$, $CH_2OCO(heteroaryl)$, or $CH_2OPO(R^{17})R^{18}$, where Z is an oxygen or a sulfur atom, or B is a group of the Formula IIIa-c:

IIIa

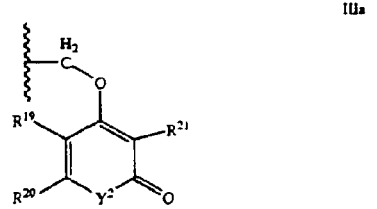

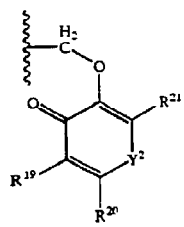

IIIb

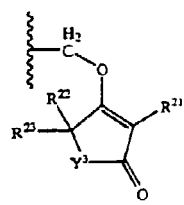

IIIc $R^1$ is phenyl, substituted phenyl, naphthyl, substituted naphthyl, heteroaryl, or substituted heteroaryl;

$R^2$ is hydrogen, alkyl, cycloalkyl, phenyl, substituted phenyl, $(CH_2)_mNH_2$, $(CH_2)_mNHCOR^{10}$, $(CH_2)_mN(C=NH)NH_2$, $(CH_2)_pCO_2R^3$, $(CH_2)_pOR^{11}$, $(CH_2)_pSR^{12}$, $(CH_2)_mcycloalkyl$, $(CH_2)_mphenyl$, $(CH_2)_m$(substituted phenyl), $(CH_2)_m$(1 or 2-naphthyl), or $(CH_2)_m$heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl;

$R^3$ is hydrogen, alkyl, cycloalkyl, (cycloalkyl)alkyl, phenylalkyl, or substituted phenylalkyl; and wherein $R^4$ is alkyl, cycloalkyl, phenyl, substituted phenyl, $(CH_2)_mNH_2$, $(CH_2)_mNHCOR^{10}$, $(CH_2)_mN(C=NH)NH_2$, $(CH_2)_pCO_2R^3$, $(CH_2)_pOR^{11}$, $(CH_2)_pSR^{12}$, $(CH_2)_mcycloalkyl$, $(CH_2)_mphenyl$, $(CH_2)_m$(substituted phenyl), $(CH_2)_m$(1 or 2-naphthyl), or $(CH_2)_m$heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl;

$R^{4a}$ is hydrogen or methyl, or $R^4$ and $R^{4a}$ taken together are $-(CH_2)_d-$ where d is an integer from 2 to 6;

$R^5$ is phenyl, substituted phenyl, $(CH_2)_p$phenyl, $(CH_2)_p$(substituted phenyl), cycloalkyl, or benzofused cycloalkyl;

$R^6$ is hydrogen, alkyl, cycloalkyl, phenyl, substituted phenyl, $(CH_2)_m$cycloalkyl, $(CH_2)_m$phenyl, $(CH_2)_m$(substituted phenyl), or $(CH_2)_m$(1 or 2-naphthyl);

$R^7$ is hydrogen, fluorine, oxo (i.e., =O), alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{11}$, $SR^{12}$, or $NHCOR^{10}$;

$R^8$ is hydrogen, oxo, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

$R^9$ is alkyl, cycloalkyl, $(CH_2)_m$cycloalkyl, $(CH_2)_m$phenyl, $(CH_2)_m$(substituted phenyl), $(CH_2)_m$(1 or 2-naphthyl), or $COR^{10}$;

$R^{10}$ is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{13}$, or $NR^{14}R^{15}$;

$R^{11}$ is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

$R^{12}$ is alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

$R^{13}$ is alkyl, cycloalkyl, $(CH_2)_m$cycloalkyl, $(CH_2)_m$phenyl, $(CH_2)_m$(substituted phenyl), or $(CH_2)_m$(1 or 2-naphthyl);

$R^{14}$ is hydrogen, alkyl, cycloalkyl, phenyl, substituted phenyl, naphthyl, substituted naphthyl, $(CH_2)_m$cycloalkyl, $(CH_2)_m$phenyl, $(CH_2)_m$(substituted phenyl), or $(CH_2)_m$(1 or 2-naphthyl);

$R^{15}$ is hydrogen or alkyl; or $R^{14}$ and $R^{15}$ taken together form a five, six or seven membered carbocyclic or heterocyclic ring, such as morpholine or N-substituted piperazine;

$R^{16}$ is phenyl, substituted phenyl, naphthyl, substituted naphthyl, heteroaryl, $(CH_2)_m$phenyl, $(CH_2)_m$(substituted phenyl), $(CH_2)_m$(1 or 2-naphthyl), or $(CH_2)_m$heteroaryl;

$R^{17}$ and $R^{18}$ are independently alkyl, cycloalkyl, phenyl, substituted phenyl, naphthyl, or phenylalkyl, substituted phenylalkyl, or (cycloalkyl)alkyl;

$R^{19}$ and $R^{20}$ are independently hydrogen, alkyl, phenyl, substituted phenyl, $(CH_2)_m$phenyl, or $(CH_2)_m$(substituted phenyl), or $R^{19}$ and $R^{20}$ taken together are $-(CH=CH)_2-$;

$R^{21}$ is hydrogen, alkyl, phenyl, substituted phenyl, $(CH_2)_m$phenyl, $(CH_2)_m$(substituted phenyl);

$R^{22}$, $R^{23}$ and $R^{24}$ are independently hydrogen or alkyl;

$Y^1$ is $CH_2$, $(CH_2)_2$, $(CH_2)_3$, or S;

$Y^2$ is O or $NR^{24}$;

$Y^3$ is $CH_2$, O, or $NR^{24}$;

a is 0 or 1 and b is 1 or 2, provided that when a is 1 then b is 1;

c is 1 or 2, provided that when c is 1 then a is 0 and b is 1;

m is 1, 2, 3 or 4; and p is 1 or 2;

or a pharmaceutically acceptable salt thereof.

Fig. 16(m)

1. An isolated compound of the following formula:

Formula I wherein:

n is 0, 1 or 2;

X is CH2, C=O, O, S or NH;

A is a moiety of Formula IIa-i:

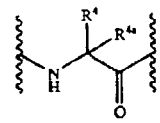
IIa

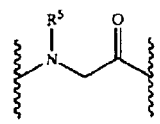
IIb

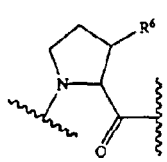
IIc

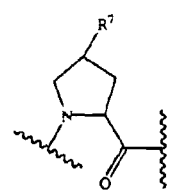
IId

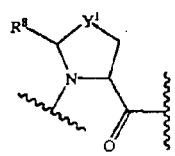
IIe

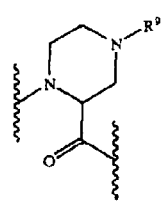
IIf

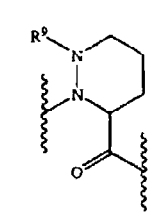
IIg

-continued

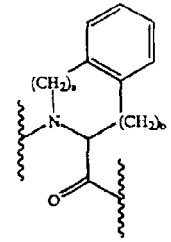
IIh

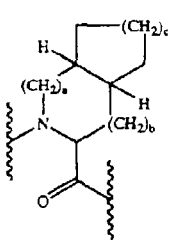
IIi

B is a hydrogen atom, a deuterium atom, $C_{1-10}$ straight chain branched alkyl, cycloalkyl, phenyl, substituted phenyl, naphthyl, substituted naphthyl, 2-benzoxazolyl, substituted 2-oxazolyl, $(CH_2)_m$ cycloalkyl, $(CH_2)_m$phenyl, $(CH_2)_m$(substituted phenyl), $(CH_2)_m$(1 or 2-naphthyl), $(CH_2)_m$heteroaryl, halomethyl, $CO_2R^{13}$, $CONR^{14}R^{15}$, $CH_2ZR^{16}$, $CH_2OCO(aryl)$, $CH_2OCO(heteroaryl)$, or $CH_2OPO(R^{17})R^{18}$, where Z is an oxygen or a sulfur atom, or B is a group of the Formula IIIa-c:

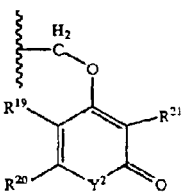
IIIa

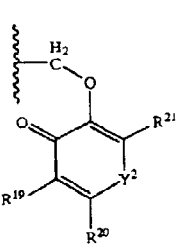
IIIb

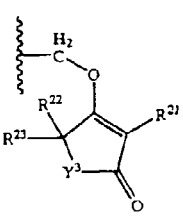
IIIc

Fig. 17(b)

R[1] is phenyl, substituted phenyl, naphthyl, substituted naphthyl, heteroaryl, or substituted heteroaryl;

R[2] is hydrogen, alkyl, cycloalkyl, phenyl, substituted phenyl, $(CH_2)_m NH_2$, $(CH_2)_m NHCOR^{10}$, $(CH_2)_m N(C=NH)NH_2$, $(CH_2)_p CO_2 R^3$, $(CH_2)_p OR^{11}$, $(CH_2)_p SR^{12}$, $(CH_2)_m$cycloalkyl, $(CH_2)_m$phenyl, $(CH_2)_m$(substituted phenyl), $(CH_2)_m$(1 or 2-naphthyl), or $(CH_2)_m$heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl;

R[3] is hydrogen, alkyl, cycloalkyl, (cycloalkyl)alkyl, phenylalkyl, or substituted phenylalkyl; and wherein R[4] is alkyl, cycloalkyl, phenyl, substituted phenyl, $(CH_2)_m NH_2$, $(CH_2)_m NHCOR^{10}$, $(CH_2)_m N(C=NH)NH_2$, $(CH_2)_p CO_2 R^3$, $(CH_2)_p OR^{11}$, $(CH_2)_p SR^{12}$, $(CH_2)_m$cycloalkyl, $(CH_2)_m$phenyl, $(CH_2)_m$(substituted phenyl), $(CH_2)_m$(1 or 2-naphthyl), or $(CH_2)_m$ heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl;

R[4a] is hydrogen, or methyl, or R[4] and R[4a] taken together are $-(CH_2)_d-$ where d is an interger from 2 to 6;

R[5] is phenyl, substituted phenyl, $(CH_2)_p$phenyl, $(CH_2)_p$(substituted phenyl), cycloalkyl, or benzofused cycloalkyl;

R[6] is hydrogen, alkyl, cycloalkyl, phenyl, substituted phenyl, $(CH_2)_m$cycloalkyl, $(CH_2)_m$phenyl, $(CH_2)_m$(substituted phenyl), or $(CH_2)_m$(1 or 2-naphthyl);

R[7] is hydrogen, fluorine, oxo, alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{11}$, $SR^{12}$, or $NHCOR^{10}$;

R[8] is hydrogen, oxo, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

R[9] is alkyl, cycloalkyl, $(CH_2)_m$cycloalkyl, $(CH_2)_m$phenyl, $(CH_2)_m$(substituted phenyl), $(CH_2)_m$(1 or 2-naphthyl), or $COR^{10}$;

R[10] is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{13}$, or $NR^{14}R^{15}$;

R[11] is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

R[12] is alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

R[13] is alkyl, cycloalkyl, $(CH_2)_m$cycloalkyl, $(CH_2)_m$phenyl, $(CH_2)_m$(substituted phenyl), or $(CH_2)_m$(1 or 2-naphthyl);

R[14] is hydrogen, alkyl, cycloalkyl, phenyl, substituted phenyl, naphthyl, substituted naphthyl, $(CH_2)_m$cycloalkyl, $(CH_2)_m$phenyl, $(CH_2)_m$(substituted phenyl), or $(CH_2)_m$(1 or 2-naphthyl);

R[15] is hydrogen or alkyl; or

R[14] and R[15] taken together form a five, six or seven membered carbocyclic or heterocyclic ring, such as morpholine or N-substituted piperazine;

R[16] is phenyl, substituted phenyl, naphthyl, substituted naphthyl, heteroaryl, $(CH_2)_m$phenyl, $(CH_2)_m$(substituted phenyl), $(CH_2)_m$(1 or 2-naphthyl), or $(CH_2)_m$heteroaryl;

R[17] and R[18] are independently alkyl, cycloalkyl, phenyl, substituted phenyl, naphthyl, or phenylalkyl, substituted phenylalkyl, or (cycloalkyl)alkyl;

R[19] and R[20] are independently hydrogen, alkyl, phenyl, substituted phenyl, $(CH_2)_m$phenyl, or $(CH_2)_m$(substituted phenyl), or R[19] and R[20] taken together are $-(CH=CH)_2-$;

R[21] is hydrogen, alkyl, phenyl, substituted phenyl, $(CH_2)_m$ phenyl, $(CH_2)_m$(substituted phenyl);

R[22], R[23] and R[24] are independently hydrogen or alkyl;

Y[1] is $CH_2$, $(CH_2)_2$, $(CH_2)_3$, or S;

Y[2] is O or $NR^{24}$;

Y[3] is $CH_2$, O, or $NR^{24}$;

a is 0 or 1 and b is 1 or 2, provided that when a is 1 then b is 1;

c is 1 or 2, provided that when c is 1 then a is 0 and b is 1;

m is 1,2,3 or 4; and p is 1 or 2;

or a salt thereof.

2. The compound of claim 1 where X is oxygen.

3. The compound of claim 1 where X is sulfur.

4. The compound of claim 1 where X is NH.

5. The compound of claim 1 where X is $CH_2$.

6. The compound of claim 1 where X is C=O.

7. The compound of claim 1 wherein A is

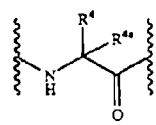

IIa

8. The compound of claim 1 wherein

R[4] is lower alkyl, cycloalkyl, phenyl, substituted phenyl, $(CH_2)_n NH_2$, $(CH_2)_n OR^{10}$, $(CH_2)_n SR^{11}$, $(CH_2)_n$cycloalkyl, $(CH_2)_n$phenyl, $(CH_2)_n$(substituted phenyl), or $(CH_2)_n$(1 or 2-naphthyl); and R[4a] is hydrogen.

9. The compound of claim 1 wherein A is

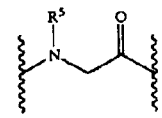

IIb

10. The compound of claim 9 wherein R[5] is phenyl, substituted phenyl, $(CH_2)_m$phenyl, $(CH_2)_m$(substituted phenyl), cycloalkyl, or 2-indanyl.

Fig. 17(c)

11. The compound of claim 1 wherein A is

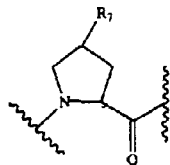
IId

12. The compound of claim 11 wherein $R^7$ is hydrogen, fluorine, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{10}$, or $SR^{11}$.

13. The compound of claim 1 wherein A is

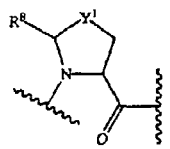
IIe

14. The compound of claim 13 wherein $R^8$ is hydrogen, oxo, cycloalkyl, phenyl, substituted phenyl, or naphthyl; and $Y^1$ is $CH_2$, $(CH_2)_2$, $(C_2)_3$, or S.

15. The compound of claim 1 wherein A is

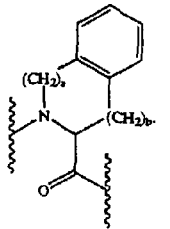
Ib

16. The compound of claim 15 wherein a is 0.

17. The compound of claim 1 wherein

B is hydrogen, 2-benzoxazolyl, substituted 2-oxazolyl, $CH_2ZR^{15}$, $CH_2OCO(aryl)$, or $CH_2OPO(R^{16})R^{17}$; and Z is O or S.

18. The compound of claim 1 wherein B is

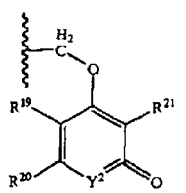
IIIa

-continued

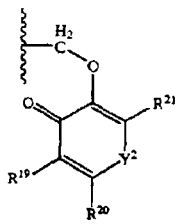
IIIb

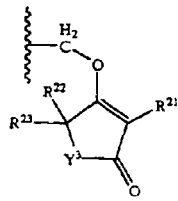
IIIc

19. The compound of claim 18 wherein $R^{19}$ and $R^{20}$ are independently hydrogen, alkyl, or phenyl, or wherein $R^{19}$ and $R^{20}$ taken together are $-(CH=CH)_2-$.

20. The compound of claim 1 wherein

X is O or NH;

n is 0 or 1;

$R^1$ is substituted phenyl, naphthyl, or substituted naphthyl;

$R^2$ is hydrogen, lower alkyl, $(CH_2)_pCO_2R^3$, $(CH_2)_m$(substituted phenyl), $(CH_2)_m$(1- or 2-naphthyl), or $(CH_2)_m$tetrazolyl; and $R^3$ is hydrogen or lower alkyl.

21. The compound of claim 20 wherein $R^1$ is 1-naphthyl.

22. The compound of claim 20 wherein $R^1$ is 2-naphthyl.

23. The compound of claim 20 wherein $R^1$ is substituted naphthyl.

24. The compound of claim 23 wherein substituted naphthyl is 2-carboxy-1-naphthyl.

25. The compound of claim 20 wherein $R^1$ is substituted phenyl.

26. The compound of claim 25 wherein substituted phenyl is 2-substituted phenyl.

27. The compound of claim 26 wherein 2-substituted phenyl is (2-phenyl)phenyl.

28. The compound of claim 20 wherein A is alanine, valine, leucine cyclohexylalanine, phenylgycine or t-butylglycine.

29. The compound of claim 28 wherein $R^1$ is 1-naphthyl.

30. The compound of claim 28 wherein $R^1$ is 2-naphthyl.

31. The compound of claim 28 wherein $R^1$ is substituted naphthyl.

32. The compound of claim 31 wherein substituted naphthyl is 2-carboxy-1-naphthyl.

33. The compound of claim 28 wherein $R^1$ is 2-substituted phenyl.

34. The compound of claim 33 wherein 2-substituted phenyl is (2-phenyl)phenyl.

35. The compound of claim 20 wherein $R^2$ is $(CH_2)_2CO_2R^3$ and n is 0.

36. A composition comprising a compound of claim 1 in combination with a carrier.

Fig. 17(d)

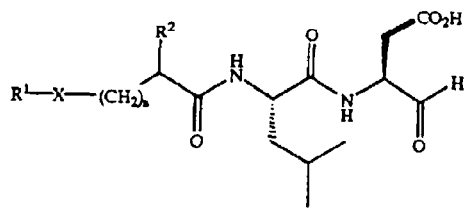

(Formula Ib)

| Ex. No. | R¹ | X | n | R² | mICE I$_{50}$(μM) | CPP32 I$_{50}$(μM) | MCH2 I$_{50}$(μM) | MCH3 I$_{50}$(μM) | MCH5 I$_{50}$(μM) |
|---|---|---|---|---|---|---|---|---|---|
| 11 | 1-naphthyl | CH₂ | 0 | H | 1.86 | 1.59 | 4.19 | 8.78 | 12.2 |
| 12 | 1-naphthyl | O | 0 | H | 0.597 | 0.139 | 0.846 | 1.95 | 0.821 |
| 13 | 2-naphthyl | O | 0 | H | 2.57 | 0.944 | 18.6 | 8.87 | >10 |
| 14 | 1-naphthyl | O | 0 | CH₃ | 3.99 | 0.376 | 1.28 | 1.32 | 2.43 |
| 15 | 6-Br-1-naphthyl | O | 0 | CH₃ | 6.84 | 4.81 | 13.8 | 32.4 | 29.1 |
| 16 | 1-naphthyl | S | 0 | H | 2.75 | 0.195 | 1.43 | 1.74 | 7.42 |
| 17 | 2-naphthyl | S | 0 | H | 0.792 | 0.269 | 3.16 | 2.52 | 11.0 |
| 18 | 2-naphthyl | CH₂ | 1 | H | 1.80 | 2.76 | 14.5 | 18.2 | >50 |
| 19 | 1-naphthyl | C=O | 1 | H | 0.408 | 0.967 | 11.8 | 11.3 | 11.2 |
| 20 | 1-naphthyl | C=O | 1 | CH₃ | 4.55 | 9.88 | 24.9 | 29.8 | 3.25 |
| 21 | 2-naphthyl | C=O | 1 | H | 0.543 | 1.42 | 10.3 | 7.43 | 5.23 |
| 22 | 1-naphthyl | O | 1 | H | 0.686 | 0.059 | 0.305 | 1.37 | 9.81 |
| 23 | 2-naphthyl | O | 1 | H | 1.32 | 0.910 | 5.90 | 9.65 | 15.2 |
| 24 | 1-naphthyl | S | 1 | H | 0.563 | 0.412 | 2.72 | 3.60 | 16.3 |
| 25 | 2-naphthyl | S | 1 | H | 0.611 | 0.837 | 1.62 | 5.89 | 15.0 |
| 26 | 2-Me-1-naphthyl | O | 0 | H | 0.843 | 0.375 | 32.4 | 4.16 | 4.14 |
| 27 | 4-MeO-1-naphthyl | O | 0 | H | 0.831 | 0.263 | 22.6 | 4.08 | 1.45 |
| 28 | 4-Cl-1-naphthyl | O | 0 | H | 0.429 | 0.231 | 12.0 | 3.38 | 1.69 |
| 29 | 2,4-diCl-1-naphthyl | O | 0 | H | 0.141 | 0.357 | 21.4 | 3.61 | 3.04 |
| 30 | 1-isoquinolinyl | O | 0 | H | 44.2 | 1.57 | >50 | 34.7 | >50 |
| 31 | 4-quinolinyl | O | 0 | H | 35.3 | 0.232 | >50 | 4.57 | >50 |
| 32 | 5-quinolinyl | O | 0 | H | 5.25 | 0.412 | >50 | 3.85 | 4.02 |
| 33 | 5-isoquinolinyl | O | 0 | H | 5.14 | 0.407 | 42.7 | 3.48 | 3.64 |
| 34 | 8-quinolinyl | O | 0 | H | 13.7 | 0.147 | 12.5 | 1.51 | 2.24 |
| 35 | phenyl | CH₂ | 0 | H | >10 | 9.74 | ND | >10 | >10 |
| 36 | phenyl | O | 0 | CH₃ | 20.4 | 1.77 | >10 | 8.27 | >10 |
| 37 | phenyl | O | 1 | H | 9.42 | 0.419 | >50 | 6.04 | >10 |
| 38 | phenyl | O | 0 | H | >10 | 3.40 | >50 | >10 | >10 |
| 39 | 2-biphenyl | O | 0 | H | 0.636 | 0.095 | 0.717 | 2.02 | 1.71 |
| 40 | 3-biphenyl | O | 0 | H | 1.10 | 0.311 | 14.5 | 3.75 | 3.86 |
| 41 | 4-biphenyl | O | 0 | H | 1.90 | 0.763 | 20.5 | 12.0 | 7.53 |
| 42 | (2-benzyl)phenyl | O | 0 | H | 0.521 | 0.490 | 10.1 | 3.36 | 6.05 |
| 43 | (4-benzyl)phenyl | O | 0 | H | 1.80 | 0.346 | 18.9 | 4.41 | 4.72 |
| 44 | (4-phenoxy)phenyl | O | 0 | H | 2.21 | 0.545 | 21.2 | 6.82 | 9.28 |
| 45 | (2-benzyloxy)phenyl | O | 0 | H | 2.40 | 0.222 | 9.75 | 2.20 | 4.34 |
| 46 | (4-benzyloxy)phenyl | O | 0 | H | 2.51 | 0.570 | 33.4 | 7.25 | 8.60 |
| 47 | (2-cyclo-pentyl)-phenyl | O | 0 | H | 0.538 | 0.197 | 3.37 | 1.49 | 1.86 |
| 48 | (4-cyclo-pentyl)-phenyl | O | 0 | H | 2.20 | 0.319 | 51.2 | 5.23 | 5.90 |
| 49 | [2-(1-adamantanyl)-4-Me]phenyl | O | 0 | H | 1.43 | 0.474 | 5.86 | 2.79 | 3.87 |
| 50 | 4-(1-adamantanyl)-phenyl | O | 0 | H | 1.83 | 0.528 | 32.5 | 8.24 | 4.35 |
| 51 | 5,6,7,8-tetrahydro-1-naphthyl | O | 0 | H | 1.81 | 0.324 | 11.8 | 2.74 | 1.75 |
| 52 | 5,6,7,8-tetrahydro-2-naphthyl | O | 0 | H | 2.57 | 0.162 | 28.6 | 2.31 | 4.95 |

Fig. 17(e)

| Ex. | R¹ | X | n | R² | Formula | MW | MS(ES) pos. | neg. |
|---|---|---|---|---|---|---|---|---|
| 54 | 2-naphthyl | O | 0 | H | $C_{22}H_{25}FN_2O_6$ | 432.45 | 433(M + H) 455(M + Na) 471(M + K) | 431(M − H) 545(M + TFA) |
| 55 | 1-naphthyl | O | 1 | H | $C_{23}H_{27}FN_2O_6$ | 446.47 | 447(M + H) 489(M + Na) | 445(M − H) 559(M + TFA) |
| 56 | (2-Ph)Ph | O | 0 | H | $C_{24}H_{27}FN_2O_6$ | 458.49 | 481(M + Na) 497(M + K) | 457(M − H) 571(M + TFA) |

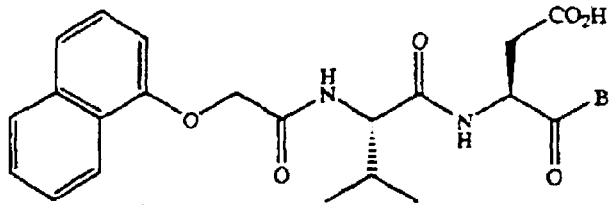

| Ex. | B | Formula | MW | MS(ES) pos. | MS(ES) neg. |
|---|---|---|---|---|---|
| 63 | CH$_2$OCO(2,6-diCl—Ph) | C$_{29}$H$_{28}$Cl$_2$N$_2$O$_8$ | 603.45 | 603/605 (M + H) | 601/603 (M - H) |
| 64 | CH$_2$OPh | C$_{28}$H$_{30}$N$_2$O$_7$ | 506.55 | 507(M + H) 529(M + Na) 545(M + K) | 505(M - H) |
| 65 | CH$_2$O(2-F—Ph) | C$_{28}$H$_{29}$FN$_2$O$_7$ | 524.54 | 525(M + H) | 523(M - H) |
| 66 | CH$_2$O(3-F—Ph) | C$_{28}$H$_{29}$FN$_2$O$_7$ | 524.54 | 525(M + H) | 523(M - H) |
| 67 | CH$_2$O(4-F—Ph) | C$_{28}$H$_{29}$FN$_2$O$_7$ | 524.54 | 547(M + Na) | 523(M - H) |
| 68 | CH$_2$O(2,3-diF—Ph) | C$_{28}$H$_{29}$F$_2$N$_2$O$_7$ | 542.54 | 543(M + H) 565(M + Na) | 541(M - H) 655(M + TFA) |
| 69 | CH$_2$O(2,4-diF—Ph) | C$_{28}$H$_{29}$F$_2$N$_2$O$_7$ | 542.54 | 543(M + H) 565(M + Na) 581(M + K) | 541(M - H) |
| 70 | CH$_2$O(2,5-diF—Ph) | C$_{28}$H$_{29}$F$_2$N$_2$O$_7$ | 542.54 | 543(M + H) 565(M + Na) 581(M + K) | 541(M - H) |
| 71 | CH$_2$O(2,6-diF—Ph) | C$_{28}$H$_{29}$F$_2$N$_2$O$_7$ | 542.54 | 543(M + H) 565(M + Na) | 541(M - H) |
| 72 | CH$_2$O(3,4-diF—Ph) | C$_{28}$H$_{29}$F$_2$N$_2$O$_7$ | 542.54 | 543(M + H) 581(M + K) | 541(M - H) |
| 73 | CH$_2$O(3,5-diF—Ph) | C$_{28}$H$_{29}$F$_2$N$_2$O$_7$ | 542.54 | 543(M + H) 565(M + Na) 581(M + K) | 541(M - H) |
| 74 | CH$_2$O(2,3,4-triF—Ph) | C$_{28}$H$_{27}$F$_3$N$_2$O$_7$ | 560.53 | 561(M + H) 583(M + Na) 599(M + K) | 559(M - H) |
| 75 | CH$_2$O(2,3,5-triF—Ph) | C$_{28}$H$_{27}$F$_3$N$_2$O$_7$ | 560.53 | 561(M + H) 583(M + Na) 599(M + K) | 559(M - H) 673(M + TFA) |
| 76 | CH$_2$O(2,3,6-triF—Ph) | C$_{28}$H$_{27}$F$_3$N$_2$O$_7$ | 560.53 | 561(M + H) 583(M + Na) 599(M + K) | 559(M - H) 673(M + TFA) |
| 77 | CH$_2$O(2,4,5-triF—Ph) | C$_{28}$H$_{27}$F$_3$N$_2$O$_7$ | 560.53 | 561(M + H) 583(M + Na) 599(M + K) | 559(M - H) |
| 78 | CH$_2$O(2,4,6-triF—Ph) | C$_{28}$H$_{27}$F$_3$N$_2$O$_7$ | 560.53 | 561(M + H) 583(M + Na) | 559(M - H) |
| 79 | CH$_2$O(2,3,5,6-tetra-Ph) | C$_{28}$H$_{26}$F$_4$N$_2$O$_7$ | 578.52 | 579(M + H) 601(M + Na) 617(M + K) | 577(M - H) |

Fig. 17(g)

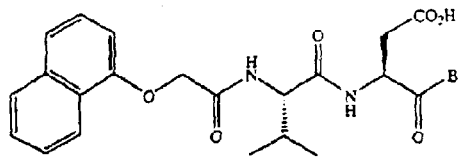

| Ex. | B | Formula | MW | MS(ES) pos. | neg. |
|---|---|---|---|---|---|
| 80 | CH₂O(2,3,4,5,6-pentaF—Ph) | C₂₈H₂₅F₅N₂O₇ | 596.51 | 619(M + Na) | 595(M − H) |
| 81 | CH₂O(2-CF₃—Ph) | C₂₉H₂₇F₃N₂O₇ | 574.55 | 597(M + Na) | 573(M − H) |
| 82 | CH₂O(3-CF₃—Ph) | C₂₉H₂₇F₃N₂O₇ | 574.55 | 597(M + Na) | 573(M − H) |
| 83 | CH₂O(4-CF₃—Ph) | C₂₉H₂₇F₃N₂O₇ | 574.55 | 597(M + Na) | 573(M − H) |
| 84 | CH₂O(3,5-diCF₃—Ph) | C₃₀H₂₆F₆N₂O₇ | 642.55 | 643(M + H) 665(M + Na) 681(M + K) | 641(M − H) |
| 85 | CH₂O(2-F,3-CF₃—Ph) | C₂₉H₂₆F₄N₂O₇ | 592.54 | 593(M + H) 615(M + Na) 631(M + K) | 591(M − H) |
| 86 | CH₂O(2,6-diCl—Ph) | C₂₈H₂₈Cl₂N₂O₇ | 575.44 | 575/577(M + H) | 573/575 (M − H) |
| 87 | CH₂O(2-NO₂—Ph) | C₂₈H₂₉N₃O₉ | 551.55 | 552(M + H) 574(M + Na) 590(M + K) | 550(M − H) |
| 88 | CH₂O(4-NO₂—Ph) | C₂₈H₂₉N₃O₉ | 551.55 | 552(M + H) 574(M + Na) | 550(M − H) |
| 89 | CH₂O(2-F,4-NO₂—Ph) | C₂₈H₂₈FN₃O₉ | 569.54 | 570(M + H) 592(M + Na) | 568(M − H) |
| 90 | CH₂O(4-CN—Ph) | C₂₉H₂₉N₃O₇ | 531.56 | 554(M + Na) | 530(M − H) |
| 91 | CH₂O(4-CF₃O—Ph) | C₂₉H₂₉F₃N₂O₈ | 590.55 | 591(M + H) | 589(M − H) 703(M + TFA) |
| 92 | CH₂O(4-H₂NCO—Ph) | C₂₉H₃₁N₃O₈ | 549.58 | 550(M + H) 572(M + Na) | 548(M − H) 662(M + TFA) |
| 93 | CH₂O(4-PhCO—Ph) | C₃₅H₃₄N₂O₈ | 610.66 | 611(M + H) 633(M + Na) | 609(M − H) |
| 94 | CH₂O(4-Ph—Ph) | C₃₄H₃₄N₂O₇ | 582.65 | 583(M + H) 605(M + Na) 621(M + K) | 581(M − H) 695(M + TFA) |
| 95 | CH₂O(4-C₆F₅-2,3,5,6-tetraF—Ph) | C₃₄H₂₅F₉N₂O₇ | 744.57 | 745(M + H) 767(M + Na) 783(M + K) | 743(M − H) |
| 96 | CH₂O(4-PhO—Ph) | C₃₄H₃₄N₂O₈ | 598.65 | 599(M + H) 621(M + Na) | 597(M − H) |
| 97 | CH₂O[4-(4'-CF₃—PhO)Ph] | C₃₅H₃₃F₃N₂O₈ | 666.65 | 667(M + H) 689(M + Na) | 665(M − H) |
| 98 | CH₂O(3-AcNH—Ph) | C₃₀H₃₃N₃O₈ | 563.61 | 564(M + H) 586(M + Na) | 562(M − H) |
| 99 | CH₂O(3,4-OCOS—Ph) | C₂₉H₂₈N₂O₉S | 580.61 | 581(M + H) 603(M + Na) 619(M + K) | 693(M + TFA) |
| 100 | CH₂O(2-pyridinyl) | C₂₇H₂₉N₃O₇ | 507.54 | 508(M + H) | 506(M − H) |
| 101 | CH₂O(4,5-diCl-3-pyridazinyl) | C₂₆H₂₆Cl₂N₄O₇ | 577.42 | 577/579(M + H) | 575/577 (M − H) 689/691 (M + TFA) |
| 102 | CH₂O(2-naphthyl) | C₃₂H₃₂N₂O₇ | 556.61 | 557(M + H) | 555(M − H) |
| 103 | CH₂OPOPh₂ | C₃₄H₃₅N₂O₈P | 630.63 | 631(M + H) 653(M + Na) | 629(M − H) |
| 104 | CH₂OPO(Me)Ph | C₂₉H₃₃N₂O₈P | 568.56 | 569(M + H) | 567(M − H) |
| 105 | CH₂OPOMe₂ | C₂₄H₃₁N₂O₈P | 506.49 | 529(M + Na) | 505(M − H) |
| 106 | CH₂OPO(n-hexyl)Ph | C₃₄H₄₃N₂O₈P | 638.28 | 639(M + H) 661(M + Na) 677(M + K) | 637(M − H) 751(M + TFA) |
| 107 | CH₂OPO(PhCH₂)Ph | C₃₅H₃₇N₂O₈P | 644.66 | 645(M + H) 667(M + Na) 683(M + K) | 643(M − H) 757(M + TFA) |
| 108 | CH₂OPO(Me)(4-F—Ph) | C₂₉H₃₂FN₂O₈P | 586.55 | 587(M + H) 609(M + Na) | 585(M − H) 699(M + TFA) |
| 109 | CH₂OPO(n-hexyl)(4-F—Ph) | C₃₄H₄₂FN₂O₈P | 656.69 | 679(M + Na) | 655(M − H) |
| 110 | CH₂OPO(Me)(1-naphthyl) | C₃₃H₃₅N₂O₈P | 618.62 | 619(M + H) 641(M + Na) | 731(M + TFA) |
| 111 | CH₂O(6-Me-2-pyron-4-yl) | C₂₈H₃₀N₂O₉ | 538.55 | 539(M + H) | |
| 112 | CH₂O(4-coumarinyl) | C₃₁H₃₀N₂O₉ | 574.59 | 575(M + H) 597(M + Na) | 537(M − H) 687(M + TFA) |

Fig. 17(h)

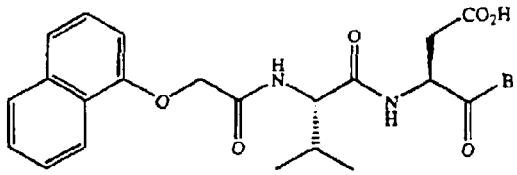

| Ex. | B | Formula | MW | MS(ES) pos. | neg. |
|---|---|---|---|---|---|
| 113 | $CH_2O$(2-Me-4-pyron-3-yl) | $C_{28}H_{30}N_2O_9$ | 538.55 | 539(M + H)<br>561(M + Na) | 537(M − H)<br>651(M + TFA) |
| 114 | $CH_2O$[1,2-diMe-4(1H)-pyridon-3-yl] | $C_{29}H_{33}N_3O_8$ | 551.59 | 552(M + H) | 550(M − H) |
| 115 | $CH_2O$(3-flavonyl) | $C_{37}H_{34}N_2O_9$ | 650.68 | 651(M + H) | 649(M − H) |
| 116 | $CH_2O$(4,6-diMe-2-pyrimidinyl) | $C_{28}H_{32}N_4O_7$ | 536.58 | 537(M + H) | 535(M − H) |
| 117 | $CH_2O$(4-$CF_3$-2-pyrimidinyl) | $C_{27}H_{27}F_3N_4O_7$ | 576.53 | 577(M + H) | 575(M − H) |
| 118 | $CH_2S$(4,6-diMe-2-pyrimidinyl) | $C_{28}H_{32}N_4O_6S$ | 552.64 | 553(M + H)<br>575(M + Na) | 551(M − H)<br>665(M + TFA) |
| 119 | $CH_2O$(2,6-diMe-4-pyrimidinyl) | $C_{28}H_{32}N_4O_7$ | 536.58 | 537(M + H) | 535(M − H) |
| 120 | $CH_2O$(6-$CF_3$-4-pyrimidinyl) | $C_{27}H_{27}F_3N_4O_7$ | 576.53 | 577(M + H) | 575(M − H) |
| 121 | $CH_2O$(2-$CF_3$-4-pyrimidinyl) | $C_{27}H_{27}F_3N_4O_7$ | 576.53 | 577(M + H) | 575(M − H) |
| 122 | $CH_2S$(2-imidazolyl) | $C_{25}H_{28}N_4O_6S$ | 512.58 | 513(M + H) | 511(M − H)<br>625(M + TFA) |
| 123 | $CH_2S$(1-Me-2-imidazolyl) | $C_{26}H_{30}N_4O_6S$ | 526.61 | 527(M + H) | 525(M − H) |
| 124 | $CH_2S$(1H-1,2,4-triazol-3-yl) | $C_{24}H_{27}N_5O_6S$ | 513.57 | 514(M + H) | 512(M − H) |
| 125 | $CH_2S$(4-Me-4H-1,2,4-triazol-3-yl) | $C_{25}H_{29}N_5O_6S$ | 527.59 | 528(M + H) | 526(M − H)<br>640(M + TFA) |
| 126 | $CH_2S$(1-Me-5-tetrazolyl) | $C_{24}H_{28}N_6O_6S$ | 528.58 | 529(M + H) | 527(M − H) |
| 127 | $CH_2S$(1-Ph-5-tetrazolyl) | $C_{29}H_{30}N_6O_6S$ | 590.65 | 591(M + H) | 589(M − H) |
| 128 | $CH_2S$(5-Me-1,3,4-thiadiazol-2-yl) | $C_{25}H_{28}N_4O_6S_2$ | 544.64 | 545(M + H) | 543(M − H) |
| 129 | $CH_2S$(5-Ph-1,3,4-oxadiazol-2-yl) | $C_{30}H_{30}N_4O_7S$ | 590.65 | 591(M + H)<br>613(M + Na) | 589(M − H)<br>703(M + TFA) |
| 130 | $CH_2S$(3-Ph-1,2,4-oxadiazol-5-yl) | $C_{30}H_{30}N_4O_7S$ | 590.65 | 591(M + H) | 589(M − H) |
| 131 | $CH_2S$(4-Ph-2-thiazolyl) | $C_{31}H_{31}N_3O_6S_2$ | 605.72 | 606(M + H)<br>628(M + Na) | 604(M − H) |
| 132 | $CH_2S$(4,5-diPh-2-imidazolyl) | $C_{37}H_{36}N_4O_6S$ | 664.77 | 665(M + H) | 663(M − H) |
| 133 | $CH_2O$(2-benzothiazolyl) | $C_{29}H_{29}N_3O_7S$ | 563.62 | 564(M + H)<br>586(M + Na) | 562(M − H) |
| 134 | $CH_2O$(2-benzimidazolyl) | $C_{29}H_{30}N_4O_7$ | 546.58 | 547(M + H)<br>569(M + Na) | 545(M − H) |
| 135 | $CH_2S$(2-benzothiazolyl) | $C_{29}H_{29}N_3O_6S_2$ | 579.68 | 580(M + H) | 578(M − H) |
| 136 | $CH_2S$(2-benzimidazolyl) | $C_{29}H_{30}N_4O_6S$ | 562.64 | 563(M + H) | 561(M − H)<br>675(M + TFA) |
| 137 | $CH_2O$(2-quinolinyl) | $C_{31}H_{31}N_3O_7$ | 557.60 | 558(M + H)<br>580(M + Na) | 556(M − H)<br>670(M + TFA) |
| 138 | $CH_2O$(3-isoquinolinyl) | $C_{31}H_{31}N_3O_7$ | 557.60 | 558(M + H) | 556(M − H) |
| 139 | $CH_2O$(1-isoquinolinyl) | $C_{31}H_{31}N_3O_7$ | 557.60 | 558(M + H)<br>580(M + Na) | 556(M − H)<br>670(M + TFA) |
| 140 | $CH_2O$(4-quinazolinyl) | $C_{31}H_{30}N_4O_7$ | 558.59 | 559(M + H) | 557(M − H) |
| 141 | $CH_2O$(8-quinolinyl) | $C_{31}H_{31}N_3O_7$ | 557.60 | 558(M + H) | 556(M − H)<br>670(M + TFA) |
| 142 | $CH_2O$(3-Me-4-$CO_2$Et-isoxazol-5-yl) | $C_{29}H_{33}N_3O_{10}$ | 583.59 | 584(M + H) | 582(M − H) |
| 143 | $CH_2O$(1-Ph-3-$CF_3$-pyrazol-5-yl) | $C_{32}H_{31}F_3N_4O_7$ | 640.61 | 641(M + H) | 639(M − H) |
| 144 | $CH_2O$(5-$CO_2$Me-isoxazol-3-yl) | $C_{27}H_{29}N_3O_{10}$ | 555.54 | 556(M + H)<br>578(M + Na) | 554(M − H) |
| 145 | $CH_2O$(5-iPr-isoxazol-3-yl) | $C_{28}H_{33}N_3O_8$ | 539.58 | 540(M + H) | 538(M − H) |
| 146 | $CH_2O$(3-benzoisoxazolyl) | $C_{29}H_{29}N_3O_8$ | 547.56 | 548(M + H) | 546(M − H) |
| 147 | $CH_2O$(1-Me-5-$CF_3$-pyrazol-3-yl) | $C_{27}H_{29}F_3N_4O_7$ | 578.54 | 579(M + H)<br>601(M + Na) | 577(M − H) |
| 148 | $CH_2O$(1-benzotriazolyl) | $C_{28}H_{29}N_5O_7$ | 547.57 | 548(M + H) | 660(M + TFA) |
| 149 | $CH_2O$(N-phthalimidyl) | $C_{30}H_{29}N_3O_9$ | 575.57 | 576(M + H) | 574(M + H)<br>688(M + TFA) |

Fig. 17(i)

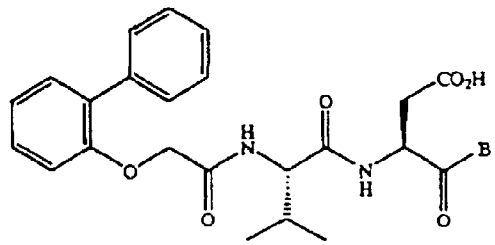

| Ex. | B | Formula | MW | MS(ES) pos. | neg. |
|---|---|---|---|---|---|
| 150 | $CH_2OCO(2,6$-di-Cl—Ph) | $C_{31}H_{30}Cl_2N_2O_8$ | 629.49 | 629/631(M + H)<br>651/653(M + Na)<br>667/669(M + K) | 627/629(M − H)<br>741/743(M + TFA) |
| 151 | $CH_2O(2,4,6$-triF—Ph) | $C_{30}H_{29}F_3N_2O_7$ | 586.57 | 587(M + H)<br>609(M + Na)<br>625(M + K) | 585(M − H)<br>699(M + TFA) |
| 152 | $CH_2O(2,3,5,6$-tetraF—Ph) | $C_{30}H_{28}F_4N_2O_7$ | 604.56 | 605(M + H) | 603(M − H)<br>717(M + TFA) |
| 153 | $CH_2OPOPh_2$ | $C_{36}H_{37}N_2O_8P$ | 656.67 | 679(M + Na)<br>695(M + K) | 655(M − H)<br>769(M + TFA) |
| 154 | $CH_2OPO(Me)Ph$ | $C_{31}H_{35}N_2O_8P$ | 594.60 | 617(M + Na)<br>633(M + K) | 593(M − H)<br>707(M + TFA) |

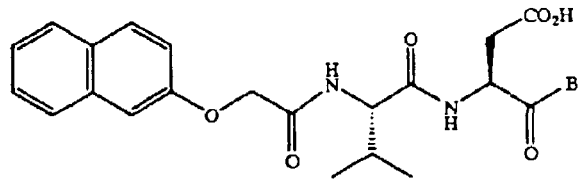

| Ex. | B | Formula | MW | MS(ES) pos. | neg. |
|---|---|---|---|---|---|
| 155 | $CH_2OCO(2,6$-di-Cl-Ph) | $C_{29}H_{28}Cl_2N_2O_8$ | 603.45 | 603/605(M + H)<br>625/627(M + Na) | 601/603(M − H)<br>715/717(M + TFA) |
| 156 | $CH_2O(2,4,6$-triF—Ph) | $C_{28}H_{27}F_3N_2O_7$ | 560.53 | 583(M + Na) | 559(M − H)<br>673(M + TFA) |
| 157 | $CH_2O(2,3,5,6$-tetraF—Ph) | $C_{28}H_{26}F_4N_2O_7$ | 578.52 | 601(M + Na) | 577(M − H)<br>891(M + TFA) |

Fig. 17(j)

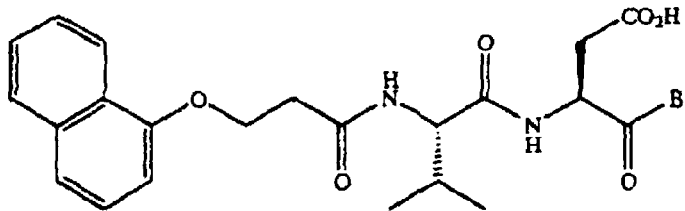
| Ex. | B | Formula | MW | MS(ES) pos. | neg. |
|---|---|---|---|---|---|
| 158 | CH₂OCO(2,6-di-Cl—Ph) | C₃₀H₃₀Cl₂N₂O₈ | 617.48 | 617/619(M + H) 639/641(M + Na) | 615/617(M − H) 729/731(M + TFA) |
| 159 | CH₂O(1-Ph-5-CF₃—pyrazol-3-yl) | C₃₃H₃₃F₃N₄O₇ | 654.64 | 677(M + Na) | 653(M − H) 767(M + TFA) |
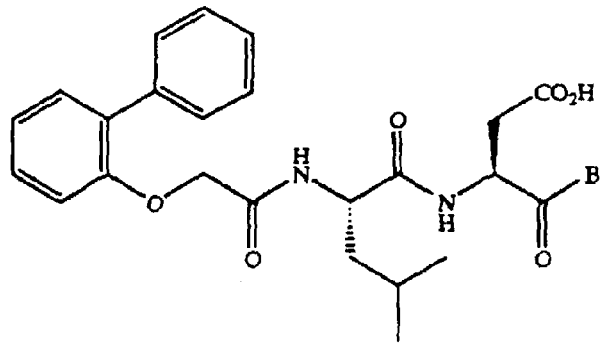
| Ex. | B | Formula | MW | MS(ES) pos. | neg. |
|---|---|---|---|---|---|
| 162 | CH₂OCO(2,6-di-Cl—Ph) | C₃₂H₃₂Cl₂N₂O₈ | 643.52 | 665/667(M + Na) | 641/643(M − H) 755/757(M + TFA) |
| 163 | CH₂O(2,4,6-triF—Ph) | C₃₁H₃₁F₃N₂O₇ | 600.60 | 623(M + Na) | 599(M − H) 713(M + TFA) |
| 164 | CH₂O(2,3,5,6-tetraF—Ph) | C₃₁H₃₀F₄N₂O₇ | 618.59 | 641(M + Na) | 731(M + TFA) |
Fig. 17(k)

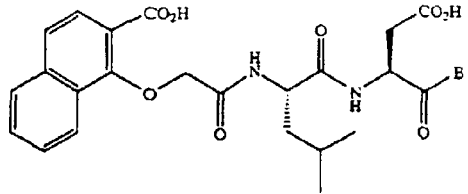

| Ex. | B | Formula | MW | MS(ES) pos. | neg. |
|---|---|---|---|---|---|
| 166 | CH₂OPOPh₂ | C₃₄H₃₇N₂O₁₀P | 688.67 | 689(M + H) | 687(M − H) |
| 167 | CH₂O(2,3,5,6-tetraF—Ph) | C₃₀H₂₉F₄N₂O₉ | 636.55 | 637(M + H)<br>659(M + Na)<br>675(M + K) | 635(M − H) |

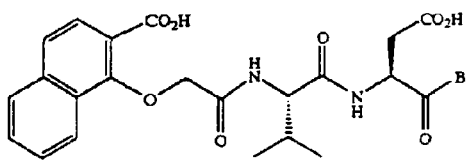

| Ex. | B | Formula | MW | MS(ES) pos. | neg. |
|---|---|---|---|---|---|
| 169 | CH₂O(2,3,5,6-tetraF—Ph) | C₂₉H₂₉F₄N₂O₉ | 622.53 | 645(M + Na) | 621(M − H) |
| 170 | CH₂OCO(2,6-diCl—Ph) | C₃₀H₂₉Cl₂N₂O₁₀ | 647.46 | 669/671<br>(M + Na) | 645/647<br>(M − H) |
| 171 | CH₂OPOPh₂ | C₃₅H₃₅N₂O₁₀P | 674.64 | 697(M + Na) | 673(M − H) |

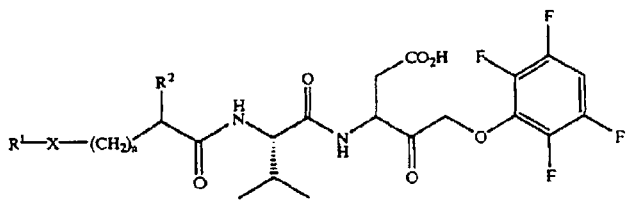

| Ex. | R¹ | X | n | R² | Formula | MW | MS(ES) pos. | neg. |
|---|---|---|---|---|---|---|---|---|
| 173 | 2-naphthyl | O | 0 | H | C₃₂H₃₂F₄N₂O₇ | 632.61 | 633(M + H)<br>655(M + Na)<br>671(M + K) | 631(M − H)<br>745(M + TFA) |
| 174 | 1-naphthyl | O | 1 | H | C₃₃H₃₄F₄N₂O₇ | 646.63 | 647(M + H)<br>669(M + Na)<br>685(M + K) | 645(M − H)<br>759(M + TFA) |
| 175 | (2-Ph)Ph | O | 0 | H | C₃₄H₃₄F₄N₂O₇ | 658.65 | 659(M + H)<br>681(M + Na)<br>697(M + K) | 657(M − H)<br>771(M + TFA) |

Fig. 17(l)

| Ex. | R⁸ | Formula | MW | MS(ES) pos. | neg. |
|---|---|---|---|---|---|
| 180 | n-propyl | $C_{23}H_{26}N_2O_6S$ | 458.53 | — | 457(M − H) |
| 181 | n-hexyl | $C_{26}H_{32}N_2O_6S$ | 500.61 | 501(M + H) 539(M + Na) | 499(M − H) |
| 182 | iso-propyl | $C_{23}H_{26}N_2O_6S$ | 458.53 | 459(M + H) | 457(M − H) |
| 183 | cyclo-hexyl | $C_{26}H_{30}N_2O_6S$ | 498.59 | 499(M + H) | 497(M − H) |
| 184 | H | $C_{20}H_{20}N_2O_6S$ | 416.45 | — | 415(M − H) |

| Ex. | R¹ | X | n | R² | Formula | MW | MS(SE) pos. | neg. |
|---|---|---|---|---|---|---|---|---|
| 190 | (2-t-Bu)Ph | O | 0 | H | $C_{21}H_{30}N_2O_6$ | 406.48 | 429(M + Na) 445(M + K) | 405(M − H) |
| 191 | (2-Ph)Ph | O | 0 | H | $C_{23}H_{26}N_2O_6$ | 426.47 | 449(M + Na) 465(M + K) | 425(M − H) |
| 192 | (2-Ph)Ph | O | 0 | CH₃ | $C_{24}H_{28}N_2O_6$ | 440.50 | 463(M + Na) | 439(M − H) |
| 193 | (2-Ph)Ph | O | 1 | H | $C_{24}H_{28}N_2O_6$ | 440.50 | 441(M + H) 463(M + Na) 479(M + K) | 439(M − H) 553(M + TFA) |
| 194 | 1-naphthyl | O | 1 | H | $C_{22}H_{26}N_2O_6$ | 414.46 | 415(M + H) 437(M + Na) 453(M + K) | 413(M − H) |

| 1 | (3S)-3-[N-((l-Naphthyloxy)Acetyl)Leucinyl]Amino-4-Oxobutanoic Acid |
|---|---|
| 2 | (3S)-3-[N-((l-Naphthyloxy)Acetyl)Valinyl]Amino-4-Oxobutanoic Acid |
| 3 | (3S,2lS)-3-[N-((2'-(l-Naphthyloxy)-4'-Carboxy)Butyryl)Leucinyl]Amino-4-Oxobutanoic Acid |
| 5 | (3S)-3-[N-((l'-Carboxy)-2'-l-Naphthyloxy)Acetyl)Valinyl]Amino-4-Oxobutanoic Acid |
| 8 | (3S)-3-[N-((l-Naphthylamino)Acetyl)Leucinyl]Amino-4-Oxobutanoic Acid |
| 9 | (3S,2tRS)-3-[N-((2'-(l-Naphthylamino)Propionyl)Leucinyl]Amino-4-Oxobutanoic Acid |
| 10 | (3S)-3-[N-((2',3-Dihydro-2,2-Dimethyl-7-Benzofuranyloxy)Acetyl)Leucinyl]Amino-4-Oxobutanoic Acid |
| 53 | (3RS)-3-[N-((l-Naphthyloxy)Acetyl)Valinyl]Amino-5-Fluoro-4-Oxopentanoic Acid |
| 57 | (3RS)-3-[N-((2-Phenylphenoxy)Acetyl)Leucinyl]Amino-5-Fluoro-4-Oxopentanoic Acid |
| 61 | (2'S,3RS)-N-[((l-Naphthyloxy)Acetyl)Indoline-2'-Carbonyl]Amino-5-Fluoro-4-Oxopentanoic Acid |
| 62 | (3S)-3-[N-((l-Naphthyloxy)Acetyl)Valinyl]Amino-5-(r,2',3'-Benzotriazin-4'(3H)-on-3'-yloxy)-4-Oxopentanoic Acid |
| 161 | (3S)-3-[N-((2-Phenoxyphenyl)Acetyl)Leucinyl]Amino-5-(Diphenylphosphinyloxy)-4-Oxopentanoic Acid |
| 165 | (3S)-3-[N-((2'-Carboxy-1'-Naphthyloxy)Acetyl)Leucinyl]Amino-5-(2',6'-(Dichlorobenzoyloxy)-4-Oxopentanoic Acid |
| 168 | (3S)-3-[N-((2'-Carboxy-1'-Naphthyloxy)AQetyl)Valinyl]Amino-5-(2'-Fluorophenoxy)-4-Oxopentanoic Acid |
| 172 | (3RS)-3-[N-((l1-Naphthyloxy)Acetyl)Cyclohexylalaninyl]-Amino-5-(2',3l,5l,Tetrafluorophenoxy)-4-Oxoxypentanoic Acid |
| 179 | (3S,2'RS,4'R)-3-[3l-((l-Naphthyloxy)Acetyl)-2l-Phenylthiazolidine-4'-Carbonyl]Amino-4-Oxobutanoic Acid |
| 185 | (3S)-3-[N-((l-Naphthyloxy)Acetyl)-4'(trans)-Hydroxyprolinyl]Amino-4-Oxobutanoic Acid |

Fig. 17(o)

| 187 | (3S)-3-[N-((3'-Trifluoromethylsulfonylamino-2'-Naphthyloxy)Acetyl)Valinyl]Amino-4-Oxobutanoic Acid |
|---|---|
| 188 | (3S)-3-[N-((5'-Trifluoromethylsulfonylammo-1'-Naphthyloxy)Acetyl)Valinyl]Amino-4-Oxobutanoic Acid |
| 189 | (3S)-3-tN-(4-( 1'-Naphthyloxy)Butyryl)Valinyl] Amino-4-Oxobutanoic Acid |

Fig. 17(p)

compounds of the Formula I:

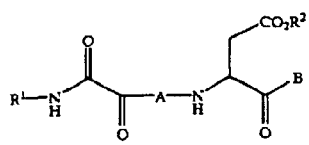
Formula I wherein:

A is a natural or unnatural amino acid of Formula IIa-i:

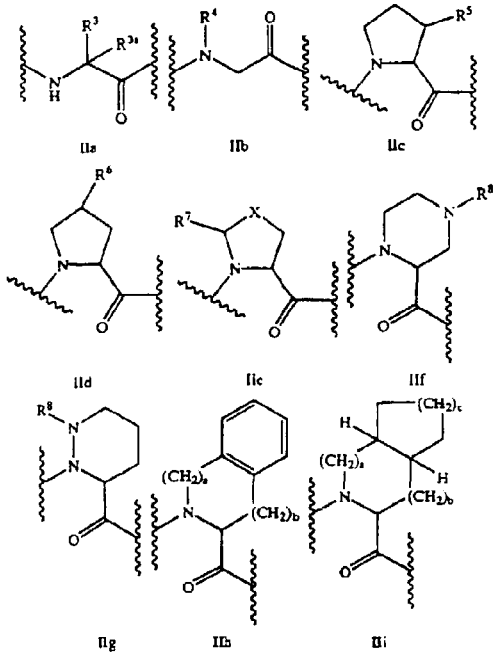

B is a hydrogen atom, a deuterium atom, alkyl, cycloalkyl, phenyl, substituted phenyl, naphthyl, substituted naphthyl, 2-benzoxazolyl, substituted 2-oxazolyl, $(CH_2)_n$cycloalkyl, $(CH_2)_n$phenyl, $(CH_2)_n$(substituted phenyl), $(CH_2)_n$(1 or 2-naphthyl), $(CH_2)_n$(heteroaryl), halomethyl, $CO_2R^{12}$, $CONR^{13}R^{14}$, $CH_2ZR^{15}$, $CH_2OCO(aryl)$, $CH_2OCO(heteroaryl)$, or $CH_2OPO(R^{16})R^{17}$, where Z is an oxygen or a sulfur atom, or B is a group of the Formula IIIa-c:

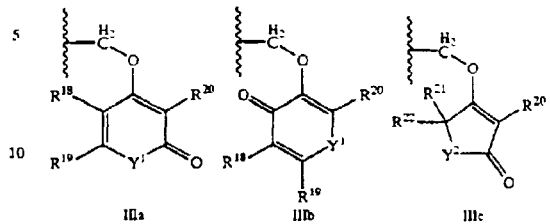

$R^1$ is alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, (heteroaryl)alkyl, $R^{1a}(R^{1b})N$, or $R^{1c}O$; and $R^2$ is hydrogen, lower alkyl, cycloalkyl, (cycloalkyl)alkyl, phenylalkyl, or substituted phenylalkyl;

and wherein:

$R^{1a}$ and $R^{1b}$ are independently hydrogen, alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, or (heteroaryl)alkyl, with the proviso that $R^{1a}$ and $R^{1b}$ cannot both be hydrogen;

$R^{1c}$ is alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, or (heteroaryl)alkyl;

$R^3$ is $C_{1-6}$ lower alkyl, cycloalkyl, phenyl, substituted phenyl, $(CH_2)_nNH_2$, $(CH_2)_nNHCOR^9$, $(CH_2)_nN(C=NH)NH_2$, $(CH_2)_nCO_2R^2$, $(CH_2)_nOR^{10}$, $(CH_2)_mSR^{11}$, $(CH_2)_n$cycloalkyl, $(CH_2)_n$phenyl, $(CH_2)_n$(substituted phenyl), $(CH_2)_n$(1 or 2-naphthyl) or $(CH_2)_n$(heteroaryl), wherein heteroaryl includes pyridyl, thienyl, furyl, thiazolyl, imidazolyl, pyrazolyl, isoxazolyl, pyrazinyl, pyrimidyl, triazinyl, tetrazolyl, and indolyl;

$R^{3a}$ is hydrogen or methyl, or $R^3$ and $R^{3a}$ taken together are $-(CH_2)_d-$ where d is an interger from 2 to 6;

$R^4$ is phenyl, substituted phenyl, $(CH_2)_m$phenyl, $(CH_2)_m$(substituted phenyl), cycloalkyl, or benzofused cycloalkyl;

$R^5$ is hydrogen, lower alkyl, cycloalkyl, phenyl, substituted phenyl, $(CH_2)_n$cycloalkyl, $(CH_2)_n$phenyl, $(CH_2)_n$(substituted phenyl), or $(CH_2)_n$(1 or 2-naphthyl);

$R^6$ is hydrogen, fluorine, oxo, lower alkyl, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{10}$, $SR^{11}$ or $NHCOR^9$;

$R^7$ is hydrogen, oxo (i.e., =O), lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

$R^8$ is lower alkyl, cycloalkyl, $(CH_2)_n$cycloalkyl, $(CH_2)_n$phenyl, $(CH_2)_n$(substituted phenyl), $(CH_2)_n$(1 or 2-naphthyl), or $COR^9$;

$R^9$ is hydrogen, lower alkyl, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{12}$, or $NR^{13}R^{14}$;

$R^{10}$ is hydrogen, lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

Fig. 17(q)

$R^{11}$ is lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

$R^{12}$ is lower alkyl, cycloalkyl, $(CH_2)_n$cycloalkyl, $(CH_2)_n$phenyl, $(CH_2)_n$(substituted phenyl), or $(CH_2)_n$(1 or 2-naphthyl);

$R^{13}$ is hydrogen, lower alkyl, cycloalkyl, phenyl, substituted phenyl, naphthyl, substituted naphthyl, $(CH_2)_n$cycloalkyl, $(CH_2)_n$phenyl, $(CH_2)_n$(substituted phenyl), or $(CH_2)_n$(1 or 2-naphthyl);

$R^{14}$ is hydrogen or lower alkyl;

or $R^{13}$ and $R^{14}$ taken together form a five to seven membered carbocyclic or heterocyclic ring, such as morpholine, or N-substituted piperazine;

$R^{15}$ is phenyl, substituted phenyl, naphthyl, substituted naphthyl, heteroaryl, $(CH_2)_n$phenyl, $(CH_2)_n$(substituted phenyl), $(CH_2)_n$(1 or 2-naphthyl), or $(CH_2)_n$(heteroaryl);

$R^{16}$ and $R^{17}$ are independently lower alkyl, cycloalkyl, phenyl, substituted phenyl, naphthyl, phenylalkyl, substituted phenylalkyl, or (cycloalkyl)alkyl;

$R^{18}$ and $R^{19}$ are independently hydrogen, alkyl, phenyl, substituted phenyl, $(CH_2)_n$phenyl, $(CH_2)_n$(substituted phenyl), or $R^{18}$ and $R^{19}$ taken together are —(CH=CH)$_2$—;

$R^{20}$ is hydrogen, alkyl, phenyl, substituted phenyl, $(CH_2)_n$phenyl, $(CH_2)_n$(substituted phenyl);

$R^{21}$, $R^{22}$ and $R^{23}$ are independently hydrogen, or alkyl;

X is $CH_2$, $(CH_2)_2$, $(CH_2)_3$, or S;

$Y^1$ is O or $NR^{23}$;

$Y^2$ is $CH_2$, O, or $NR^{23}$;

a is 0 or 1 and b is 1 or 2, provided that when a is 1 then b is 1;

c is 1 or 2, provided that when c is 1 then a is 0 and b is 1;

m is 1 or 2; and n is 1, 2, 3 or 4;

or a pharmaceutically acceptable salt thereof.

Fig. 17(r)

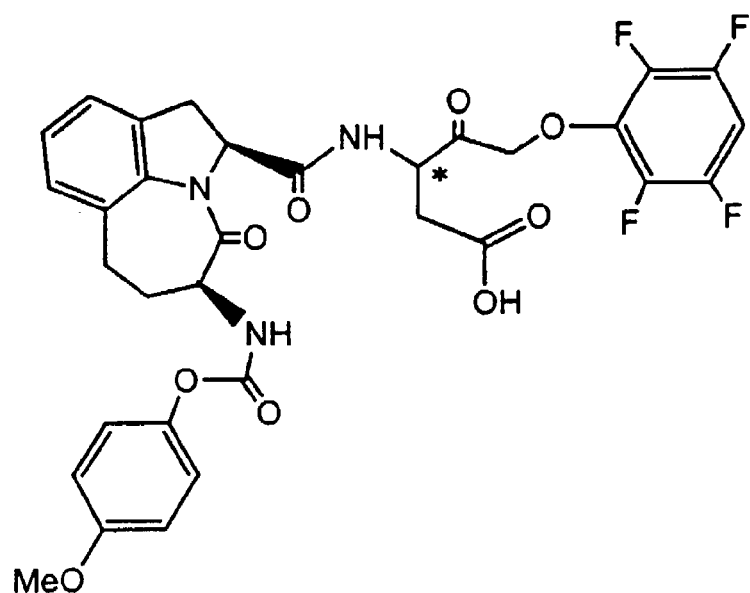
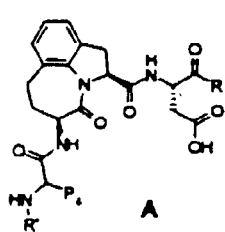
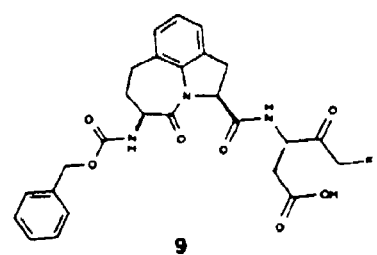
P = amino acid
Fig. 18(a)

G(n=1)

H(n=2)

fmk = fluoromethyl ketone

| Compound | Formula |
|---|---|
| 1 | 1-naphthylO Ac -E- Asp-aldehyde |
| 2 | z-F-Asp-aldehyde |
| 3 | z-E-D- Asp- fmk |
| 4 | (1-Naphthyl)O Ac-E- Asp-fmk |
| 5 | z-Glu(tetrazolyl)-Glu-D-CH2O(F2-Ph) |
| 6 | z-G- Asp-aldehyde |
| 7 | acetyl-G- Asp-aldehyde |
| 8 | z-Asp-G-aldehyde |
| 9 | z-G- Asp-fmk |
| 10 | z-G-Asp-CH2OPOPh2 |
| 11 | z-G-Asp-CH2O(2,3,5,6-F4Ph) |

G (n=1)

R-G-Asp-tfpmk analogues (tfpmk = tetra fluoro phenoxy methyl ketone)

| Compound | "R" group |
|---|---|
| 12 | (l-Naphthyl)CH2CO |
| 13 | PhCH2CO |
| 14 | PropargylOCO |
| 15 | 3,4,5-(MeO)3PhOCO |
| 16 | 3,4-MethylenedioxyPhOCO |
| 17 | 4-CH3OPHOCO |
| 18 | 4-CH3OBenzylNCO |
| 19 | PhSCO |
| 20 | F3COPhSO2 |
| 21 | Me2NS02 |
| 22 | Ph2PO |

2. A compound of formula I:

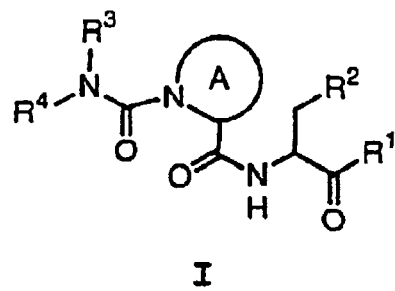

I wherein:

Ring A is an optionally substituted piperidine, tetrahydroquinoline or tetrahydroisoquinoline ring;

$R^1$ is hydrogen, CN, CHN2/ R> or CH2Y;

R is an optionally substituted group selected from an aliphatic group, an aryl group, or an aralkyl group;

Y is an electronegative leaving group;

$R^2$ is CO2H, CH2CO2H, or esters, amides or isosteres thereof; and $R^3$ is hydrogen, an optionally substituted aryl group, an optionally substituted aralkyl group or an optionally substituted Ci_6 aliphatic group, R4 is an optionally substituted group selected from an aryl group or a heterocyclyl group, or R3 and R4 taken together with the nitrogen to which they, are attached optionally form a substituted or unsubstituted monocyclic, bicyclic or tricyclic ring.

3. The compound according to claim 1 having one or more features selected from the group consisting of:

(a) R1 is CH2Y where Y is an electronegative leaving group;

(b) R2 is CO2H , esters, amides or isosteres thereof; and

Fig. 19(a)

(c) $R^3$ is a hydrogen atom, an optionally substituted aryl group, an optionally substituted aralkyl group or an optionally substituted $C_{1-6}$ aliphatic group, $R^4$ is an optionally substituted group selected from an aryl group or a heterocyclyl group, or $R^3$ and $R^4$, taken together with the nitrogen to which they are attached, optionally form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine, purine, quinolizine, quinoline, isoquinoline, cinnoline, phthalazine, guinazoline, guinoxaline, 1,8-naphthyridine, pteridine, quinuclidine, and phenazine.

4. The compound of claim 2, wherein:

(a) $R^1$ is $CH_2Y$ where Y is an electronegative leaving group;

(b) $R^2$ is $CO_2H$, esters, amides or isosteres thereof; and (c) $R^3$ is a hydrogen atom, an optionally substituted aryl group, an optionally substituted aralkyl group or an optionally substituted $C_{1-6}$ aliphatic group, $R^4$ is an optionally substituted group selected from an aryl group, or a heterocyclyl group; or $R^3$ and $R^4$, taken together with the nitrogen to which they are attached, optionally form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline,

Fig. 19(b)

pyrazolidine, triazole, piperidine, morpholine, thiomorpholine, piperazine, carbazole, phenothiazine, phenoxazine, phenanthridine, acridine, purine, quinolizine, quinoline, isoquinoline, cinnoline, phthala z ine, quinazoline, guinoxaline, 1,8-naphthyri dine, pteridine, quinuclidine, and phenazine.

5. The compound according to claim 3 wherein -$CH_2Y$ is -$CH_2F$.

6. The compound according to claim 4 wherein $R^3$ and $R^4$, taken together with the nitrogen to which they are attached, form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine. purine, quinolizine, quinoline, isoquinoline, cinnoline, phthalazine, quinazoline, quinoxaline, 1,8-naphthyridine, pteridine, quinuclidine, and phenazine.

Fig. 19(c)

Table 1. Representative Compounds

| No. | R¹ | R² | Ring A Type | R³R⁴N- |
|---|---|---|---|---|
| I-1 | $CH_2F$ | $CO_2H$ | Ia | phenothiazinyl |
| I-2 | $CH_2F$ | $CO_2H$ | Ia | chloro-phenothiazinyl |
| I-3 | $CH_2F$ | $CO_2H$ | Ia | chloro-phenothiazinyl |

| No. | R¹ | R² | Ring A Type | R³R⁴N- |
|---|---|---|---|---|
| I-4 | $CH_2F$ | $CO_2H$ | Ia | 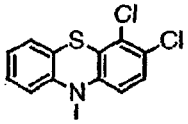 |
| I-5 | $CH_2F$ | $CO_2H$ | Ia | 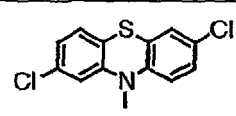 |
| I-6 | $CH_2F$ | $CO_2H$ | Ia | 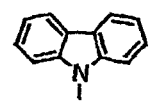 |
| I-7 | $CH_2F$ | $CO_2H$ | Ia | 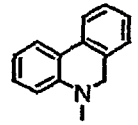 |
| I-8 | $CH_2F$ | $CO_2H$ | Ia | 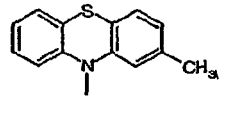 |
| I-9 | $CH_2F$ | $CO_2H$ | Ia | 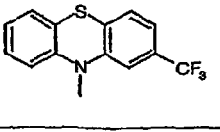 |
| I-10 | $CH_2F$ | $CO_2H$ | Ia | 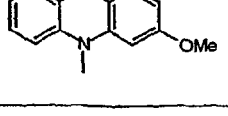 |
| I-11 | $CH_2F$ | $CO_2NH_2$ | Ia | 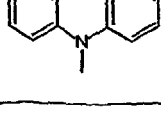 |
| I-12 | $CH_2F$ | $CO_2NHEt$ | Ia | 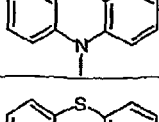 |
| I-13 | $CH_2F$ | $CO_2NEt_2$ | Ia |  |
Fig. 19(e)

| No. | $R^1$ | $R^2$ | Ring A Type | $R^3R^4N-$ |
|---|---|---|---|---|
| I-14 | $CH_2F$ | $CONHCH_2CH_2N(CH_3)_2$ | Ia | 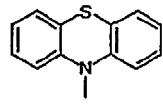 |
| I-15 | $CH_2F$ | $CO_2H$ | Ib | 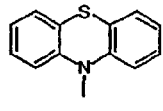 |
| I-16 | $CH_2F$ | $CO_2H$ | Ic | 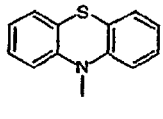 |
| I-17 | $CH_2F$ | $CO_2H$ | Ib | 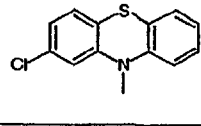 |
| I-18 | $CH_2F$ | $CO_2H$ | Ic | 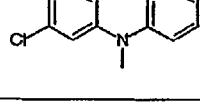 |
| I-19 | $CH_2F$ | $CO_2H$ | Ia | 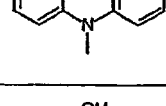 |
| I-20 | $CH_2F$ | $CO_2H$ | Ia | 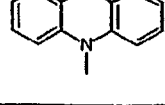 |
| I-21 | $CH_2F$ | $CO_2H$ | Ia | 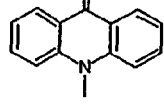 |
| I-22 | $CH_2F$ | $CO_2H$ | Ia | 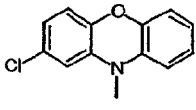 |
Fig. 19(f)

| No. | R$^1$ | R$^2$ | Ring A Type | R$^3$R$^4$N- |
|---|---|---|---|---|
| I-23 | CH$_2$F | CO$_2$H | Ia | 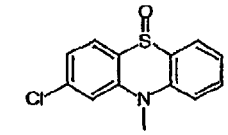 |
| I-24 | CH$_2$F | CO$_2$H | Ia | 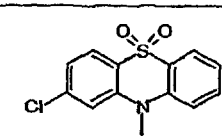 |
| I-25 | CH$_2$F | CO$_2$H | Ia | 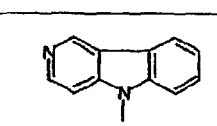 |
| I-26 | CH$_2$F | CO$_2$H | Ia | 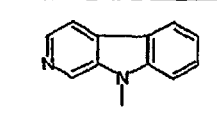 |
| I-27 | CH$_2$F | CO$_2$H | Ia |  |
| I-28 | CH$_2$F | CO$_2$H | Ia | 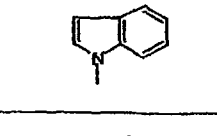 |
| I-29 | CH$_2$F | CO$_2$H | Ia | 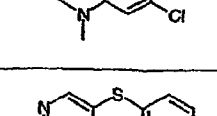 |
| I-30 | CH$_2$F | CO$_2$H | Ia | 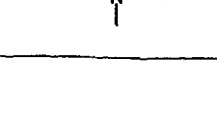 |
Fig. 19(g)

1. A compound of the formula I:

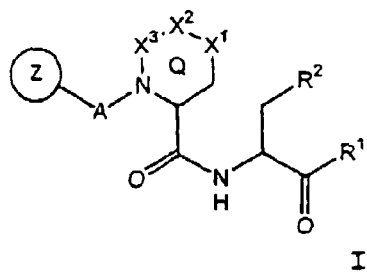

wherein:

$R^1$ is hydrogen, CN, CHN$_2$, R, or -CH$_2$Y;

R is an aliphatic group, a substituted aliphatic group, an aryl group, a substituted aryl group, an aralkyl group, a substituted aralkyl group, a non-aromatic heterocyclic group, or a substituted non-aromatic heterocyclic group;

Y is an electronegative leaving group, -OR, -SR, -OC=O(R), or -OPO(R$^3$)(R$^4$);

$R^3$ and $R^4$ are independently R or OR;

$R^2$ is CO$_2$H, CH$_2$CO$_2$H, or optionally substituted esters, amides or isosteres thereof;

A is C=O or SO$_2$;

$X^1$ is oxygen, sulfur, -NH, or -CH$_2$, wherein -NH is optionally substituted by an alkyl group, a cycloalkyl group, a(cycloalkyl)alkyl group, an amino acid N-terminal protecting group, or COR and -CH2 is optionally substituted by fluorine, an alkyl group, a cycloalkyl group, a(cycloalkyl)alkyl group, an aralkyl group, an aryl group, an alkyloxy group, an

Fig. 20(a)

alkylthioxy group, an aryloxy group, an arylthioxy croup, an oxo croup(i.e., «O), or a NHCOR group;

$X^2$ is oxygen, sulfur, -NH, or -$CK_2$, wherein -NH is optionally substituted by an alkyl group, or an amino acid N-terminal protecting group and -CKj is optionally substituted by an alkyl group, an aryl group, an alkyloxy group, an alkylthioxy group, an aryloxy group, an arylthioxy group, or an oxo(i.e., =O)group, a KHCOR group; $X^1$ and $X^2$ optionally form part of a phenyl ring that is fused to the adjoining ring Q;

$X^3$ is $CH_2$ or $X^2$ and $X^3$ optionally form part of a phenyl ring that is fused to the adjoining ring Q, provided that when $X^2$ forms a ring with $X^3$, then $X^2$ does not form a ring with $X^1$;

any two hydrogens attached to adjacent positions in ring Q are optionally replaced by a double bond; and Z is an optionally substituted ring selected from the group consisting of a carbocyclic, an aryl, a saturated heterocycle, a partially saturated heterocycle, and a heteroaryl wherein the ring is connected to A at a ring carbon;

or a pharmaceutically acceptable derivative thereof.

2. The compound of claim 1 wherein $R^1$ is $CH_2Y$ and Y is F, OR, SR, or -OC(=O)(R).

3. The compound of claim 2 wherein Y is F.

4. The compound of claim 2 wherein $R^2$ is $CO_2H$, an ester, amide, or carboxylic acid isostere.

Fig. 20(b)

5. The compound of claim 4 wherein $R^2$ is $CO_2H$.

6. The compound of claim 4 wherein $X^1$ and $X^2$ are each $CH_2$, or $X^1$ and $X^2$ combine to form part of an optionally substituted phenyl ring fused to ring Q.

7. The compound of claim 6 wherein $X^1$ and $X^2$ are each $CH_2$.

8. The compound of claim 7 wherein A is CO.

9. The compound of claim 8 wherein Z is an optionally substituted aryl which is connected to A at a ring carbon.

10. The compound of claim 1 selected from Table 1 below:

Table 1. Representative Compounds

| No. | Z |
|---|---|
| 1 | 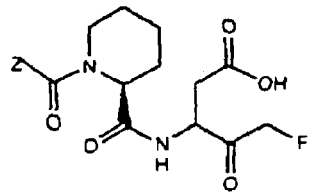 |

Fig. 20(c)

REGULATION OF TNF-ALPHA

CROSS-REFERENCE TO RELATED APPLICATION

This application claims the benefit of U.S. provisional application No. 60/374,434 filed Apr. 19, 2002 which is hereby incorporated by reference herein in its entirety.

FIELD OF THE INVENTION

This invention relates to compounds and pharmaceutical compositions that regulate TNF-alpha levels and activity and methods for using them. The invention also relates to kits comprising a compound or pharmaceutical composition of this invention and a tool for measuring TNF-alpha levels and/or activity.

BACKGROUND OF THE INVENTION

Generally, the term tumor necrosis factor (TNF) refers to two closely related cytokines (encoded by separate genes) known as tumor necrosis factor-alpha (TNF, cachectin) and tumor necrosis factor-beta (lymphotoxin, TNF-beta). Both cytokines interact with the same cell membrane receptors, and both have been implicated as pathogenic mediators of human illness.

TNF-alpha participates in the signaling pathways that regulate cell apoptosis and inflammation. TNF-alpha is also known as TNFSF2, TNFA and DIF. TNF-alpha is a pro-inflammatory mammalian protein capable of inducing cellular effects by virtue of its interaction with specific cellular receptors. It is produced primarily by activated monocytes and macrophages. Lipopoly-sacccharide (LPS, also called endotoxin), derived from the cell wall of gram negative bacteria, is a potent stimulator of TNF-alpha synthesis.

Due to the deleterious effects which can result from an over-production or an unregulated production of TNF-alpha, considerable efforts have been made to regulate the tissue or serum level of TNF-alpha. The pathology of a number of diseases are affected by TNF-alpha, including, restinosis, inflammatory diseases of the central nervous system, demyelinating diseases of the nervous system, multiple sclerosis, septic arthritis, aneurysmal aortic disease, traumatic joint injury, periodontal disease, macular degeneration, diabetic retinopathy, occular inflammation, keratoconus, Sjogren's syndrome, corneal graft rejection, cachexia, and anorexia.

While a number of inhibitors of TNF-alpha levels and activity have been reported, it is not clear whether they possess the appropriate pharmacological properties to be therapeutically useful. Therefore, there is a continued need for small molecule TNF-alpha inhibitors that are potent, stable, and have good penetration through membranes to provide effective inhibition of apoptosis in vivo. Such compounds would be extremely useful in treating the aforementioned disease states where TNF-alpha cytokines play a role.

SUMMARY OF THE INVENTION

The present invention relates to compounds that are potent inhibitors of TNF activity. In addition, these compounds are expected to have improved cell penetration and pharmacokinetic properties and, as a consequence of their potency, have improved efficacy against diseases where caspases and/or TNF-alpha are implicated.

The invention also relates to methods for inhibiting the release of TNF-alpha from various cells and decreasing TNF-alpha levels or activity using the compounds and compositions of this invention. The invention also relates to methods for identifying agents useful for decreasing TNF-alpha levels or activity and treating TNF-alpha mediated diseases. The invention additionally relates to kits comprising the compounds and compositions disclosed herein and a tool for measuring TNF-alpha levels or activity.

BRIEF DESCRIPTION OF THE FIGURES

FIG. 1 depicts compounds and pharmaceutical compositions of this invention, which are depicted as a series of partial views extended over FIGS. 1 (a-f). FIGS. 1 (a-f), taken together in sequence, are intended to form one complete view of said compounds and pharmaceutical compositions, in which like reference characters and numbers therein refer to like parts throughout FIGS. 1 (a-f). Said compounds and compositions are also described in PCT Publication WO 00/55114.

FIGS. 2-1 (a) to 2-2 (8), taken together in sequence, are intended to form one complete view of said compounds and pharmaceutical compositions, in which like reference characters therein and numbers refer to like parts throughout FIGS. 2-1 (a) to 2-2 (s). Said compounds and compositions are also described in PCT Publication WO 00/55127.

FIG. 3 depicts compounds and pharmaceutical compositions of this invention, which are depicted as a series of partial views extended over FIGS. 3 (a-j). FIGS. 3 (a-j), taken together in sequence, are intended to form one complete view of said compounds and pharmaceutical compositions, in which like reference characters and numbers therein refer to like parts throughout FIGS. 3 (a-j). Said compounds and compositions are also described in PCT Publication WO 00/61542.

Figure 4C:
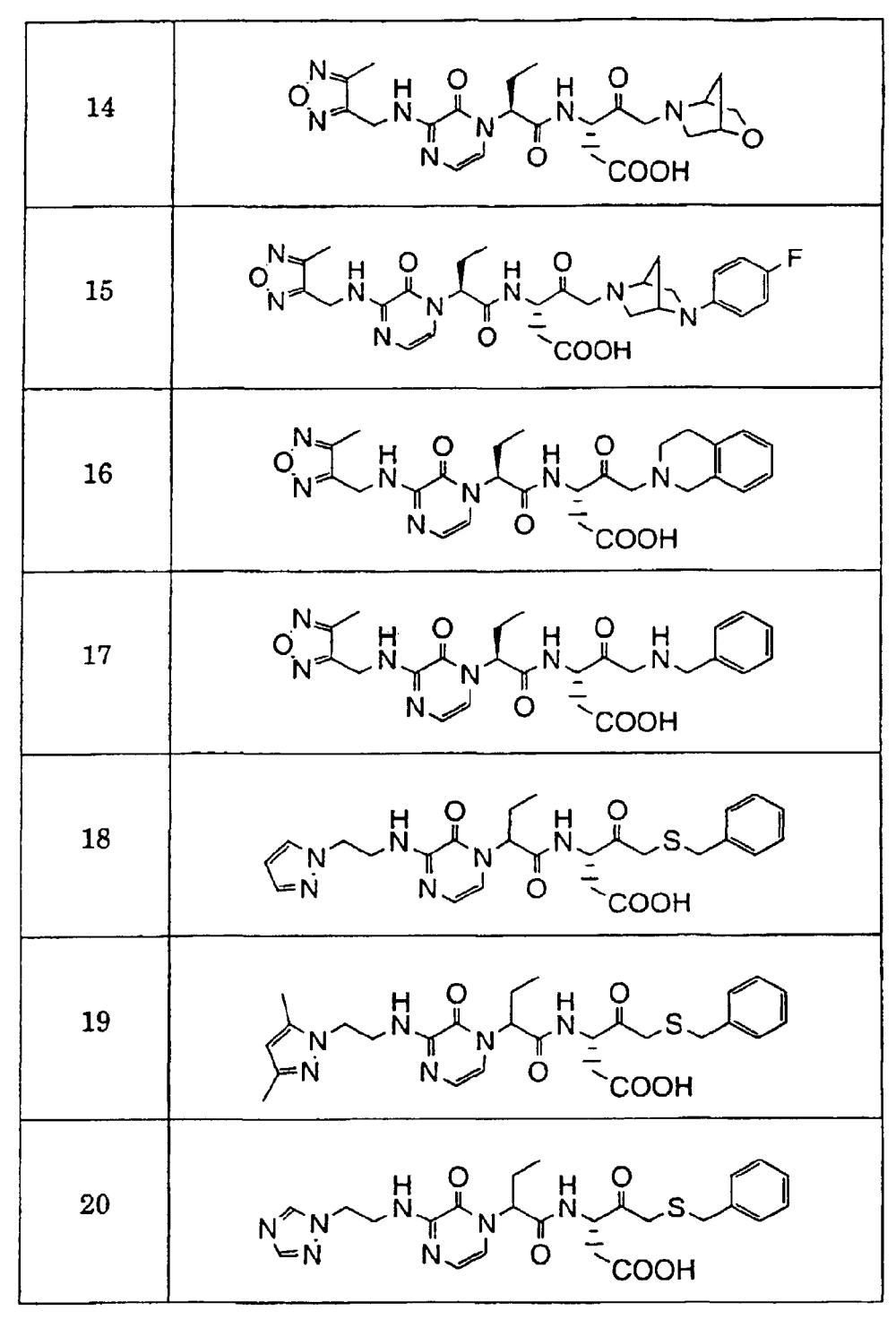
Figure 4D:
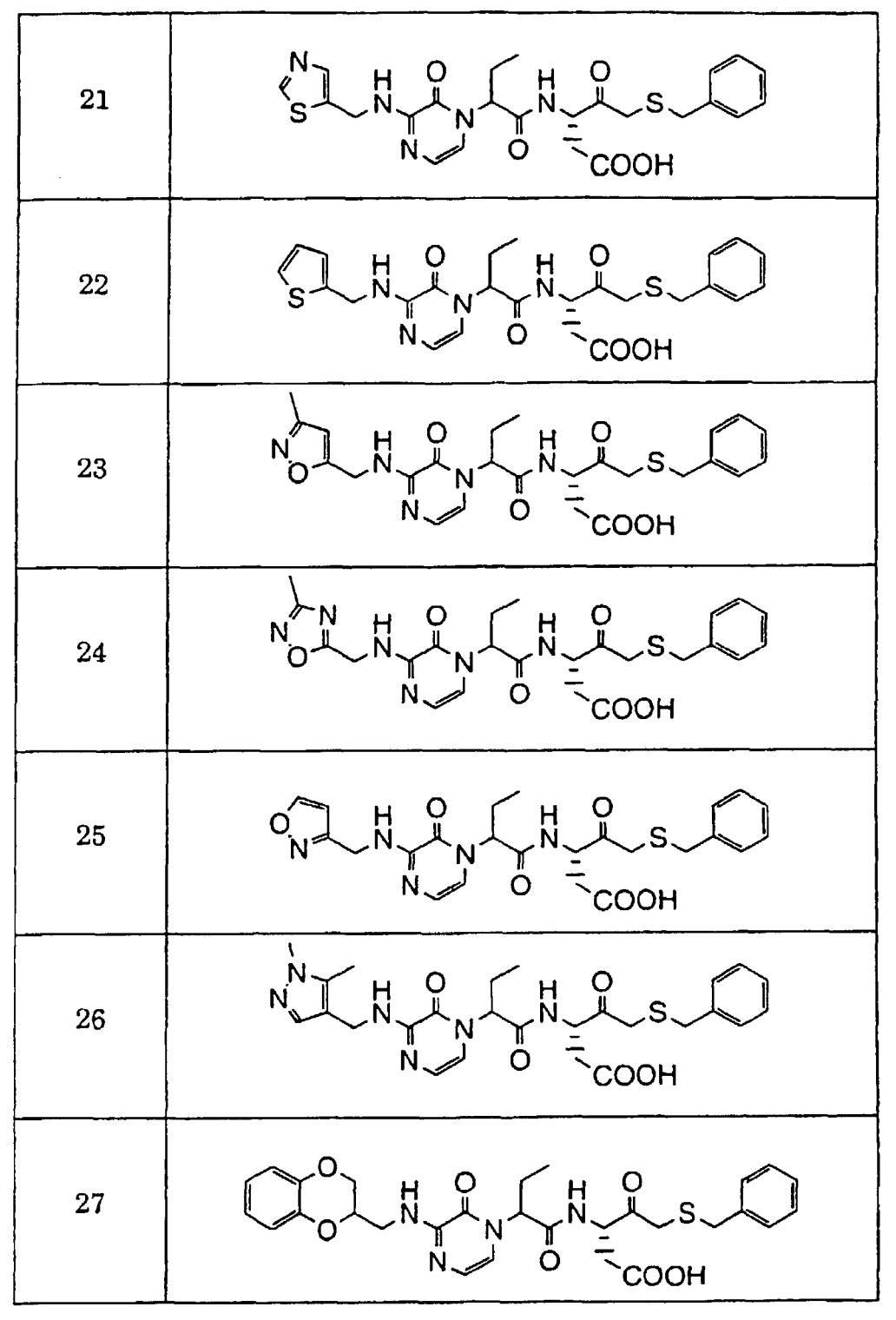
Figure 4G:
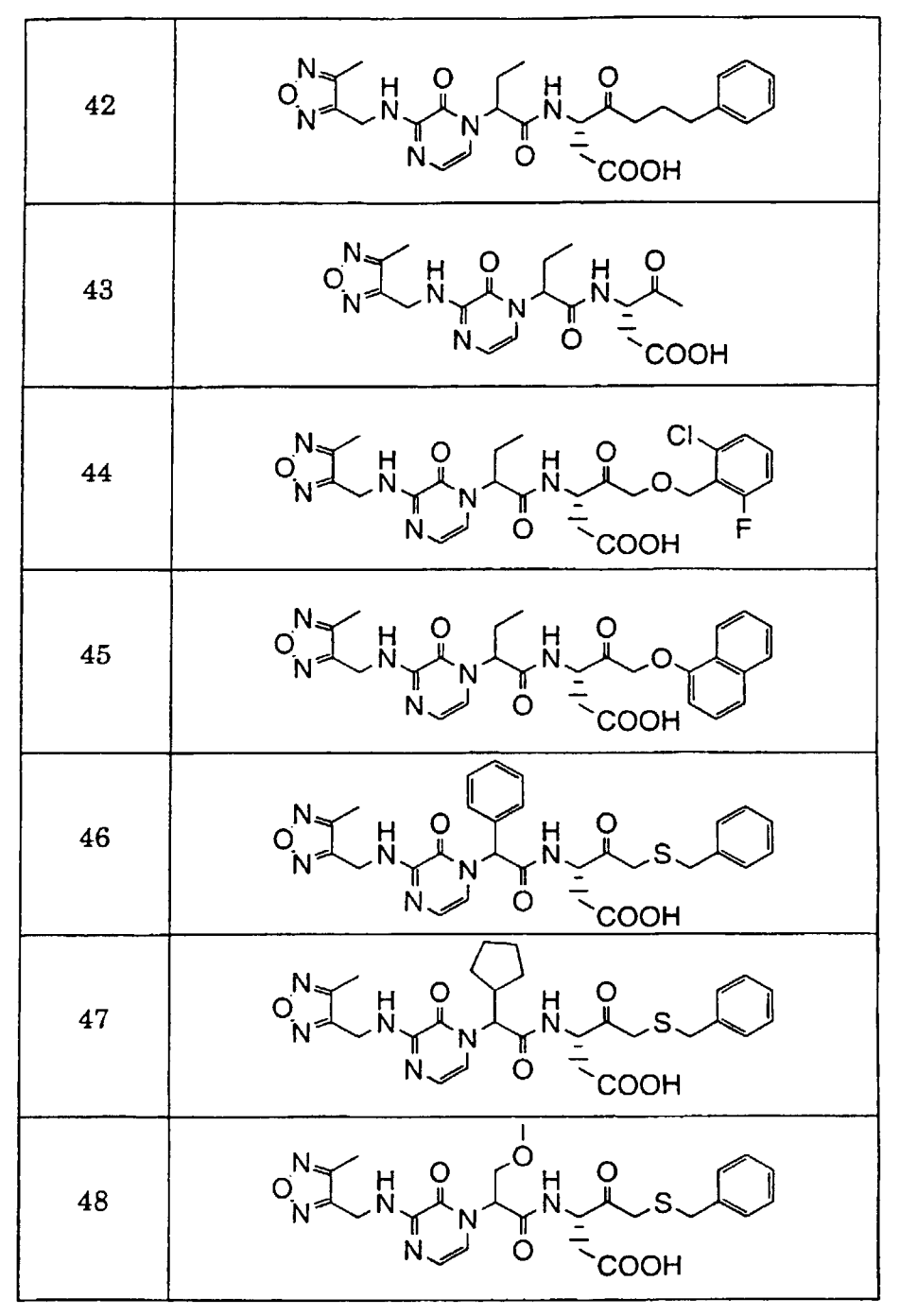
Figure 4H:
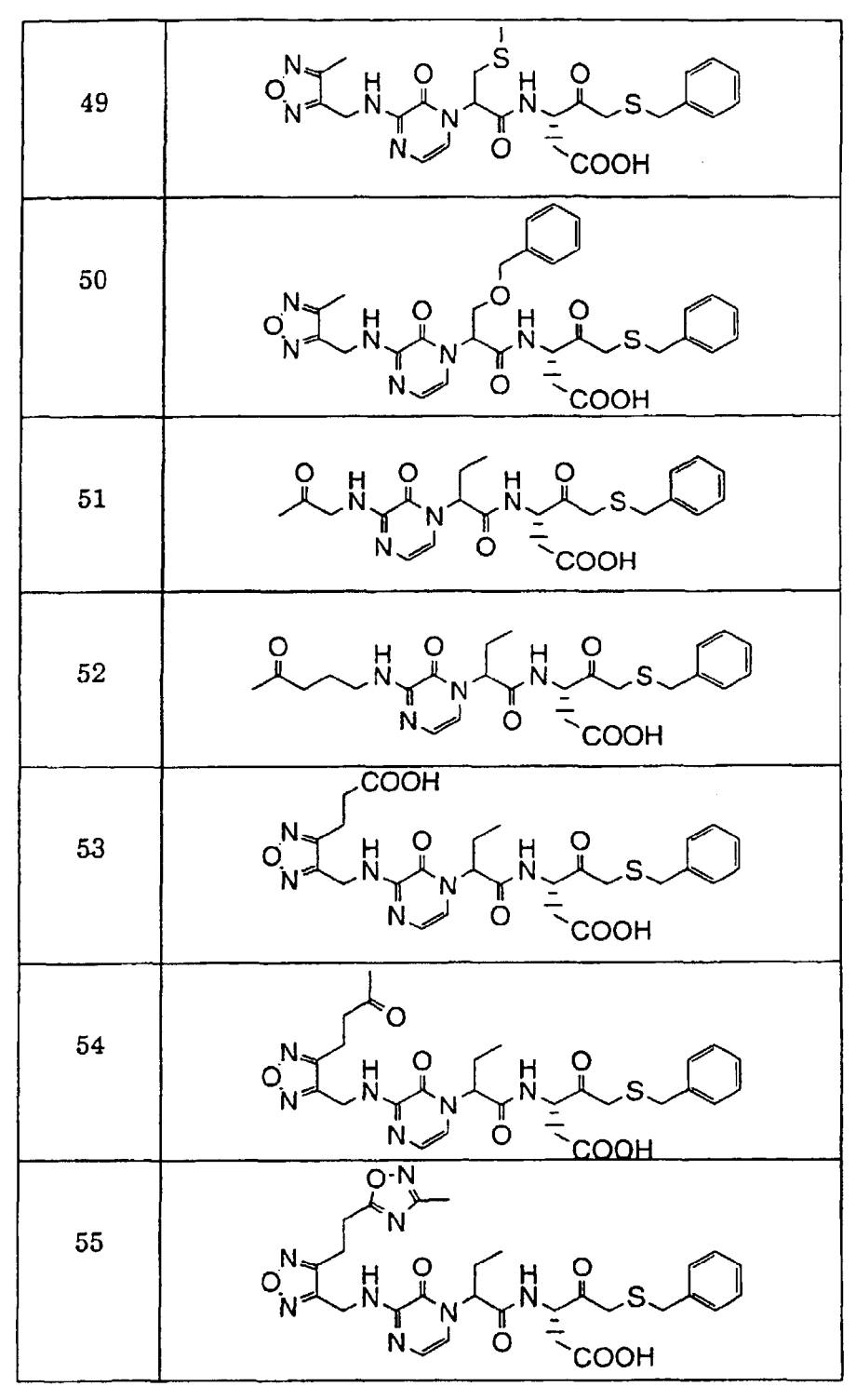
Figure 4I:
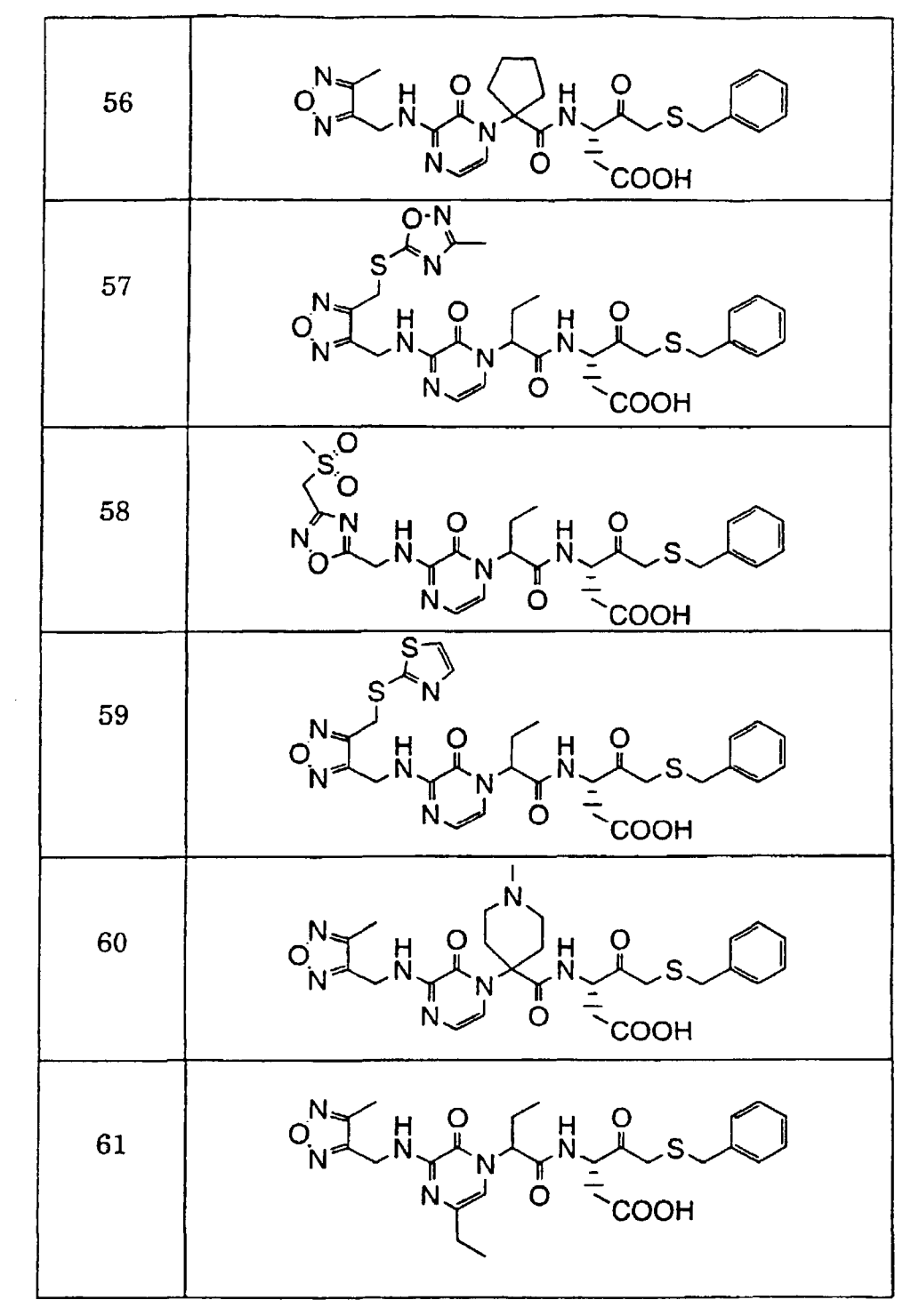

FIGS. 4 (a-v), taken together in sequence, are intended to form one complete view of said compounds and pharmaceutical compositions, in which like reference characters and numbers therein refer to like parts throughout FIGS. 4 (a-v). Said compounds and compositions are also described in PCT Publication WO 01/05772.

FIG. 5 depicts compounds and pharmaceutical compositions of this invention, which are depicted as a series of partial views extended over FIGS. 5 (a-c). FIGS. 5 (a-c), taken together in sequence, are intended to form one complete view of said compounds and pharmaceutical compositions, in which like reference characters and numbers therein refer to like parts throughout FIGS. 5 (a-c). Said compounds and compositions are also described in PCT Publication WO 01/10383.

FIG. 6 depicts compounds and pharmaceutical compositions of this invention, which are depicted as a series of partial views extended over FIGS. 6 (a-f). FIGS. 6 (a-f), taken together in sequence are intended to form one complete view of said compounds and pharmaceutical compositions, in which like reference characters and numbers therein refer to like parts throughout FIGS. 6 (a-f). Said compounds and compositions are also described in PCT Publication WO 01/16093.

FIG. 7 depicts compounds and pharmaceutical compositions of this invention, which are depicted as a series of partial views extended over FIGS. 7 (a-k). FIGS. 7 (a-k), taken together in sequence, are intended to form one complete view of said compounds and pharmaceutical compositions, in which like reference characters and numbers therein refer to like parts throughout FIGS. 7 (a-k). Said compounds and compositions are also described in PCT Publication WO 01/42216.

FIGS. 8 (a-h), taken together in sequence, are intended to form one complete view of said compounds and pharmaceutical compositions, in which like reference characters and numbers therein refer to like parts throughout FIGS. 8 (a-h). Said compounds and compositions are also described in PCT Publication WO 01/72707.

FIG. 9 depicts compounds and pharmaceutical compositions of this invention, which are depicted as a series of partial views extended over FIGS. 9 (a-e). FIGS. 9 (a-e), taken together in sequence, are intended to form one complete view of said compounds and pharmaceutical compositions, in which like reference characters and numbers therein refer to like parts throughout FIGS. 9 (a-e). Said compounds and compositions are also described in PCT Publication WO 01/90070.

FIGS. 10 (a-e), taken together in sequence, are intended to form one complete view of said compounds and pharmaceutical compositions, in which like reference characters and numbers therein refer to like parts throughout FIGS. 10 (a-e). Said compounds and compositions are also described in PCT Publication WO 01/94351.

Figure 11L:
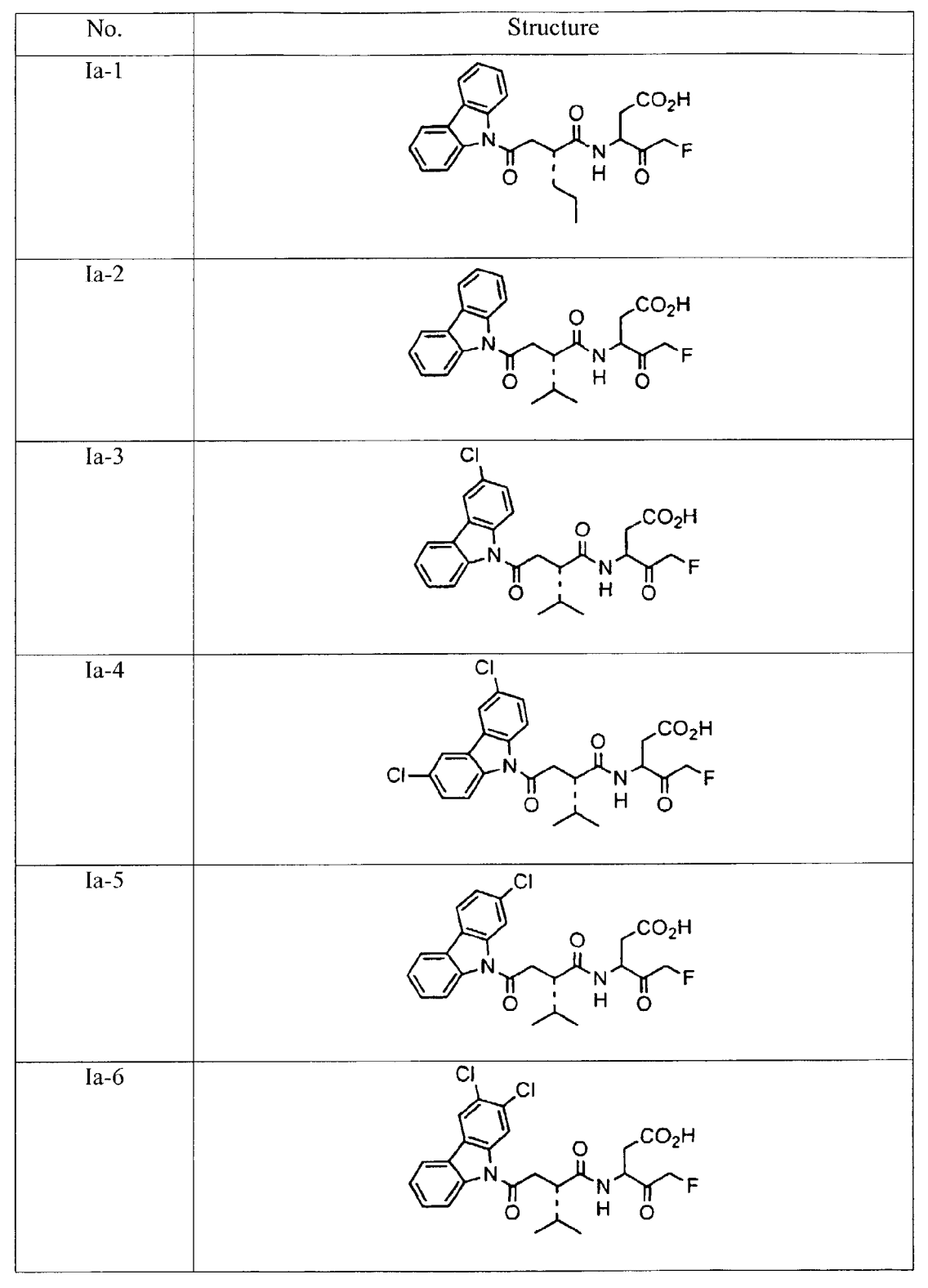
Figure 11N:
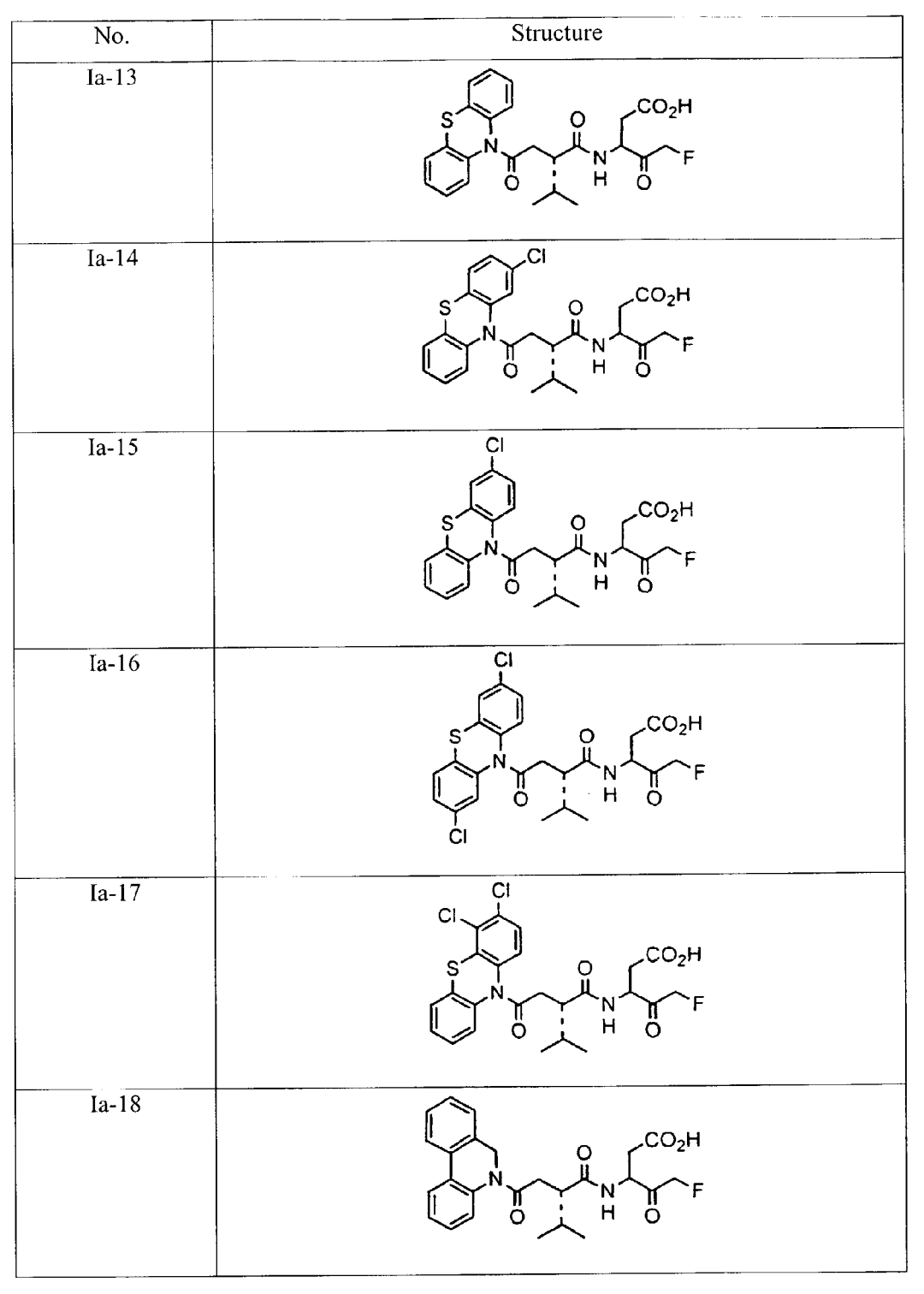
Figure 11O:
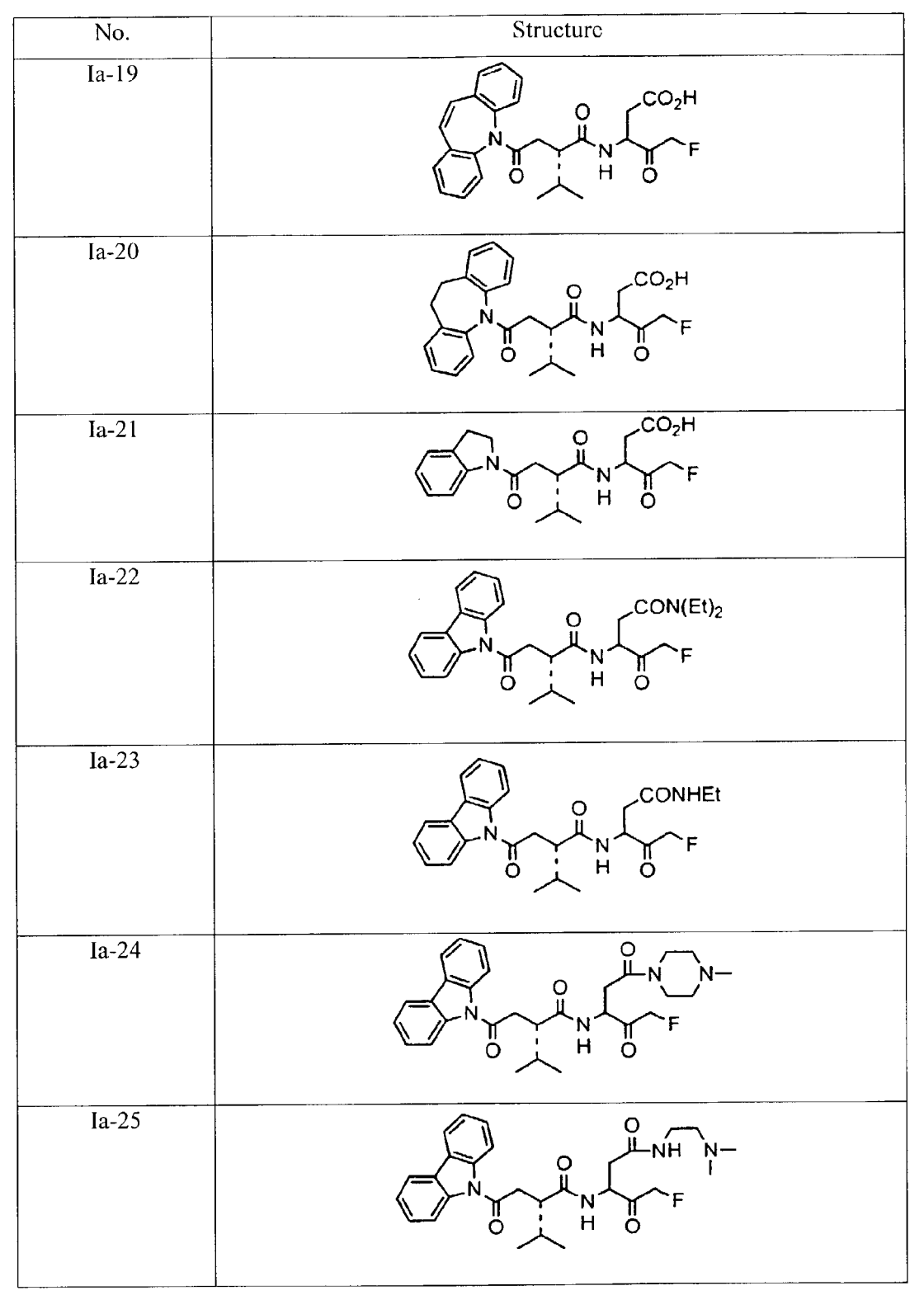
Figure 11R:
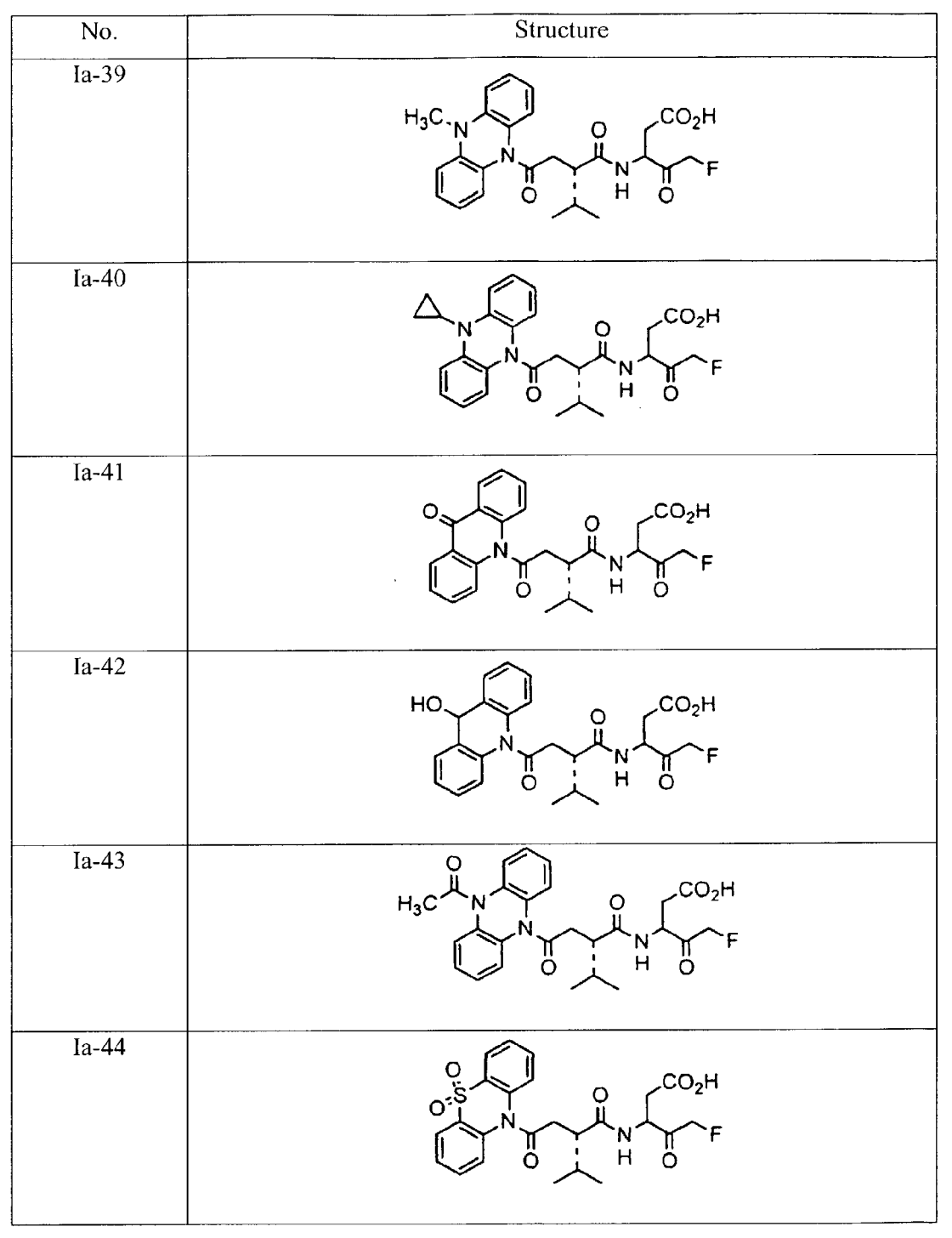

FIG. 11 depicts compounds and pharmaceutical compositions of this invention, which are depicted as a series of partial views extended over FIGS. 11 (a-s). FIGS. 11 (a-s), taken together in sequence, are intended to form one complete view of said compounds and pharmaceutical compositions, in which like reference characters and numbers therein refer to like parts throughout FIGS. 11 (a-s). Said compounds and compositions are also described in U.S. Patent Application 60/292,969 and PCT Publication WO 02/094263.

FIG. 12 depicts compounds and pharmaceutical compositions of this invention, which are depicted as a series of partial views extended over FIGS. 12 (a-c). FIGS. 12 (a-c), taken together in sequence, are intended to form one complete view of said compounds and pharmaceutical compositions, in which like reference characters and numbers therein refer to like parts throughout FIGS. 12 (a-c). Said compounds and compositions are also described in U.S. patent application Ser. No. 10/012,722 and PCT Publication WO 02/42278.

FIG. 13 depicts compounds and pharmaceutical compositions of this invention, which are depicted as a series of partial views extended over FIGS. 13 (a-c). FIGS. 13 (a-c), taken together in sequence, are intended to form one complete view of said compounds and pharmaceutical compositions, in which like reference characters and numbers therein refer to like parts throughout FIGS. 13 (a-c). Said compounds and compositions are also described in U.S. Pat. No. 6,184,210.

FIG. 14 depicts compounds and pharmaceutical compositions of this invention, which are depicted as a series of partial views extended over FIGS. 14 (a-j). FIGS. 14 (a-j) taken together in sequence, are intended to form one complete view of said compounds and pharmaceutical compositions, in which like reference characters and numbers therein refer to like parts throughout FIGS. 14 (a-j). Said compounds and compositions are also described in U.S. Pat. No. 6,184,244.

FIG. 15 depicts compounds and pharmaceutical compositions of this invention, which of partial views extended over FIGS. 15 (a-f). FIGS. 15 (a-f), taken together in sequence, are intended to form one complete view of said compounds and pharmaceutical compositions, in which like reference characters and numbers therein refer to like parts throughout FIGS. 15 (a-f). Said compounds and compositions are also described in U.S. Pat. No. 6,187,771.

FIG. 16 depicts compounds and pharmaceutical compositions of this invention, which are depicted as a series of partial views extended over FIGS. 16 (a-m). FIGS. 16 (a-m), taken together in sequence, are intended to form one complete view of said compounds and pharmaceutical compositions, in which like reference characters and numbers therein refer to like parts throughout FIGS. 16 (a-m). Said compounds and compositions are also described in U.S. Pat. No. 6,197,750.

FIGS. 17 (a-r), taken together in sequence, are intended to form one complete view of said compounds and pharmaceutical compositions, in which like reference characters and numbers therein refer to like parts throughout FIGS. 17 (a-r). Said compounds and compositions are also described in U.S. Pat. No. 6,242,422.

FIGS. 18 (a-c), taken together in sequence, are intended to form one complete view of said compounds and pharmaceutical compositions, in which like reference characters and numbers therein refer to like parts throughout FIGS. 18 (a-c). Said compounds and compositions were also described at the April 2001 American Chemical Society (ACS) meeting in San Diego, Calif., USA.

FIGS. 19 (a-g), taken together in sequence, are intended to form one complete view of said compounds and pharmaceutical compositions, in which like reference characters and numbers therein refer to like parts throughout FIGS. 19(a-g). Said compounds and compositions are also described in PCT Publication WO 02/22611 and in U.S. Patent Application Publication US2002/0058630.

FIGS. 20 (a-g), taken together in sequence, are intended to form one complete view of said compounds and pharmaceutical compositions, in which like reference characters and numbers therein refer to like parts throughout FIGS. 20 (a-g). Said compounds and compositions are also described in U.S. patent application Ser. No. 10/127324.

DETAILED DESCRIPTION OF THE INVENTION

Figures 1G, 2:
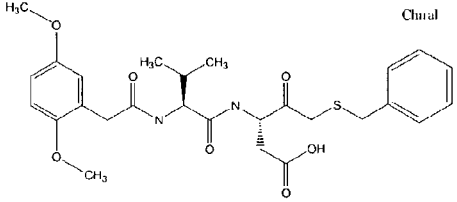
FIG. 2 depicts compounds and pharmaceutical compositions of this invention, which are depicted as a series of partial views extended over FIGS. 2-1 (a) to 2-2 (s).
Figures 1H, 2:
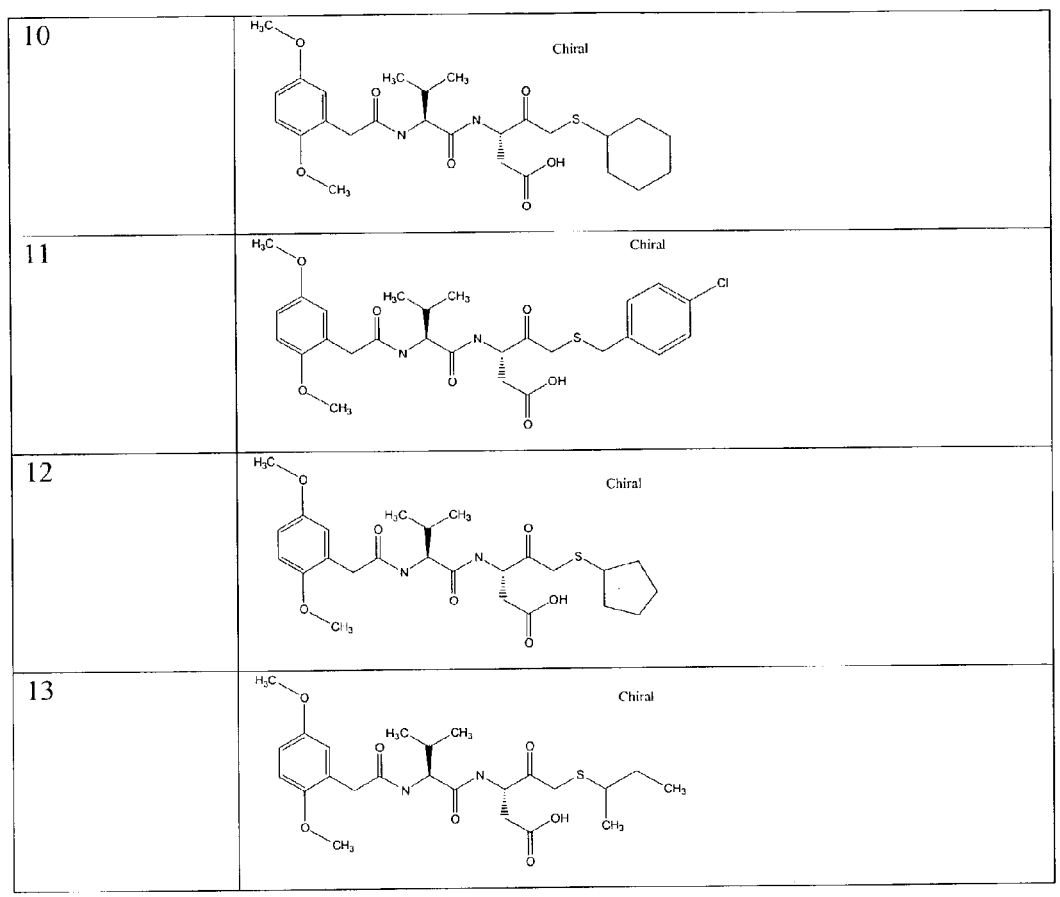
Figures 1I, 2:
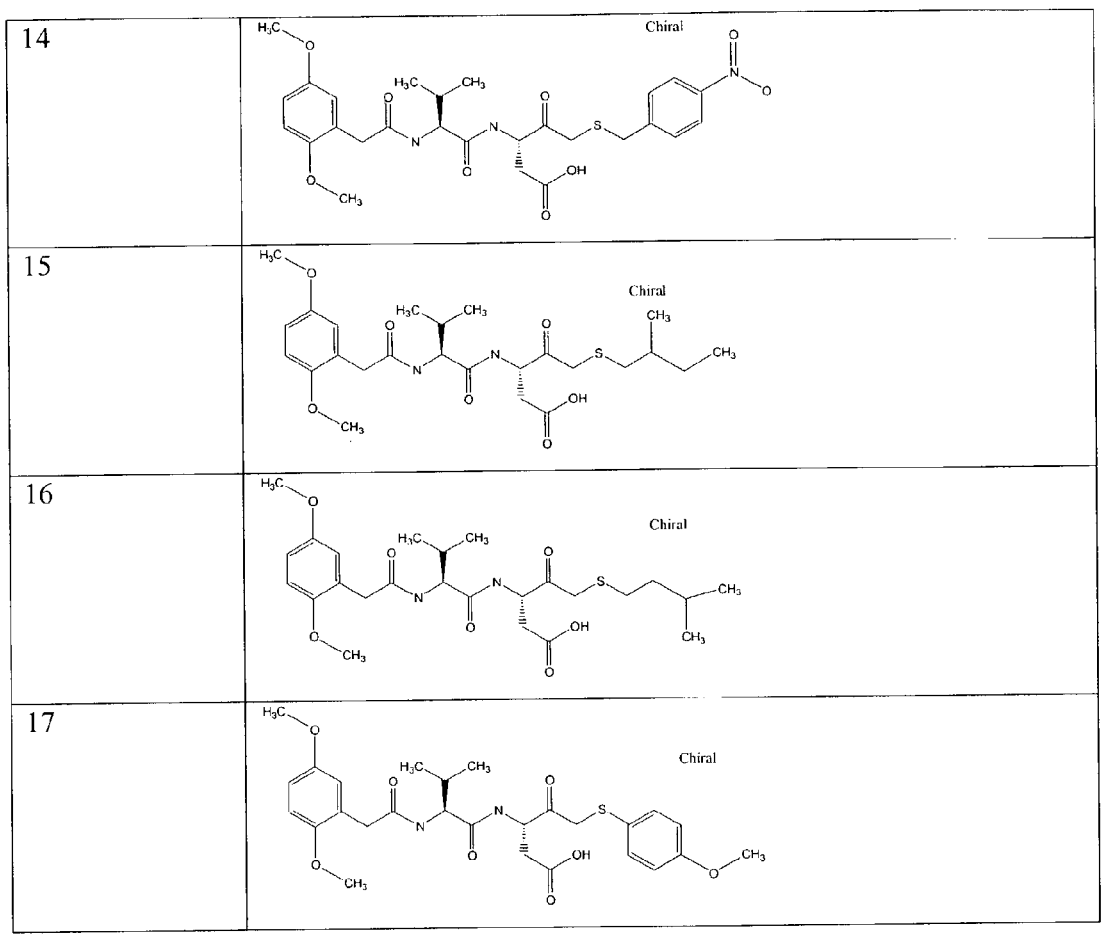
Figures 1K, 2:
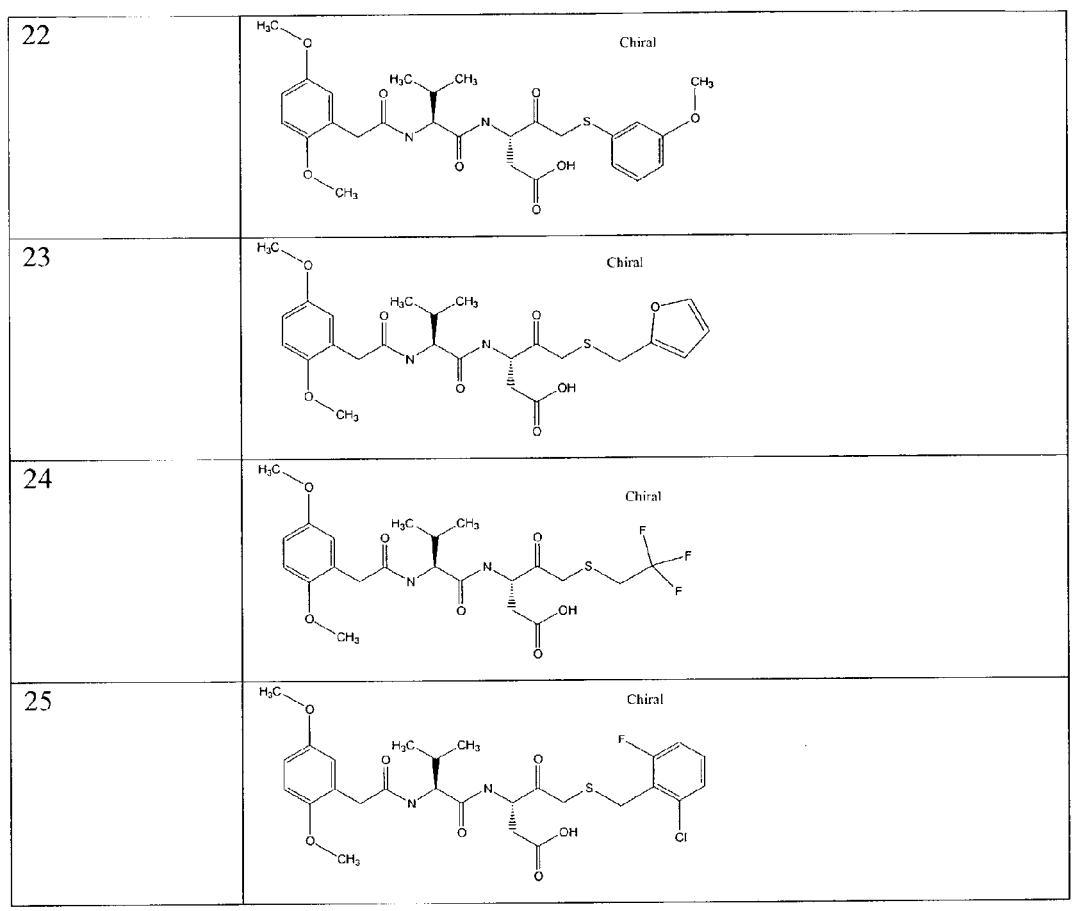
Figures 1M, 2:
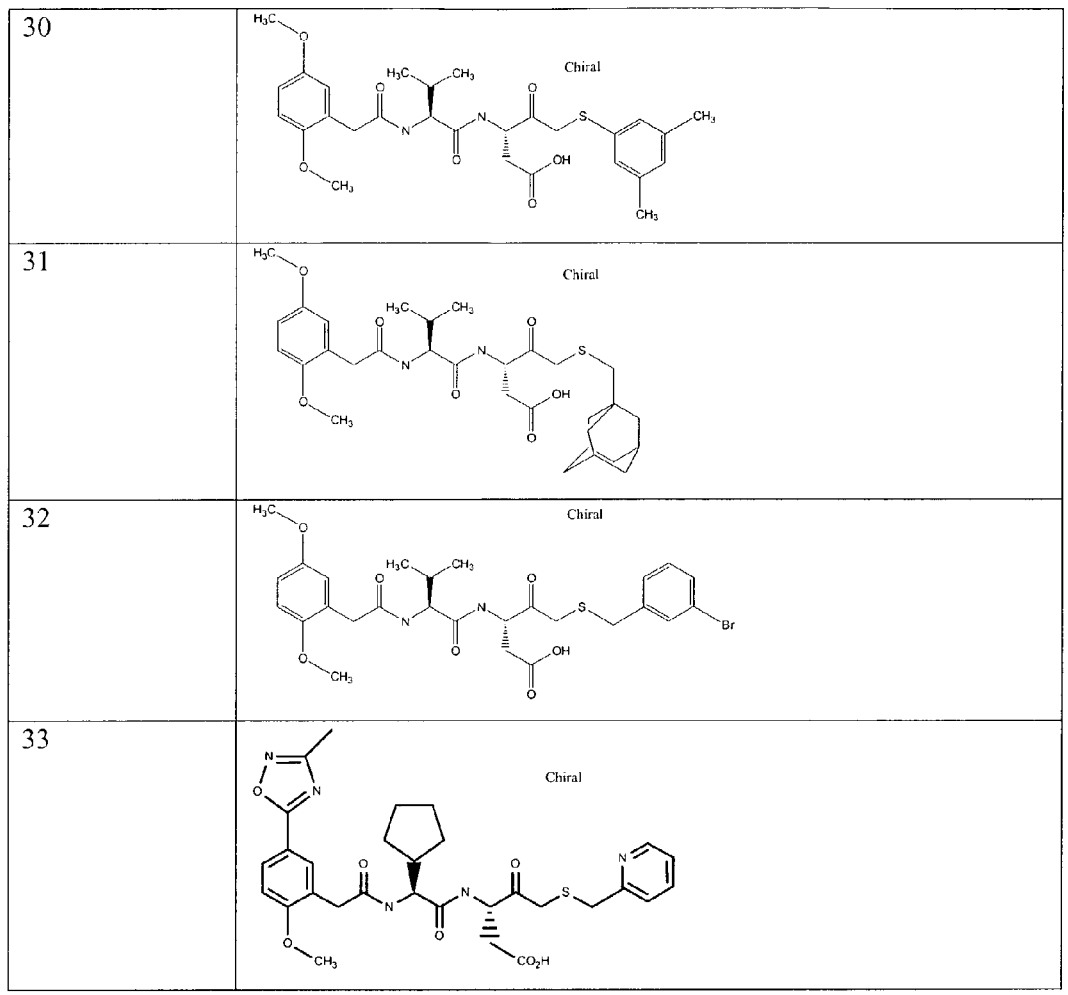
Figures 1O, 2:
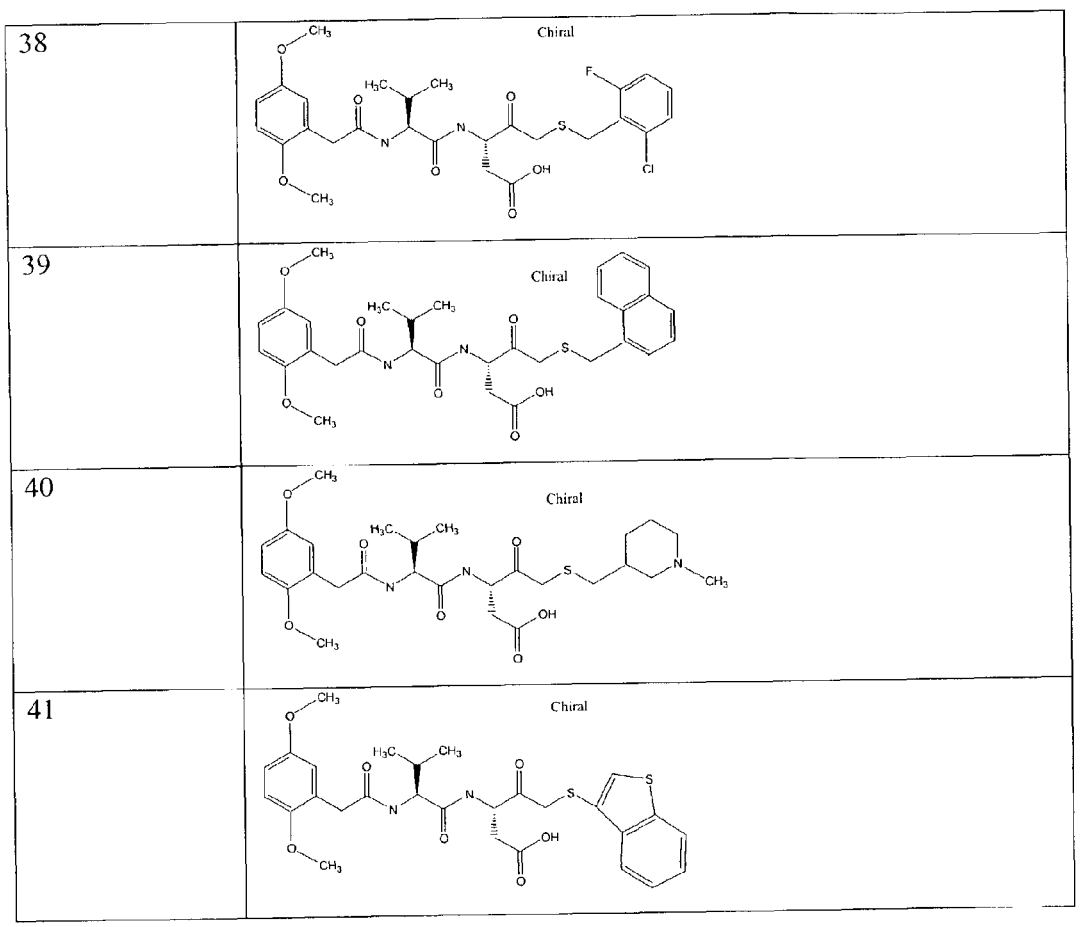
Figures 1P, 2:
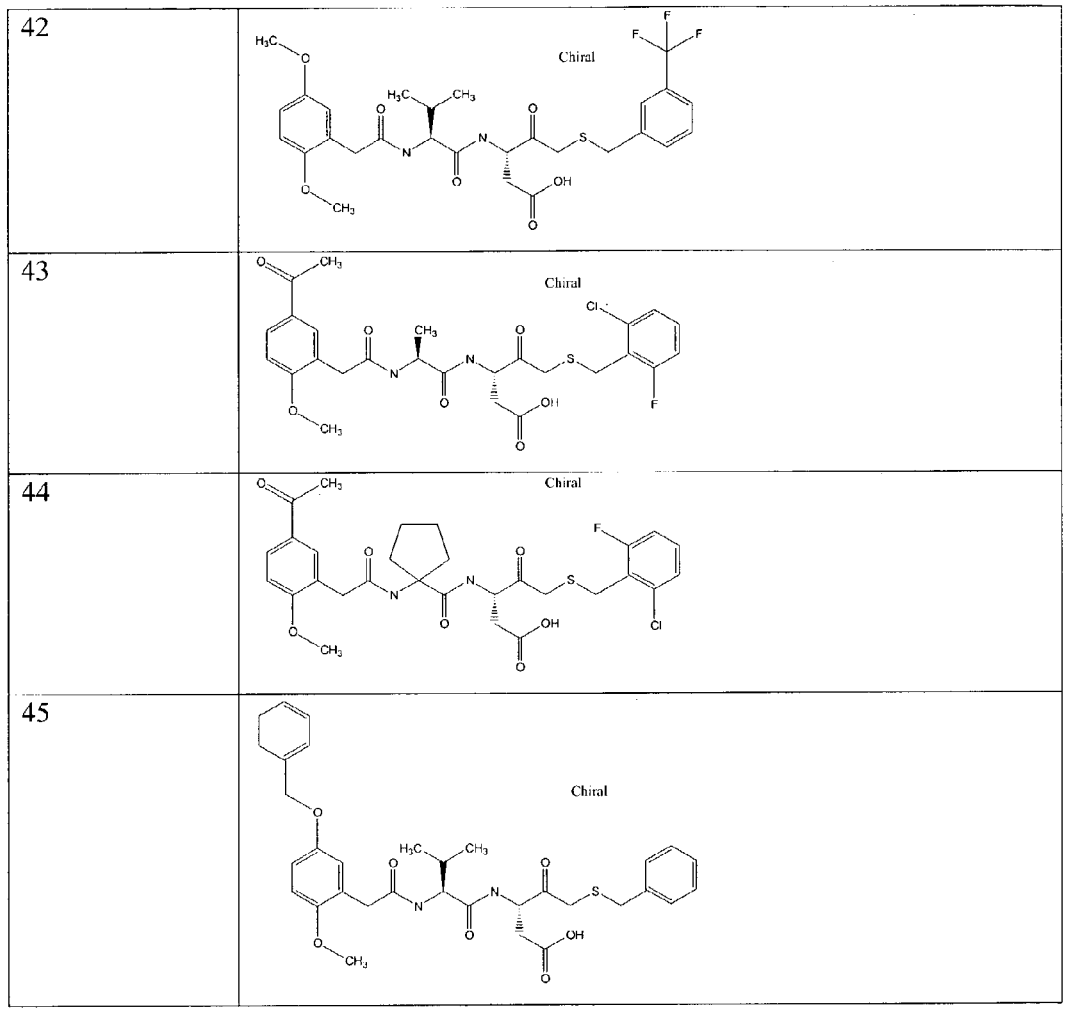
Figures 1R, 2:
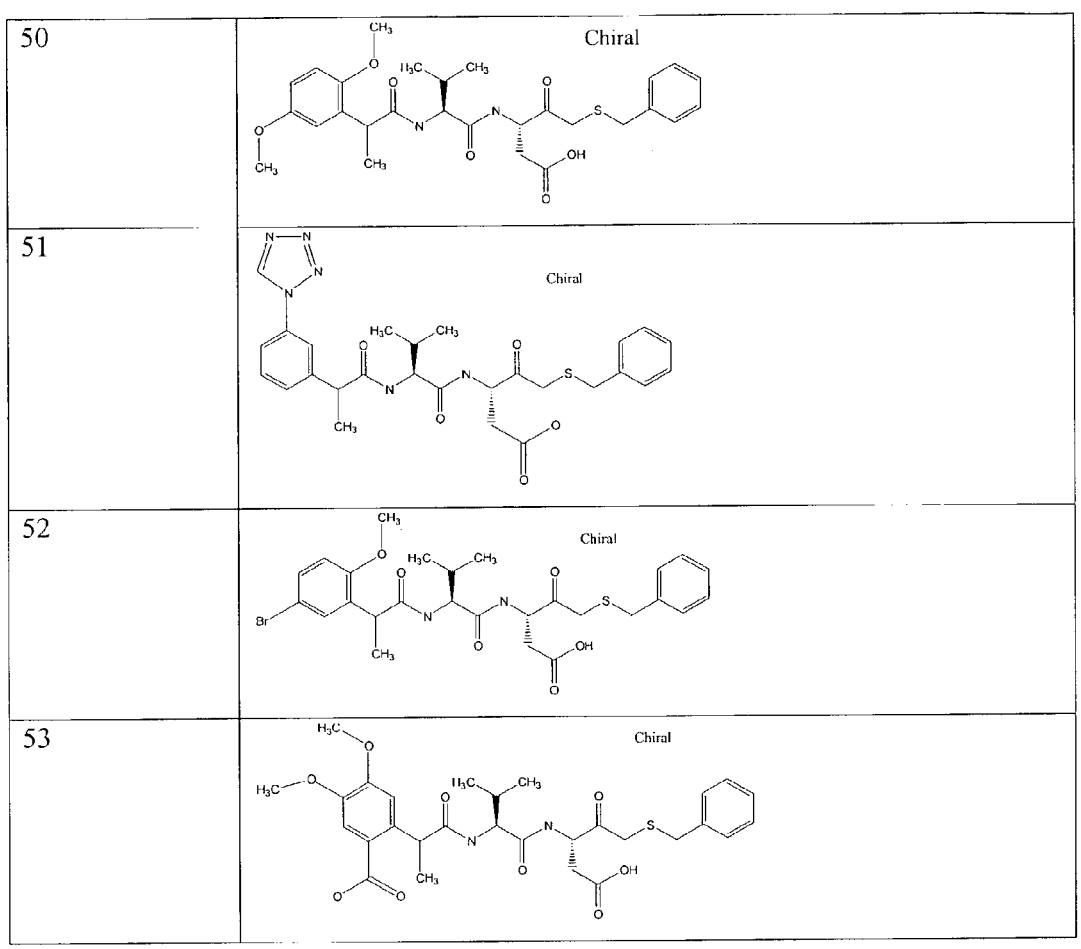
Figures 1U, 2:
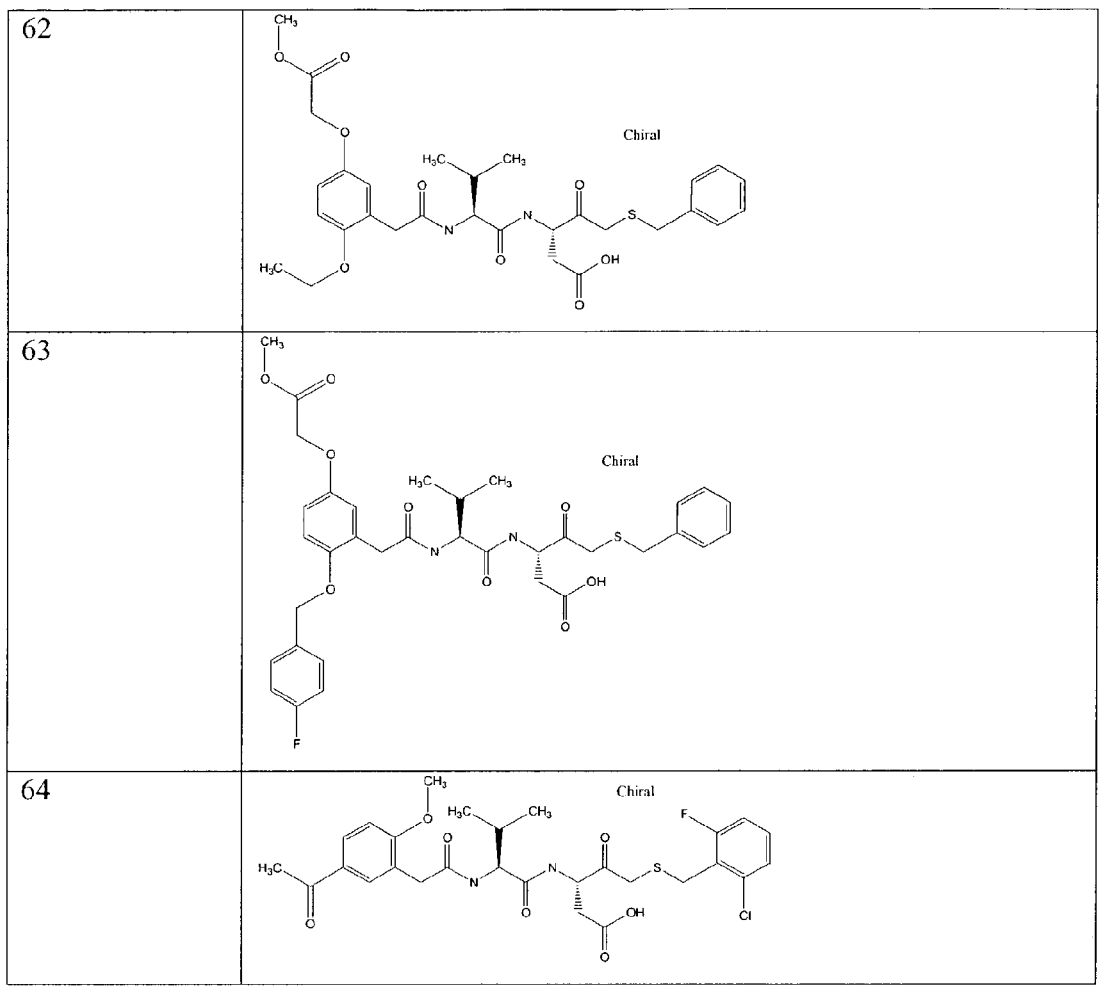
Figures 1V, 2:
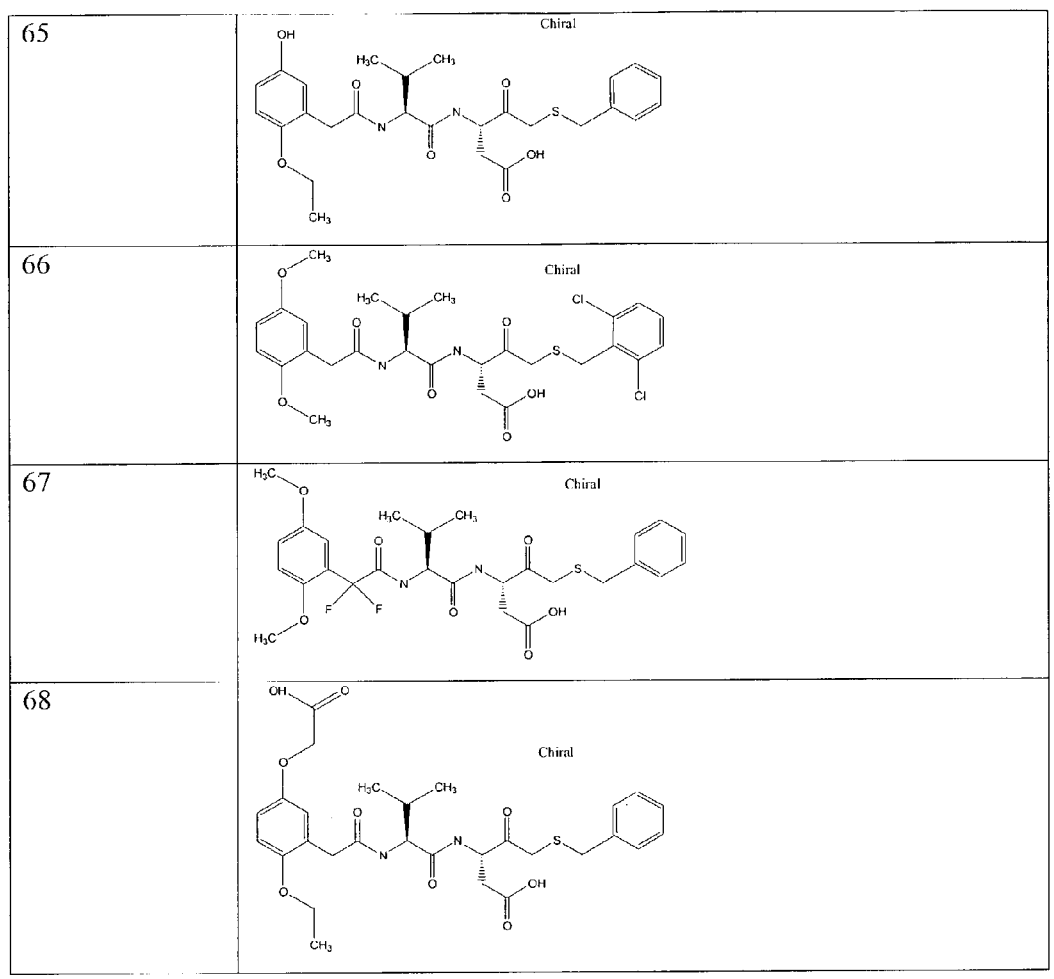
Figures 1W, 2:
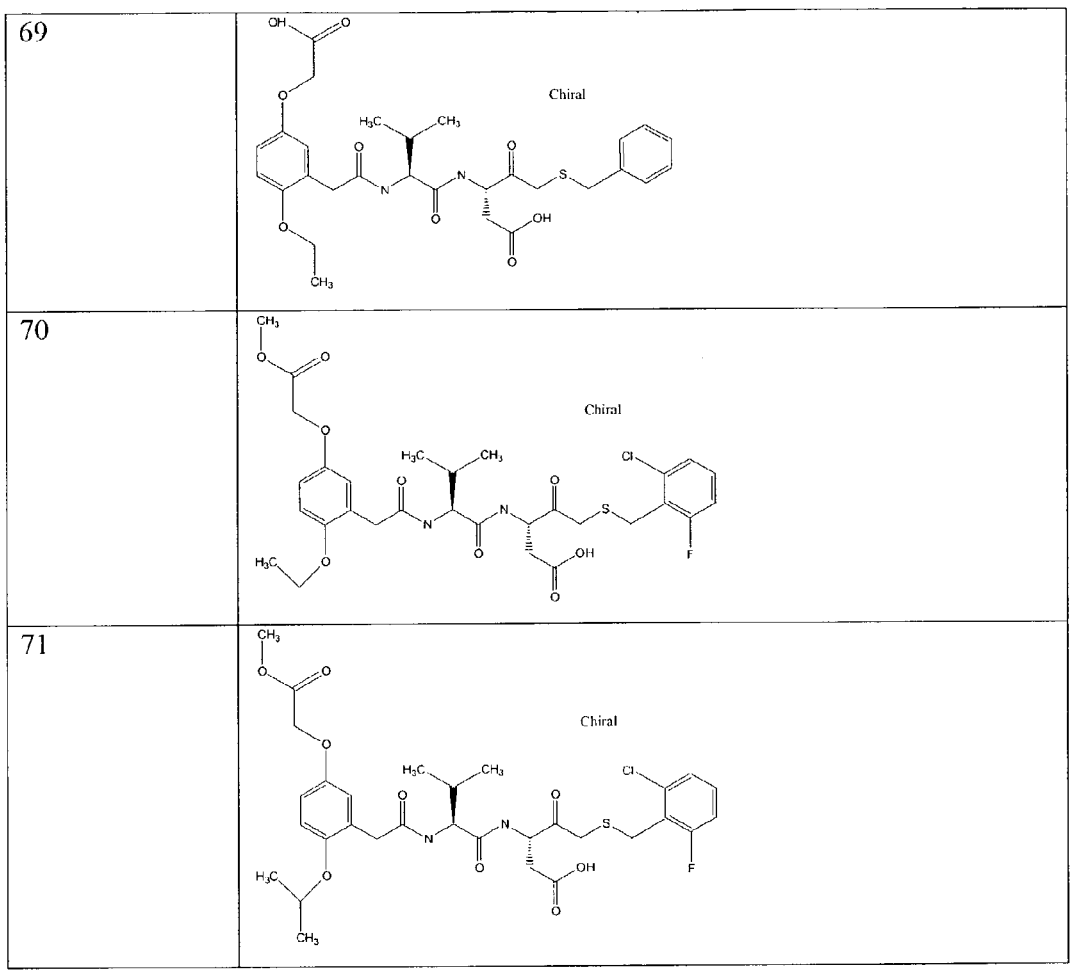
Figures 1X, 2:
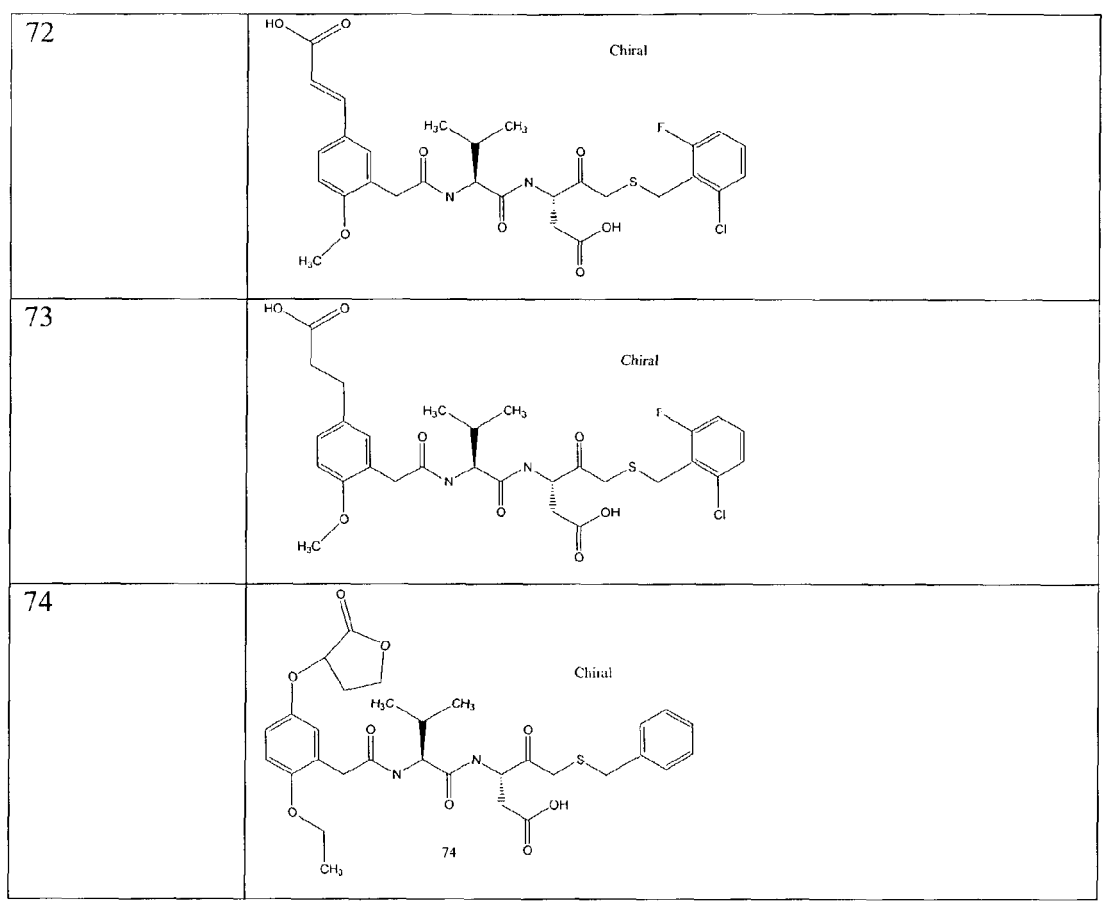
Figures 1Y, 2:
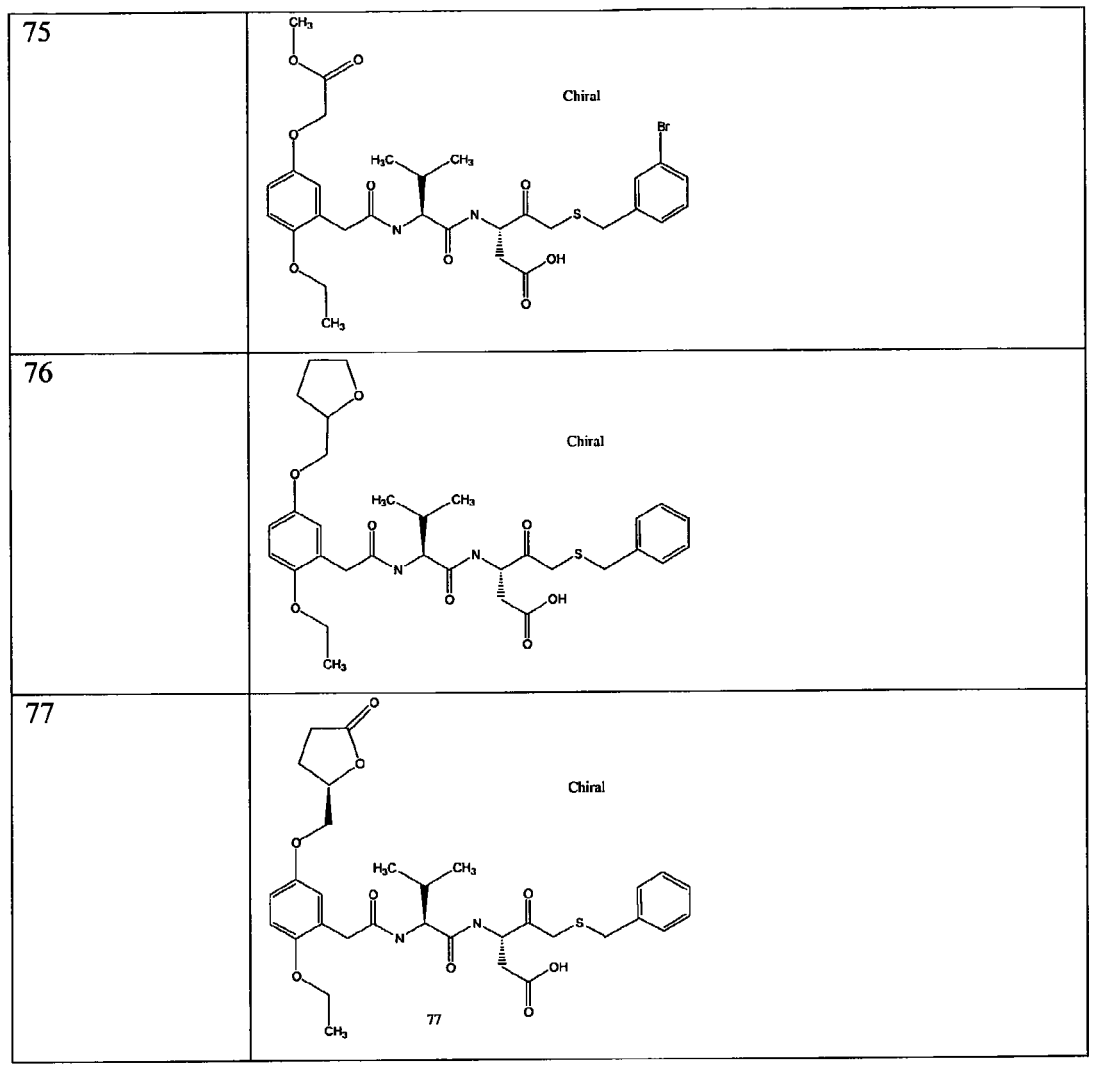
Figures 1Z, 2:
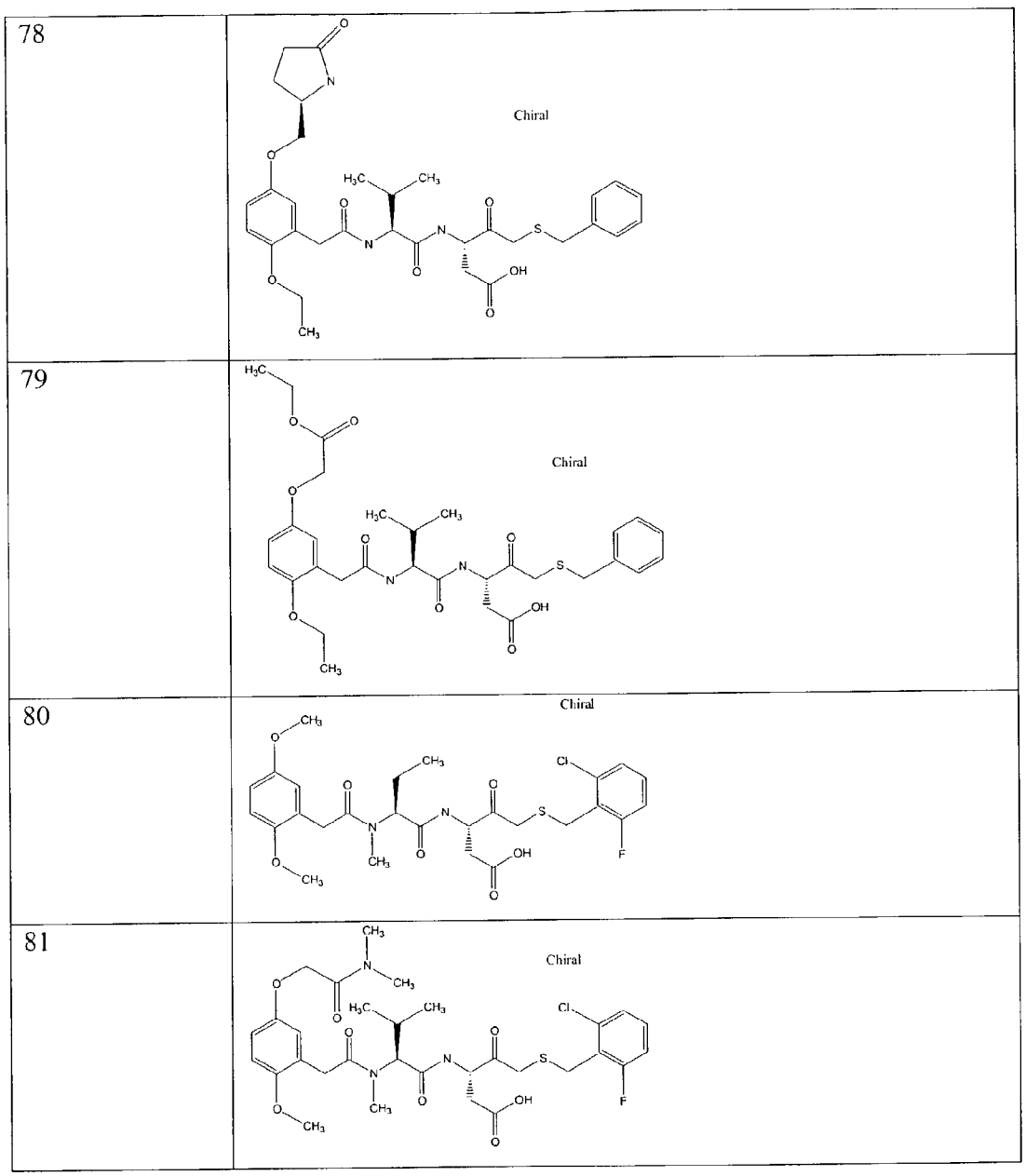
Figures 2, 2A:
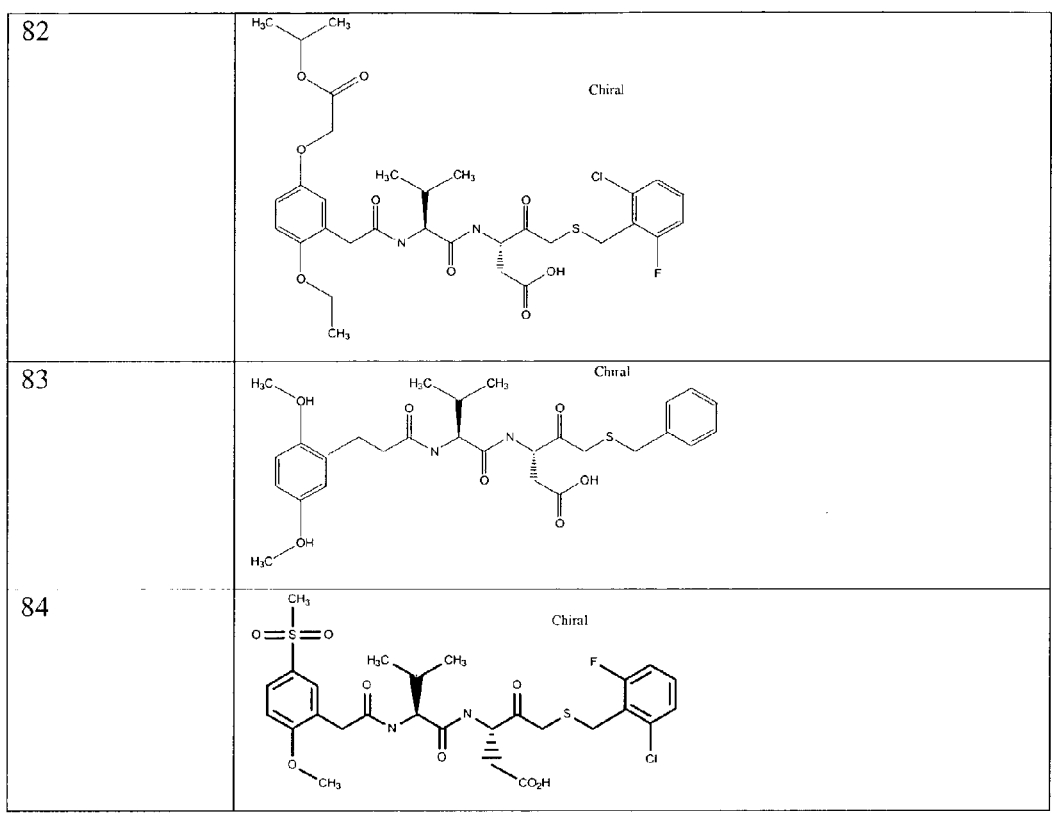
Figures 2, 2B:
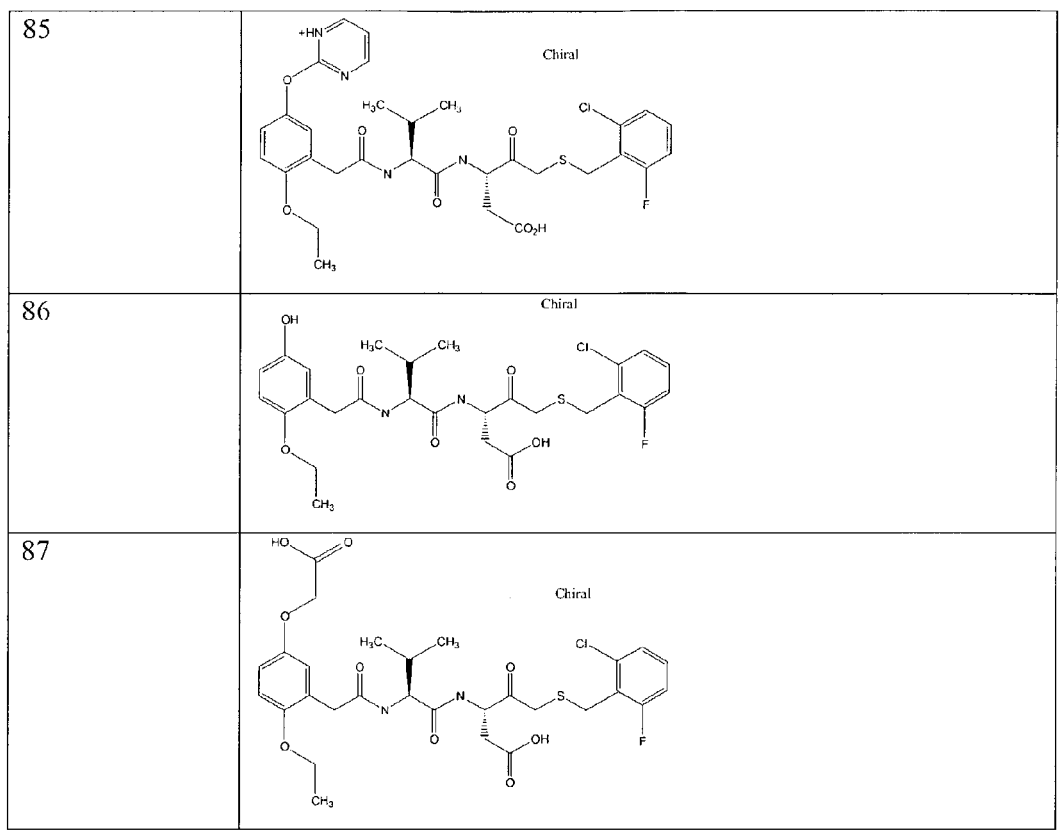
Figures 2, 2C:
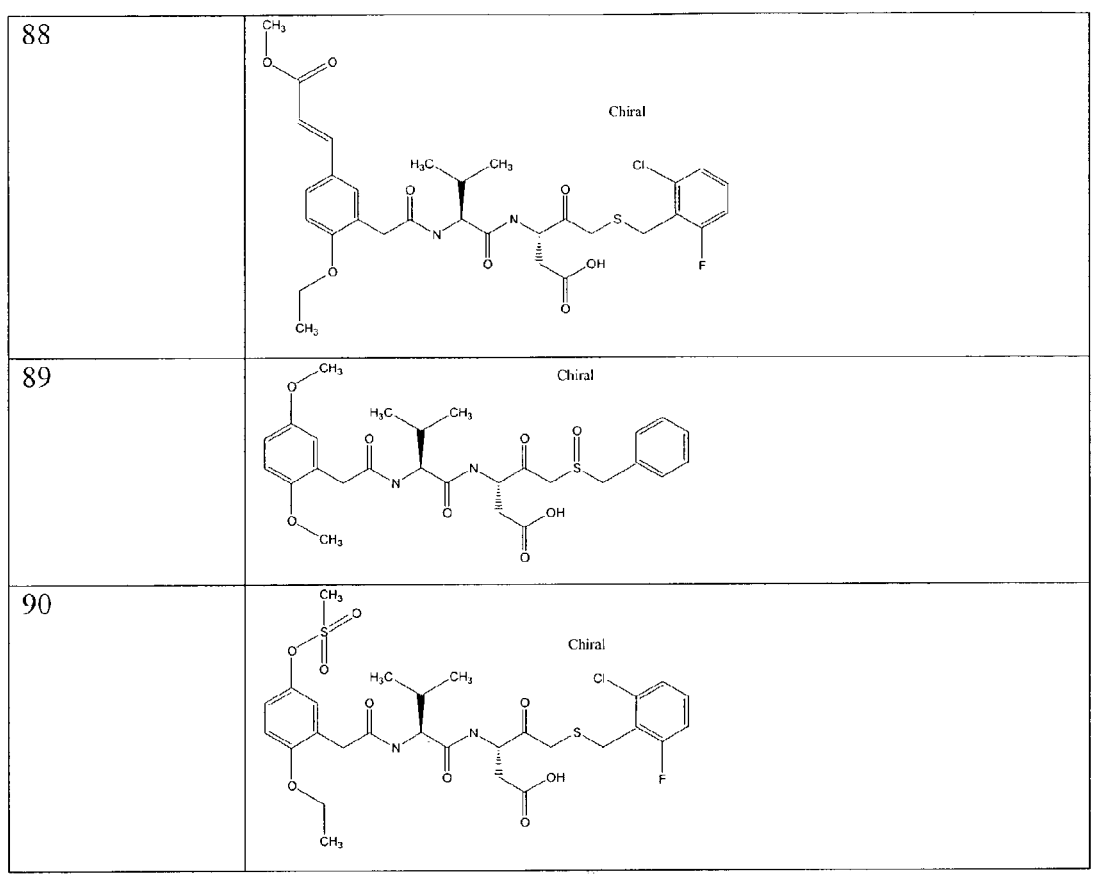
Figures 2, 2F:
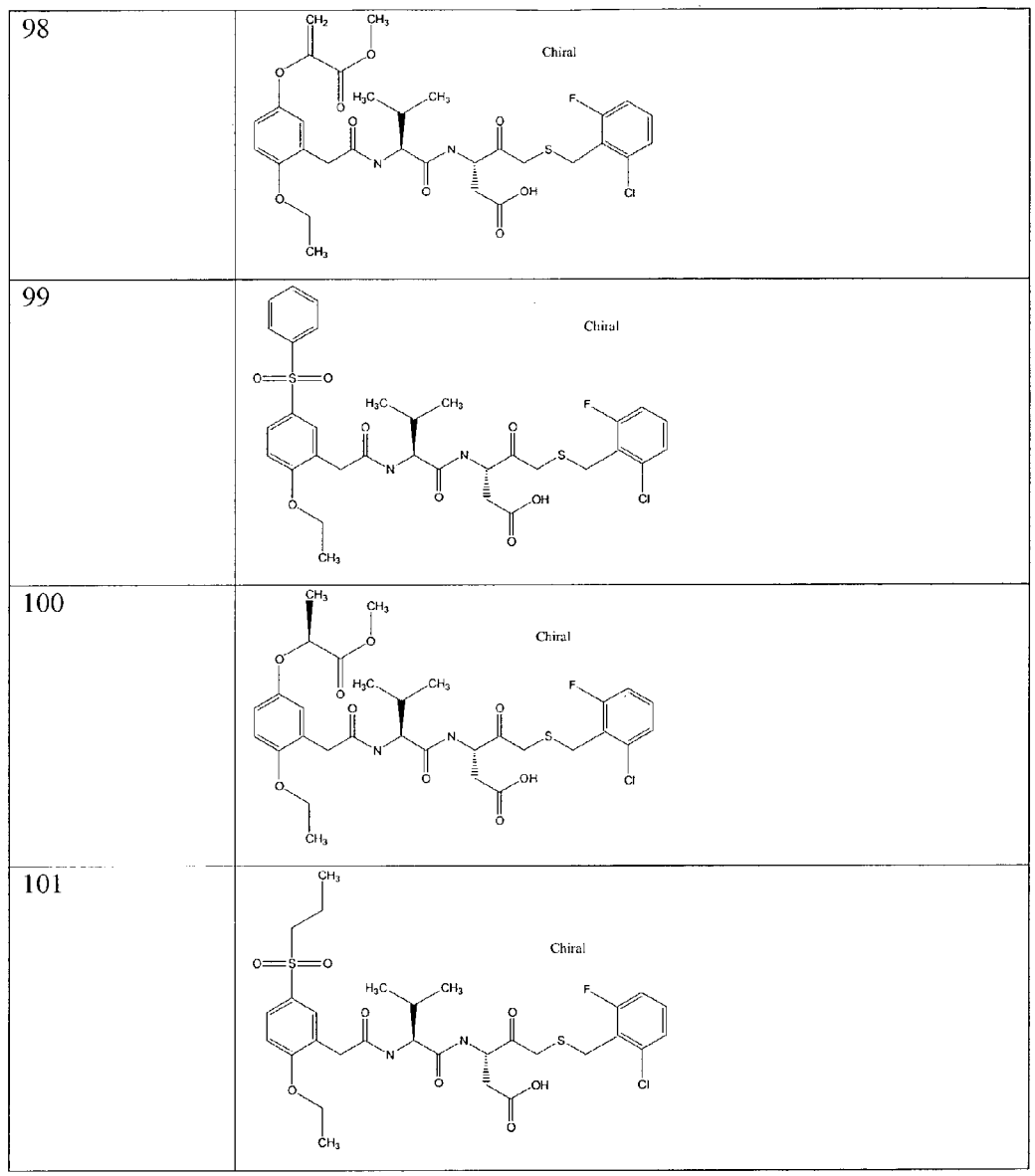
Figures 2, 2G:
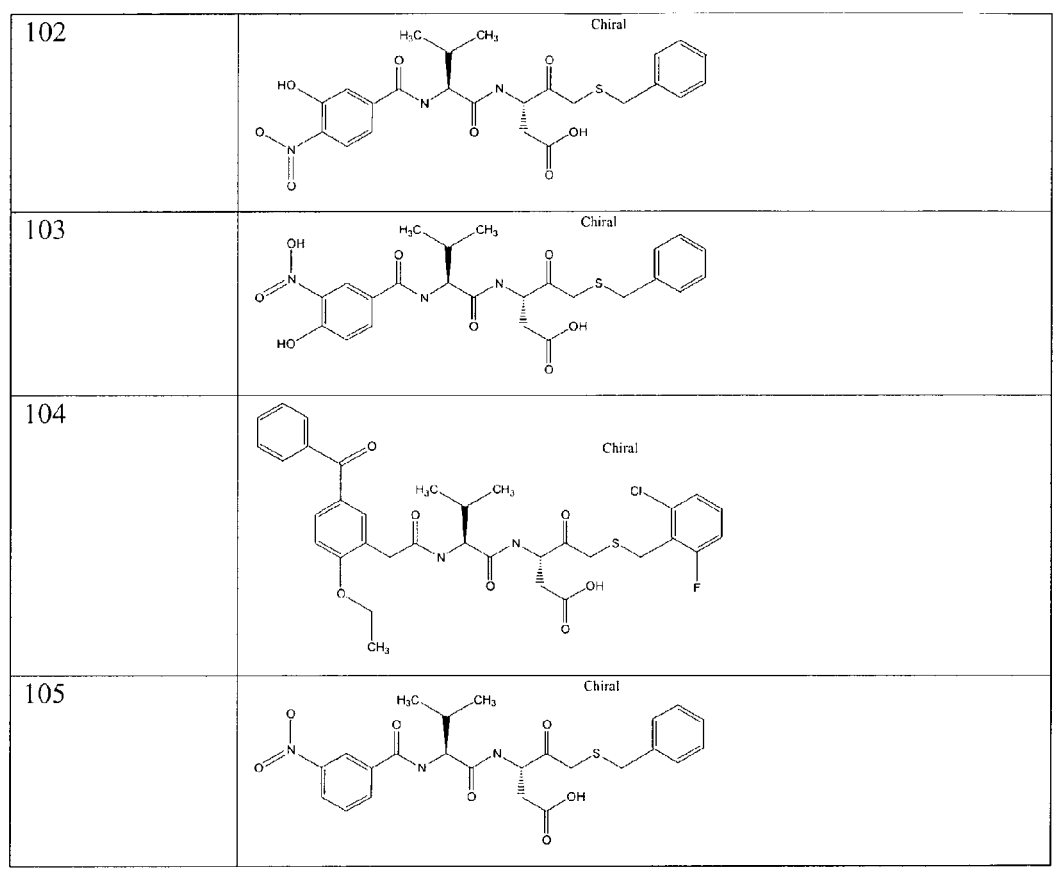
Figures 2, 2I:
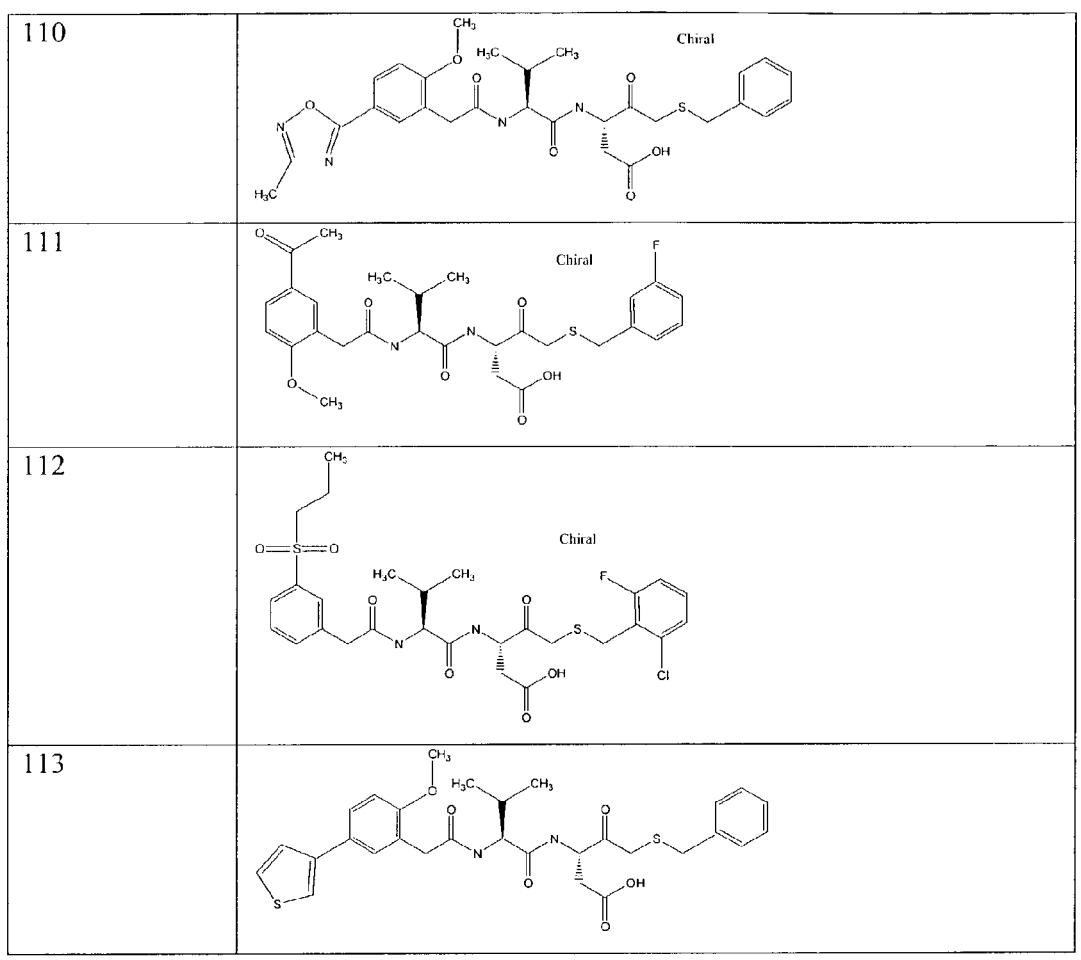
Figures 2, 2K:
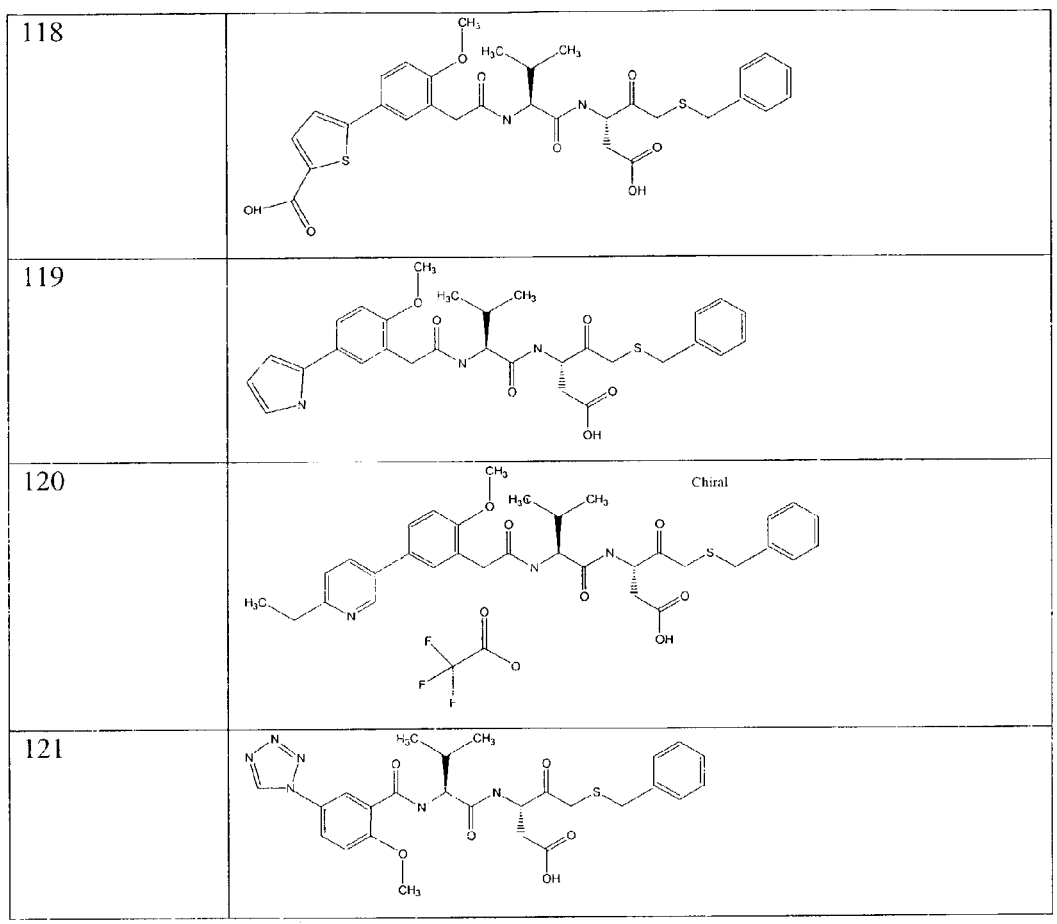
Figures 2, 2M:
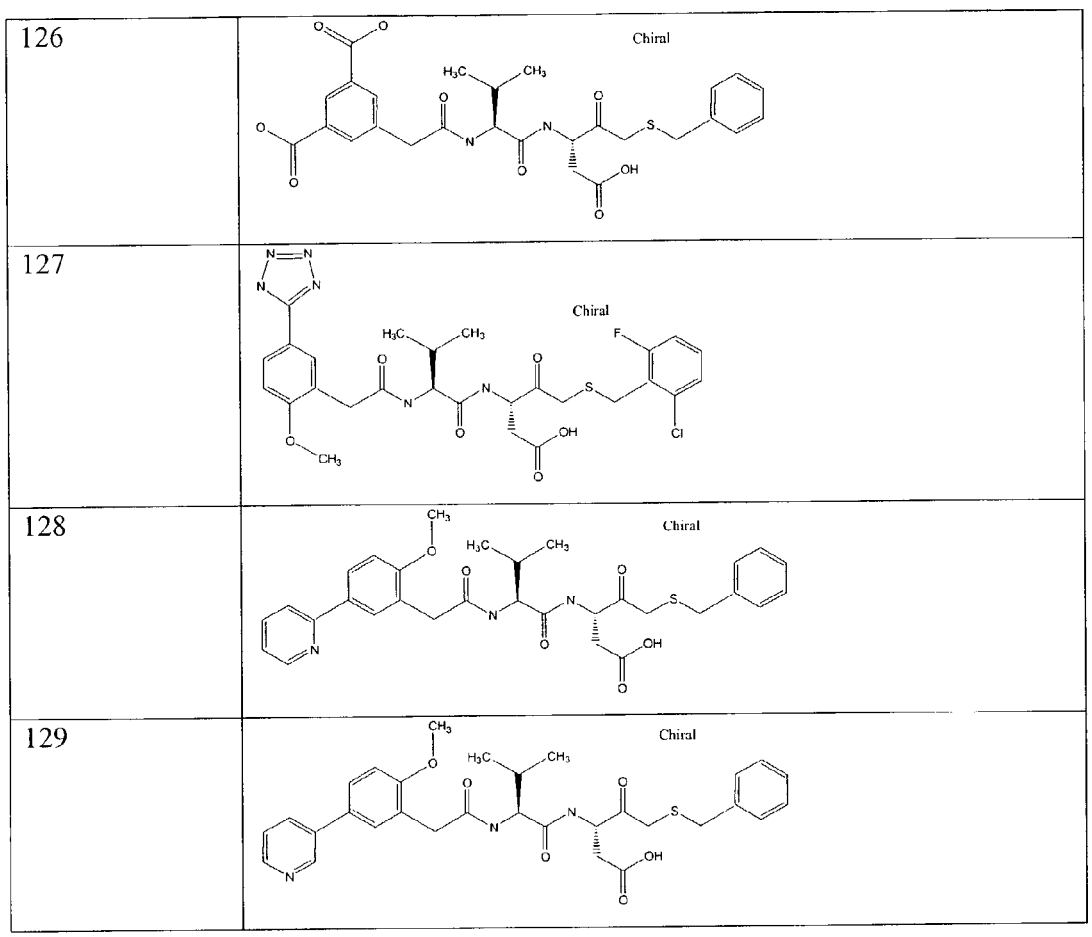
Figures 2, 2N:
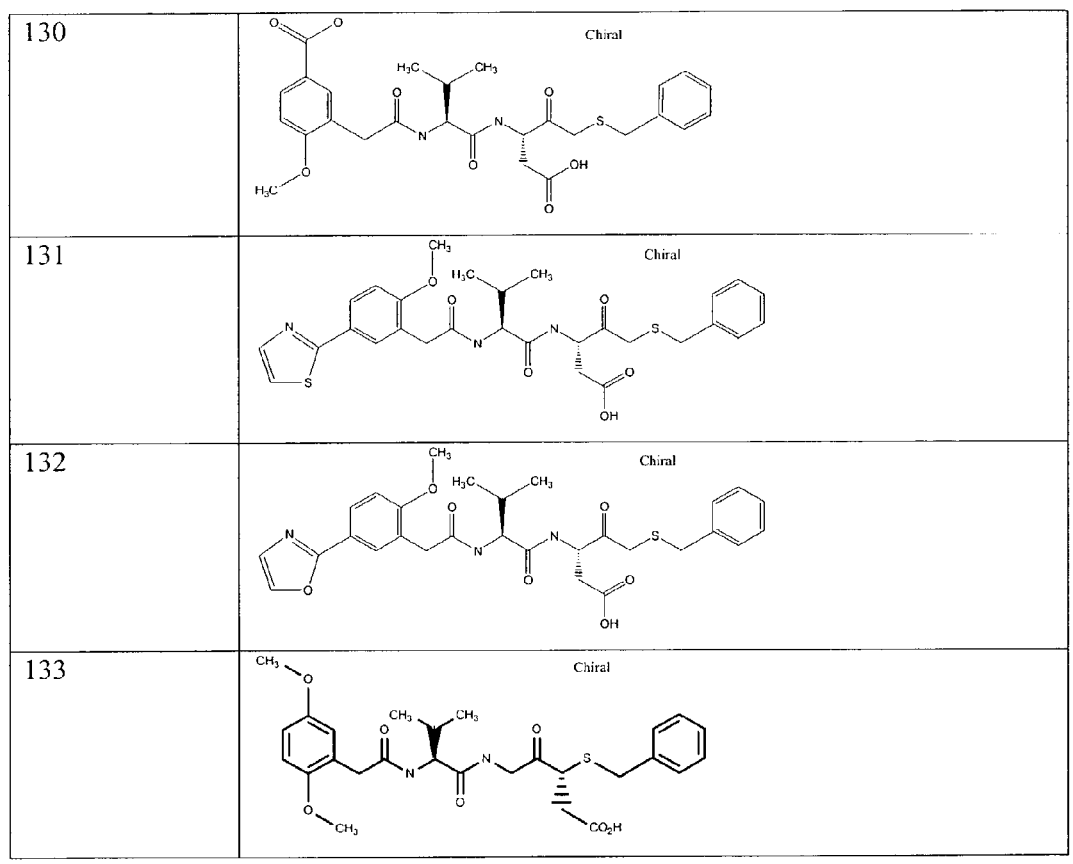
Figures 2, 2O:
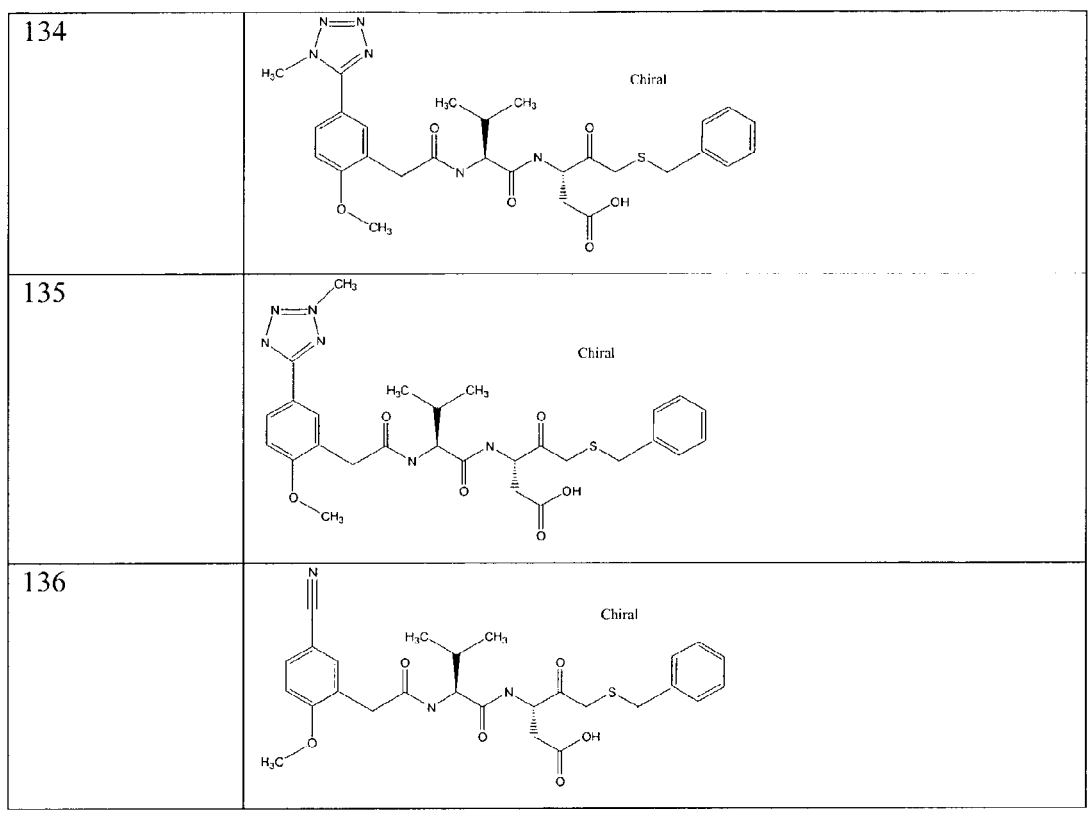
Figures 2, 2S:
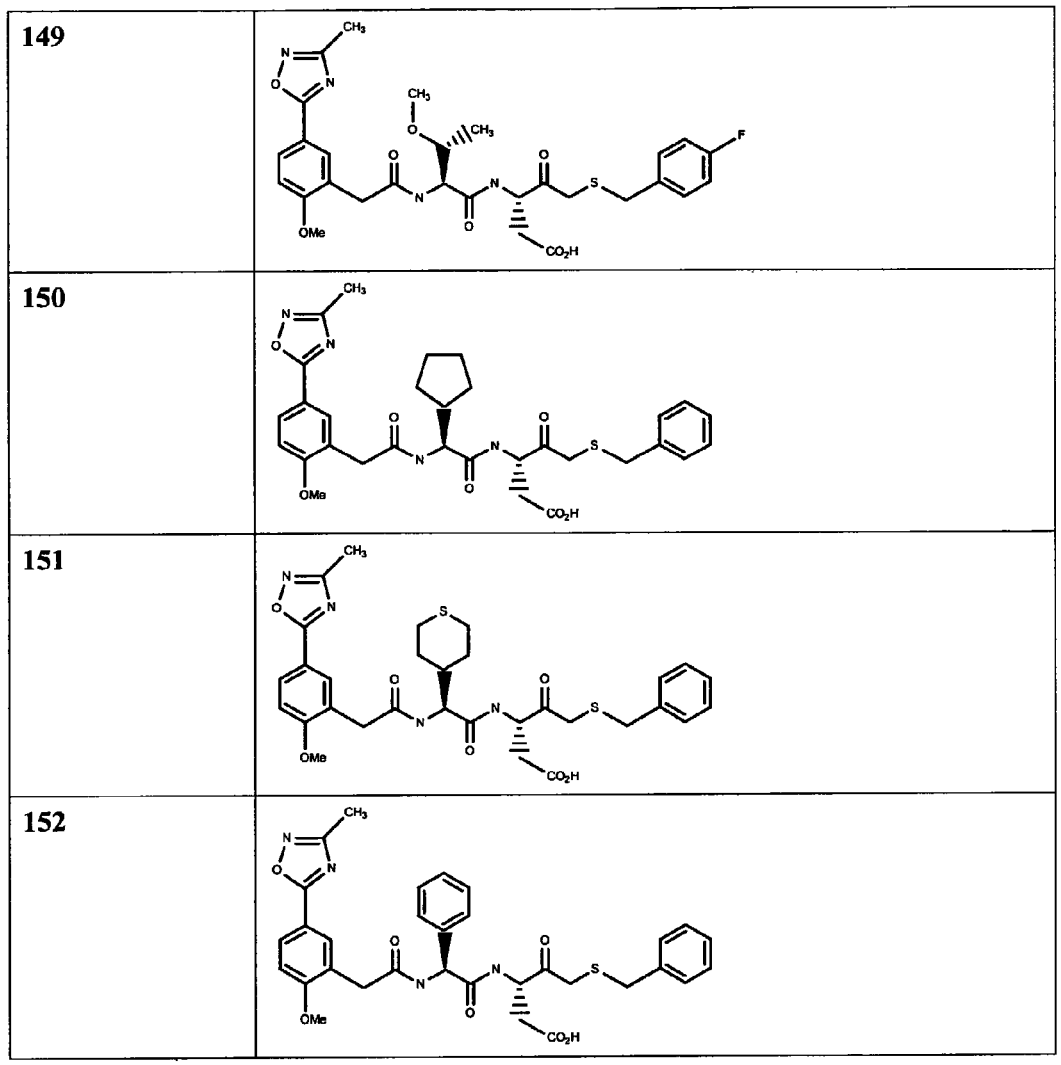
Figure 4B:
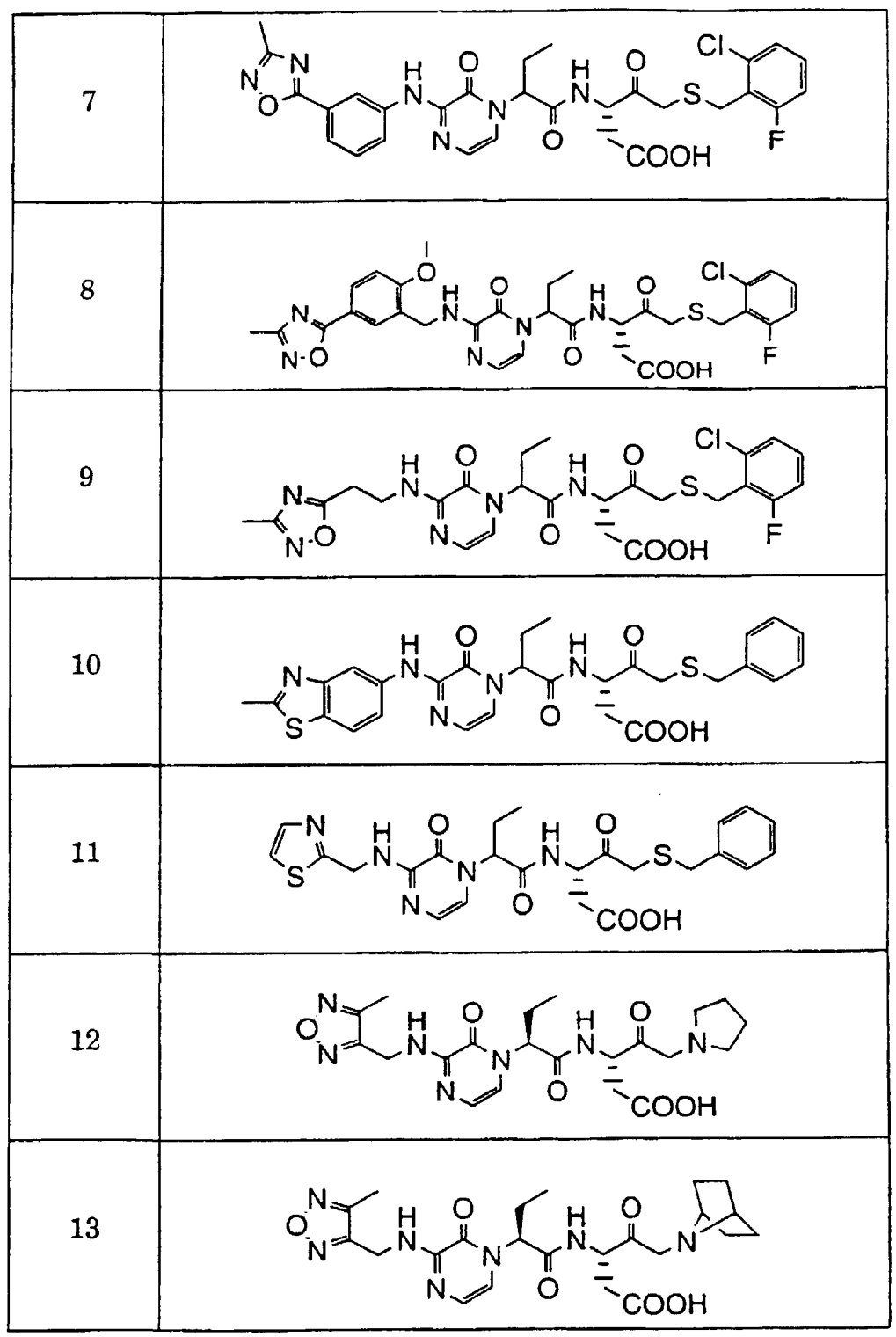
FIG. 4 depicts compounds and pharmaceutical compositions of this invention, which are depicted as a series of partial views extended over FIGS. 4 (a-v).
Figure 4E:
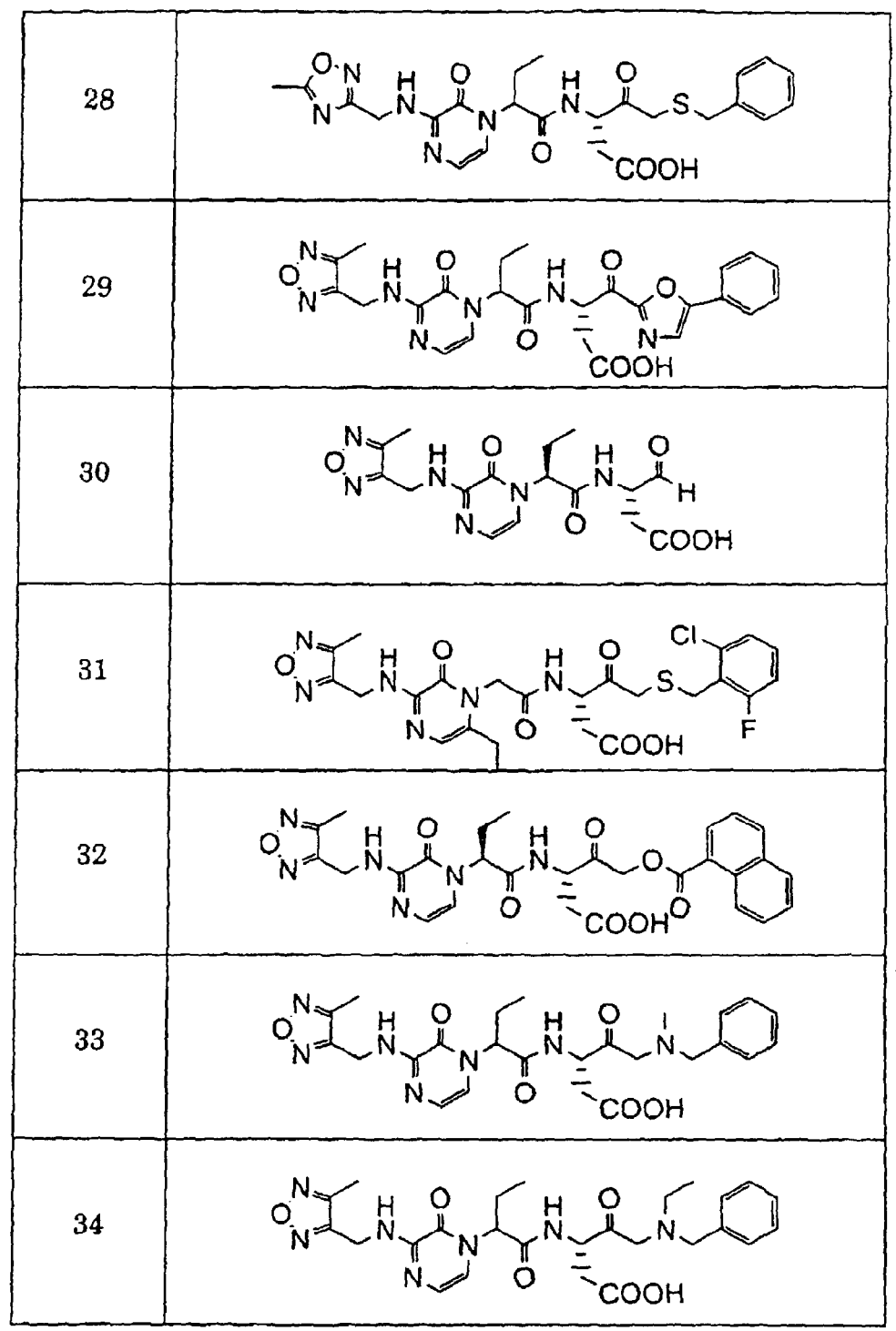
Figure 4K:
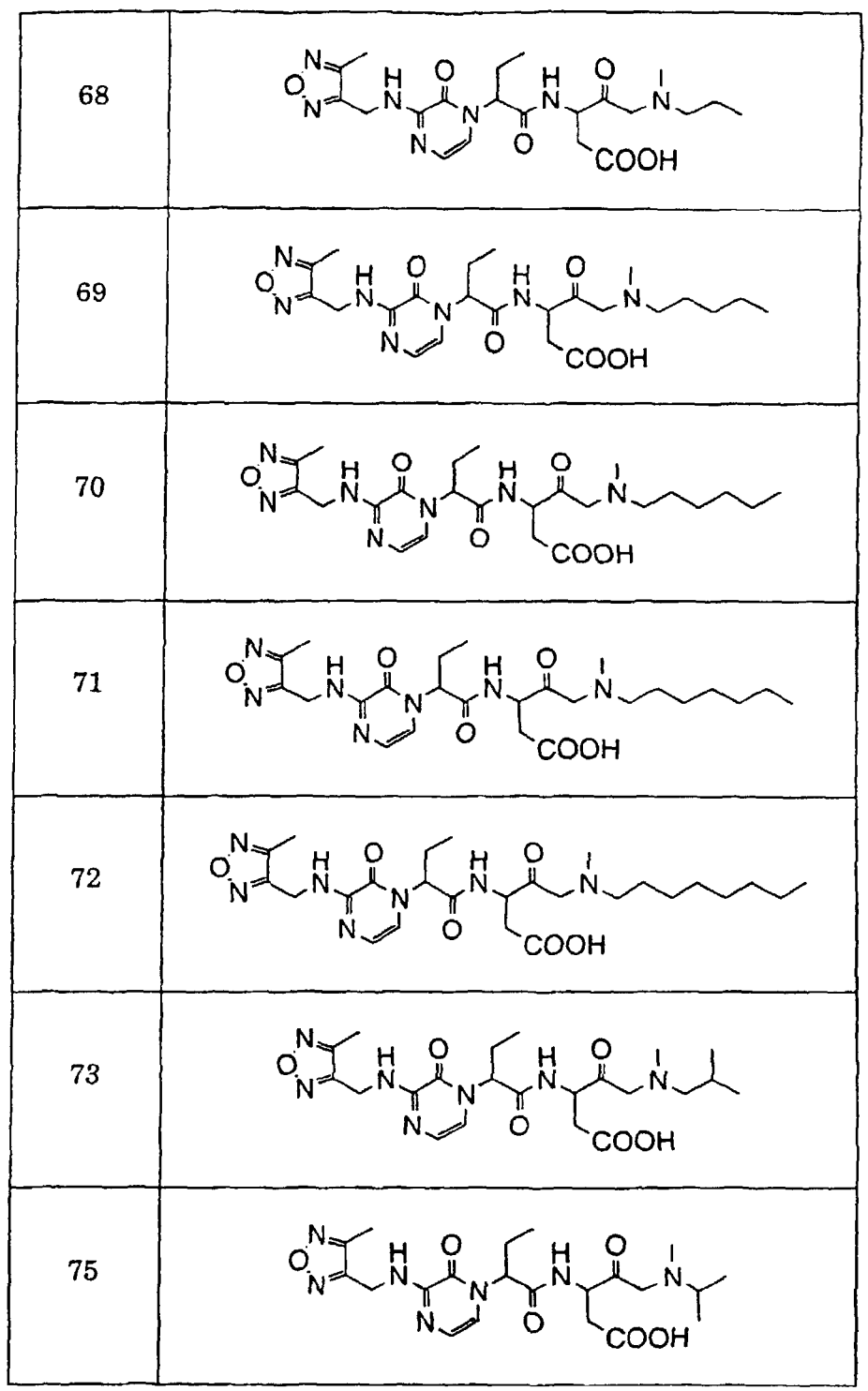
Figure 4N:
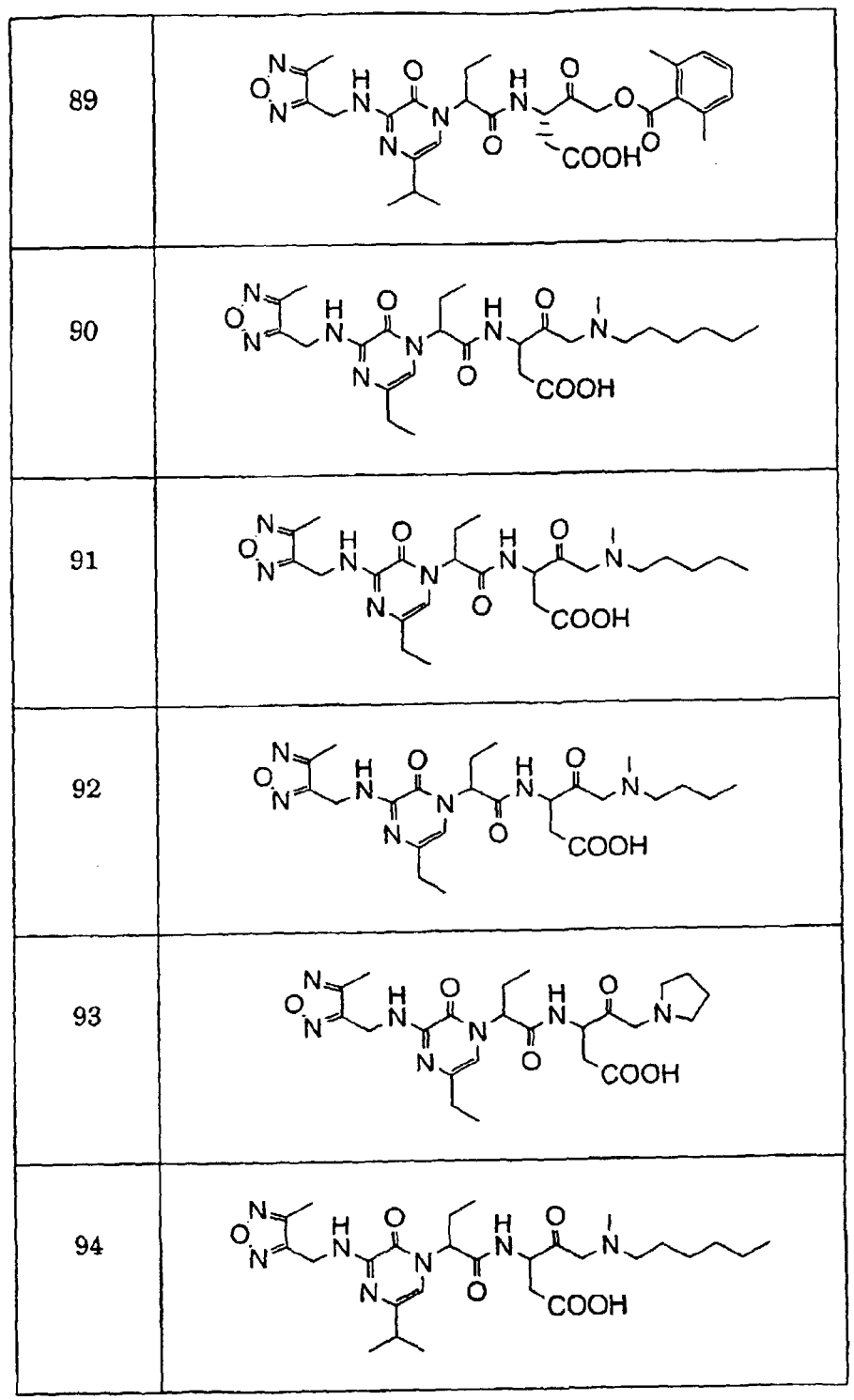
Figure 8F:
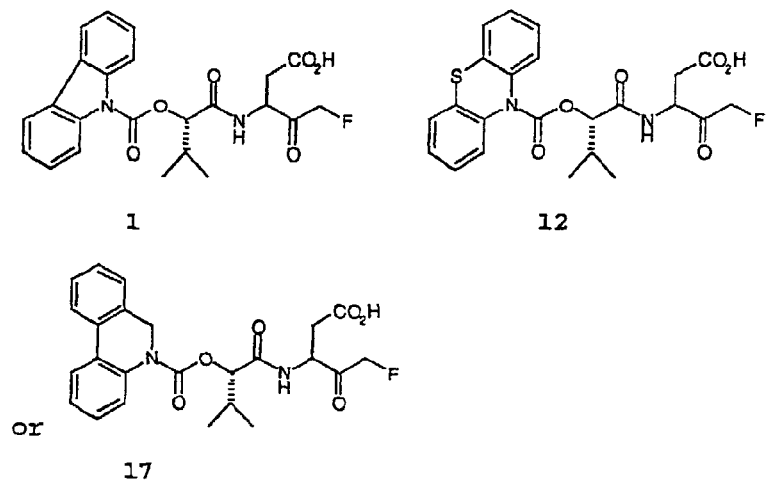
FIG. 8 depicts compounds and pharmaceutical compositions of this invention, which are depicted as a series of partial views extended over FIGS. 8 (a-h).
Figure 10E:
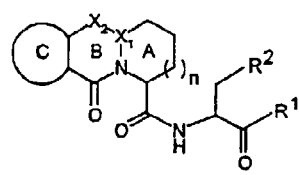
FIG. 10 depicts compounds and pharmaceutical compositions of this invention, which are depicted as a series of partial views extended over FIGS. 10 (a-e).
Figure 17A:
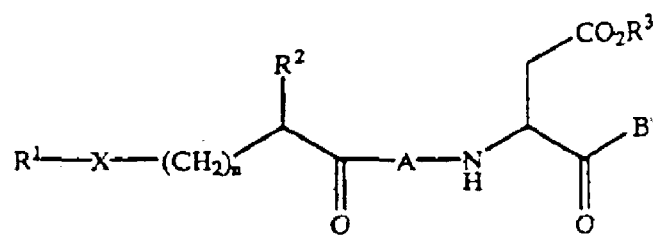
FIG. 17 depicts compounds and pharmaceutical compositions of this invention, which are depicted as a series of partial views extended over FIGS. 17 (a-r).
Figure 17F:
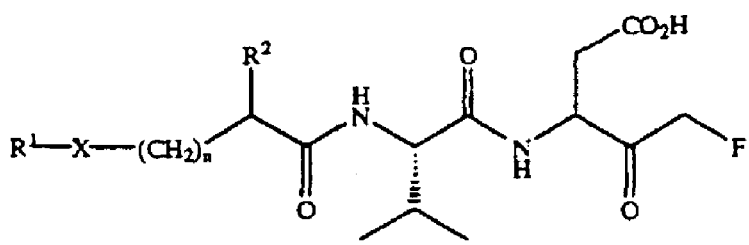
Figure 17M:
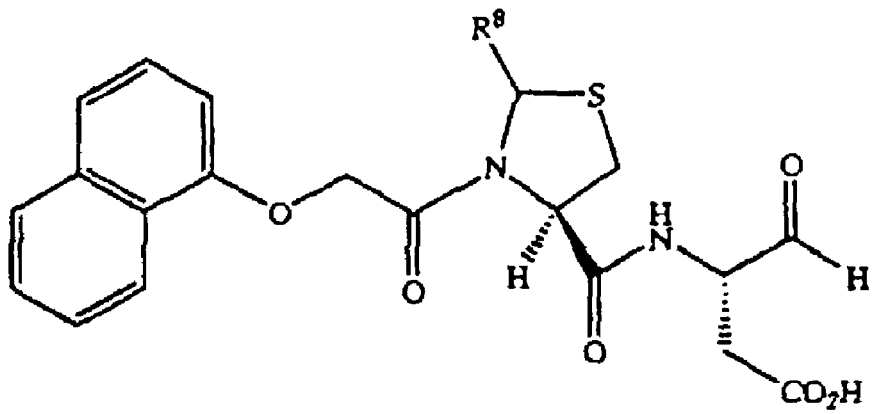
Figure 17N:
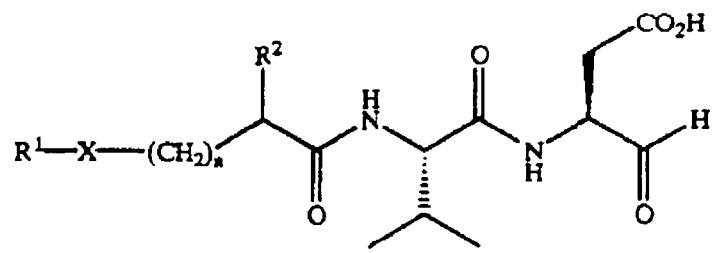
Figure 18B:
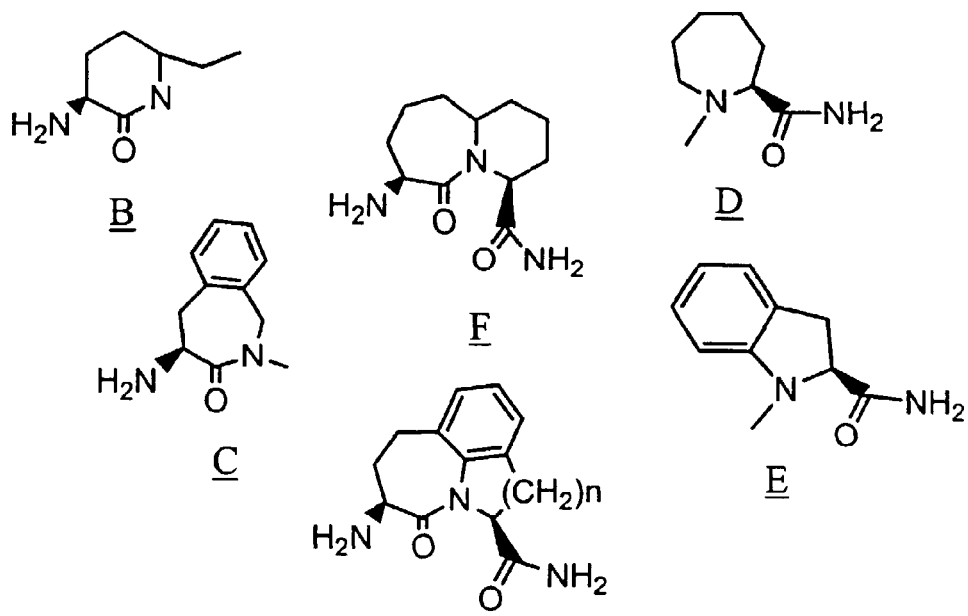
FIG. 18 depicts compounds and pharmaceutical compositions of this invention, which are depicted as a series of partial views extended over FIGS. 18 (a-c).
Figure 18C:
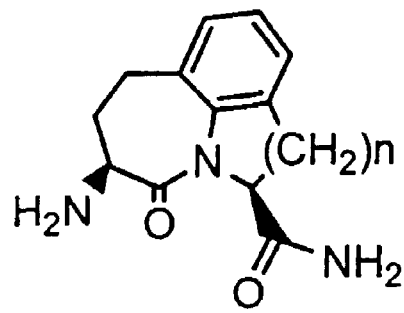
Figure 19D:
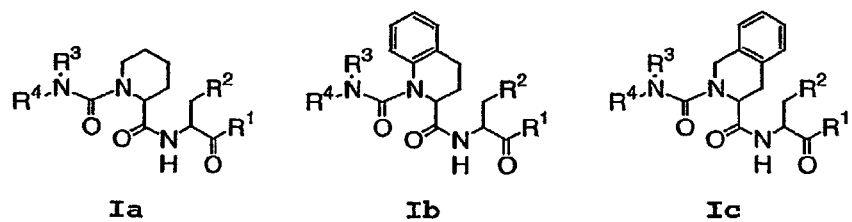
FIG. 19 depicts compounds and pharmaceutical compositions of this invention, which are depicted as a series of partial views extended over FIGS. 19 (a-g).
Figure 20D:
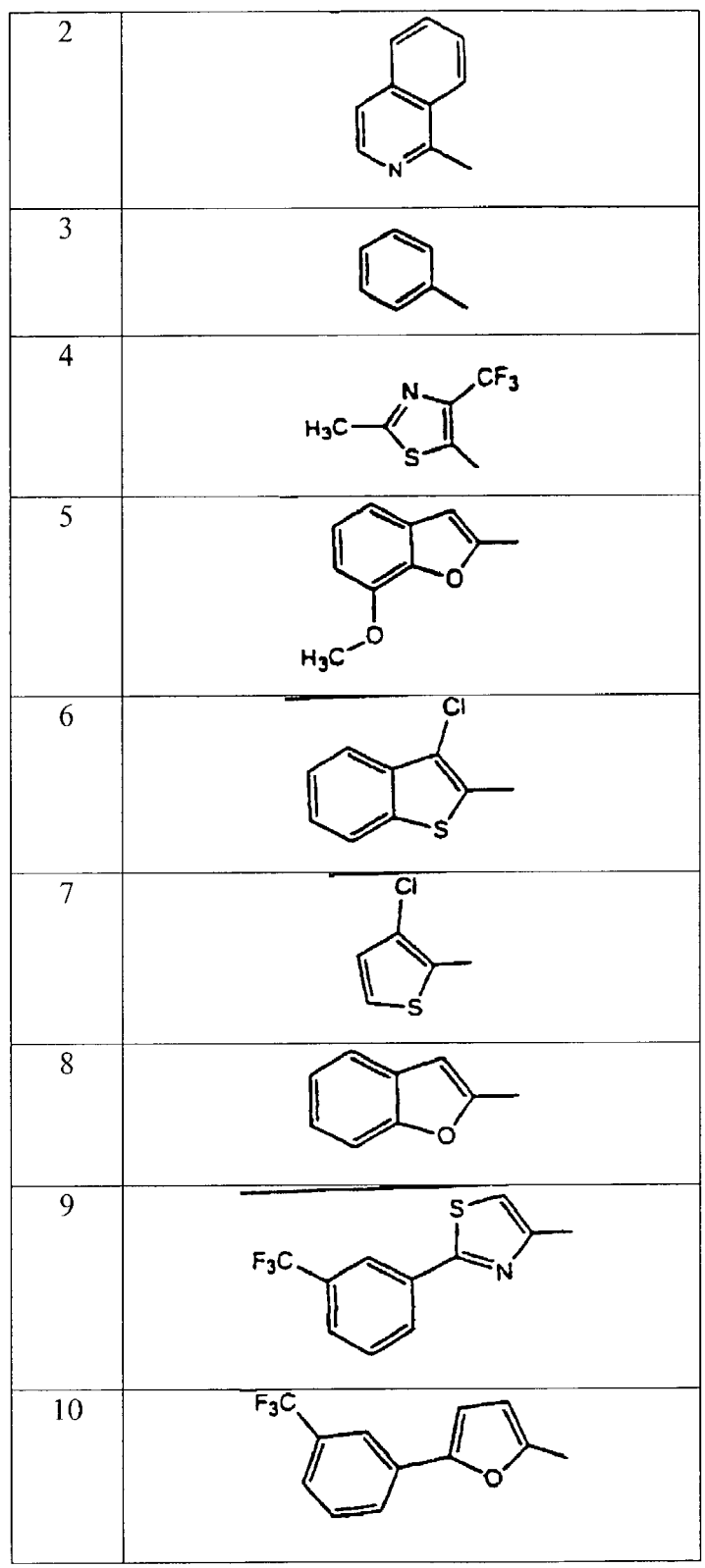
FIG. 20 depicts compounds and pharmaceutical compositions of this invention, which are depicted as a series of partial views extended over FIGS. 20 (a-g).
Figure 20E:
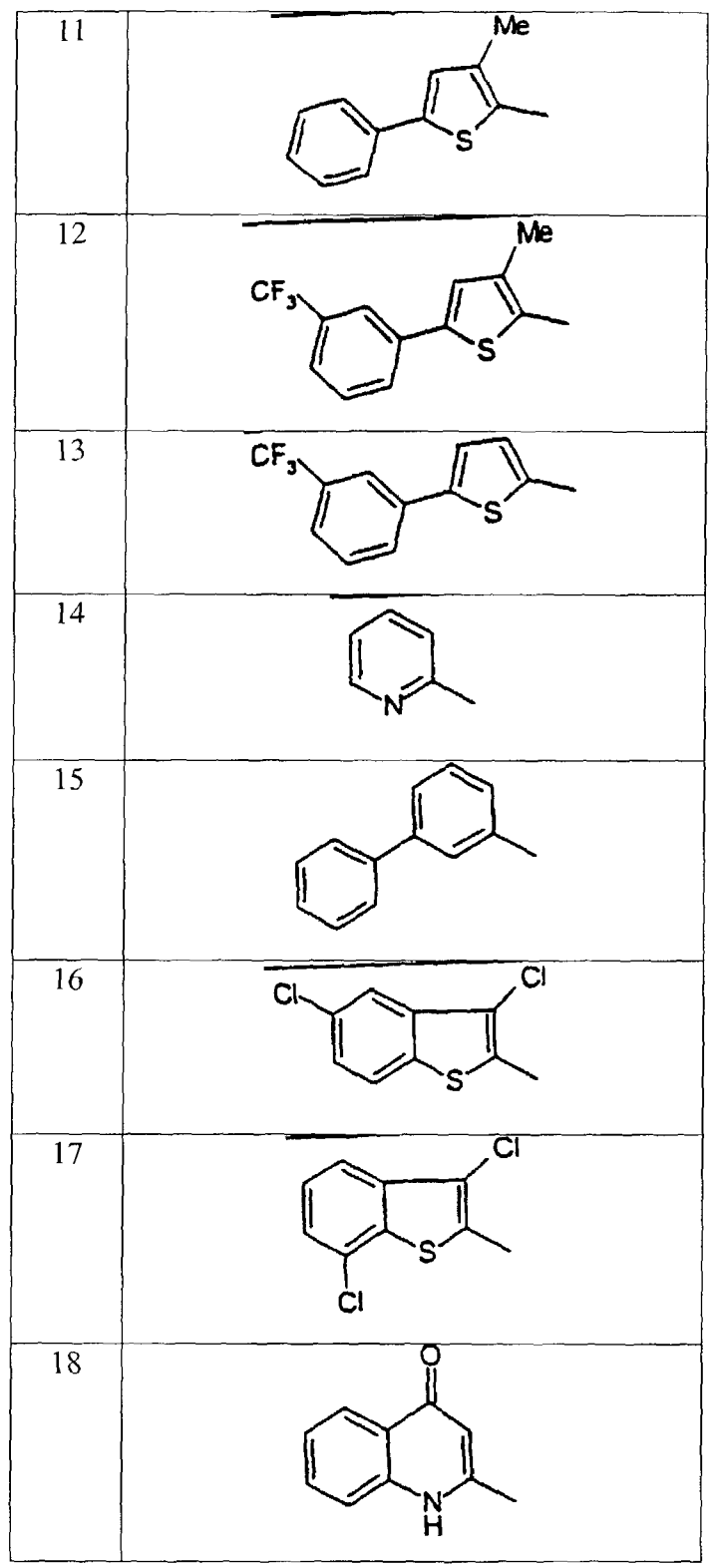
Figure 20F:
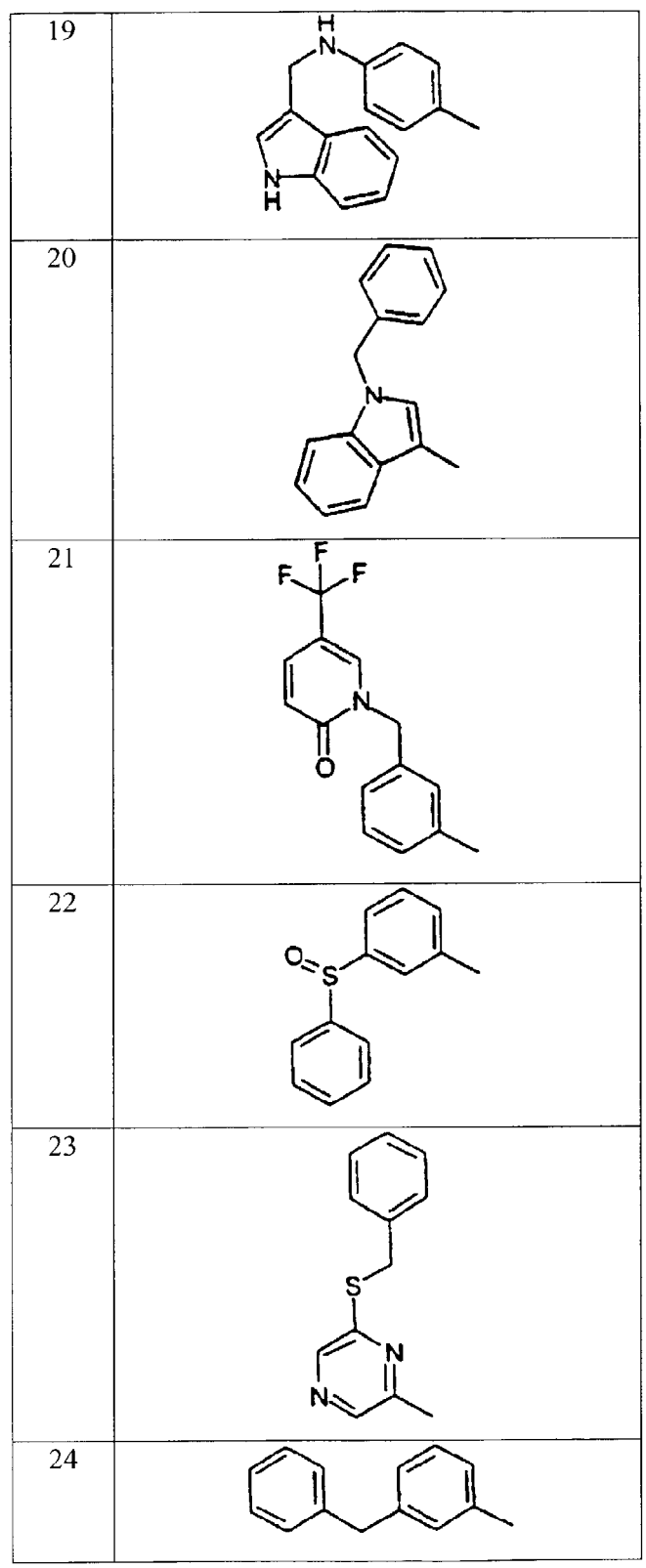
Figure 20G:
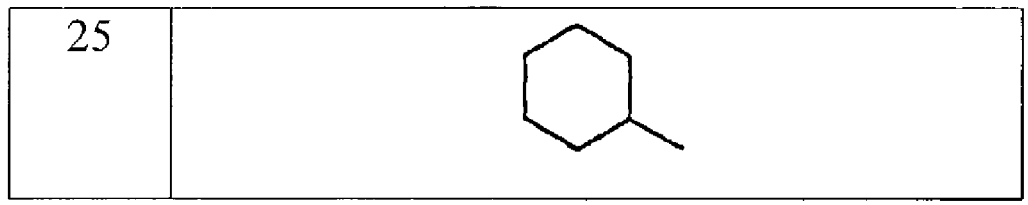

This invention provides compounds disclosed herein and pharmaceutically acceptable derivatives thereof that are particularly effective as regulators of TNF alpha levels and/or activity. The compounds can be useful to treat TNF-alpha mediated disease states in mammals. The compounds of this invention are recited in FIGS. 1-20.

The compounds of this invention inhibit TNF-alpha activity and/or decrease TNF-alpha levels. These compounds can be assayed, for example, for their ability to inhibit the release of TNF-alpha, and/or regulate TNF-alpha levels and/or TNF-alpha activity. Assays for each of the activities are known in the art, including those described below in detail in the Examples. Accordingly, these compounds are capable of targeting and inhibiting events in TNF-alpha mediated diseases, and the ultimate activity of the relevant protein in a number of diseases, such as inflammatory diseases, autoimmune diseases, destructive bone, proliferative disorders, infectious diseases, and degenerative diseases.

Compounds of this invention also inhibit the release of TNF-alpha from activated cells. For example, cells activated to produce TNF-alpha due to the presence of lipopolysaccharide, bacteria and/or virus will release less TNF-alpha after exposure to the compounds of this invention.

The pharmaceutical compositions and methods of this invention, therefore, will be useful for controlling TNF-alpha levels and/or activity in vitro or in vivo. The compositions and methods of this invention will thus be useful for controlling TNF-alpha levels in vivo and for treating or reducing the advancement, severity or effects of TNF-alpha mediated conditions, including diseases, disorders or effects.

According to another embodiment, the invention provides a composition comprising a compound of this invention or a pharmaceutically acceptable derivative (e.g., salt) thereof, as described above, and a pharmaceutically acceptable carrier.

According to another embodiment, the compositions of this invention may further comprise another therapeutic agent. Such agents include, but are not limited to, a thrombolytic agent such as tissue plasminogen activator and streptokinase, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator (e.g., bropirimine, anti-human alpha interferon antibody, IL-2, GM-CSF, methionine enkephalin, interferon alpha, diethyldithiocarbamate, tumor necrosis factor, naltrexone and rEPO), a prostaglandin, or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In pharmaceutical compositions comprising only a compound of this invention as the active component, methods for administering these compositions may additionally comprise the step of administering to the subject an additional agent. Such agents include, but are not limited to, a thrombolytic agent such as tissue plasminogen activator and streptokinase, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator (e.g., bropirimine, anti-human alpha interferon antibody, IL-2, GM-CSF, methionine enkephalin, interferon alpha, diethyldithiocarbamate, tumor necrosis factor, naltrexone and rEPO), a prostaglandin, or an anti-vascular hyperproliferation compound. When a second agent is used, the second agent may be administered either as a separate dosage form or as part of a single dosage form with the compounds or compositions of this invention.

The amount of compound present in the above-described compositions should be sufficient to cause a detectable decrease in the severity of the disease, or in TNF-alpha levels or activity.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chlorides, bromides and iodides; dialkyl sulfates, such as dimethyl, diethyl, dibutyl and diamyl sulfates; long chain halides such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, or central nervous system), increase oral availability, increase solubility to allow administration by injection, alter metabolism and/or alter rate of excretion.

According to a preferred embodiment, the compositions of this invention are formulated for pharmaceutical administration to a subject, e.g., a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection and infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. Fatty acids, such as oleic acid and its glyceride derivatives are useful in the preparation of injectables, as are natural pharmaceutically-acceptable oils, such as olive oil and castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

If a solid carrier is used, the preparation can be tableted, placed in a hard gelatin capsule in powder or pellet form, or in the form of a troche or lozenge. The amount of solid carrier will vary, e.g., from about 25 mg to 400 mg. When a liquid carrier is used, the preparation can be, e.g., in the form of a syrup, emulsion, soft gelatin capsule, sterile injectable liquid such as an ampule or nonaqueous liquid suspension. Where the composition is in the form of a capsule, any routine encapsulation is suitable, for example, using the aforementioned carriers in a hard gelatin capsule shell.

A syrup formulation can consist of a suspension or solution of the compound in a liquid carrier for example, ethanol, glycerin, or water with a flavoring or coloring agent. An aerosol preparation can consist of a solution or suspension of the compound in a liquid carrier such as water, ethanol or glycerin; whereas in a powder dry aerosol, the preparation can include e.g., a wetting agent.

Formulations of the present invention comprise an active ingredient together with one or more acceptable carrier(s) thereof and optionally any other therapeutic ingredient(s). The carrier(s) should be "acceptable" in the sense of being compatible with the other ingredients of the formulation and not deleterious to the recipient thereof.

The pharmaceutical compositions of this invention may be orally administered in any orally acceptable dosage form including, but not limited to, capsules, tablets, and aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents known in the art.

It will be recognized by one of skill in the art that the form and character of the pharmaceutically acceptable carrier or diluent is dictated by the amount of active ingredient with which it is to be combined, the route of administration, and other well-known variables.

The above-described compounds and compositions are also useful in therapeutic applications relating to a TNF mediated disease. The phrase "TNF-alpha mediated disease" means, all diseases states in which TNF-alpha plays a role, either by excessive production or release of TNF-alpha itself, or by TNF-alpha causing an event such as production or release of another pathophysiological biochemical agent or cytokine. In one preferred embodiment, TNF-alpha plays a direct role in the disease.

Such diseases can include, e.g., restinosis, inflammatory diseases such as inflammatory diseases of the central nervous system, demyelinating diseases of the nervous system, multiple sclerosis, septic arthritis, aneurysmal aortic disease, traumatic joint injury, peridontal disease, macular degeneration, diabetic retinopathy, occular inflammation, keratoconus, Sjogren's syndrome, corneal graft rejection, cachexia, and anorexia.

Excessive TNF-alpha tissue levels have been implicated in mediating or exacerbating a number of diseases including: rheumatoid arthritis, rheumatoid spondylitis, osteoarthritis, gouty arthritis and other arthritic conditions, general sepsis, gram-negative sepsis, septic shock, endotoxic shock, toxic shock syndrome, adult respiratory distress syndrome (ARDS), cerebral malaria, chronic pulmonary inflammatory disease, silicosis, asbestosis, pulmonary sarcoidosis, bone resorption diseases, graft vs. host reactions, allograft rejections, fever and myalgias due to bacterial or viral infections, influenza, cachexia secondary to acquired immune deficiency syndrome (AIDS), keloid formation, scar tissue formation, Crohn's disease, ulcerative colitis, pyresis, a number of "autoimmune diseases", multiple sclerosis, autoimmune diabetes, and systemic lupus erythematosus.

TNF-alpha inhibitors are useful in the treatment of a variety of allergic, traumatic and other injurious disorders including: asthma, chronic bronchitis, atopic dermatitis, urticaria, allergic rhinitis, allergic conjunctivitis, eosiniophilic granuloma, ulcerative colitis, Crohn's disease, reperfusion injury of the myocardium and brain, chronic glomerulonephritis, and adult respiratory distress syndrome (ARDS).

The compounds of this invention can inhibit the release of TNF-alpha and thus can be useful for inhibiting or blocking several pathophysiological effects of TNF-alpha at injury or surgery sites and thus also inhibit the release of other pathophysiological biochemical products from cells such as histamines, prostaglandins, bradykinins, and peroxidases.

As discussed above, TNF-alpha inhibitors can be very effective in the treatment of disorders which follow cellular, tissue or organ injury or surgery, and can be as effective, or even more potent, than corticosteroids or immunosuppressants without producing the side effects common to these agents.

This invention also relates to a therapeutic method of (1) inhibiting TNF-alpha release from cells and/or (2) preventing the untoward, toxic or lethal effects of excessively high tissue levels of TNF-alpha in a mammal, including a human. This method comprises administering to a mammal an effective TNF-alpha inhibiting quantity of one or more of the above compounds. This method also can be used for the prophylactic treatment or prevention of certain TNF-alpha mediated or exacerbated diseases amenable thereto. The invention provides a method for the treatment of allergic, traumatic, radiation, chemical, microbial and other injurious disorders by administering to a mammal, including a human, in need thereof an effective amount of such compounds.

The compounds, by inhibiting or blocking the release of TNF-alpha or decreasing TNF-alpha levels and activity, as well as the pathophysiologic actions of excessive levels of TNF-alpha in each of these circumstances, directly facilitate the arrest or resolution of the tissue or organ damage, and facilitates the restoration of normal function. Together, these actions relate their novel use in treating tissue trauma, or other injury disorders caused by infection, allergy, immunologic phenomena, burns, radiation exposure, neoplastic disease, toxic chemicals and expressed as cardiovascular damage, neurologic injury, renal damage, liver damage, pancreatic damage, as well as ascites, localized edema, dermal damage and dermal blister.

The term "inhibiting the release of TNF-alpha", means:
a) decrease of in vivo TNF-alpha levels in a mammal such as a human;
b) a down regulation of TNF-alpha levels in vitro or in-vivo; or
c) a down regulation of TNF-alpha activity, by inhibition of the direct synthesis of TNF-alpha or a post-translation event in vivo or in vitro.

The compounds can be useful in inhibiting the release of TNF-alpha by monocytes, macrophages, neuronal cells, endothelial cells, epidermal cells, mesenchymal cells (for example: fibroblasts, skeletal myocytes, smooth muscle myocytes, cardiac myocytes) and many other types of cells.

The term "condition" or "state" refers to any disease, disorder or effect that produces deleterious biological consequences in a subject.

The level of TNF-alpha protein in the blood or cell of a patient or a cell culture (i.e., within the cell or the cell culture media) can be determined by for example, assaying for immunospecific binding to TNF-alpha or to other proteins known to be produced as a result of the presence of active TNF-alpha. Such methods are known in the art. For example, immunoassays which can be used include, but are not limited to competitive and non-competitive assay systems, western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis with labeled antibodies. Such assays well known in the art (see, e.g., Ausubel et al, eds, 1994, Current Protocols in Molecular Biology, Vol. 1, John Wiley & Sons, Inc., New York, which is incorporated by reference herein in its entirety).

Competitive binding assays can also be used to determine the level of TNF-alpha. One example of a competitive binding assay is a radioimmunoassay comprising the incubation of labeled proteins from cells expressing TNF-alpha (e.g., $^3$H or $^{125}$I) with a TNF-alpha antibody in the presence of increasing amounts of unlabeled TNF-alpha, and the detection of the TNF-alpha antibody bound to the labeled TNF-alpha. The affinity of the antibody of interest for a particular antigen and the binding off-rates can be determined from the data by Scatchard plot analysis. Competition with a second antibody can also be determined using radioimmunoassays. In this case, the antigen is incubated with antibody of interest conjugated to a labeled compound (e.g., $^3$H or $^{125}$I) in the presence of increasing amounts of an unlabeled second antibody.

TNF-alpha levels can also be assayed by activity, for example, TNF-alpha levels can be assayed by a cell line that is capable of detecting bioactive levels of cytokines like TNF-alpha or a growth factor. According to one embodiment, the levels of bioactive TNF-alpha in a biological sample is detected by incubating a cell line genetically engineered with isopropyl-b-D-thiogalactopyranoside. The cell line is incubated with the sample to be tested and cell death in the cell line is monitored by determining the intensity of blue color which is indicative of a bioactive cytokine or growth factor in the sample tested. See also, e.g., Burns (1994) 20(1):40-44 for TNF activity assay of serum of patients.

A cytotoxicity assay can be used to e.g., determine TNF-alpha activity with actinomycin D-treated ME180 cells and L929 cells can be used in an assay described by Ostrove and Gifford (Proc. Soc. Exp. Biol. Med. 160, 354-358 (1979)), Aggarwal and Essalu (J. Biol. Chem. 262, 10000-10007 (1987)) and Levesque et al. (J. Immun. Meth. 178, 71-76 (1995)). L929 cells (CCLI: American Type Culture Collection) are maintained in McCoy's 5A medium containing 10% fetal bovine serum. Confluent cultures were treated briefly with 0.25% trypsin in physiological solution and resuspended in a fresh medium. The trypsinized cells per well are plated in 96-Well plates (Corning) and incubated for 24 hours at 37° C. Then actinomycin D was added to a final concentration of 0.25 ug/ml. Samples containing the compounds to be tested are added to the wells and incubation is continued overnight at the same temperature. After microscopic evaluation, the medium is decanted, and the wells are rinsed with PBS. The wells are then filled with a crystal violet dye solution. The dye is extracted and the absorbance of the dye retained in viable cells is determined at 570 nm.

Dosage levels of between about 0.01 and about 100 mg/kg body weight per day, preferably between about 0.5 and about 75 mg/kg body weight per day and most preferably between about 1 and about 50 mg/kg body weight per day of the active ingredient compound are useful in a monotherapy.

Typically, the pharmaceutical compositions of this invention will be administered from about 1 to 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of this invention and one or more additional therapeutic agents, both the compound and the additional agent should be present at dosage levels of between about 10% to about 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence or disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

Accordingly, a method for treating or preventing a disease of this invention in a subject comprises the step of administering to the subject any compound, pharmaceutical composition, or combination described herein.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent, it may be delivered together with the compound of this invention in a single dosage form, or, as a separate dosage form. When administered as a separate dosage form, the other therapeutic agent may be administered prior to, at the same time as, or following administration of a pharmaceutically acceptable composition comprising a compound of this invention.

A kit according to this invention comprises a compound or pharmaceutical composition of this invention and a tool for measuring TNF-alpha levels or activity in vitro or in vivo. The kit can further comprise instructions for using the contents of the kit. A tool for measuring TNF-alpha levels or activity according to this invention refers to materials that can be used to measure the TNF gene product (i.e., RNA or protein) or activity. Such methods are described for example above. Thus, a tool according to this invention can include, e.g., an anti-TNF antibody, a TNF-alpha DNA probe or a genetically engineered cell line responsive to TNF-alpha levels described above.

The methods for identifying a compound or composition that decreases TNF-alpha activity and/or levels according to this invention include methods for screening of a plurality of compounds or compositions for their ability to decrease TNF-alpha activity and/or levels. For example, high-throughput screening is a desired embodiment of this invention. According to one embodiment of this invention, high throughput screening can be achieved by having cells in culture in a plurality of wells in a microtiter plate, adding a different compound or composition to each well and comparing the TNF-alpha levels and/or activity in each cell culture to the TNF-alpha levels or activity present in a cell culture in a control well. Controls that are useful for the comparison step according to this invention include cells or subjects that have not been treated with a compound or composition and cells or subjects have been treated with a compound or composition that is known to have no effect on TNF-alpha levels or activity. According to one embodiment of this invention, the high throughput screening is automated so that the steps including the addition of the cells to the plate up to the data collection and analysis after addition of the compound or composition are done by machine. Instruments that are useful in the comparison step of this invention, e.g., instruments that can detect labeled objects (e.g., radiolabelled, fluorescent or colored objects) or objects that are themselves detectable, are commercially available and/or known in the art. Accordingly, compounds and compositions according to this invention that are useful for decreasing TNF-alpha levels and/or activity can be quickly and efficiently screened.

All applications, patents and references disclosed herein are incorporated by reference. In order that this invention be more fully understood, the following preparative and testing examples are set forth. These examples are for the purpose of illustration only and are not to be construed as limiting the scope of the invention in any way.

EXAMPLES

Example 1

[3S/R, (2S)]-5-Fluoro-4-oxo-3-{[1-(phenothiazine-10-carbonyl)piperidine-2-carbonyl]amino}-pentanoic acid

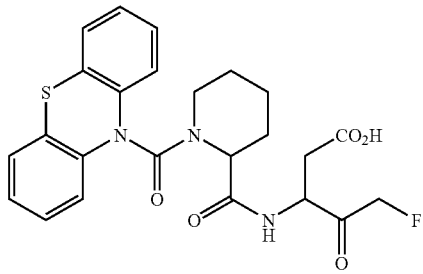

Method A (S)-(1-Phenothiazine-10-carbonyl)piperidine-2-carboxylic acid methyl ester

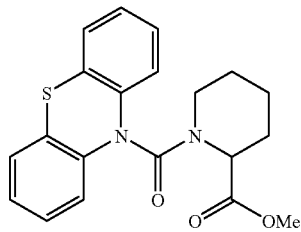

To a stirred solution of methyl pipecolate hydrochloride (1 g, 5.57 mmol) in THF (10 ml) was added phenothiazine carbonyl chloride (1.457 g, 5.57 mmol) followed by diisopropylethylamine (2.02 ml, 11.68 mmol). The resulting solution was stirred for 16 h before being partitioned between ethyl acetate and aq. sat. NH$_4$Cl. The organic layer was washed with brine, dried (MgSO$_4$), filtered and evaporated. The residue was purified by flash chromatography (15% ethyl acetate in hexane) to afford the sub-title compound as a colorless oil which crystallized upon standing (1.823 g, 89%): $^1$H NMR (400 MHz, CDCl$_3$) δ 1.13-1.48 (3H, m), 2.57-2.69 (2H, m), 2.16 (1H, m), 3.00 (1H, m), 3.74 (4H, s+m), 5.00 (1H, m), 7.11 (2H, t), 7.22-7.34 (4H, m), 7.76 (2H, d); $^{13}$C NMR (100 MHz, CDCl$_3$) δ 21.3 (CH$_2$), 24.8 (CH$_2$), 27.3 (CH$_2$), 44.9 (CH$_2$), 52.5 (CH$_3$), 55.9 (CH), 122.8 (CH), 125.5 (CH), 127.8 (CH), 128.0 (CH), 129.2 (C), 141.7 (C), 158.4 (C), 172.2 (C).

Method B

(S)-(1-Phenothiazine-10-carbonyl)piperidine-2-carboxylic acid

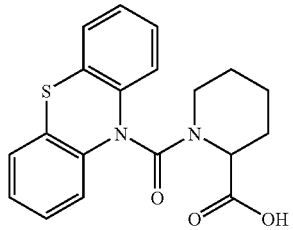

To a stirred solution of (S)-(1-phenothiazine-10-carbonyl)piperidine-2-carboxylic acid methyl ester (0.912 g) in THF (15 ml) and water (8 ml) was added 2M NaOH (3.71 ml) and the reaction mixture was stirred for 16 hours. The reaction mixture was poured into sodium hydrogen carbonate solution (50 ml) and extracted with ethyl acetate (40 ml). Aqueous phase was made acidic and extracted with ethyl acetate (2×75 ml). Organic extracts were combined, dried (MgSO$_4$) and concentrated to give the sub-title compound as a white solid (0.709 g, 81%): $^1$H NMR (400 MHz, CDCl$_3$) δ 0.99-1.72 (5H, m), 2.23 (1H, m), 2.97 (1H, m), 3.58 (1H, m), 4.93 (1H, m), 7.16 (2H, t), 7.28 (2H, t), 7.37 (2H, d), 7.78 (2H, d); $^{13}$C NMR (100 MHz, CDCl$_3$) δ 21.0 (CH$_2$), 24.2 (CH$_2$), 26.7 (CH$_2$), 45.7 (CH$_2$), 56.0 (CH), 123.8 (CH), 126.0 (CH), 127.9 (CH), 128.1 (CH), 130.3 (C), 141.2 (C), 160.1 (C), 175.9 (C).

Method C

[3S/R, 4S/R (2S)]-5-Fluoro-4-hydroxy-3-{[1-(phenothiazine-10-carbonyl)piperidine-2-carbonyl]amino}-pentanoic acid tert-butyl ester

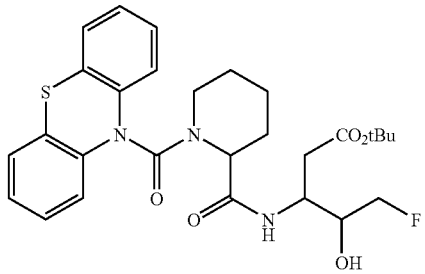

A stirred mixture of (S)-(1-phenothiazine-10-carbonyl)piperidine-2-carboxylic acid (233 mg, 0.658 mmol), 3-amino-5-fluoro-4-hydroxy-pentanoic acid tert-butyl ester (150 mg, 0.724 mmol), HOBt (98 mg, 0.724 mmol), DMAP (88 mg, 0.724 mmol) and anhydrous THF (10 ml) was cooled to 0° C. before EDC (139 mg, 0.724 mmol) was added. The mixture was allowed to warm to room temperature during 16 h then concentrated under reduced pressure. The residue was purified by flash chromatography (50% ethyl acetate in hexane) to afford the sub-title compound as a pale pink foam (294 mg, 82%): $^1$H NMR (400 MHz, CDCl$_3$) δ 1.96 (1H, m), 1.18-1.60 (13H, m), 2.10-2.25 (1H, m), 2.48-2.70 (2H, m), 2.78-2.94 (1H, m), 3.51-4.72 (7H, m), 7.03-7.36 (7H, m), 7.71-7.76 (2H, m); $^{19}$F (376 MHz, CDCl$_3$) δ −228.9 (t), −229.3 (t), −230.1 (t), −230.2 (t).

Method D

[3S/R, (2S)]-5-Fluoro-4-oxo-3-{[1-(phenothiazine-10-carbonyl)piperidine-2-carbonyl]amino}-pentanoic acid tert-butyl ester

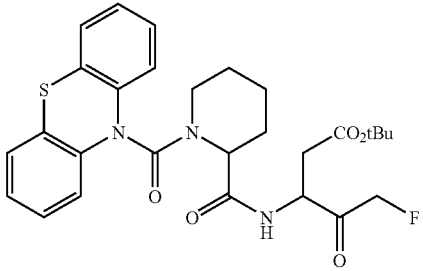

A stirred solution of [3S/R, 4S/R (2S)]-5-Fluoro-4-hydroxy-3-{[1-(phenothiazine-10-carbonyl)piperidine-2-carbonyl]amino}-pentanoic acid tert-butyl ester (294 mg, 0.541 mmol) in anhydrous DCM (10 mL) was treated with 1,1,1-triacetoxy-1,1-dihydro-1,2-benziodoxol-3(1H)-one (344 mg, 0.812 mmol) at 0° C. The resulting mixture was allowed to warm to room temperature over 2 h, diluted with ethyl acetate, then poured into a 1:1 mixture of saturated aqueous sodium hydrogen carbonate and saturated aqueous sodium thiosulphate. The organic layer was removed and the aqueous layer was re-extracted with ethyl acetate. The combined organic extracts were dried (Na$_2$SO$_4$) and concentrated. The residue was purified by flash chromatography (30% ethyl acetate in hexane) to afford the sub-title compound as a pale pink foam (220 mg, 75%): $^1$H NMR (400 MHz, CDCl$_3$) δ 0.84-0.96 (1H, m), 1.20-1.40 (10H, m+2 s), 1.51-1.56 (3H, m), 2.20-2.27 (1H, m), 2.70-2.98 (3H, m), 3.49-3.63 (1H, m), 4.74-5.24 (4H, m), 7.14-7.18 (2H, m), 7.28-7.38 (4H, m), 7.48-7.79 (3H, m); $^{13}$C (100 MHz, CDCl$_3$) δ 20.8/21.0 (CH$_2$), 23.7/23.9 (CH$_2$), 25.8/25.9 (CH$_2$), 28.2/28.3 (CH$_3$), 36.8/36.9 (CH$_2$), 46.0/46.1 (CH$_2$), 52.9 (CH), 56.8 (CH), 82.6 (C), 84.4/84.5 (2d, J 184.0/183.3, CH$_2$F), 123.7/123.8 (CH) 126.1 (CH), 128.0/128.1 (CH), 128.2/128.3 (CH), 130.4/130.5 (C), 141.4 (C), 160.0 (C), 170.0 (C), 171.7 (C), 202.9 (C); $^{19}$F (376 MHz, CDCl$_3$) δ −231.9 (t), −232.2 (t).

Method E

[3S/R, (2S)]-5-Fluoro-4-oxo-3-{[1-(phenothiazine-10-carbonyl)piperidine-2-carbonyl]amino}-pentanoic acid

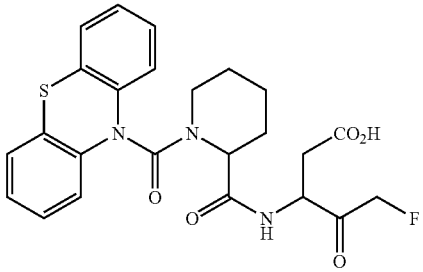

Trifluoroacetic acid (5 mL) was added to a stirred ice cold solution of [3S/R, (2S)]-5-fluoro-4-oxo-3-{[1-(phenothiazine-10-carbonyl)piperidine-2-carbonyl]amino}-pentanoic acid tert-butyl ester (130 mg, 0.24 mmol) in anhydrous DCM (5 mL). The mixture was stirred at 0° C. for 0.5 h then at room temperature for 0.5 h. The mixture was concentrated under reduced pressure and then the residue was dissolved in dry DCM. This process was repeated several times in order to remove excess trifluoroacetic acid. The gum was lyophilized twice from HPLC grade water to afford the title compound as a white powder (77 mg, 66%): IR (solid) 1670, 1716, 1782 cm$^{-1}$; $^1$H NMR (400 MHz, d$_6$-DMSO) δ 0.96-0.99 (1H, m), 1.23-1.26 (2H, m), 1.42-1.44 (1H, m), 1.60 (1H, m), 1.91-1.98 (1H, m), 2.51-2.89 (2H, m), 3.11-3.22 (1H, m), 3.57-3.60 (1H, m), 4.30-4.72 and 5.05-5.29 (4H, 2 m), 7.11-7.17 (2H, m), 7.24-7.30 (2H, m), 7.34-7.38 (2H, m), 7.57-7.63 (2H, m), 8.07-8.61 (1H, m); $^{13}$C NMR (100 MHz, DMSO) δ (DMSO+TFA) 18.8/18.9 (CH$_2$), 22.2/22.3 (CH$_2$), 25.8/26.1 (CH$_2$), 31.5/33.2 (CH$_2$) 43.2 (CH$_2$), 50.6/51.1 (CH), 54.4/54.5 (CH), 82.8/82.9 (2d, J 178.6/178.1, CH$_2$F), 119.9/120.0 (CH), 120.4/120.5 (CH), 124.0/124.1 m (CH), 125.9/126.0 (C), 126.4/126.5 (CH), 139.6/139.7 (C), 156.0/156.4 (CO), 170.3 (CO), 170.7/170.8 (CO), 202.2/202.3 (2d, J 14.6/15.1, CO).; $^{19}$F (376 MHz, DMSO) δ chemical shift (multiplicity, relative intensity) −226.7 (t, 3), −226.9 (t, 3), −230.4 (t, 1), −231.2 (t, 1), −232.7 (t, 10), −233.0 (t, 10).

Example 2

[3S/R, (2S)]-3-{[1-(2-Chlorophenothiazine-10-carbonyl)piperidine-2-carbonyl]amino}-4-fluoro-4-oxo-pentanoic acid

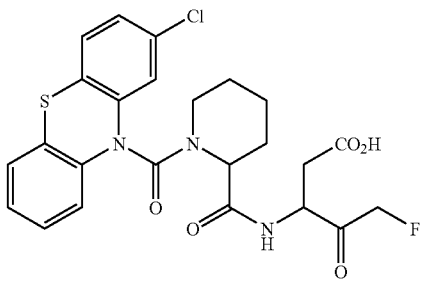

This was prepared from 2-chlorophenothiazine carbonyl chloride using procedures similar to those described above in Methods A-E (73 mg, 69%): IR (solid, cm$^{-1}$) 1738, 1660, 1555, 1363, 1224; $^1$H NMR (400 MHz, d$_6$-DMSO+TFA) δ 0.98-1.61 (4H, m), 1.94-2.03 (1H, m), 2.53-2.89 (2H, m), 3.12-3.24 (1H, m), 3.51-3.61 (1H, m), 4.31-4.73 and 5.10-5.24 (4H, 2 m), 7.15-7.49 (6H, m), 7.77-7.81 (1H, m), 8.13-8.64 (1H, m); $^{13}$C NMR (100 MHz, DMSO+TFA) δ 18.7/18.8 (CH$_2$), 22.3/22.6 (CH$_2$), 25.9/26.2 (CH$_2$), 31.5/33.2 (CH$_2$), 43.0/43.2 (CH$_2$), 50.6/51.1 (CH) 54.4/54.5 (CH), 82.8/82.9 (2d, J 178.7/178.3, CH$_2$F), 119.3/119.8 (CH), 120.2/120.3 (CH), 123.6/123.7 (CH), 124.4/124.5 (CH), 124.6/124.8 (C), 126.6 (CH), 126.9 (CH), 127.5 (CH), 131.0 (C), 139.2/139.2 (C), 140.7/140.7 (C), 155.5/155.9 (C), 170.1/170.2 (C), 170.7/170.8 (C), 201.2/201.3 (2d, J 14.3/13.9, CO); $^{19}$F NMR (376 MHz, DMSO+TFA) δ −226.7 (t), −226.9 (t), −230.3 (t), −232.7 (t), −233.0 (t).

Example 3

[3S/R, (2S)]-3-{[1-(3-Chlorophenothiazine-10-carbonyl)piperidine-2-carbonyl]amino}-4-fluoro-4-oxo-pentanoic acid

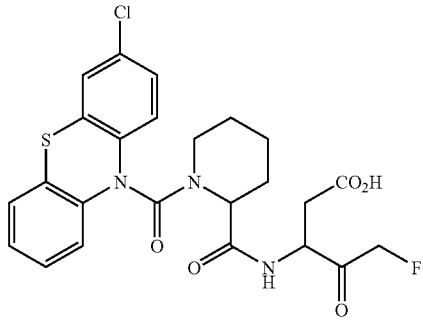

This was prepared from 3-chlorophenothiazine carbonyl chloride using procedures similar to those described above in Methods A-E (108 mg, 65%): IR (solid, cm$^{-1}$) 1737, 1655, 1455, 1373, 1224; $^1$H NMR (400 MHz, d$_6$-DMSO+TFA) δ 0.99-1.61 (5H, m), 1.91-2.04 (1H, m), 2.54-2.90 (2H, m), 3.12-3.24 (1H, m), 3.48-3.60 (1H, m), 4.26-5.28 (4H, m), 7.15-7.68 (7H, m), 8.10-8.62 (1H, m); $^{13}$C NMR (100 MHz, DMSO+TFA) δ 18.8 (CH$_2$), 22.2/22.3 (CH$_2$), 25.8 (CH$_2$), 33.1/33.2 (CH$_2$), 43.2 (CH$_2$), 50.6/51.0 (CH), 54.3/54.4 (CH), 82.7/82.8 (2d, CH$_2$F), 120.2/120.3 (CH), 121.3/121.4 (CH), 124.2/124.3 (CH), 124.8/125.0 (C), 125.7 (CH), 126.3 (CH), 126.6 (CH), 126.8 (CH), 127.7/127.9 (C), 127.9/128.0 (C), 138.5 (C), 139.3 (C), 156.0 (CO), 170.1 (CO), 170.6/170.7 (CO), 201.1/201.2 (2d, CO); $^{19}$F NMR (376 MHz, DMSO+TFA) δ −226.6 (t), −226.9 (t), −232.6 (t), −232.9 (t).

Example 4

[3S/R, (2S)]-3-{[1-(3,4-Dichlorophenothiazine-10-carbonyl)piperidine-2 carbonyl]amino}-4-fluoro-4-oxo-pentanoic acid

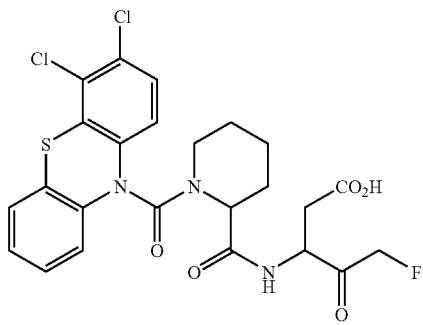

This was prepared from 3,4-dichlorophenothiazine carbonyl chloride using procedures similar to those described above in Methods A-E (91 mg, 66%): IR (solid, cm$^{-1}$) 1737, 1439, 1363, 1219; $^1$H NMR (400 MHz, d$_6$-DMSO+TFA) δ 1.03-1.62 (5H, m) 1.97-2.06 (1H, m), 2.54-2.86 (2H, m), 3.14-3.28 (1H, m), 3.59-3.66 (1H, m), 4.30-5.26 (4H, m), 7.15-7.68 (6H, m), 8.14-8.96 (1H, m); $^{13}$C NMR (100 MHz, DMSO+TFA) δ 20.2 (CH$_2$), 23.8 (CH$_2$), 27.3 (CH$_2$), 34.6/34.7 (CH$_2$), 44.5 (CH$_2$), 52.1/52.5 (CH), 55.7/55.9 (CH), 84.2/84.3 (2d, CH$_2$F), 120.2/120.3 (CH), 120.8/120.9 (CH), 124.2/124.4 (C), 125.9 (CH), 127.7/127.8 (C), 128.2 (CH), 128.4/128.5 (C), 128.8 (CH), 128.9 (CH), 140.0 (C), 140.1 (C), 140.6 (C), 156.8/156.8 (CO), 171.5 (CO), 172.1/172.1 (CO), 202.6/202.7 (2d, CO); $^{19}$F NMR (376 MHz, DMSO+TFA) δ −226.6 (t), −226.8 (t), −232.6 (t), −232.9 (t).

Example 5

[3S/R, (2S)]-3-{[1-(2,6-Dichlorophenothiazine-10-carbonyl)piperidine-2-carbonyl]amino}-4-fluoro-4-oxo-pentanoic acid

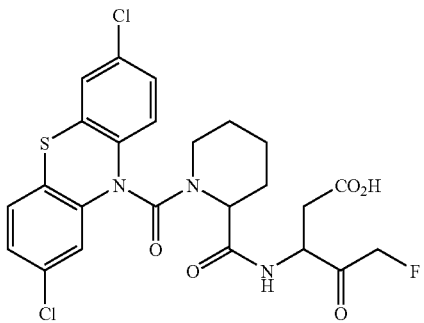

This was prepared from 2.7 g dichlorophenothiazine carbonyl chloride using procedures similar to those described above in Methods A-E (91 mg, 70%): IR (solid, cm$^{-1}$) 1737, 1660, 1555, 1363, 1224; $^1$H NMR (400 MHZ, d$_6$-DMSO+TFA) δ 1.02-1.62 (5H, m), 1.91-2.02 (1H, m), 2.53-2.90 (2H, m), 3.13-3.25 (1H, m), 3.51-3.62 (1H, m), 4.31-5.29 (4H, m), 7.22-7.75 (6H, m), 8.18-8.65 (1H, m); $^{13}$C NMR (100 MHz, DMSO+TFA) δ 20.2 (CH$_2$), 23.8 (CH$_2$), 27.3 (CH$_2$), 34.6 (CH$_2$), 44.7 (CH$_2$), 52.5 (CH), 55.8 (CH), 84.3 (d, J 178.2, CH$_2$F), 120.7/121.2 (CH), 122.7/122.8 (CH), 124.7/125.1 (C), 125.3/125.4 (CH), 127.4 (CH), 128.1 (CH), 128.7/128.9 (C), 129.1 (CH), 129.8 (C), 132.7 (C), 139.5/139.6 (C), 141.8/141.9 (C), 157.0 (CO), 171.5 (CO), 172.1 (CO), 202.6 (d, J 14.3, CO); $^{19}$F NMR (376 MHz, DMSO+TFA) δ −226.6 (t), −226.9 (t), −232.6 (t), −232.9 (t)

Example 6

[3S/R, (2S)]-3-{[1-(Carbazole-9-carbonyl)piperidine-2-carbonyl]amino}-4-fluoro-4-oxo-pentanoic acid

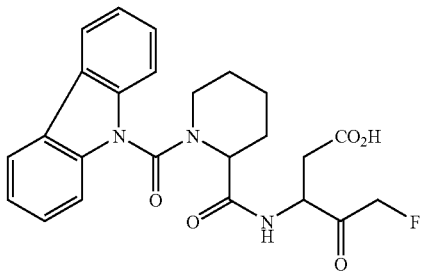

This was prepared from 9-carbazole carbonyl chloride using procedures similar to those described above in Methods A-E (180 mg, 75%): IR (solid, cm$^{-1}$) 1737, 1655, 1419, 1373, 1224; $^1$H NMR (400 MHz, d$_6$-DMSO+TFA) δ 1.36-1.65 (6H, m), 1.94-1.99 (1H, m), 2.12-2.21 (1H, m), 2.59-2.89 (2H, m), 4.32-5.27 (4H, m), 7.30-7.36 (2H, m), 7.48-7.54 (2H, m), 7.63-7.76 (2H, m), 8.17-8.72 (3H, m); $^{13}$C NMR (100 MHz, DMSO+TFA) δ 19.0 (CH$_2$), 23.7/23.8 (CH$_2$), 26.5/26.8 (CH$_2$), 33.3/33.5 (CH$_2$) 44.1 (br, CH$_2$), 50.9/51.4 (CH), 54.5 (br, CH), 82.9/83.1 (2d, J 178.7/178.7, CH$_2$F), 111.0/111.1 (CH) 111.9 (CH), 119.5/119.7 (CH), 120.6/120.7 (CH), 122.5/122.7 (C), 125.8/125.9 (CH), 137.1/137.4 (C), 153.2/153.3 (C), 170.3/170.4 (C), 170.8/170.9 (C), 201.4/201.5 (2d, J 14.6/14.6, CO); $^{19}$F NMR (376 MHz, DMSO+TFA) δ d (J, % I) −226.6 (t, 3), −226.8 (t, 3), −230.0 (t, 1), −232.7 (t, 10), −232.7 (t, 10).

Example 7

[3S/R, (2S)]-5-Fluoro-4-oxo-3-{[1-(6H-phenanthridine-5-carbonyl)-piperidine-2-carbonyl]amino}-pentanoic acid

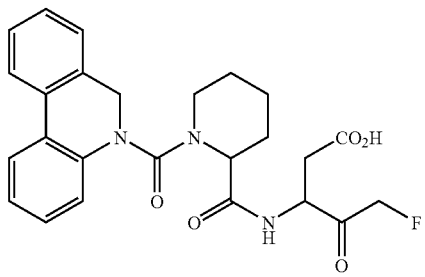

This was prepared from 9,10-dihydrophenanthrinine carbonyl chloride using procedures similar to those described above in Methods A-E (115 mg, 61%): IR (solid, cm$^{-1}$) 1731, 1419, 1363, 1219; $^1$H NMR (400 MHz, d$_6$-DMSO+TFA) δ 1.27-1.69 (5H, m), 1.90-2.06 (1H, m), 2.55-2.87 (2H, m), 3.13-3.21 (2H, m), 4.31-5.26 (6H, m), 7.12-7.48 (6H, m), 7.84-7.86 (2H, m), 8.08-8.58 (1H, m); $^{13}$C NMR (100 MHz, DMSO+TFA) δ 20.5 (CH$_2$), 24.2 (CH$_2$), 27.73 (CH$_2$), 34.6/34.8 (CH$_2$) 44.9 (CH$_2$), 48.5/48.7 (CH), 52.1/52.5 (CH), 55.4/55.7 (CH), 84.2 (d, CH$_2$F), 120.2 (CH), 123.3 (CH), 123.6 (CH), 124.7 (CH), 126.1 (C), 126.3 (CH), 128.0 (CH), 128.3 (CH), 128.7 (CH), 131.6 (C), 134.6 (C), 140.2 (C), 172.1/172.2 (CO), 172.4/172.4 (CO), 203.0 (d, CO); $^{19}$F NMR (376 MHz, DMSO+TFA) δ −226.8 (t), −226.9 (t), −232.7 (t), −232.9 (t).

Example 8

[3S/R, (2S)]-5-Fluoro-3-{2-[(1H-imidazole-2-carbonyl)-amino]-propionylamino}-4-oxo-pentanoic acid, trifluoroacetate salt (Compound 1)

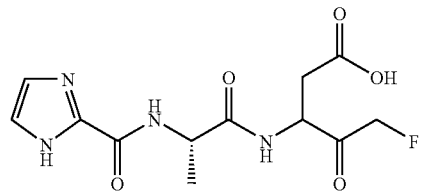

Method A

(2S)-2-[(1H-Imidazole-2-carbonyl)-amino]-propionic acid tert-butyl ester

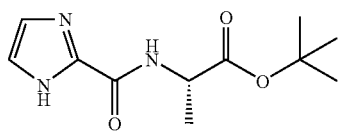

To a solution of 1H-imidazole-2-carboxylic acid (0.17 g) in N,N-dimethylformamide (DMF) (3 mL) was added alanine tert-butyl ester hydrochloride (0.22 g), diisopropylethyl amine (0.27 mL) and HOBT (0.41 g) before cooling to 0° C. and the reaction mixture was then treated with EDC HCl (0.32 g). The cooling bath was removed and the reaction mixture was stirred at ambient temperature for 18 hrs before being diluted with ethyl acetate and washed with water and brine, dried (MgSO$_4$) and concentrated at reduced pressure. The residue was purified by silica gel chromatography (30% ethyl acetate in hexanes) to afford the sub-title compound as a colourless oil (0.263 g, 73%): $^1$H NMR 400 MHz CDCl$_3$ 1.50 (9H, s), 1.51 (3H, d, J 7.2), 3.70 (1H, m), 7.28 (2H, s), 7.78 (1H, d, J 7.6), 11.49 (1H, br s).

Method B

[3S/R, 4S/R, (2S)]-5-Fluoro-4-hydroxy-3-{2-[(1H-imidazole-2-carbonyl)-amino]-propionylamino}-pentanoic acid tert-butyl ester

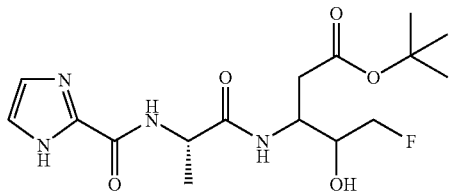

A solution of (2S)-2-[(1H-imidazole-2-carbonyl)-amino]-propionic acid tert-butyl ester (0.257 g) in dichloromethane (2 ml) was cooled to 0° C. before dropwise addition of trifluoroacetic acid and the reaction mixture was warmed to room temperature and stirred for 2 hr before evaporation under reduced pressure. The residue was co-evaporated with dichloromethane (twice) and toluene (twice) to leave the required (2S)-2-[(1H-imidazole-2-carbonyl)-amino]-propionic acid that was used without further purification (0.40 g).

A solution of (2S)-2-[(1H-imidazole-2-carbonyl)-amino]-propionic acid and 3-amino-5-fluoro-4-hydroxy-pentanoic acid tert-butyl ester (0.254 g) in THF (7 mL) was cooled to 0° C. before addition of DMAP (0.151 g), diisopropylethyl amine (0.56 mL), HOBT (0.16 g) and EDC HCl (0.23 g). The reaction mixture was stirred at ambient temperature for 18 hrs before being concentrated at reduced pressure. The residue was purified by silica gel chromatography (5% methanol in dichloromethane) to afford the sub-title compound as a colourless solid (0.386 g, 97%): $^1$H NMR 400 MHz CDCl$_3$/CD$_3$OD 1.40 (12H, m), 3.92 (1H, m), 4.20-4.55 (4H, m), 7.11 (2H, d, J 15); $^{19}$F NMR CDCl$_3$ −229.74 (m), −229.84 (m), −230.54 (m), −230.87 (m).

Method C:

[3S/R, (2S)]-5-Fluoro-3-{2-[(1H-imidazole-2-carbonyl)-amino]-propionylamino}-4-oxo-pentanoic acid tert-butyl ester

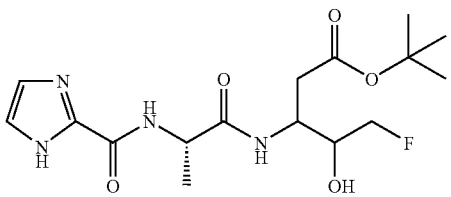

A solution of [3S/R, (2S)]-5-fluoro-4-hydroxy-3-{2-[(1H-imidazole-2-carbonyl)-amino]-propionylamino}-pentanoic acid tert-butyl ester (0.381 g) in dichloromethane was cooled to 0° C. before addition of 1,1,1 triacetoxy-1,1-dihydro-1,2-benziodoxol-3(1H)-one (0.476 g). The mixture was stirred at room temperature for 2 h before addition of an additional portion of 1,1,1 triacetoxy-1,1-dihydro-1,2-benziodoxol-3 (1H)-one (0.05 g) and reaction mixture was then stirred for 90 min before being concentrated at reduced pressure. The residue was dissolved in ethyl acetate and washed with a 1:1 mixture of aqueous NaHSO$_4$ and aqueous Na$_2$S$_2$O$_3$. The organic layer was collected, dried (MgSO$_4$) and concentrated. The residue was purified by flash chromatography (5% methanol in dichloromethane) to give the sub-title compound as a colourless foam (319 mg, 84%): $^1$H NMR 400 MHz CDCl$_3$ 1.37+1.43 (9H, 2×s), 1.54 (3H, m), 2.85 (1H, m), 3.03 (1H, m), 4.85-5.30 (4H, m), 7.18 (2H, d, J 16), 7.90 (1H, m), 7.98 (1H, m), 11.37+11.45 (1H, 2×s); $^{19}$F NMR 376 MHz CDCl$_3$ −231.85 (t, J 48), −232.12 (t, J 48).

Method D:

Compound 1

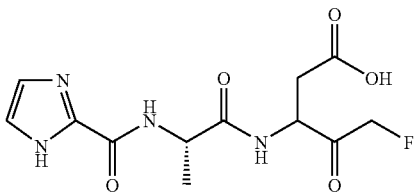

A solution of [3S/R, (2S)]-5-Fluoro-3-{2-[(1H-imidazole-2-carbonyl)-amino]-propionylamino}-4-oxo-pentanoic acid tert-butyl ester (0.31 g) in dichloromethane (2 ml) was cooled to 0° C. before dropwise addition of trifluoroacetic acid and the reaction mixture was warmed to room temperature and stirred for 2 hr before evaporation under reduced pressure. The residue was co-evaporated with dichloromethane (twice) and triturated under ether to give the title compound as a colourless solid (0.35 g): IR 1785.7, 1730.1, 1653.7, 1538.1, 1458.2, 1384.2, 1268.7, 1188.4, 1150.9, 1053.3, 992.13, 931.8, 867.9, 847.0, 768.5 cm$^{-1}$; $^1$H NMR 400 MHz DMSO-d₆ 1.37 (3H, d), 2.40-2.85(2H,m,asp CH₂), 4.34-4.75(2.5H, m, 2×CH+0.5CH₂F), 5.13-5.41 (1.5H,m,CH₂F), 7.50(2H,s, imidazole CHs), 8.58-8,79(2H,m,NHs); $^{13}$C NMR 100 MHz DMSO-d₆ 18.13, 18.85(ala CH₃); 33.13, 34.75(asp CH₂), 48.68, 52.41(CHs), 83.46, 85.21(CH₂F), 123.67(CH imidazole), 139.57, 158.86, 172.35(m) (C=Os), 202.70(5 peaks ketone); $^{19}$F NMR 376 MHz DMSO-d₆ decoupled −75.19 (3F,s,CF₃COOH), −(226.89, 226.96, 230.80, 231.59, 232.95, 233.06 (1F,6×s, COCH₂F ring opened and ring closed).

Example 9

[3S/R, (2S)]-3-{2-[(1H-Benzoimidazole-2-carbonyl)-amino]-propionylamino}-5-fluoro-4-oxo-pentanoic acid, trifluoroacetate salt (Compound 2)

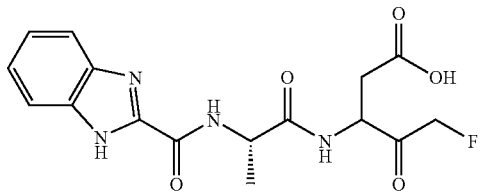

This was prepared from 1H-benzoimidazole-2-carboxylic acid using procedures similar to those described in Methods A-D above (142 mg, 90% for final step): (compound isolated as the TFA salt) off-white solid; IR (solid, cm⁻¹) 3277.9, 1654.6, 1526.6, 1188.6, 1142.5, 1050.4, 927.5, 748.2, 712.4; $^1$H NMR (DMSO-d₆) 1.42 (3H, d), 2.51-2.95 (2H, m), 4.21-4.75(2H, m), 4.76-5.60 (3H, brm), 7.41 (2H, m), 7.65 (2H, m), 8.21-9.05 (2H, m); $^{13}$C NMR (DMSO-d₆) 18.0, 18.7, 18.8 (Ala CH₃), 37.2, 34.6, 34.7 (Asp CH₂), 47.6, 48.8, 48.85, 49.1 (Asp CH), 52.0, 52.5 (Ala CH), 83.5, 85.2, 85.3, 103.8, 106.0 (CH₂F), 116.6, 123.9 (Aryl CH), 145.3, 145.4, (Aryl C), 158.4, 158.7, 158.8, 172.1, 172.2, 172.4, 172.5, 172.6, 172.7, 173.2 (NC=O), 202.6, 202.7, 202.8, 202.9 (C=O); Found M⁺ 364.1177. C₁₆H₁₇FN₄O₅ requires M⁺ 364.1183 (1.8 ppm).

Example 10

[3S/R, (2S)]-5-Fluoro-3-{2-[(1H-imidazole-2-carbonyl)-amino]-butyrylamino}-4-oxo-pentanoic acid, trifluoroacetate salt (Compound 3)

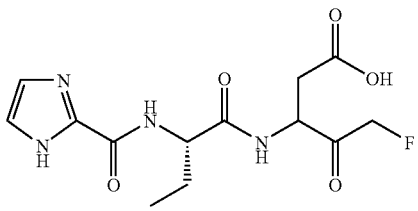

This was prepared from 1H-benzoimidazole-2-carboxylic acid using procedures similar to those described in Methods A-D above (147 mg, 64% for final step): IR(cm⁻¹) 3280.0, 1659.5, 157.9, 1192.5, 1141.6, 784.7, 721.1; $^1$H NMR 400 MHz DMSO-d₆ 0.95 (3H, m), 1.78 (2H, m), 2.58-2.98 (2H, m), 4.30-4.78 (2.5H, m), 5.10-5.42 (1.5H, m), 7.41 (2H, s), 8.44+8.75 (2H, 2xm); $^{13}$C NMR 100 MHz DMSO-d₆ 10.19, 10.29, 15.52 (CH₃), 25.42, 25.49, 26.03, 33.06, 33.13, 34.65, 34.80 (CH₂), 47.45, 47.53, 52.0, 53.96, 54.13 (CH) 65.27 (CH₂), 84.38 (d, J 177, CH₂F), 103.81, 104.00 (C), 123.89 (CH), 139.74 (C=O), 156.90, 158.39, 158.74, 171.51, 171.80, 171.83, 172.02, 173.11 (C=O), 202.51, 202.66, 202.76, 202.90 (CH₂FC=O); $^{19}$F NMR 376 MHz DMSO-d₆ −226.82 (t, J 45), −226.84 (t, J 45), −230.67 (t, J 45), −231.43 (t, J 45), −232.79 (t, J 45), −232.82 (t, J 45).

Example 11

[3S/R, (2S)]-5-Fluoro-3-{2-[(1H-imidazole-2-carbonyl)-amino]-3-methylbutyrylamino}-4-oxo-pentanoic acid (Compound 4)

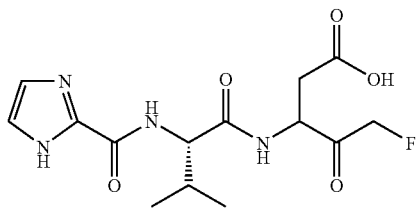

This was prepared from 1H-benzoimidazole-2-carboxylic acid using procedures similar to those described in Methods A-D above (80 g, 85% for final step): white powder, IR (solid, cm⁻¹) 1736, 1649, 1557, 1511, 1455, 1434, 1393; 1H NMR (DMSO+TFA) 0.92-0.95 (6H, m), 2.06-2.15 (1H, m), 2.56-2.90 (2H, m), 4.33-5.36 (4H, m), 7.79 (2H, s), 8.58-8.90 (2H, m); $^{19}$FNMR (DMSO+TFA) −226.8 (t), −230.6 (t), −231.0 (t), −232.5 (t), −232.6 (t); $^{13}$C NMR (DMSO+TFA) 18.1/18.4 (CH₃), 19.2/19.3 (CH₃), 34.5/34.8 (CH₂), 51.9/52.2 (CH), 58.5/58.8 (CH), 84.3/84.4 (2d, J 178.7/178.7, CH₂F), 122.0 (CH), 137.5 (C), 153.7 (C), 170.6 (C), 171.9/172.0 (C), 202.5/202.8 (2d, J 14.6/14.6, CO)

Example 12

[3S/R, (2S)]-3-{2-[(1H-Benzoimidazole-2-carbonyl)-amino]-3-methylbutyrylamino}-5-fluoro-4-oxo-pentanoic acid (Compound 5)

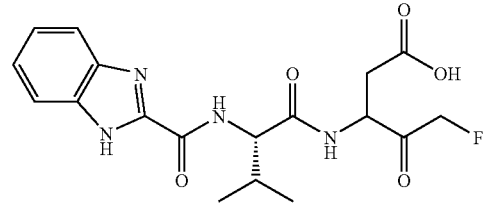

This was prepared from 1H-benzoimidazole-2-carboxylic acid using procedures similar to those described in Methods A-D above (90 mg, 87% for final step): white powder, IR (solid, cm⁻¹) 1737, 1665, 1527, 1373, 1194, 1137; $^1$H NMR (DMSO-d₆) 0.90-0.95 (6H, m), 2.15-2.18 (1H, m), 2.59-2.92 (2H, m), 4.33-4.76 and 5.12-5.38 (4H, 2 m), 7.31-7.35 (2H, m), 7.66-7.68 (2H, m), 8.36-8.82 (2H, m); $^{19}$FNMR (DMSO+TFA) −226.7 (t), −226.9 (t), −232.4 (t), −232.6 (t); $^{13}$C NMR (DMSO-d₆) 18.3/18.4/18.5/18.7 (CH₃), 19.4/19.5 (CH₃) 31.0/31.1/31.6 (CH), 34.7/34.8 (CH2), 51.8/52.1 (CH), 57.9/58.3/58.6 (CH), 84.3/84.4 (2d, J 178.7/178.7, CH₂F), 124.0 (CH), 145.2/145.2 (C) 158.4/158.5/158.7/158.8 (C), 170.9/171.1/171.2 (C), 172.0/172.0 (C), 173.1 (C), 173.9 (C), 202.06/202.6 (2d, J 13.8, CO).

Example 13

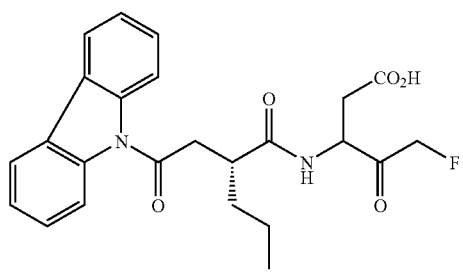

[3S/R (2S)]-3-[2-(Carbazol-9-yl-2-oxo-ethyl)-pentanoylamino]-5-fluoro-4-oxo-pentanoic acid

Method A (4S)-Benzyl-3-pentanoyl-oxazolidin-2-one

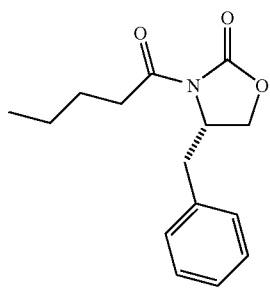

A solution of 4(S)-(−)-benzyl-2-oxazolidinone (10 g, 56.43 mmol) in anhydrous THF (200 ml) at −78° C. was treated with a 2.5M solution of n-butyl lithium in hexanes (23.70 ml, 59.26 mmol) with stirring. The reaction mixture was allowed to stir at −78° C. for 30 min before valeryl chloride (7.57 ml, 62.10 mmol) was added. The reaction mixture was then allowed to warm to ambient temperature over 15 h after which it was diluted with $NH_4Cl$ solution, diluted with ethyl acetate and washed with brine. The organic phase was dried ($Na_2SO_4$) and concentrated to give a gum. This was purified by flash chromatography (10% EtOAc in 40/60 hexanes) to give the sub-title compound (14.61 g, 99%) as a colourless oil: $^1$H NMR (400 MHz, $CDCl_3$) δ 0.94-1.20 (3H, m), 1.35-1.50 (2H, m), 1.62-1.80 (2H, m), 2.74-2.84 (1H, m), 2.86-3.08 (2H, m), 3.27-3.39 (1H, m), 4.11-4.26 (2H, m), 4.62-4.76 (1H, m), 7.18-7.40 (5H, m).

Method B

[4S(3R)]-3-(4-Benzyl-2-oxo-oxazolidine-3-carbonyl)-hexanoic acid tert-butyl ester

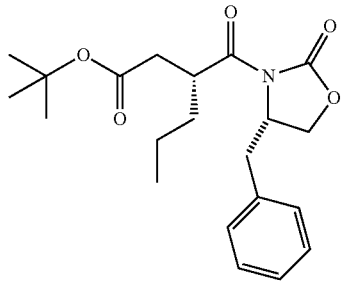

A solution of (4S)-benzyl-3-pentanoyl-oxazolidin-2-one (14.20 g, 54.34 mmol) in THF (100 ml) at −78° C. was treated over 10 min with a 1M solution of sodium bis(trimethylsilyl) amide in THF (59.80 ml, 59.77 mmol) with stirring. The reaction mixture was allowed to stir at −78° C. for 30 min before tert-butyl bromoacetate (10.43 ml, 70.64 mmol) was added. The reaction mixture was then allowed to stir for a further 3.5 h at −78° C. after which it was diluted with $NH_4Cl$ solution, diluted with ethyl acetate and washed sequentially with $NaHCO_3$ solution and brine. The organic phase was dried ($Na_2SO_4$) and concentrated to give a gum. On standing a white solid was formed and this was recrystallized from 40/60 DCM/hexanes to give the sub-title compound (14.62 g, 72%) as a white solid: $^1$H NMR (400 MHz, $CDCl_3$) δ 0.81-1.20 (3H, m), 1.21-1.76 (13H, m), 2.41-2.55 (1H, m), 2.66-2.92 (2H, m), 3.27-3.40 (1H, m), 4.05-4.26 (2H, m), 4.61-4.72 (1H, m), 7.12-7.40 (5H, m).

Method C (2R)-2-Propyl-succinic acid 1-benzyl ester 4-tert-butyl ester

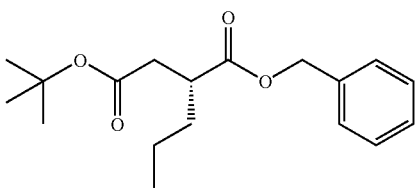

A solution of benzyl alcohol (4.62 ml, 44.64 mmol) in THF (80 ml) at −20° C. was treated with a 2.5M solution of n-butyl lithium in hexanes (13.36 ml, 33.48 mmol) with stirring. The reaction mixture was allowed to warm to −5° C. over 40 min before a solution of [4S (3R)]-3-(4-benzyl-2-oxo-oxazolidine-3-carbonyl)-hexanoic acid tert-butyl ester (8.38 g, 22.32 mmol) in THF (20 ml) was added. The reaction mixture was warmed to ambient temperature over 15 h after which it was diluted with $NH_4Cl$ solution and ethyl acetate and washed with brine. The organic phase was dried ($Na_2SO_4$) and concentrated to give a gum. This was purified by flash chromatography (11% EtOAc in 40/60 hexanes) to give the sub-title compound (4.56 g, 67%) as a colourless oil: $^1$H NMR (400 MHz, $CDCl_3$) δ 0.83-1.00 (3H, m), 1.21-1.71 (13H, m), 2.34-2.45 (1H, m), 2.75-2.95 (1H, m), 5.09-5.25 (2H, m), 7.30-7.43 (5H, m).

Method D (2R)-2-Propyl-succinic acid 1-benzyl ester

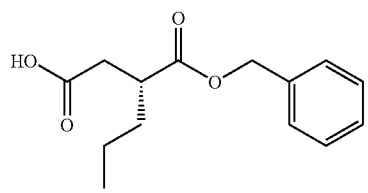

A stirred solution of (2R)-2-propyl-succinic acid 1-benzyl ester 4-tert-butyl ester (4.56 g, 14.88 mmol) in anhydrous DCM (20 ml) at 0° C. was treated with a solution of trifluoroacetic acid (10 ml) in anhydrous DCM (10 ml). The reaction mixture was allowed to warm to ambient temperature over 3 h before being concentrated under reduced pressure. The residue was dissolved in dry DCM, before concentrating again. This process was repeated several times in order to remove excess trifluoroacetic acid to leave the sub-title compound (3.70 g, 99%) as a gum: $^1$H NMR (400 MHz, CDCl$_3$) δ 0.82-0.99 (3H, m), 1.21-1.76 (4H, m), 2.45-2.60 (1H, m), 2.76-3.00 (2H, m), 5.10-5.21 (2H, m), 7.28-7.43 (5H, m), 7.83-8.18 (1H, m).

Method E (2R)-2-(2-carbazol-9-yl-2-oxo-ethyl)-pentanoic acid benzyl ester

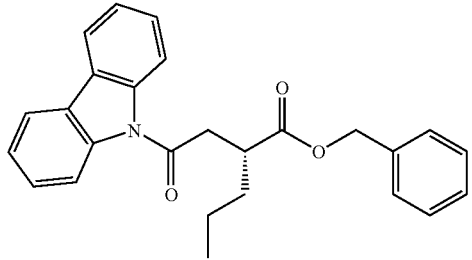

A stirred solution of carbazole (2.49 g, 14.88 mmol) in anhydrous THF (30 ml) at −78° C. was treated with a 1.0M solution of lithium bis(trimethylsilyl)amide in THF (14.88 ml, 14.88 mmol). The reaction mixture was allowed to warm to ambient temperature over 2 h before being re-cooled to −78° C.

A solution of (2R)-2-propyl-succinic acid 1-benzyl ester (3.70 g, 14.78 mmol) in anhydrous DCM (20 ml), stirring at 0° C., was treated with oxalyl chloride (1.43 ml, 16.37 mmol) and DMF (14 drops). The reaction mixture was stirred at 0° C. for 1 h before being concentrated in vacuo. The residue was dissolved in anhydrous THF (10 ml) and added to the lithium anion of carbazole previously prepared at −78° C. The reaction mixture was warmed to ambient temperature over 40 h after which it was diluted with NH$_4$Cl solution, and ethyl acetate and washed sequentially with 2N HCl, NaHCO$_3$ solution and brine. The organic phase was dried (Na$_2$SO$_4$) and concentrated to give a gum which was purified by flash chromatography (10% EtOAc in 40/60 hexanes) to give the sub-title compound (4.50 g, 76%) as a semi-solid/oil which also contained carbazole: $^1$H NMR (400 MHz, CDCl$_3$) δ 0.82-1.05 (3H, m), 1.11-1.99 (4H, m), 3.18-3.38 (2H, m), 3.56-3.71 (1H, m), 5.10-5.30 (2H, m), 7.11-7.60 (9H, m), 7.92-8.29 (4H, m).

Method F (2R)-2-(2-carbazol-9-yl-2-oxo-ethyl)-pentanoic acid

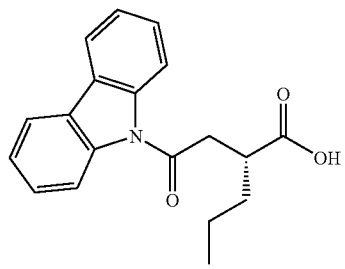

A stirred solution of (2R)-2-(2-carbazol-9-yl-2-oxo-ethyl)-pentanoic acid benzyl ester (4.50 g, 11.26 mmol) in EtOAc (60 ml) was treated with 10% Pd on carbon (~400 mg) and the reaction mixture was then placed under an atmosphere of hydrogen. After 1 h further 10% Pd on carbon (~300 mg) was added and the reaction mixture was placed under hydrogen, with stirring, for a further 3 h after which the reaction mixture was filtered through a celite pad and concentrated to give the sub-title compound (2.94 g, 84%) as a white solid which also contained carbazole: $^1$H NMR (400 MHz, CDCl$_3$) δ 0.92-1.04 (3H, m), 1.32-2.00 (4H, m), 3.19-3.34 (2H, m), 3.58-3.70 (1H, m), 7.30-7.53 (4H, m), 8.00-8.30 (4H, m).

Method G

[3S/R, 4S/R, (2R)]-3-[2-(2-carbazol-9-yl-2-oxo-ethyl)-pentanoylamino]-5-fluoro-4-hydroxy-pentanoic acid tert-butyl ester

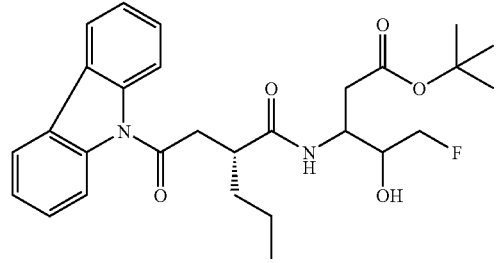

A stirred mixture of (2R)-2-(2-carbazol-9-yl-2-oxo-ethyl)-pentanoic acid (2.94 g, 9.50 mmol), 3-amino-5-fluoro-4-hydroxy-pentanoic acid tert-butyl ester (2.07 g, 9.99 mmol), HOBT (1.41 g, 10.43 mmol), DMAP (1.34 g, 10.97 mmol) and anhydrous THF (40 ml) was cooled to 0° C. before EDC (2.00 g, 10.43 mmol) was added. The mixture was allowed to warm to room temperature during 16 h then concentrated under reduced pressure. The residue purified by flash chromatography (33% EtOAc in 40/60 hexanes) to give the sub-title compound (2.51 g, 53%) as a foam: $^1$H NMR (400 MHz, CDCl$_3$) δ 0.90-1.03 (3H, m), 1.20-1.90 (13H, m), 2.50-3.00 (3H, m), 3.12-3.26 (1H, m), 3.59-3.80 (2H, m), 4.00-4.68 (3H, m), 6.53-6.89 (1H, m), 7.30-7.52 (4H, m), 7.95-8.05 (2H, m), 8.15-8.26 (2H, m); $^{19}$F NMR (376 MHz, CDCl$_3$) −229.10, −229.34, −230.95, −231.09.

Method H

[3S/R, (2R)]-3-[2-(2-carbazol-9-yl-2-oxo-ethyl)-pentanoylamino]-5-fluoro-4-oxo-pentanoic acid tert-butyl ester

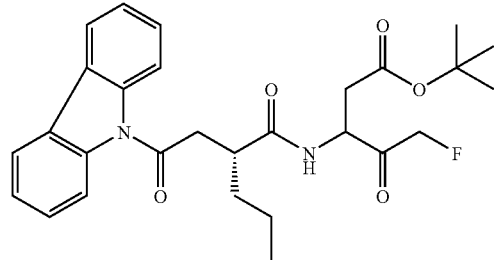

A stirred solution of [3S/R, 4S/R, (2R)]-3-[2-(2-carbazol-9-yl-2-oxo-ethyl)-pentanoylamino]-5-fluoro-4-hydroxy-pentanoic acid tert-butyl ester (2.51 g, 5.03 mmol) in anhydrous DCM (60 ml) was treated with 1,1,1-triacetoxy-1,1- dihydro-1,2-benziodoxol-3(1H)-one (2.35 g, 5.53 mmol) at 0° C. The resulting mixture was kept at 0° C. for 3 h, diluted with DCM, and then washed sequentially with saturated aqueous sodium thiosulphate, NaHCO$_3$ solution and brine. The organics were dried (Na$_2$SO$_4$) and concentrated. The residue was purified by flash chromatography (25% ethyl acetate in 40/60 hexanes) to afford the sub-title compound as an off white solid (1.437 g, 57%): IR (solid, cm$^{-1}$) 1722, 1689, 1636, 1531, 1441, 1365, 1279, 1155; $^1$H NMR (400 MHz, CDCl$_3$) δ 0.85-1.50 (3H, m), 1.35-1.54 (11H, m) 1.55-1.69 (1H, m), 1.78-1.95 (1H, m), 2.67-3.28 (4H, m), 3.60-3.79 (1H, m), 4.80-5.59 (3H, m), 6.89-7.04 (1H, m), 7.33-7.54 (4H, m), 7.98-8.04 (2H, m), 8.15-8.28 (2H, m); $^{13}$C (100 MHz, CDCl$_3$) δ 14.12, 14.40, 14.47, 14.60, 20.78, 20.84, 21.47, 28.32, 28.42, 28.48, 29.77, 33.63, 34.58, 34.91, 40.05, 43.05, 43.26, 43.29, 52.60, 53.00, 53.64, 66.90, 66.99, 82.62, 82.69, 85.53, 116.88, 116.94, 120.28, 120.31, 124.27, 127.76, 127.86, 128.69, 128.77, 128.99, 138.80, 171.21, 171.29, 172.21, 172.25, 175.53, 176.03, 203.04, 203.20, 203.30, 203.46; $^{19}$F (376 MHz, CDCl$_3$) δ −232.12, −233.24.

Method I

[3S/R, (2R)]-3-[2-(2-Carbazol-9-yl-2-oxo-ethyl)-pentanoylamino]-5-fluoro-4-oxo-pentanoic acid

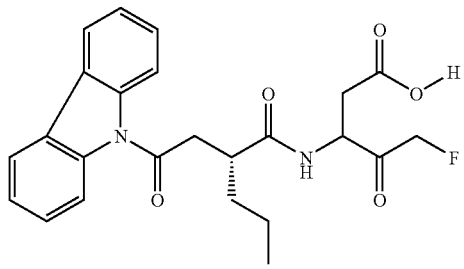

A solution of [3S/R, (2R)]-3-[2-(2-carbazol-9-yl-2-oxo-ethyl)-pentanoylamino]-5-fluoro-4-oxo-pentanoic acid tert-butyl ester (1.43 g, 2.88 mmol) in anhydrous DCM (20 ml) was treated with a solution of TFA (10 ml) in anhydrous DCM (10 ml) with stirring. The mixture was stirred at 0° C. for 2 h then at room temperature for 2 h. The mixture was concentrated under reduced pressure and then the residue was dissolved in dry DCM. This process was repeated several times in order to remove excess trifluoroacetic acid. The off-white solid was recrystallized from Et$_2$O/40/60 hexanes to give the title compound as a white powder (71 mg): IR (solid, cm$^{-1}$) 1746, 1689, 1641, 1541, 1436, 1374, 1284, 1207, 1160 cm-1; $^1$H NMR (400 MHz, d$_6$-DMSO) δ 0.80-1.00 (3H, m), 1.20-1.76 (4H, m), 2.30-2.90 (2H, m), 2.95-3.24 (1H, m), 3.26-3.59 (2H, m), 4.25-4.79 (1.5H, m) 5.02-5.43 (1.5H, m), 7.36-7.58 (4H, m), 8.10-8.30 (4H, m), 8.54-8.91 (1H, m); $^{13}$C NMR (100 MHz, DMSO) δ 14.31, 20.03, 20.13, 21.92, 22.51, 34.36, 34.77, 41.20, 41.62, 44.06, 51.77, 52.84, 83.45, 85.22, 116.70, 120.54, 123.91, 124.01, 127.85, 126.01, 138.20, 172.15, 172.36, 172.96, 173.00, 175.32, 175.48, 202.60, 203.10; $^{19}$F (376 MHz, DMSO) δ −226.68, −226.73, −231.21, −232.95, −233.38, −233.52.

Example 14

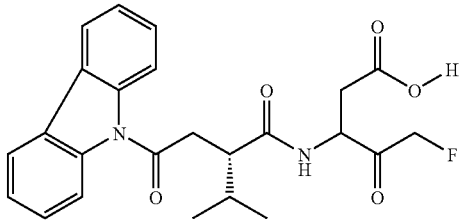

[3S/R(2S)]-3-[2-(2-Carbazol-9-yl-2-oxo-ethyl)-3-methyl-butyrylamino]-5-fluoro-4-oxo-pentanoic acid This was prepared using procedures similar to those described in Methods A-I. The product was isolated as a white powder (71% for final step): IR (solid, cm$^{-1}$) 1739, 1682, 1646, 1545, 1447, 1381, 1290, 1209, 1170 cm$^{-1}$; $^1$H NMR (400 MHz, DMSO+TFA) δ 0.79-1.08 (6H, m), 1.89-2.15 (1H, m), 2.31-3.60 (5H, m), 4.21-4.78 (1.25H, m), 4.98-5.45 (1.75H, m), 7.38-7.60 (4H, m), 8.14-8.35 (4H, m), 8.56-8.90 (1H, m); $^{13}$C NMR (100 MHz, DMSO) δ 20.46, 20.84, 21.04, 21.21, 30.77, 30.85, 33.37, 34.83, 35.24, 38.16, 38.89, 47.67, 48.23, 52.19, 53.43, 83.96, 84.01, 85.72, 85.77, 117.16, 121.02, 124.43, 126.42, 126.52, 128.42, 138.75, 172.64, 172.90, 173.85, 173.90, 174.74, 174.93, 175.16, 202.91, 203.04, 203.51, 203.65; $^{19}$F (376 MHz, DMSO) δ −226.63, −226.68, −231.24, −233.16, −233.38, −233.55.

Biological Method

Example 15

Inhibition of TNF Release From Whole Blood

Human blood was freshly drawn from healthy donors and collected in vacutainers. Blood was diluted 1:2 in PBS (tissue culture, pyrogen free) in a sterile bottle and inverted to mix well. Aliquots of 0.5 ml of blood mixture were dispensed into cluster tubes in 96 well format.

Dilutions of the test compounds were prepared in RPMI by taking 100 mM DMSO stocks of the compounds and diluting 1:10 in RPMI medium in eppendorfs, to give a 10 mM stock. 1:5 serial dilutions were prepared from the stock solutions.

LPS was kept at a frozen stock (−20 degrees C.) at 1 mg/ml in PBS and then diluted to 1:10 with RPMI medium and finally diluted in the medium again 1:350. 50 µl of each test compound (first concentration was 100 uM) were added to the blood samples and then stimulated with 10 µl LPS (final concentration in the well is 5 ng/ml). The contents were gently mixed using an 8 well multi-channel pipette and incubated at 37° C. overnight. At the end of the incubation time, contents were gently mixed, then spun down at 1000×g for 5 mins at 20° C. The serum supernatants were transferred to a fresh plate without disturbing the RBCs and diluted 1:2 with the diluent RD6C.

TNF-alpha levels of supernatants were assayed using the R+D systems ELISA kit, using R+D systems protocol. Samples were read at 450 nm. The compounds shown in Table 1 were tested in the above assay. In this TNF-alpha assay, category "A" indicates an IC50 value of <500 nM. Category "B" indicates an IC50 value of 500-1000 nM. Category "C" indicates an IC50 value of 1001-2000 nM. Category "D" indicates an IC50 value of >2000 nM. See Table 1.

TABLE 1
TNF-alpha IC50 Data of Exemplary Compounds
| Example | TNF-alpha IC50 (nM) |
|---|---|
| 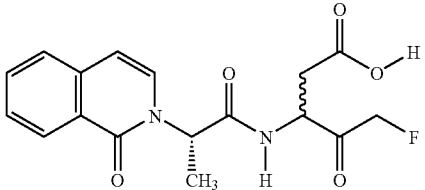 | C |
| 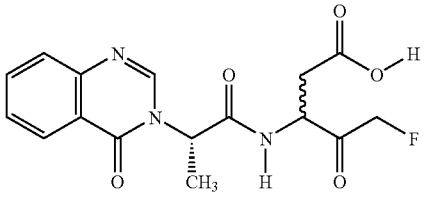 | A |
| 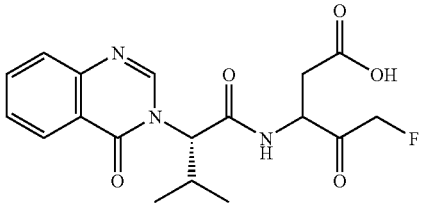 | B |
| 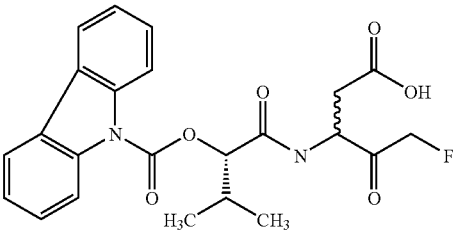 | C |
| 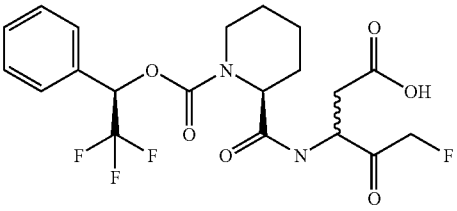 | A |
| 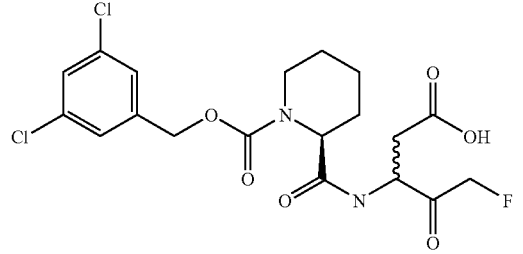 | C |

TABLE 1-continued
TNF-alpha IC50 Data of Exemplary Compounds
| Example | TNF-alpha IC50 (nM) |
|---|---|
| 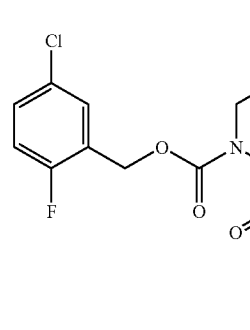 | D |
| 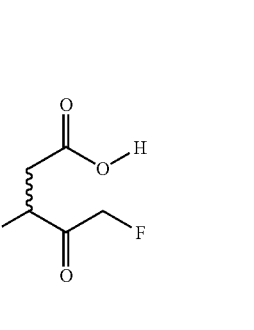 | A |
| 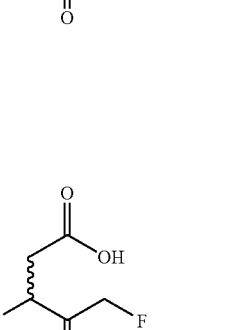 | A |
| 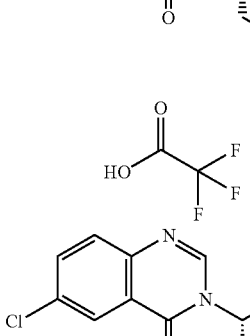 | A |
| 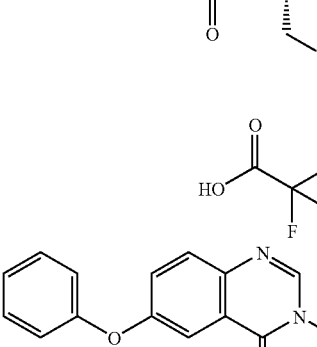 | B |

TABLE 1-continued

TNF-alpha IC50 Data of Exemplary Compounds

| Example | TNF-alpha IC50 (nM) |
|---|---|
| (structure) | C |
| (structure) | C |
| (structure) | A |
| (structure) | A |
| (structure) | A |

TABLE 1-continued

TNF-alpha IC50 Data of Exemplary Compounds

| Example | TNF-alpha IC50 (nM) |
|---|---|
| [structure: 2-methylbenzyl carbamate of piperidine-2-carboxamide linked to aspartyl fluoromethyl ketone] | A |
| [structure: 6-(2-chlorophenoxy)quinazolin-4(3H)-one with butyl side chain, coupled to aspartyl fluoromethyl ketone; TFA salt] | D |
| [structure: 6-(3-chlorophenoxy)quinazolin-4(3H)-one with butyl side chain, coupled to aspartyl fluoromethyl ketone; TFA salt] | D |
| [structure: 6-(3-fluorophenoxy)quinazolin-4(3H)-one with butyl side chain, coupled to aspartyl fluoromethyl ketone; TFA salt] | D |
| [structure: 6-(3-fluorophenylthio)quinazolin-4(3H)-one with butyl side chain, coupled to aspartyl fluoromethyl ketone; TFA salt] | C |

TABLE 1-continued
TNF-alpha IC50 Data of Exemplary Compounds
| Example | TNF-alpha IC50 (nM) |
|---|---|
| 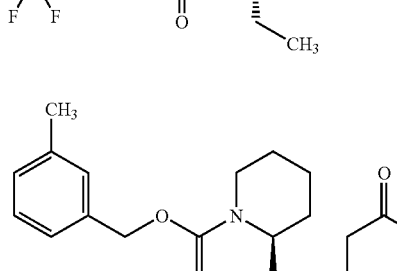 | B |
| 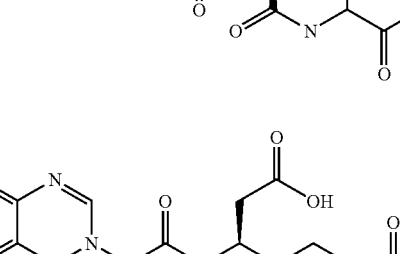 | B |
| 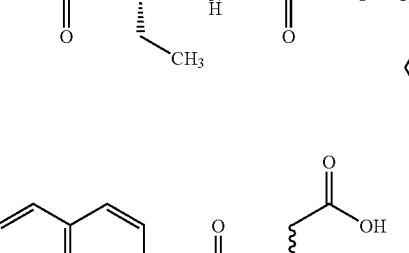 | D |
| 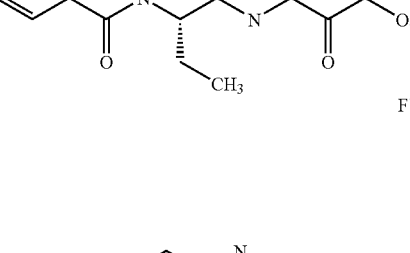 | C |
| 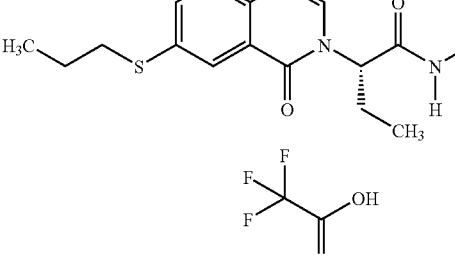 | A |

TABLE 1-continued
TNF-alpha IC50 Data of Exemplary Compounds
| Example | TNF-alpha IC50 (nM) |
|---|---|
| 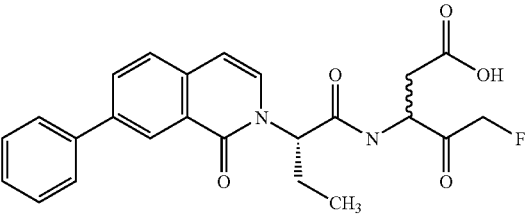 | A |
| 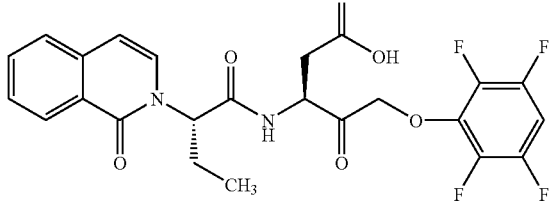 | B |
| 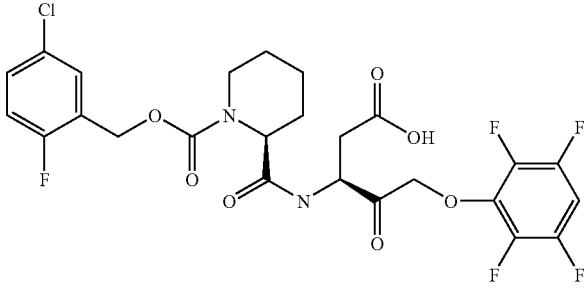 | D |
| 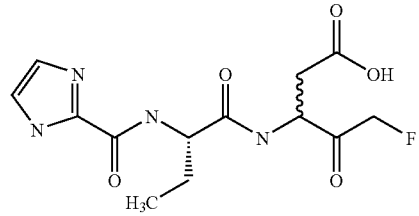 | A |
| 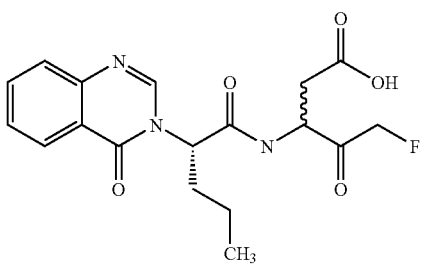 | A |
| 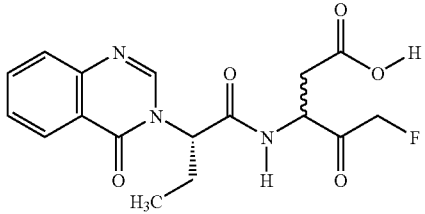 | A |

TABLE 1-continued
TNF-alpha IC50 Data of Exemplary Compounds
| Example | TNF-alpha IC50 (nM) |
|---|---|
| 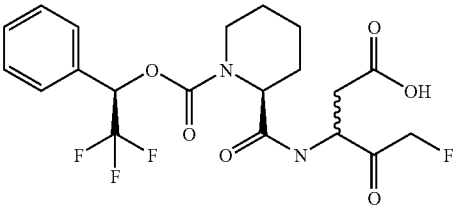 | A |
| 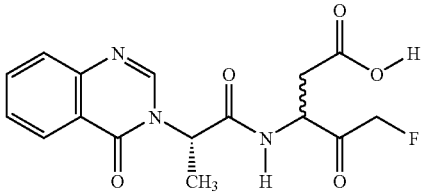 | A |
| 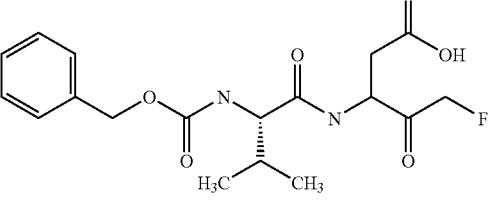 | A |
| 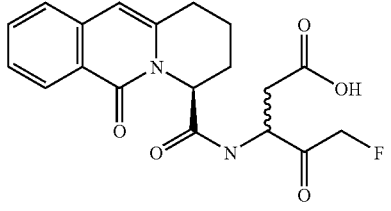 | A |
| 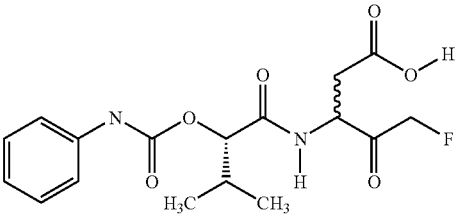 | A |
| 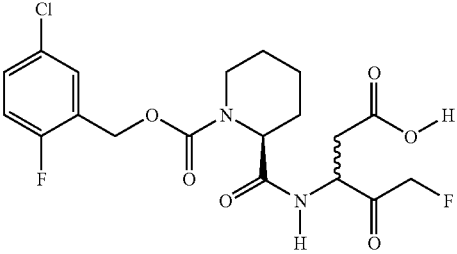 | A |

TABLE 1-continued
TNF-alpha IC50 Data of Exemplary Compounds
| Example | TNF-alpha IC50 (nM) |
|---|---|
| 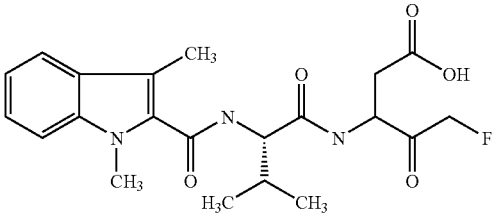 | A |
| 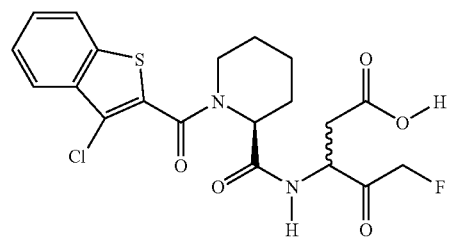 | A |
| 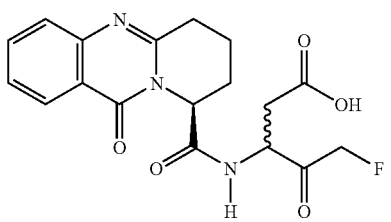 | B |
| 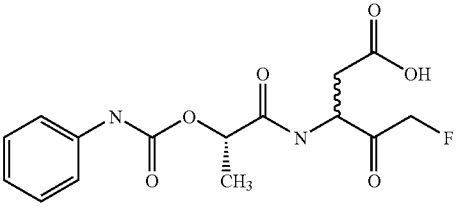 | B |
| 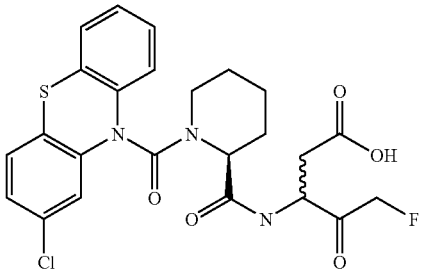 | B |
| 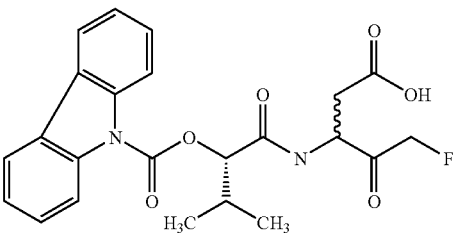 | C |

TABLE 1-continued

TNF-alpha IC50 Data of Exemplary Compounds

| Example | TNF-alpha IC50 (nM) |
|---|---|
| 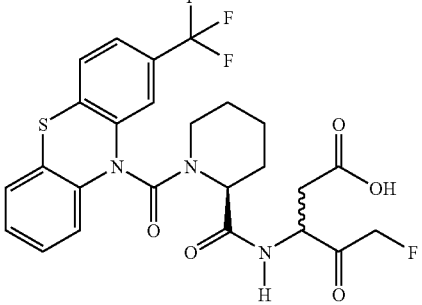 | D |
| 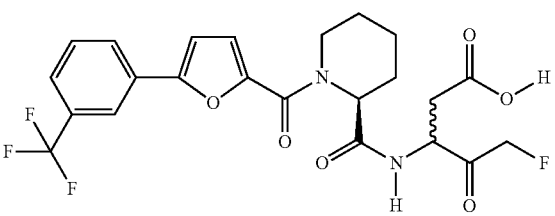 | D |

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

We claim:

1. A method for inhibiting TNF-alpha activity or decreasing TNF-alpha activity in a subject suffering from restinosis, inflammatory disease of the central nervous system, aneurysmal aortic disease, traumatic joint injury, peridontal disease, macular degeneration, diabetic retinopathy, occular inflammation, keratoconus, Sjogren's syndrome, cachexia, anorexia, cerebral malaria, silicosis, asbestosis, pulmonary sarcoidosis, influenza, keloid formation, pyresis, chronic bronchitis, urticaria, allergic rhinitis, allergic conjunctivitis, eosiniophilic granuloma, or reperfusion injury of the myocardium and brain; said method comprising administering a compound according to FIG. 7 or a pharmaceutical composition comprising said compound to said subject.

* * * * *